United States Patent
Lioux et al.

(10) Patent No.: US 9,295,732 B2
(45) Date of Patent: Mar. 29, 2016

(54) CONJUGATED TLR7 AND/OR TLR8 AND TLR2 POLYCATIONIC AGONISTS

(71) Applicant: CAYLA, Toulouse (FR)

(72) Inventors: Thierry Lioux, Balma (FR); Daniel Drocourt, Saint-Orens de Gameville (FR); Fabienne Vernejoul, Toulouse (FR); Gerard Tiraby, Toulouse (FR); Eric Perouzel, Toulouse (FR)

(73) Assignee: INVIVOGEN, Toulouse (FR)

( * ) Notice: Subject to any disclaimer, the term of this patent is extended or adjusted under 35 U.S.C. 154(b) by 21 days.

(21) Appl. No.: 13/774,155

(22) Filed: Feb. 22, 2013

(65) Prior Publication Data

US 2014/0242108 A1    Aug. 28, 2014

(51) Int. Cl.
*A61K 31/52*    (2006.01)
*A61K 47/48*    (2006.01)

(52) U.S. Cl.
CPC ........... *A61K 47/48338* (2013.01); *A61K 31/52* (2013.01); *A61K 47/48038* (2013.01)

(58) Field of Classification Search
CPC .................................................... A61K 31/52
See application file for complete search history.

(56) References Cited

U.S. PATENT DOCUMENTS

| | | | |
|---|---|---|---|
| 4,689,338 A | 8/1987 | Gerster | |
| 2007/0197478 A1 | 8/2007 | Jones et al. | |
| 2010/0210598 A1 | 8/2010 | Carson et al. | |
| 2010/0297165 A1 | 11/2010 | Berzofsky et al. | |
| 2011/0282061 A1 | 11/2011 | Johnson | |
| 2012/0003298 A1 | 1/2012 | Barberis et al. | |
| 2012/0135963 A1 | 5/2012 | Johnson | |
| 2012/0178743 A1 | 7/2012 | Isobe et al. | |
| 2012/0294885 A1 | 11/2012 | David et al. | |
| 2013/0202629 A1 | 8/2013 | Carson et al. | |

FOREIGN PATENT DOCUMENTS

| | | | |
|---|---|---|---|
| WO | 2007093901 A1 | 8/2007 | |
| WO | 2009088401 A2 | 7/2009 | |
| WO | 2010048520 A1 | 4/2010 | |
| WO | 2011017611 A1 | 2/2011 | |
| WO | 2011134669 A1 | 11/2011 | |
| WO | 2011139348 A2 | 11/2011 | |

OTHER PUBLICATIONS

Long et al., "Lipoteichoic Acid Induces Unique Inflammatory Responses when Compared to Other Toll-Like Receptor 2 Ligands", Plos One, 2009, vol. 4, No. 5, e5601, XP002695160.
Kaiser et al.: "Fully Synthetic Vaccines Consisting of Tumor-Associated MUC1 Glycopeptides and a Lipopeptide Ligand of the Toll-like Receptor 2", Angewandte Chemie International Edition, vol. 49, No. 21, 2010, pp. 3688-3692.
Zeng et al., "Lipidation of intact proteins produces highly immunogenic vaccine candidates", Molecular Immunology, vol. 48, No. 4, 2011, pp. 490-496, XP027578517.
Ghosh et al.: "TLR-TLR cross talk in human PBMC resulting in synergistic and antagonistic regulation of type-1 and 2 interferons, IL-12 and TNF-alpha", International Immunopharmacology, vol. 7, No. 8, 2007, pp. 1111-1121, XP022113162.
Wenink et al., "TLR2 Promotes Th2/Th17 Responses via TLR4 and TLR7/8 by Abrogating the Type I IFN Amplification Loop", The Journal of Immunology, vol. 183, No. 11, 2009, pp. 6960-6970 XP055050689.
Liu et al.: "TLR2 Signaling Depletes IRAK1 and Inhibits Induction of Type I IFN by TLR7/9", The Journal of Immunology, vol. 188, No. 3, 2012, pp. 1019-1026, XP055050692.
Hemmi et al., "Small anti-viral compounds activate immune cells via the TLR7 MyD88—dependent signaling pathway", Nature Immunology, 2002, vol. 3, No. 2, pp. 196-200.
Jones et al., "Discovery of a highly potent series of TLR7 agonists", Bioorganic & Medicinal Chemistry Letters, 2011, vol. 21, pp. 5939-5943.
Kurimoto et al., "Synthesis and evaluation of 2-substituted 8-hydroxyadenines as potent interferon inducers with improved oral bioavailabilities", Bioorganic & Medicinal Chemistry, 2004, No. 12, pp. 1091-1099.
Lee et al., "Molecular basis for the immunostimulatory activity of guanine nucleoside analogs: Activation of Toll-like receptor 7", PNAS, 2003, vol. 100, No. 11, pp. 6646-6651.

*Primary Examiner* — Jeffrey S Lundgren
*Assistant Examiner* — Chris Simmons
(74) *Attorney, Agent, or Firm* — Young & Thompson

(57) ABSTRACT

A conjugated compound of Formula I: $Q\text{-}Z\text{—}R^4$ wherein Q is a TLR7 and/or TLR8 agonist and $Z\text{—}R^4$ is a TLR2 agonist, the conjugated compound being chosen among compounds of Formula II:

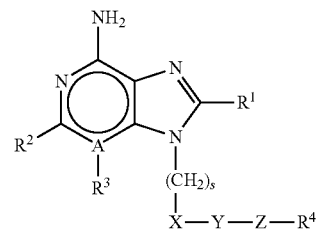

Formula II

4 Claims, 12 Drawing Sheets

CONJUGATED TLR7 AND/OR TLR8 AND TLR2 POLYCATIONIC AGONISTS

FIELD OF THE INVENTION

Figure 1A:
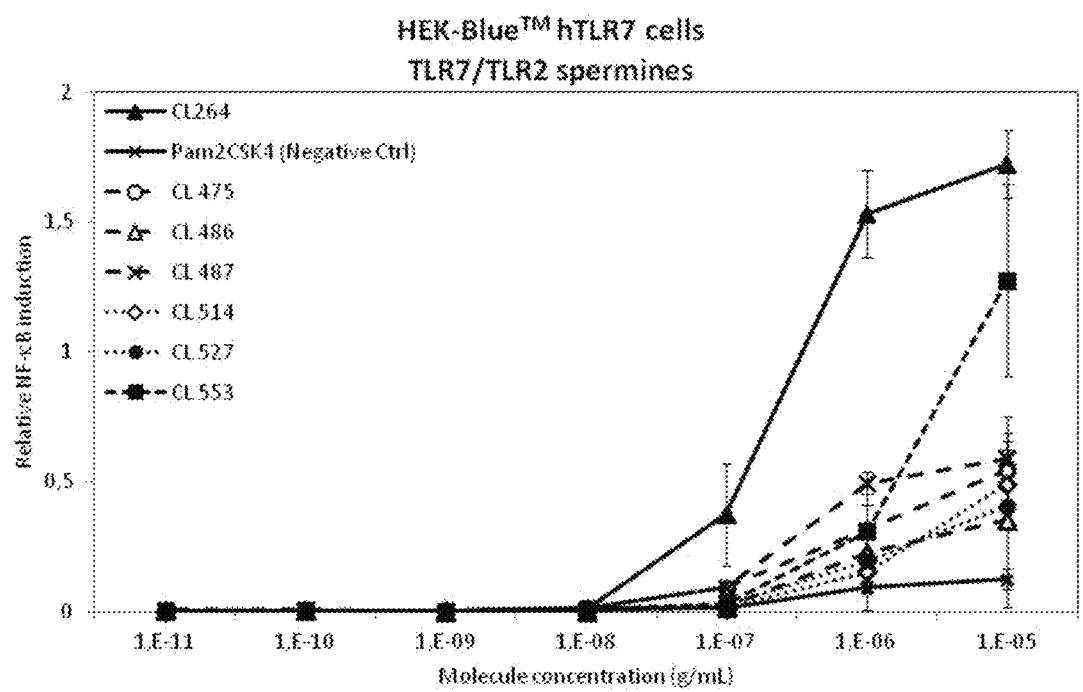

The present invention provides covalent conjugates of TLR7 and/or TLR8 and TLR2 agonists and their use in therapeutic applications. The present invention further provides novel TLR2 agonists.

The present invention further provides polycationic molecules able to bind polyanionic molecules.

The present invention further provides compositions and methods for treating diseases by administering such molecules to a subject.

BACKGROUND OF THE INVENTION

Toll-like receptors (TLRs) are pattern recognition receptors (PRRs) expressed by diverse cell types that play an important role in both innate and adaptive immunity. TLRs are type I membrane proteins with distinct sub-cellular localization and recognize a range of highly conserved molecular structures present on microbial pathogens termed pathogen-associated molecular patterns (PAMPs) or microbe-associated molecular patterns (MAMPs) (Beutler 2009; Kawai and Akira 2011). To date, 13 TLR isoforms have been identified in mammals, 10 in humans, and the individual receptors have been characterized to recognize specific ligands. Ligands can broadly be categorized into three groups; lipids and lipopeptides, proteins and nucleic acids. Lipid-based bacterial cell wall components such as lipoproteins are recognized by TLR1, 2, 6 and lipopolysaccharides by TLR4. Microbial proteins such as flagellin are recognized by TLR5. Exogenous nucleic acids in the form of CpG DNA are recognized by TLR9 and single or double stranded RNA are recognized by TLR7 and TLR3, respectively. Certain TLRs bind not only to microbial products but also recognize 'self' ligands known as damage-associated molecular patterns (DAMPs), which are proteins or nucleic acids released from stressed, damaged or dying cells and tissues. Cells of the innate immune system respond to PAMPs/MAMPs and DAMPs by producing proinflammatory cytokines and chemokines that signal for the clearance of the pathogens and damaged-self. Upon engagement with specific ligands, TLR activation leads to the activation of transcription factors such as nuclear factor kappa B (NF)-B, activating protein-1 (AP-1) and interferon regulatory factors (IRFs) through several adaptor molecules including myeloid differentiation primary response gene 88 MyD88, Toll-interleukin 1 receptor (TIR) domain containing adaptor protein TIRAP and TIR-domain containing adaptor inducing interferon-beta TRIF, to regulate cytokine expression. The production and secretion of cytokines such as interferons (IFNs), TNF-α and interleukins, as well as co-stimulatory molecules, contribute to the death and clearance of the pathogenic invasion and dead cells. In addition to TLRs, the innate immune system comprises other germline-encoded PRRs families, which include the Nod-like receptors (NLRs), RIG-I-like receptors (RLRs), C-type lectin receptors (CLRs) and cytosolic DNA sensors (CDSs). The recognition of exogenous nucleic acids in the cytoplasm of cells by CDSs and RLRs has been recently understood to play a major role in triggering innate immune responses (Keating et al. 2011). Stimulation of multiple receptors of the innate immune system can effectively drive a more specific adaptive immune response, which is responsible for developing antigen-specific memory. Novel therapeutic strategies attempt to harness receptors of the innate immune system to systematically shape an immune response to fight infections, immune disorders and diseases such as cancer.

Targeting PRRs and more particularly TLRs and cytosolic nucleic sensors for therapeutic purposes is a growing interest in the prevention and treatment of infections, immune-diseases and cancers.

SUMMARY OF THE INVENTION

Now, the Applicants have synthesized and developed novel compounds that are TLR7 and/or TLR8 agonists covalently conjugated to TLR2 agonists.

These molecules of the invention are in addition, polycations at physiological pH. By virtue of being polycationic, the molecules of the invention have the ability to form a complex with polyanionic molecules such as nucleic acids.

Due to their ability to complex with nucleic acid molecules, these molecules induce an immune response via cytosolic nucleic sensors pathways, in addition to the TLR7 and TLR2 pathways.

Furthermore, some molecules of the invention function as transfection agents and carriers of DNA into cells. Thus, the molecules of the invention may also enable the introduction of therapeutic genes into cells concomitant with triggering a strong innate immune response through the stimulation of multiple receptors of the innate immune system.

Moreover, by virtue of being polycationic, the conjugated TLR agonists of the invention have improved uptake by targeted cells.

Provided herein are molecules and compositions of, and methods for the modulation of the innate immune system. Furthermore, the present invention provides a means for gene delivery. More specifically, the invention is designed to effectively combine the action of TLR7 and/or TLR8, TLR2, and cytosolic nucleic acid sensors to mount a robust innate immune response in order to trigger an adaptive immune response. One application of the molecules of the invention is to be used as anti-cancer agents to eliminate tumors by inducing tumor antigen-specific CD4+ and CD8+ T cells. This invention provides novel conjugated agonists that are TLR7 and/or TLR8 agonists covalently attached to TLR2 agonists, The synthetic molecules of the present invention are conjugated compounds of Formula I:

  Formula I which are polycationic with the ability to complex polyanionic molecules, such as nucleic acids.

One application of the molecules of the invention includes their use as anti-cancer agents.

One aspect of the invention is the ability of the novel molecules to complex with nucleic acids such as linear or circular DNA, which can in turn be introduced into cells to trigger IFN production by the activation of cytosolic nucleic acid sensors. Furthermore, the molecules of the invention may be used to introduce and express a plasmid DNA encoding a gene of interest into cells. In this regard, the molecules of the invention may be used for gene therapy. Overall, the molecules of the invention, and compositions thereof, stimulate a primary innate immune response and have the ability to trigger a secondary immune response of the adaptive immune system. Triggering the secondary adaptive immune response is required for immunological memory, which is imperative to prevent tumor metastases and relapse.

Toll-Like Receptors 7 and 8

TLR7 and TLR8 are endosomal TLRs that recognize single-stranded RNA and play a major role in the anti-viral response during viral infection. TLR7 is expressed predominantly in plasmacytoid dendritic cells (pDCs), macrophages and B cells, whereas TLR8 is expressed predominantly in myeloid dendritic cells (mDCs) and monocytes. Activation of TLR7 and TLR8 play an important role in shaping adaptive immunity and several low molecular weight agonists of TLR7 and/or TLR8 have been employed in therapeutics. The different classes of TLR7 and/or TLR8 agonists include imidazoquinolines, nucleoside analogs of purines and 3-deazapurine derivatives (Hemmi et al. 2002; Lee et al. 2003; Jones et al. 2011). The class of TLR7 and/or TLR8 agonists that have received a considerable attention are imidazoquinolines particularly Imiquimod, which is a IH-imidazo[4,5-c]quinoline (described in U.S. Pat. No. 4,689,338 Gerster et al.—Riker). Imiquimod, also known as Aldara™, R-837, S-26308, was found to be effective against basal cell carcinoma, actinic keratosis and genital papilloma virus infections when applied topically in cream form. The other members of this class of TLR7 agonists are Resiquimod (R-848, S-28609), Gardiquimod, and CL097 (InvivoGen), which in contrast to Imiquimod are also ligands for the TLR8 receptor. A second class are purine-like molecules that include 8-hydroxyadenines, such as 9-benzyl-8-hydroxy-2-(2-methoxyethoxy) adenine (SM-360320) and CL264 (InvivoGen), and have been identified as potent and specific TLR7 agonists (Kurimoto et al. 2004). The third class, 3-deazapurine derivatives, include compounds that are modified purines with an amine functional group on the benzyl moiety (WO Pat. No. 2007/093901 Jones et al. (Pfizer)). The activation of TLR7 and/or TLR8 in immune cells has been shown to contribute to anti-tumor immune response (So and Ouchi 2010). TLR7 and/or TLR8 agonists have shown to induce apoptosis in cancer cells of skin and bladder. Induced apoptosis further recruits cytotoxic T lymphocytes (CTLs) to induce death of tumor cells. TLR7 and/or TLR8 agonists have also been demonstrated to induce local cytokine production altering the tumor microenvironment to make it more conducive for the action of anti-tumoral agents. The understanding of the activation of TLR7 and TLR8 in tumor cells and its relationship to cancer progression is accumulating and facilitating the development of therapeutic drugs. To date, a number of TLR7 agonists, namely purine or imidazoquinoline derivatives, have been reported for the treatment of diseases and infections. Conjugating TLR7 agonists to a lipidic moiety has been an approach taken to facilitate uptake into cells (Wu et al. US Pat. No. 2011/0053893 (Novartis); Isobe et al. U.S. Pat. No. 8,044,056 (Sumitomo); Fink et al. U.S. Pat. No. 7,485,432 (3M); Gorden et al US Pat. No. 2011/0070575 (Coley); Johnson US Pat. No. 2011/0282061 (Glaxo); Biggadike et al. US Pat. No. 2011/0229500 (Glaxo); Cook et al. US Pat. No. 2010/0240623 (AstraZeneca); Carson et al. US Pat. No. 2010/0210598).

Current delivery methods of TLR7 agonists as medicines are intramuscular injections and the use of topically applied creams (Hemmi et al. 2002; Ambach et al. 2004). The major challenges faced by TLR agonists as anti-cancer agents include the penetration into tumor-protective niches and, for agonists of endosomal TLRs, their cellular uptake into the endosomal compartment. These are aspects that require careful attention in the design of novel TLR agonists for effective targeting and delivery.

Toll-Like Receptor 2

TLR2 is the most ubiquitous of the TLRs expressed on the cell surface of monocytes, mature macrophages, DCs, and B cells (Lee and Kim 2007). TLR2 recognizes a large set of structurally diverse ligands including peptidoglycan, lipoteichoic acid and lipoprotein from Gram-positive bacteria, lipoarabinomannan from mycobacteria, and zymosan from yeast cell wall. TLR2 is functionally active as a heterodimer in combination with either TLR1 or TLR6 (Ozinsky, Underhill et al. 2000; Takeuchi, Kawai et al. 2001). TLR2 dimerization with either TLR1 or TLR6 confers specificity for ligand binding; TLR2/TLR1 for tri-acylated lipopeptides and TLR2/TLR6 for diacylated lipopeptides (Zahringer et al. 2008). The signaling elicited by ligand bound TLR2 is dependent on key accessory molecules such as CD14. A number of TLR2 ligands are exploited as vaccine adjuvants. The synthetic tri-acylated lipopeptide $Pam_3CSK_4$ has been proven to be a potent adjuvant for various vaccines, including a sublingual allergy vaccine, flu vaccine and leishmaniasis vaccine (Lombardi et al. 2008; Jayakumar et al. 2011; Caproni et al. 2012). The implication of TLR2 in diseases such as rheumatoid arthritis, lung disease, and cancer (Schmidt et al. 2007), has encouraged the design of new synthetic TLR2 immunomodulatory agents to be effective as therapeutics (Nakaar et al. US Pat No. 2009/0028889 (Vaxinnate); Finberg et al. US Pat. No. 2011/0152251). TLR2 agonists have been shown to be effective in tumor regression and prolong survival in cancer patients (Garay et al. 2007; Curtin et al. 2009; Zhang et al. 2011). The role of TLR2 in cancer is clearly context-dependent. Recent studies have indicated that TLR2 promotes gastric cancer proliferation, and through a non-inflammatory mechanism (Tye et al. 2012). Indeed, the modulation of TLR2 for therapeutic reasons has also been complicated due to the diversity of TLR2 ligands and the implication of TLR2 signaling in auto-immune diseases. Interestingly small molecule TLR2 agonists have been reported to exhibit potent adjuvantic activity in a model of immunization without inducing an inflammatory response (Agnihotri et al. 2011; Salunke et al. 2012).

It has been demonstrated that combinations of agonists of the innate immune system can effectively enhance adjuvancy. For instance combining ligands for TLRs may better mimic viral recognition (Whitmore et al. 2004) or induce effective tumor-specific responses (Garaude et al. 2012). Furthermore a TLR2/6 agonist with a TLR9 agonist has been reported to induce a synergistic response in the resistance to pneumonia (Duggan et al. 2011; Tuvim et al. 2012).

The present invention provides novel conjugated compounds comprising a TLR7 and/or TLR8 agonist covalently attached to a TLR2 agonist. In addition, the molecules of the invention contain at least two secondary amines and possibly a primary amine, which at physiological pH, are polycations that have the ability to form a complex with polyanionic molecules such as nucleic acids. Therefore, compositions of the certain molecules of the invention with DNA can also serve as transfection agents or carriers of DNA, introducing DNA into cells and triggering innate immune responses.

Innate Immune Sensors of Nucleic Acids

Recent advances indicate a prominent role of nucleic acid sensors in the detection of exogenous, foreign or synthetic, cytosolic DNA or RNA, and in triggering an innate immune response (Takeshita and Ishii 2008; Barber 2011a). A number of sensors of double-stranded DNA, single-stranded DNA, double-stranded RNA, single-stranded RNA and oligodeoxynucleotides are involved in the proinflammatory response particularly of IFN type I (Keating et al. 2011). Single-stranded CpG-rich DNA is recognized by TLR9, whereas double-stranded and specific motifs in single-stranded RNA are recognized by TLR3 and TLR7/TLR8, respectively. In addition to the TLRs, increasing evidence has highlighted the importance of a number of cytosolic nucleic acids sensors.

The first identified cytosolic DNA sensor, named DNA-dependent activator of IFN-regulatory factors (DAI), binds cytosolic double stranded DNA and leads to the production of type I IFNs through the Interferon Regulatory Factor 3 (IRF3)

pathway (Takaoka et al. 2007; Wang et al. 2008). DAI and other DNA sensors such as IFI16 and DDX41 act through the endoplasmic reticulum (ER)-resident transmembrane protein stimulator of IFN genes (STING), an essential signalling adaptor activating IRF3 to trigger transcriptional induction of type I IFN genes and interferon inducible proteins (Barber 2011b; Burdette et al. 2011). A number of cyclic nucleotides that act as second messengers and their analogs have been demonstrated to activate STING, which in turn activates the type I IFN pathway (Burdette et al 2011; Wu et al. 2012; Sun et al. 2012). Another double-stranded DNA sensor Leucine-rich repeat in flightless I-interacting protein-1 (LRRFIP1) can recognize AT-rich B-forms as well as GC-rich Z-forms of double-stranded DNA (Yang et al. 2010). LRRFIP1 triggers the production of IFN-β in a β-catenin-dependent manner. Another DNA sensing pathway leads to the activation of the multi-protein scaffold inflammasome that contains Absent In Melanoma 2 (AIM2), which functions to process proinflammatory cytokines IL-13 and IL-18 to active forms via cleavage by caspase-1 (Muruve et al. 2008).

Cytosolic RNA sensors comprise the retinoic acid-inducible gene (RIG-I)-like receptors (RLRs), which include RIG-I and the melanoma differentiation associated gene 5 protein (MDA-5). RIG-I and MDA-5 signal through TKK-binding kinase (TBK1) upon recognition of foreign cytosolic double-stranded RNA, leading to the activation of transcription factors such as IRF3 to control the transcription of genes encoding interferons and other cytokines (Takeuchi and Akira 2009). Another RNA sensor, the protein laboratory of genetics and physiology 2 (LGP2) has recently been described to facilitate RNA recognition by RIG-I and MDA-5 (Satoh et al. 2010). These RNA sensors can also be activated indirectly upon the introduction of foreign DNA into the cytosol following infection with DNA viruses or bacteria, which are able to be converted to a double stranded 5' triphosphate RNA species in the cytosol by RNA polymerase III (Chiu et al. 2009; Caviar et al. 2012). In summary, coding or non-coding DNA, or RNA, which when complexed with molecules of the invention and consequently delivered into cells, act as immunomodulatory molecules.

The present invention provides novel TLR7 and/or TLR8 agonist covalently conjugated to TLR2 agonist having affinity for nucleic acids.

Thus, in one embodiment, provided herein is a compound having a structure according to Formula II:

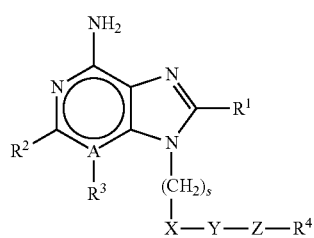

Formula II wherein A, $R^1$, $R^2$, $R^3$, X, Y, Z, and $R^4$ are as defined hereafter.

Purine, imidazoquinoline or 3-deazapurine derivatives described herein can disclose modulators of TLR7 and/or TLR8, and Z—$R^4$ modulators of TLR2.

Compositions of the molecules of the invention include complexing with nucleic acids to deliver coding or non-coding DNA, or RNA, to cells as well as retaining TLR7 and/or TLR8 and TLR2 activity.

Some of the molecules can be used as nucleic acid transfection agents.

In one embodiment, administering a TLR7 and/or TLR8 agonist conjugated to a TLR2 agonist and compositions of the polycationic molecule, activates multiple receptors giving rise to an effective and amplified immune response implicating both the innate and adaptive arms of the immune system. In one embodiment, molecules of the invention in complex with nucleic acids mediate the synergistic activation of TLR7 and/or TLR8 and TLR2 and cytosolic nucleic acid sensors to induce a strong interferon response. In one embodiment, molecules of the invention are transfection agents to complex with plasmid DNA for gene transfer.

DETAILED DESCRIPTION OF THE INVENTION

The present invention provides conjugated compound comprising a TLR7 and/or TLR8 agonist covalently conjugated to a TLR2 agonist, and compositions thereof, that induce innate immune responses. The compounds of the invention are therefore interferon inducers, anti-cancer agents, anti-infectious agents, therapeutic agents for immunological diseases and vaccine adjuvants. More particularly, the molecules of the invention comprise heterocyclic compounds that are TLR7 and/or TLR8 agonists and lipidic polyamine molecules that are TLR2 agonists of Formula II as defined below, or pharmaceutically acceptable salt thereof. In addition, the molecules of the invention contain at least two secondary amines and possibly a primary amine, which at physiological pH, are polycations that have the ability to form a complex with polyanionic molecules such as nucleic acids.

Furthermore, the present invention relates to a process for preparing heterocyclic lipidic polyamine compounds of the Formula II, or pharmaceutically acceptable salts thereof. Unless stated otherwise, the following terms used in the specification and claims have the meanings indicated below.

$C_i$-$C_j$ alkyl means a linear or branched alkyl group comprising from i to j carbon atoms. Alkyl groups include for instance methyl, ethyl, n-propyl, isopropyl, n-butyl, isobutyl, pentyl, and hexyl.

$C_{i-j}$ alkenyl means an unsaturated hydrocarbon chain wherein i denotes the number of carbon atoms in the hydrocarbon chain and j denotes the number of double bonds in the hydrocarbon chain. Alkenyl groups include for instance vinyl, allyl, octenyl, oleyl, arachidonyl.

$C_i$-$C_j$ alkylamino means a $C_i$-$C_j$ alkyl-NH— group wherein $C_i$-$C_j$ alkyl is defined as above. Alkylamino groups include for instance methylamino, ethylamino, n-propylamino, or n-butylamino.

Di($C_i$-$C_j$ alkyl)amino means a ($C_i$-$C_j$ alkyl)$_2$N— group wherein $C_i$-$C_j$ alkyl is as defined above. Dialkylamino groups include for instance di methylamino or diethylamino.

$C_i$-$C_j$ alkoxy means a $C_i$-$C_j$ alkyl-O— group wherein $C_i$-$C_j$ alkyl is defined as above. Alkoxy groups include for instance methoxy or ethoxy.

$C_i$-$C_j$ cycloalkyl means a non-aromatic saturated carbocyclic radical, consisting of one or several rings, comprising from i to j carbon atoms. Cycloalkyl groups include for instance cyclopropyl, cyclobutyl, cyclopentyl, cyclohexyl, cycloheptyl, decahydronaphthalene, or octahydro-1H-indene.

$C_i$-$C_j$ carbocyclic means a non-aromatic saturated carbocyclic ring comprising from i to j carbon atoms. Carbocyclic groups include for instance cyclopropyl, cyclobutyl, cyclopentyl, cyclohexyl, cycloheptyl.

$C_i$-$C_j$ cycloalkyl-$C_m$-$C_n$ alkyl means a $C_i$-$C_j$ cycloalkyl-R— group wherein R is a linear or branched alkyl group comprising from m to n carbon atoms. $C_3$-$C_6$cycloalkyl-$C_1$-$C_6$alkyl groups include for instance ethylcyclopentyl, propylcyclopentyl, ethylcyclohexyl, or propylcyclohexyl.

$C_i$-$C_j$ cycloalkyl-$C_m$-$C_n$ alkylamino means a $C_i$-$C_j$ cycloalkyl-R—NH— group wherein R is a linear or branched alkyl group comprising from m to n carbon atoms. $C_3$-$C_6$cycloalkyl-$C_1$-$C_6$alkylamino groups include for instance cyclopentylmethanamino, 2-cyclopentylethanamino, cyclohexylmethanamino, or 2-cyclohexylethanamino.

$C_i$-$C_j$ alkoxy$C_m$-$C_n$ alkylamino means a $C_i$-$C_j$ alkoxy-R—NH— group wherein R is a linear or branched alkyl group comprising from m to n carbon atoms. $C_1$-$C_{10}$alkoxy$C_1$-$C_{10}$alkylamino groups include for instance 2-ethoxyethanamino, 2-propoxyethanamino, 3-ethoxypropan-1-amino, 3-propoxypropan-1-amino.

$C_i$-$C_j$ alkoxy$C_m$-$C_n$ alkoxy means a $C_i$-$C_j$ alkoxy-R— group wherein R is a $C_m$-$C_n$ alkoxy group as defined above. $C_1$-$C_{10}$alkoxy$C_1$-$C_{10}$alkoxy groups include for instance 2-ethoxyethoxy, 2-propoxyethoxy, 3-ethoxypropoxy, or 3-propoxypropoxy.

$C_i$-$C_j$ aryl means an aromatic carbocyclic radical consisting of one or several rings, containing from i to j carbon atoms. Aryl groups include for instance phenyl.

$C_i$-$C_j$ heterocyclyl and $C_i$-$C_j$ heterocycle respectively means a non-aromatic saturated cyclic radical and cycle consisting of one or several rings, comprising from i to j atoms including one or several heteroatoms chosen among N, O and S. Heterocyclyl groups include for instance tetrahydrofuranyl, tetrahydropyranyl, tetrahydrothioaziridinyl, N-pyrrolidinyl, N-piperidinyl, or N-morpholinyl.

$C_i$-$C_j$ alkoxycarbonyl means a $C_i$-$C_j$ alkoxy-CO— group wherein the $C_i$-$C_j$ alkoxy group is as defined above.

$C_i$-$C_j$ alkanoyl means a $C_i$-$C_j$ alkyl-CO— group wherein the $C_i$-$C_j$ alkyl group is as defined above.

The suffix "ene" means that the radical is divalent. For instance, $C_1$-$C_6$ alkylene means a linear or branched divalent hydrocarbon chain comprising from 1 to 6 carbon atoms, or $C_6$-$C_{20}$ arylene means an aromatic carbocyclic divalent radical consisting of one or several rings, containing from 6 to 20 carbon atoms.

The "specific side chain of an amino acid" means the R group of an amino acid having the generic Formula $H_2$NCHRCOOH. Amino acids include for instance the L or D isomers of alanine, valine, leucine, isoleucine, phenylalanine, tryptophan, methionine, glycine, serine, threonine, cysteine, tyrosine, asparagine, glutamine, aspartic acid, glutamic acid, lysine, arginine, proline and histidine.

"Complex" means the chemical entity formed by the association of two or more compounds.

The term "agonist," as used herein, refers to a compound that can combine with a receptor (e.g., a TLR) to produce a cellular activity. An agonist may be a ligand that directly binds to the receptor. Alternatively, an agonist may combine with a receptor indirectly by, for example, (a) forming a complex with another molecule that directly binds to the receptor, or (b) otherwise results in the modification of another compound so that the other compound directly binds to the receptor. An agonist may be referred to as an agonist of a particular TLR (e.g., a TLR7 agonist or a TLR2 agonist) or a particular combination of TLRs (e.g., a TLR 7/8 agonist—an agonist of both TLR7 and TLR8).

An agonist that selectively modulates biological activity through a particular TLR may be a TLR-selective agonist.

A TLR agonist is any compound or substance that functions to activate a TLR, e.g., to induce a signaling event mediated by a TLR signal transduction pathway. Suitable TLR agonists include TLR2 agonists, TLR3 agonists, TLR4 agonists, TLR7 agonists, TLR8 agonists, and TLR9 agonists.

"TLR7 and/or TLR8" agonist refers to a molecule that is an agonist of TLR7 only, TLR8 only or both TLR7 and TLR8. TLR7 and/or TLR8 agonists are well known in the art. Examples of TLR7 agonists are purine or purine like molecules such as 8-hydroxyadenine, imidazoquinoline and it derivatives such as imiquimod, and pyridinomidazol or 3-deazapurine. Examples of TLR8 agonists are resiquimod and 3M-002. Some molecules are both TLR7 and TLR8 agonists such as Resiquimod.

TLR2 agonist refers to synthetic TLR2 agonists. Suitable synthetic TLR2 agonists include synthetic diacylated and triacylated lipopeptides. An exemplary, non-limiting TLR2 ligand is $Pam_2Cys$ (dipalmitoyl-S-glyceryl cysteine) or S-[2,3-bis(palmitoyloxy)-(2RS)-propyl]-(R)-cysteine, where "$Pam_2$" is "dipalmitoyl-S-glyceryl"). Derivatives of $Pam_2Cys$ are also suitable TLR2 agonists, where derivatives include, but are not limited to $Pam_2CSK_4$. $Pam_2CSK_4$ (dipalmitoyl-S-glyceryl cysteine-serine-(lysine)$_4$; or $Pam_2Cys$-Ser-(Lys)$_4$ is a synthetic diacylated lipopeptide. Synthetic TLRs agonists have been described in the literature. (Kellner et al. 1992; Seifert et al. 1990; Lee et al. 2003). TLR2 agonist refers also to synthetic $Pam_3Cys$ (tripalmitoyl-S-glyceryl cysteine) or S-[2,3-bis(palmitoyloxy)-(2RS)-propyl]-N-palmitoyl-(R)-cysteine, where "$Pam_3$" is "tripalmitoyl-S-glyceryl") (Aliprantis et al. 1999). Derivatives of $Pam_3Cys$ are also suitable TLR2 agonists, where derivatives include, but are not limited to, $Pam_3Cys$-Ser-(Lys)$_4$S-[2,3-bis(palmitoyloxy)-(2-R,S)-propyl]-N-palmitoyl-(R)-Cys-(S)-Ser-(Lys)$_4$.

Another non-limiting example of a suitable TLR2 agonist is a monoacyl amino acid or lipopeptides where the thioglycerol motif is replaced with a thioethanol bridge. These TLR2 derivatives have been described in the literature. (Agnihotri et al. 2011; Salunke D B et al. 2012).

In some embodiments, a suitable TLR2 agonist activates a TLR2, and may also activate one or more other Toll-like receptors. Such agonists are "relatively" selective, e.g., such agonists may activate two or more other TLR in addition to TLR2, but do not activate receptors other than TLR.

Assays for detecting TLR7, TLR8 or TLR2 activity are known in the art and include for example cell-based assays using respectively TLR7, TLR8 or TLR2 reporter cell lines (InvivoGen). The reporter cell lines are engineered HEK293 cells, a human embryonic kidney cell line (ATCC, CRL-1573) that stably express either murine TLR7 (HEK-Blue™ mTLR7) or human TLR7 (HEK-Blue™ hTLR7), human TLR8 (HEK-Blue™ hTLR8) or human TLR2 (HEK-Blue™ hTLR2) with an NF-κB-inducible secreted embryonic alkaline phosphatase (SEAP) as the reporter gene.

Such assays are disclosed in more detail in the examples below.

Suitable compound TLR agonists include TLR2 agonists that are attached, covalently, to a TLR7 and/or TLR8 agonist via a polyamine spacer.

"Treatment or treating" refers to both curative treatment and prophylactic or preventive measures, wherein the object is to prevent or slow down the targeted pathologic condition or disorder. Those in need of treatment include those already with the disorder as well as those prone to have the disorder or those in whom the disorder is to be prevented. Hence, the subject to be treated herein may have been diagnosed as having the disorder or may be predisposed or susceptible to the disorder.

"Pharmaceutically acceptable salts" of a compound means salts that are pharmaceutically acceptable and that possess the desired pharmacological activity of the parent compound. Such salts include: acid addition salts formed with inorganic acids such as hydrochloric acid, hydrobromic acid, sulfuric acid, nitric acid, phosphoric acid, and the like; or formed with organic acids such as acetic acid, benzenesulfonic acid, benzoic, camphorsulfonic acid, citric acid, ethanesulfonic acid, fumaric acid, glucoheptonic acid, gluconic acid, glutamic acid, glycolic acid, hydroxynaphtoic acid, 2-hydroxyethanesulfonic acid, lactic acid, maleic acid, malic acid, malonic acid, mandelic acid, methanesulfonic acid, muconic acid, 2-naphthalenesulfonic acid, propionic acid, salicylic acid, succinic acid, tartaric acid, p-toluenesulfonic acid, trimethylacetic acid, and the like; or salts formed when an acidic proton present in the parent compound either is replaced by a metal ion, e.g., an alkali metal ion, an alkaline earth ion, or an aluminum ion; or coordinates with an organic or inorganic base. Acceptable organic bases include diethanolamine, ethanolamine, N-methylglucamine, triethanolamine, trimethylamine, and the like. Acceptable inorganic bases include aluminum hydroxide, calcium hydroxide, potassium hydroxide, sodium carbonate and sodium hydroxide.

"Solvates" means solvent additions forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate.

Polymorphs as referred to herein can include crystalline and amorphous forms, which can be further characterised as follows:

i) Crystalline forms have different arrangements and/or conformations of the molecules in the Crystal lattice, (ii) Amorphous forms consist of disordered arrangements of molecules that do not possess a distinguishable crystal lattice.

A first object of the present invention is a conjugated compound of Formula I $$Q\text{-}Z\text{—}R^4 \qquad \text{Formula I}$$

wherein:

Q is a TLR7 and/or TLR8 agonist, and $Z\text{—}R^4$ is a TLR2 agonist selected from the group consisting of:

Formula III

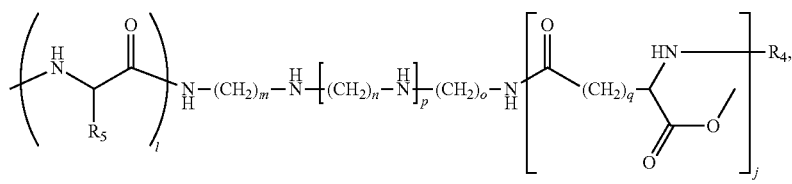

Formula IV

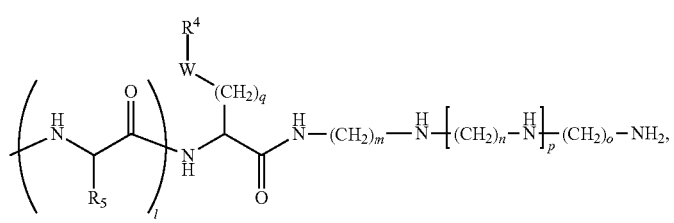

Formula V

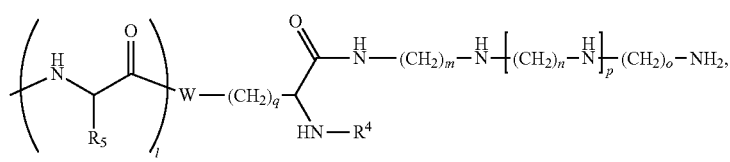

Formula VI

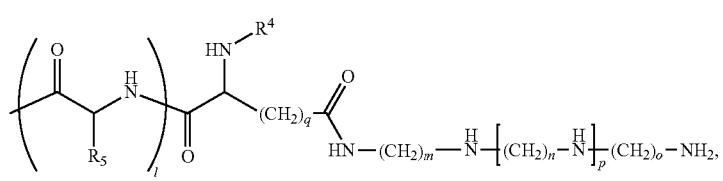

Formula VII

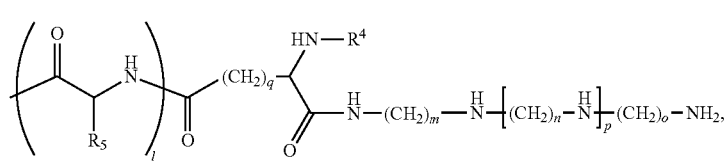

-continued

Formual VIII

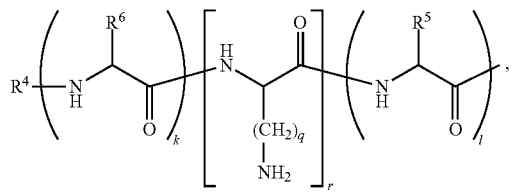

Formula IX

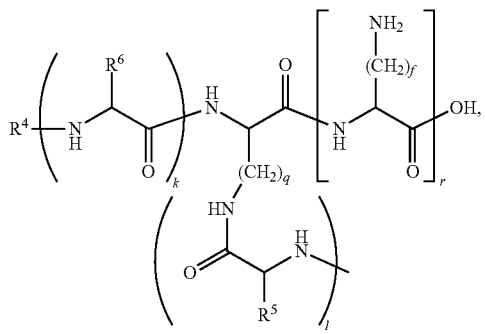

Formula X

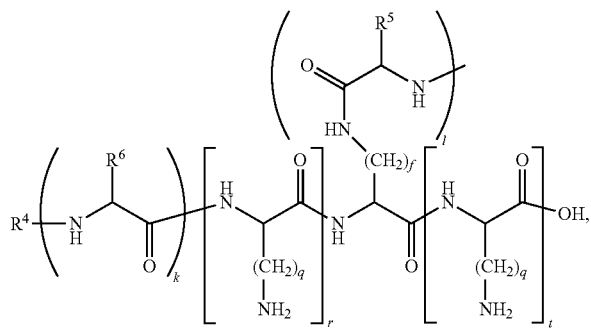

wherein:
$R^5$ and $R^6$, identical or different, are the specific side chain of an amino acid;
W is —O—, —NH—, or —S—;
j and l, identical or different, are 0 or 1;
p is integer from 0 to 6;
f, g, k, m, n, o, and q, identical or different, are integers from 1 to 4;
r and t, identical or different, are integers from 1 to 6;
$R^4$ is a lipid of Formula XI:

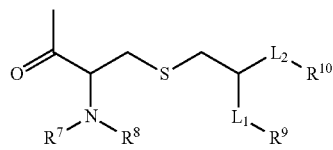

Formula XI wherein:
$R^7$ and $R^8$ are independently from each other H, $C_1$-$C_{30}$alkyl, $C_2$-$C_{30}$alkylenyl, —C(O)—$C_1$-$C_{30}$alkyl, —C(O)—$C_2$-$C_{30}$alkylenyl, or —C(O)—O—$C_1$-$C_{30}$alkyl;
$R^9$ is H, $C_1$-$C_{30}$alkyl or $C_2$-$C_{30}$alkylenyl;
$R^{10}$ is H, $C_1$-$C_{30}$alkyl or $C_2$-$C_{30}$alkylenyl;
$R^9$ and $R^{10}$ are not both H;
$L_1$ is absent, —OC(O)—, —O—, —$NR^{11}$C(O)—, —OC(O)$NR^{11}$— or —CH2- wherein $R^{11}$ is H, $C_1$-$C_{30}$alkyl or $C_2$-$C_{30}$alkylenyl;
$L_2$ is —$CH_2$OC(O)—, —$CH_2$O—, —$CH_2NR^{11}$C(O)— or —$CH_2$—, if $L_1$ is absent $L_2$ is —OC(O)—, —O—, —$NR^{11}$C(O)—, —$NR^{10}R^{11}$, —OC(O)$NR^{11}$— or —CH2- wherein $R^{11}$ is as defined above.

Preferably, the compounds of Formula I are imidazoquinoline, purine or 3-deazapurine derivatives, i.e. the radical Q of Formula I contains a moiety which is selected from the group consisting of imidazoquinoline, purine and 3-deazapurine derivatives.

Hence, the radical Q may be represented by the following formula:

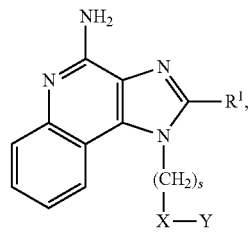

(imidazoquinoline derivative)

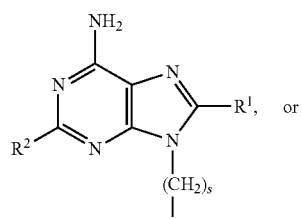

or (purine derivative)

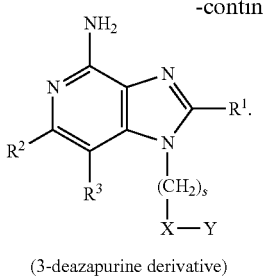

(3-deazapurine derivative)

A preferred class of compounds provided by the present invention comprises those of the general Formula II:

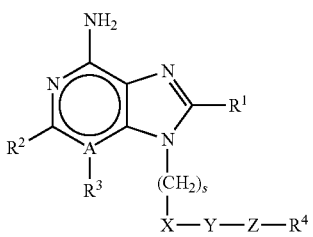

Formula II a tautomer thereof or a pharmaceutically acceptable salt, solvate or polymorph of said compound or tautomer, wherein:

A is a carbon or nitrogen atom;

$R^1$ is —H, —OH, —SH, —NH$_2$, —CF$_3$, halogen, or a group chosen from C$_1$-C$_6$alkyl, C$_1$-C$_6$alkylamino, C$_1$-C$_6$alkoxy, C$_3$-C$_6$cycloalkyl-C$_1$-C$_6$alkyl, C$_3$-C$_6$cycloalkyl-C$_1$-C$_6$alkylamino, C$_3$-C$_6$cycloalkyl, C$_1$-C$_6$alkoxyC$_1$-C$_6$alkylamino, or C$_1$-C$_6$alkoxyC$_1$-C$_6$alkoxy, (C$_1$-C$_6$alkyl)-E-(C$_1$-C$_6$alkylene)- wherein E is —O—, —S—, —N(R$^{12}$)—, —C(O)— or —S(O)$_2$— and R$^{12}$ is —H, carboxyl, —NH$_2$, C$_1$-C$_6$alkyl, C$_1$-C$_6$alkoxy, C$_1$-C$_6$alkanoyl, C$_6$-C$_{20}$aryl, C$_6$-C$_{20}$ heteroaryl, or C$_1$-C$_6$alkoxycarbonyl, said group being optionally terminally substituted with a hydroxyl, amino, thiol, hydrazino, hydrazido, azido, acetylenyl, carboxyl, or maleimido group;

$R^2$ and $R^3$ independently from each other are H, OH, SH, NH$_2$, CF$_3$, halogen, C$_1$-C$_{10}$alkyl, C$_1$-C$_{10}$alkylamino, C$_1$-C$_{10}$dialkylamino, C$_1$-C$_{10}$alkoxy, C$_1$-C$_{10}$alkoxy-C$_1$-C$_{10}$ alkylamino, C$_1$-C$_{10}$alkoxy-C$_1$-C$_{10}$alkoxy, C$_1$-C$_{10}$alkoxy-C$_6$-C$_7$heterocycle, C$_1$-C$_{10}$alkylamino-C$_6$-C$_7$heterocycle, —NH—SO$_2$—C$_1$-C$_6$alkyl, —C(O)—C$_1$-C$_6$alkyl, —O—C(O)—C$_1$-C$_6$alkyl, —C(O)—C$_1$-C$_{10}$alkylamino, —C(O)—C$_1$-C$_{10}$dialkylamino, C$_6$-C$_{10}$aryl, C$_5$-C$_9$heterocyclyl, C$_3$-C$_9$ carbocyclyl, C$_1$-C$_{10}$alkylamino-C$_2$-C$_7$heterocycle, (C$_1$-C$_6$alkoxy)-E-(C$_1$-C$_6$alkylene), wherein E is as defined above, or when taken together, $R^2$ and $R^3$ form a fused C$_6$-C$_{20}$ aryl, C$_4$-C$_{20}$ heteroaryl, C$_6$-C$_7$carbocycle or a C$_4$-C$_7$heterocycle; where carbocycle, heterocycle, aryl, and heteroaryl are optionally substituted with one or more groups independently selected from F, Cl, Br, I, —CH$_3$, —CH$_2$CH$_3$, CH$_2$CH(CH$_3$)$_2$, —CH$_2$OH, —CH$_2$CH$_2$OH, —O(CH$_3$)$_2$OH, —CH(OH)CH(CH$_3$)$_2$, —O(CH$_3$)$_2$CH$_2$OH, —CH$_2$CH$_2$SO$_2$CH$_3$, —CN, —CF$_3$, —CHF$_2$, —CO$_2$H, —COCH$_3$, —CO$_2$CH$_3$, —C(CH$_3$)$_2$CO$_2$CH$_3$, —CO$_2$C(CH$_3$)$_3$, —COCH(OH)CH$_3$, —COCH(CH$_3$)$_2$, —CONH$_2$, —CONHCH$_3$, —CON(CH$_3$)$_2$, —C(CH$_3$)$_2$CONH$_2$, —NO$_2$, —NH$_2$, —NHCH$_3$, —N(CH$_3$)$_2$, —NHCOCH$_3$, —N(CH$_3$)COCH$_3$, —NHS(O)$_2$CH$_3$, —N(CH$_3$)C(CH$_3$)$_2$CONH$_2$, —N(CH$_3$)CH$_2$CH$_2$S(O)$_2$CH$_3$, —OH, —OCH$_3$, —S(O)$_2$N(CH$_3$)$_2$, —SCH$_3$, —CH$_2$OCH$_3$, —S(O)$_2$CH$_3$, cyclopropyl, oxetanyl, and morpholino;

$R^3$ is absent when A is a nitrogen atom;

s is an integer from 1 to 4 (thus s is 0, 1, 2, 3 or 4);

X is an unbranched —C$_1$-C$_6$ alkylene)-, —(C$_6$-C$_{20}$arylene)-, —(C$_4$-C$_{20}$heteroarylene)-, —(C$_1$-C$_6$ alkylene)-E-(C$_1$-C$_6$alkylene)-,—(C$_1$-C$_6$ alkylene)-(C$_3$-C$_7$-carbocyclylene)-, —(C$_1$-C$_6$ alkylene)-(C$_3$-C$_7$-heterocyclylene)-, —(C$_1$-C$_6$ alkylene)-(C$_6$-C$_{20}$ arylene)-, —(C$_1$-C$_6$ alkylene)-(C$_4$-C$_{20}$ heteroarylene)-, —(C$_1$-C$_6$ alkylene)-E-(C$_1$-C$_7$ carbocyclylene)-, —(C$_1$-C$_6$ alkylene)-E-(C$_3$-C$_7$-heterocyclylene)-, —(C$_1$-C$_6$ alkylene)-E-(C$_6$-C$_{20}$ arylene)-,—(C$_1$-C$_6$ alkylene)-E-(C$_4$-C$_{20}$ heteroarylene)-, where alkylene, carbocyclylene, heterocyclylene, arylene, and heteroarylene are optionally substituted with one or more groups independently selected from F, Cl, Br, I, —CH$_3$, —CH$_2$CH$_3$, CH$_2$CH(CH$_3$)$_2$, —CH$_2$OH, —CH$_2$CH$_2$OH, —C(CH$_3$)$_2$OH, —CH(OH)CH(CH$_3$)$_2$, —C(CH$_3$)$_2$CH$_2$OH, —CH$_2$CH$_2$SO$_2$CH$_3$, —CN, —CF$_3$, —CHF$_2$, —CO$_2$H, —COCH$_3$, —CO$_2$OH$_3$, —O(CH$_3$)$_2$CO$_2$CH$_3$, —CO$_2$O(OH$_3$)$_3$, —COCH(OH)CH$_3$, —COOH(CH$_3$)$_2$, —CONH$_2$, —CONHCH$_3$, —CON(CH$_3$)$_2$, —C(CH$_3$)$_2$CONH$_2$, —NO$_2$, —NH$_2$, —NHCH$_3$, —N(CH$_3$)$_2$, —NHCOCH$_3$, —N(CH$_3$)COCH$_3$, —NHS(O)$_2$CH$_3$, —N(CH$_3$)C(CH$_3$)$_2$CONH$_2$, —N(CH$_3$)CH$_2$CH$_2$S(O)$_2$CH$_3$, —OH, —OCH$_3$, —S(O)$_2$N(CH$_3$)$_2$, —SCH$_3$, —CH$_2$OCH$_3$, —S(O)$_2$CH$_3$, cyclopropyl, oxetanyl, and morpholino, and E is as defined above;

Y is a single bond, —O—, —S—, —N(R$^{12}$)—, —C(O)—, or —S(O)$_2$— and R$^{12}$ is as defined above;

Z—$R^4$ is selected from the group consisting of:

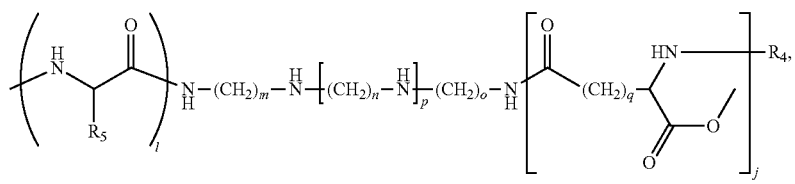

Formula III

-continued
Formula IV
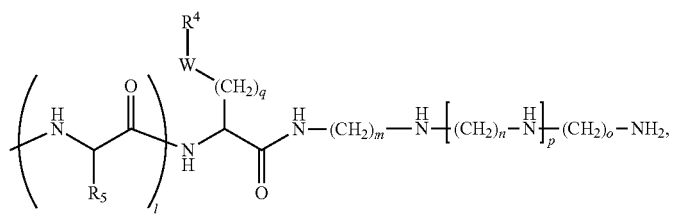
Formula V
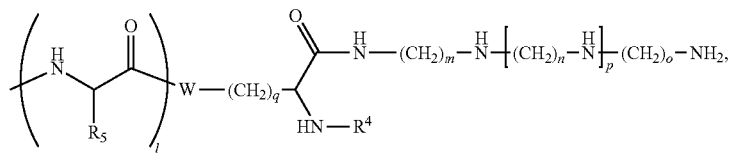
Formula VI
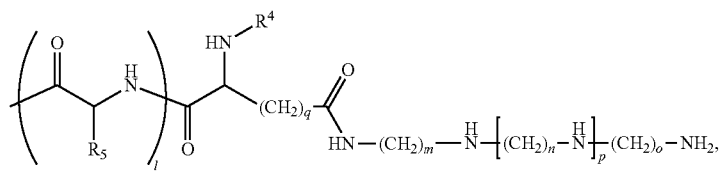
Formula VII
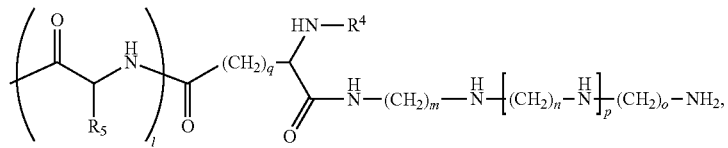
Formual VIII
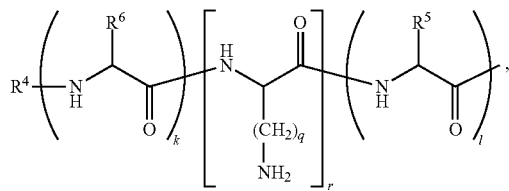
Formula IX
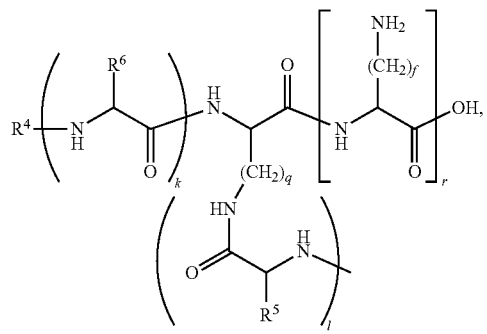
Formula X
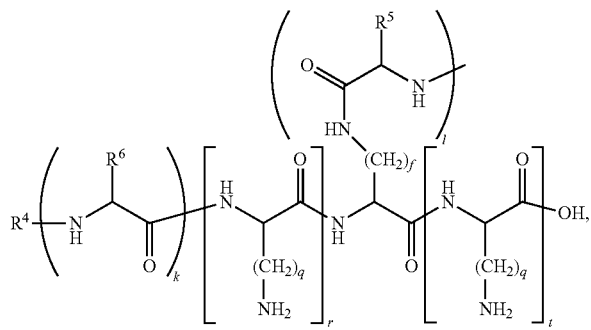
wherein:
$R^5$ and $R^6$, identical or different, are the specific side chain of an amino acid;
W is —O—, —NH—, or —S—;
j and l, identical or different, are 0 or 1;
p is integer from 0 to 6;
f, g, k, m, n, o, and q, identical or different, are integers from 1 to 4;
r and t, identical or different, are integers from 1 to 6;

$R^4$ is a lipid of Formula XI:

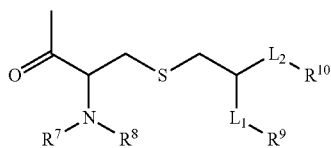

Formula XI wherein:
R$^7$ and R$^8$ are independently from each other H, $C_1$-$C_{30}$alkyl, $C_2$-$C_{30}$alkylenyl, —C(O)—$C_1$-$C_{30}$alkyl, —C(O)—$C_2$-$C_{30}$alkylenyl, or —C(O)—O—$C_1$-$C_{30}$alkyl;
$R^9$ is H, $C_1$-$C_{30}$alkyl or $C_2$-$C_{30}$alkylenyl;
$R^{10}$ is H, $C_1$-$C_{30}$alkyl or $C_2$-$C_{30}$alkylenyl;
$R^9$ and $R^{10}$ are not both H;
$L_1$ is absent, —OC(O)—, —O—, —NR$^{11}$C(O)—, —OC(O)NR$^{11}$— or —CH2- wherein R$^{11}$ is H, $C_1$-$C_{30}$alkyl or $C_2$-$C_{30}$alkylenyl;
$L_2$ is —CH$_2$OC(O)—, —CH$_2$O—, —CH$_2$NR$^{11}$C(O)— or —CH$_2$—, if $L_1$ is absent $L_2$ is —OC(O)—, —O—, —NR$^{11}$C(O)—, —NR$^{10}$R$^{11}$, OC(O)NR$^{11}$— or —CH2- wherein R$^{11}$ is as defined above.

In one embodiment, the compounds of the invention are chosen among purine derivatives wherein A is a nitrogen atom, R$^3$ is absent and R$^2$ is H, OH, SH, NH$_2$, CF$_3$, halogen, $C_1$-$C_{10}$alkyl, $C_1$-$C_{10}$alkylamino, $C_1$-$C_{10}$dialkylamino, $C_1$-$C_{10}$alkoxy, $C_1$-$C_{10}$alkoxy-$C_1$-$C_{10}$alkylamino, $C_1$-$C_{10}$alkoxy-$C_1$-$C_{10}$alkoxy, $C_1$-$C_{10}$alkoxy-$C_5$-$C_7$heterocycle, $C_1$-$C_{10}$alkylamino-$C_5$-$C_7$heterocycle, —NH—SO$_2$—$C_1$-$C_6$alkyl, —C(O)—$C_1$-$C_6$alkyl, —O—C(O)—$C_1$-$C_6$alkyl, —C(O)—$C_1$-$C_{10}$alkylamino, —C(O)—$C_1$-$C_{10}$dialkylamino, $C_5$-$C_{10}$aryl, $C_5$-$C_9$heterocyclyl, $C_3$-$C_9$carbocyclyl, $C_1$-$C_{10}$alkylamino-$C_2$-$C_7$heterocycle, ($C_1$-$C_6$alkoxy)-E-($C_1$-$C_6$alkylene) and R$^1$ is —H, —OH, —SH, —NH$_2$, $C_1$-$C_6$alkyl, such as methyl, ethyl, propyl or butyl, $C_1$-$C_6$alkylamino such as methylamino, ethylamino, propylamino or butylamino, $C_1$-$C_6$alkoxy such as methoxy, ethoxy, propoxy or butoxy, ($C_1$-$C_6$alkyl)-E-($C_1$-$C_6$alkylene), wherein E is —O— or —NH—, such as —CH$_2$—NH—C$_2$H$_5$, —CH$_2$—O—C$_2$H$_5$, —(CH$_2$)$_2$—NH—CH$_3$, or —(CH$_2$)$_2$—O—CH$_3$, more preferably R$^1$ is —OH.

In another embodiment, the compounds of the invention are chosen among imidazoquinoline derivatives wherein A is a carbon atom and R$^2$ and R$^3$ form together a fused phenyl optionally substituted with one or more groups independently selected from F, Cl, Br, I, —CH$_3$, —CH$_2$CH$_3$, CH$_2$CH(CH$_3$)$_2$, —CH$_2$OH, —CH$_2$CH$_2$OH, —C(CH$_3$)$_2$OH, —CH(OH)CH(CH$_3$)$_2$, —C(CH$_3$)$_2$CH$_2$OH, —CH$_2$CH$_2$SO$_2$CH$_3$, —CN, —CF$_3$, —CHF$_2$, —CO$_2$H, —COCH$_3$, —CO$_2$OH$_3$, —C(CH$_3$)$_2$CO$_2$CH$_3$, —CO$_2$O(CH$_3$)$_3$, —COCH(OH)CH$_3$, —COCH(CH$_3$)$_2$, —CONH$_2$, —CONHCH$_3$, —CON(CH$_3$)$_2$, —C(CH$_3$)$_2$CONH$_2$, —NO$_2$, —NH$_2$, —NHCH$_3$, —N(CH$_3$)$_2$, —NHCOCH$_3$, —N(CH$_3$)COCH$_3$, —NHS(O)$_2$CH$_3$, —N(CH$_3$)C(CH$_3$)$_2$CONH$_2$, —N(CH$_3$)CH$_2$CH$_2$S(O)$_2$CH$_3$, —OH, —OCH$_3$, —S(O)$_2$N(CH$_3$)$_2$, —SCH$_3$, —CH$_2$OCH$_3$, —S(O)$_2$CH$_3$, cyclopropyl, oxetanyl, and morpholino, and R$^1$ is —H, —OH, —SH, —NH$_2$, $C_1$-$C_6$alkyl, such as methyl, ethyl, propyl or butyl, $C_1$-$C_6$alkylamino such as methylamino, ethylamino, propylamino or butylamino, $C_1$-$C_6$alkoxy such as methoxy, ethoxy, propoxy or butoxy, ($C_1$-$C_6$alkyl)-E-($C_1$-$C_6$alkylene), wherein E is —O— or —NH—, such as —CH$_2$—NH—C$_2$H$_5$, —CH$_2$—O—C$_2$H$_5$, —(CH$_2$)$_2$—NH—CH$_3$, or —(CH$_2$)$_2$—O—CH$_3$.

In another embodiment, the compounds of the invention are chosen among 3-deazapurine derivatives wherein A is a carbon atom and R$^2$ and R$^3$ independently from each other are H, OH, SH, NH$_2$, CF$_3$, halogen, $C_1$-$C_{10}$alkyl, $C_1$-$C_{10}$alkylamino, $C_1$-$C_{10}$dialkylamino, $C_1$-$C_{10}$alkoxy, $C_1$-$C_{10}$alkoxy-$C_1$-$C_{10}$alkylamino, $C_1$-$C_{10}$alkoxy-$C_1$-$C_{10}$alkoxy, $C_1$-$C_{10}$alkoxy-$C_5$-$C_7$heterocycle, $C_1$-$C_{10}$alkylamino-$C_5$-$C_7$heterocycle, —NH—SO$_2$—$C_1$-$C_6$alkyl, —C(O)—$C_1$-$C_6$alkyl, —O—C(O)—$C_1$-$C_6$alkyl, —C(O)—$C_1$-$C_{10}$alkylamino, —C(O)—$C_1$-$C_{10}$dialkylamino, $C_5$-$C_{10}$aryl, $C_5$-$C_9$heterocyclyl, $C_3$-$C_9$carbocyclyl, $C_1$-$C_{10}$alkylamino-$C_2$-$C_7$heterocycle, ($C_1$-$C_6$alkoxy)-E-($C_1$-$C_6$alkylene) and R$^1$ is —H, —OH, —SH, —NH$_2$, $C_1$-$C_6$alkyl, such as methyl, ethyl, propyl or butyl, $C_1$-$C_6$alkylamino such as methylamino, ethylamino, propylamino or butylamino, $C_1$-$C_6$alkoxy such as methoxy, ethoxy, propoxy or butoxy, ($C_1$-$C_6$alkyl)-E-($C_1$-$C_6$alkylene), wherein E is —O— or —NH—, such as —CH$_2$—NH—C$_2$H$_5$, —CH$_2$—O—C$_2$H$_5$, —(CH$_2$)$_2$—NH—CH$_3$, or —(CH$_2$)$_2$—O—CH$_3$, more preferably R$^1$ is —OH.

A specific class of compounds of Formula II comprises those where s is 1.

A specific class of compounds of Formula II comprises those where X is a —($C_6$-$C_{20}$arylene) (preferably a phenylene), a —($C_1$-$C_6$ alkylene)-(preferably an ethylene or a propylene), or a —($C_4$-$C_{20}$heteroarylene)-(preferably a pyridinylene, a pyrimidinylene, or a pyridazylene), in particular a —($C_6$-$C_{20}$arylene). X is preferably a —($C_6$-$C_{20}$arylene), in particular a phenylene.

A specific class of compounds of Formula II comprises those where Y is —NH—, —O—, —S—, or —C(O)—, in particular —NH— or —C(O)—.

A specific class of compounds of Formula II comprises those where A is a nitrogen atom, R$^3$ is absent and R$^2$ is a $C_1$-$C_6$alkylamino, such as propylamino or butylamino, $C_1$-$C_6$alkoxy such as propoxy, or butoxy, ($C_1$-$C_6$alkoxy)-E-($C_1$-$C_6$alkylene), wherein E is —O— or —NH— such as —O—(CH$_2$)$_2$—O—CH$_3$. A is preferably a nitrogen atom, R$^3$ is absent, and R$^2$ is a $C_1$-$C_6$alkylamino, such as propylamino or butylamino, and R$^1$ is —OH.

A specific class of compounds of Formula II comprises those where A is a carbon atom and R$^2$ and R$^3$ form a fused $C_6$-$C_{20}$ aryl, preferably a phenyl, a —($C_4$-$C_{20}$heteroaryl)-(preferably a pyridinyl, a pyrimidinyl, or a pyridazyl), or a —($C_5$-$C_7$carbocycle)-(preferably a cyclohexyl), and R$^1$ is ($C_1$-$C_6$alkyl)-E-($C_1$-$C_6$alkylene), wherein E is —O— or —NH—, such as —CH$_2$—NH—C$_2$H$_5$, —CH$_2$—O—C$_2$H$_5$, —(CH$_2$)$_2$—NH—CH$_3$, or —(CH$_2$)$_2$—O—CH$_3$.

A specific class of compounds of Formula II comprises those where A is a carbon atom and R$^3$ is a hydrogen atom and R$^2$ is $C_1$-$C_6$alkylamino, such as propylamino or butylamino, $C_1$-$C_{10}$alkylamino-$C_2$-$C_7$heterocycle, such as —NH—CH$_2$—$C_2$-$C_7$heterocyclic group, in particular —NH—CH$_2$-tetrahydropyranyl or —NH—CH$_2$-tetrahydrofuranyl, $C_1$-$C_6$alkoxy such as propoxy or butoxy, $C_1$-$C_{10}$alkoxy-$C_2$-$C_7$heterocycle, such as —O—CH$_2$—$C_2$-$C_7$heterocyclic group in particular —O—CH$_2$-tetrahydropyranyl or —O—CH$_2$-tetrahydrofuranyl, ($C_1$-$C_6$alkoxy)-E-($C_1$-$C_6$alkylene)-, wherein E is —O— or —NH— such as —O—(CH$_2$)$_2$—O—CH$_3$, and R$^1$ is —OH.

A specific class of compounds of Formula I or II comprises those where R$^4$ is a lipid of formula XI wherein:
R$^7$ and R$^8$ are independently from each other H or —C(O)—$C_1$-$C_{30}$alkyl such as —COCH$_3$, —COC$_{13}$H$_{27}$, —COC$_{15}$H$_{31}$, or —COC$_{17}$H$_{35}$;
$R^9$ and $R^{10}$ are independently from each other H or $C_1$-$C_{30}$alkyl, such as —C$_{13}$H$_{27}$, —C$_{15}$H$_{31}$, or —C$_{17}$H$_{35}$;
$R^9$ and $R^{10}$ are not both H;

and $L_1$ is absent and $L_2$ is —OC(O)—; or $L_1$ and $L_2$ are —OC(O)—.

Preferred compounds of the invention are those wherein Z is a derivative of spermine or poly(lysine).

A specific class of compounds of Formula I or II comprises those wherein:

Z is of formula III wherein l=1, $R^5$=H, m=3, n=4, p=1, o=3 and j=0 or 1 and q=2;

Z is of formula IV wherein l=0 or 1, $R^5$=H, W=NH, q=4, m=3, n=4 p=1, and o=3;

Z is of formula V wherein l=0 or 1, $R^5$=H, W=NH or O, q=1 or 4, m=3, n=4, p=1, and o=3;

is of formula VI wherein l=0, q=2, m=3, n=4, p=1, and o=3;

Z is of formula VII wherein l=0, q=2, m=3, n=4, p=1, and o=3;

Z is of formula VIII wherein $R^6$=—CH$_2$—OH, k=1, r=4, q=4, l=0.

Z is of formula IX wherein $R^6$=—CH$_2$-0H, k=1, q=4, l=0, r=3, f=4 and

Z is of formula X wherein $R^6$=—CH$_2$—OH, k=1, q=4, r=1 or 2, f=4, l=0, g=4, t=1 or 2.

In one embodiment, the compounds of the invention are chosen among purine derivatives wherein:

A is a nitrogen atom, $R^3$ is absent and $R^2$ is H, OH, SH, NH$_2$, CF$_3$, halogen, $C_1$-$C_{10}$alkyl, $C_1$-$C_{10}$alkylamino, $C_1$-$C_{10}$dialkylamino, $C_1$-$C_{10}$alkoxy, $C_1$-$C_{10}$alkoxy-$C_1$-$C_{10}$ alkylamino, $C_1$-$C_{10}$alkoxy-$C_1$-$C_{10}$alkoxy, $C_1$-$C_{10}$alkoxy-$C_5$-$C_7$heterocycle, $C_1$-$C_{10}$alkylamino-$C_5$-$C_7$heterocycle, —NH—SO$_2$—$C_1$-$C_6$alkyl, —C(O)—$C_1$-$C_6$alkyl, —O—C(O)—$C_1$-$C_6$alkyl, —C(O)—$C_1$-$C_{10}$alkylamino, —C(O)—$C_1$-$C_{10}$dialkylamino, $C_5$-$C_{10}$aryl, $C_5$-$C_9$heterocyclyl, $C_3$-$C_3$ carbocyclyl, $C_1$-$C_{10}$alkylamino-$C_2$-$C_7$heterocycle, ($C_1$-$C_6$alkoxy)-E-($C_1$-$C_6$alkylene), $R^1$ is —H, —OH, —SH, —NH$_2$, $C_1$-$C_6$alkyl, such as methyl, ethyl, propyl or butyl, $C_1$-$C_6$alkylamino such as methylamino, ethylamino, propylamino or butylamino, $C_1$-$C_6$alkoxy such as methoxy, ethoxy, propoxy or butoxy, ($C_1$-$C_6$alkyl)-E-($C_1$-$C_6$alkylene), wherein E is —O— or —NH—, $R^4$ is a lipid of formula XI wherein:

$R^7$ and $R^8$ are independently from each other H or —C(O)—$C_1$-$C_{30}$alkyl such as —COCH$_3$, —COC$_{13}$H$_{27}$, —COC$_{15}$H$_{31}$, or —COC$_{17}$H$_{35}$;

$R^9$ and $R^{10}$ are independently from each other H or $C_1$-$C_{30}$alkyl, such as —C$_{13}$H$_{27}$, —C$_{15}$H$_{31}$, or —C$_{17}$H$_{35}$; and $L_1$ is absent and $L_2$ is —OC(O)—; or $L_1$ and $L_2$ are —OC(O)—;

Z is as defined previously.

In one preferred embodiment of Formula II:

A is nitrogen, $R^1$ is —OH, $R^2$ is a $C_1$-$C_6$alkylamino, such as NH—(CH$_2$)$_3$CH$_3$, $R^3$ is absent, X is a phenylene, Y is —NH— or —C(O)—, s=1, Z—$R^4$ is as defined previously.

In another embodiment of Formula II:

A is carbon, $R^1$ is a H, or ($C_1$-$C_6$alkyl)-E-($C_1$-$C_6$alkylene)-, wherein E is —O— or —NH—, such as —CH$_2$—NH—C$_2$H$_5$ or —CH$_2$—O—C$_2$H$_5$, $R^2$ and $R^3$ form a fused $C_6$-$C_{20}$ aryl, preferably a phenyl, X is an ethylene, Y is —NH— or —C(O)—, s=1, Z—$R^4$ is as defined previously.

In another embodiment of Formula II:

A is carbon, $R^1$ is a OH, $R^2$ is CF$_3$, $C_1$-$C_{10}$alkylamino-$C_5$-$C_7$heterocycle such as —NH—CH$_2$—$C_5$-$C_7$heterocyclic group, in particular —NH—CH$_2$-tetrahydropyranyl or —NH—CH$_2$-tetrahydrofuranyl, or $C_1$-$C_{10}$alkoxy-$C_5$-$C_7$heterocycle such as —O—CH$_2$—$C_5$-$C_7$heterocyclic group, in particular —O—CH$_2$-tetrahydropyranyl or —O—CH$_2$-tetrahydrofuranyl, $R^3$ is H, X is an phenylene, or a pyridinylene, Y is —NH— or —C(O)—, s=1, Z—$R^4$ is as defined previously.

The nature of the lipophilic conjugated compounds of Formula I according to the invention is likely to promote the destabilization of endosomal vesicles in the cytoplasm following cellular osmosis, due to their impact on endosomal proton pumps. Endosomal disruption enhances the delivery of DNA to the cytosol of the cell.

Preferred compounds of Formula I or II are selected from the group consisting of:

CL553

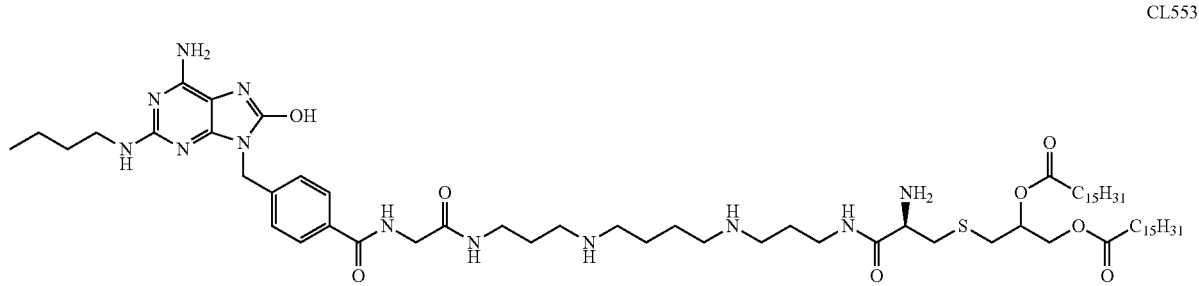

(20R)-20-amino-1-(4-((6-amino-2-(butylamino)-8-hydroxy-9H-purin-9-yl)methyl)phenyl)-1,4,19-trioxo-22-thia-2,5,9,14,18-pentaazapentacosane-24,25-diyl dipalmitate,
CL-554
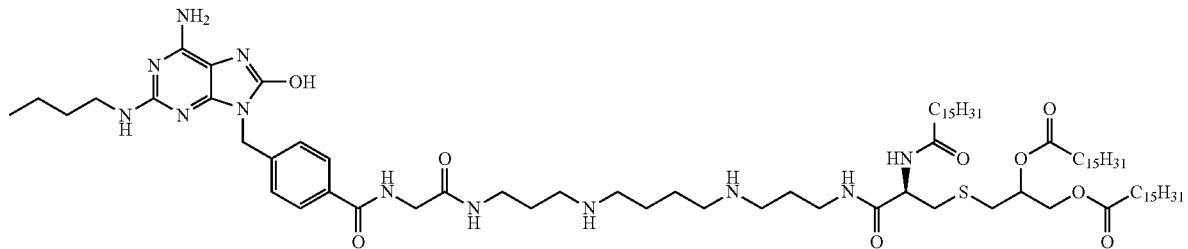
(20R)-1-(4-((6-amino-2-(butylamino)-8-hydroxy-9H-purin-9-yl)methyl)phenyl)-1,4,19-trioxo-20-palmitamido-22-thia-2,5,9,14,18-pentaazapentacosane-24,25-diyldipalmitate,
CL514
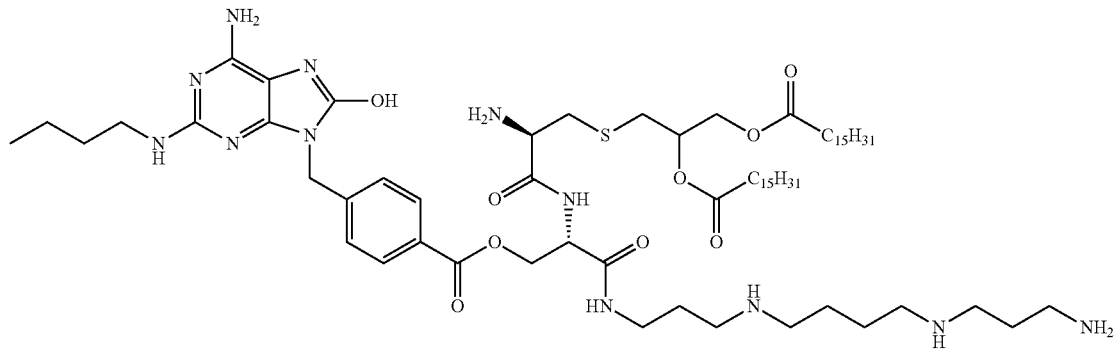
(6R,9S)-6,23-diamino-9-((4-((6-amino-2-(butylamino)-8-hydroxy-9H-purin-9-yl)methyl)benzoyloxy)methyl)-7,10-dioxo-4-thia-8,11,15,20-tetraazatricosane-1,2-diyldipalmitate,
CL486
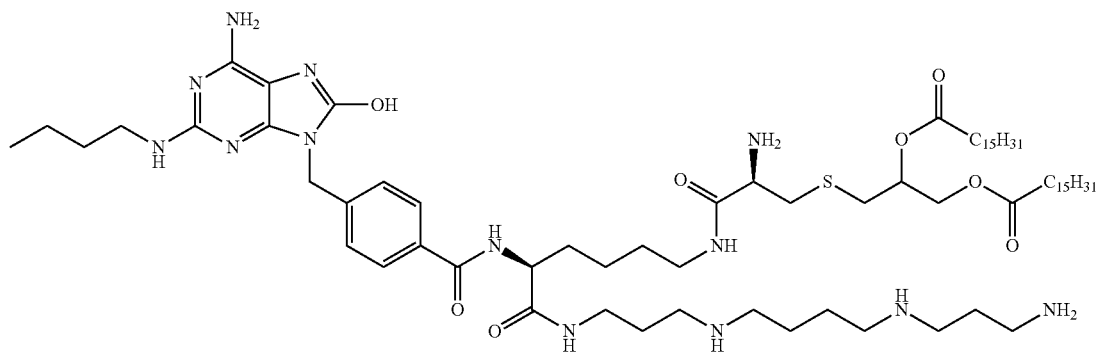

(6R,13S)-6,27-diamino-13-(4-((6-amino-2-(butylamino)-8-hydroxy-9H-purin-9-yl)methyl)benzamido)-7,14-dioxo-4-thia-8,15,19,24-tetraazaheptacosane-1,2-diyldipalmitate,

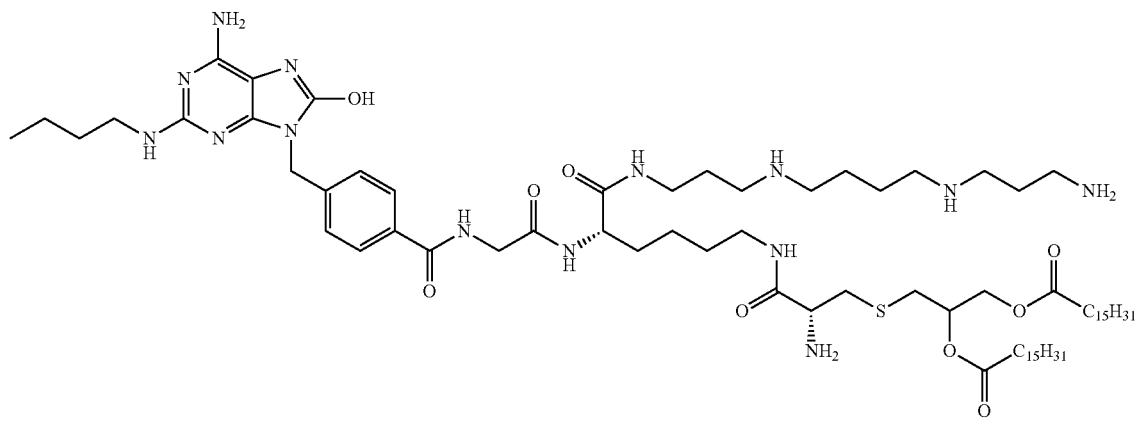

CL-487

(6R,13S)-6,27-diamino-13-(2-(4-((6-amino-2-(butylamino)-8-hydroxy-9H-purin-9-yl)methyl)benzamido)acetamido)-7,14-dioxo-4-thia-8,15,19,24-tetraazaheptacosane-1,2-diyldipalmitate,

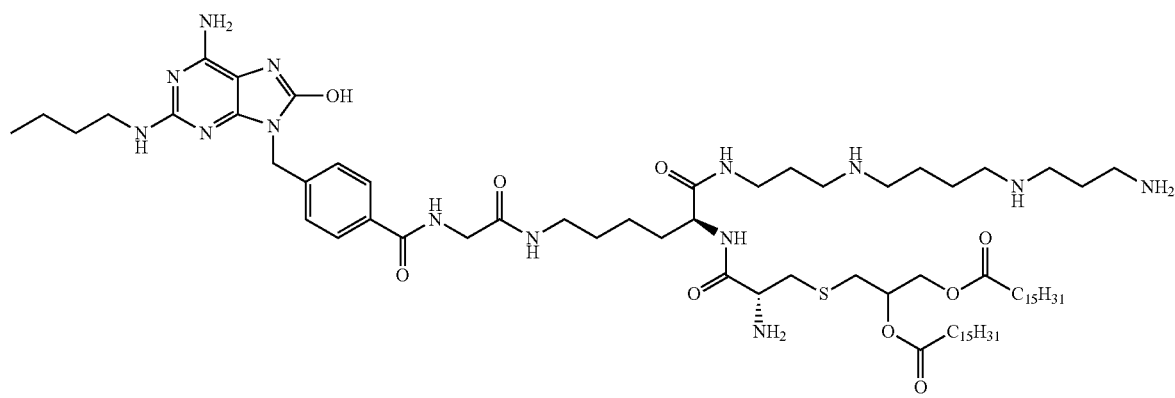

CL475

(6R,9S)-6,23-diamino-9-(4-(2-(4-((6-amino-2-(butylamino)-8-hydroxy-9H-purin-9-yl)methyl)benzamido)acetamido)butyl)-7,10-dioxo-4-thia-8,11,15,20-tetraazatricosane-1,2-diyldipalmitate,

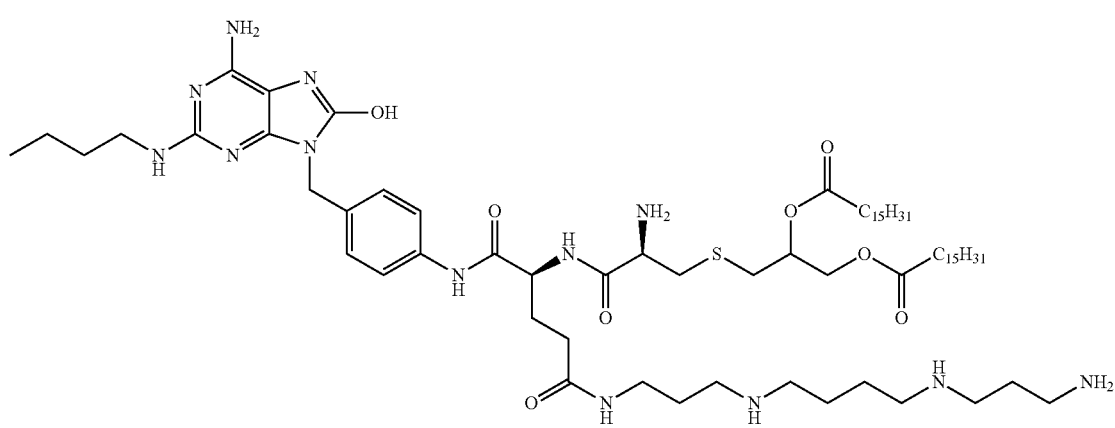

CL527

(6R,9S)-6,25-diamino-9-(4-((6-amino-2-(butylamino)-8-hydroxy-9H-purin-9-yl)methyl)phenyl carbamoyl)-7,12-dioxo-4-thia-8,13,17,22-tetraazapentacosane-1,2-diyldipalmitate,
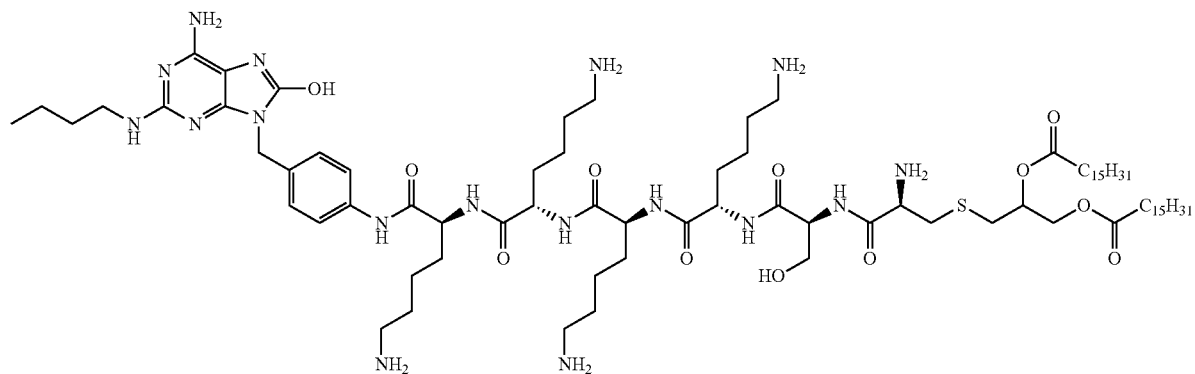
CL413
(6S,9S,12S,15S,18S,21R)-6,25-diamino-21-(4-((6-amino-2-(butylamino)-8-hydroxy-9H-purin-9-yl)methyl)phenyl-carbamoyl)-12,15,18-tris(4-aminobutyl)-9-(hydroxy methyl)-7,10,13,16,19-pentaoxo-4-thia-8,11,14,17,20-pentaazapentacosane-1,2-diyl dipalmitate,
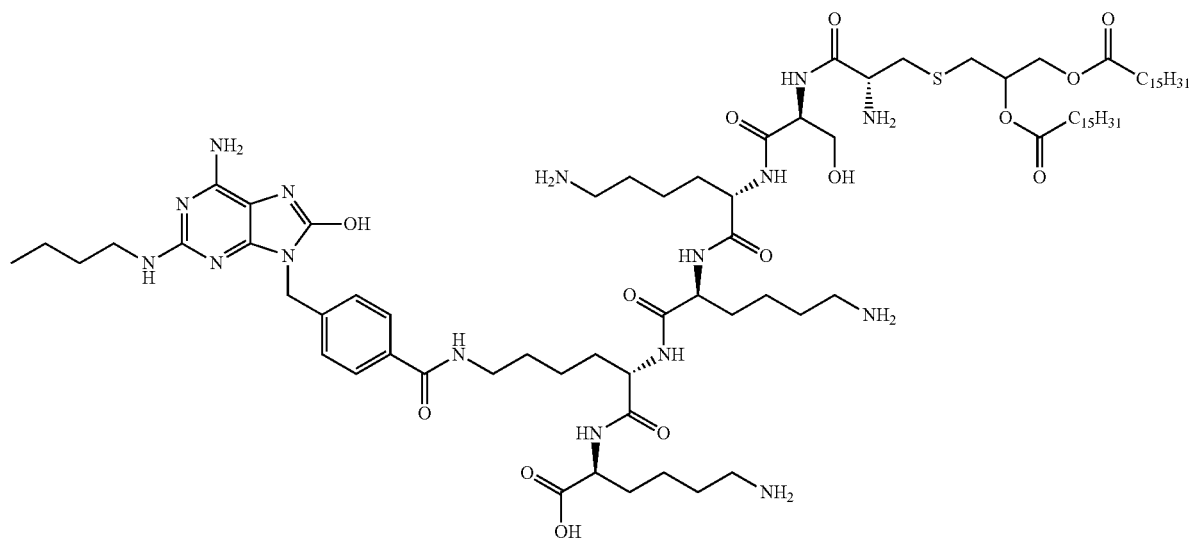
CL530

27
(2S,5S,8S,11S,14S,17R)-17-amino-5-(4-(4-((6-amino-2-(butylamino)-8-hydroxy-9H-purin-9-yl)methyl)benzamido)butyl)-2,8,11-tris(4-aminobutyl)-14-(hydroxym-
28
ethyl)-4,7,10,13,16,24-hexaoxo-21-(palmitoyloxy)-23-oxa-19-thia-3,6,9,12,15-pentaazanona triacontan-1-oic acid,
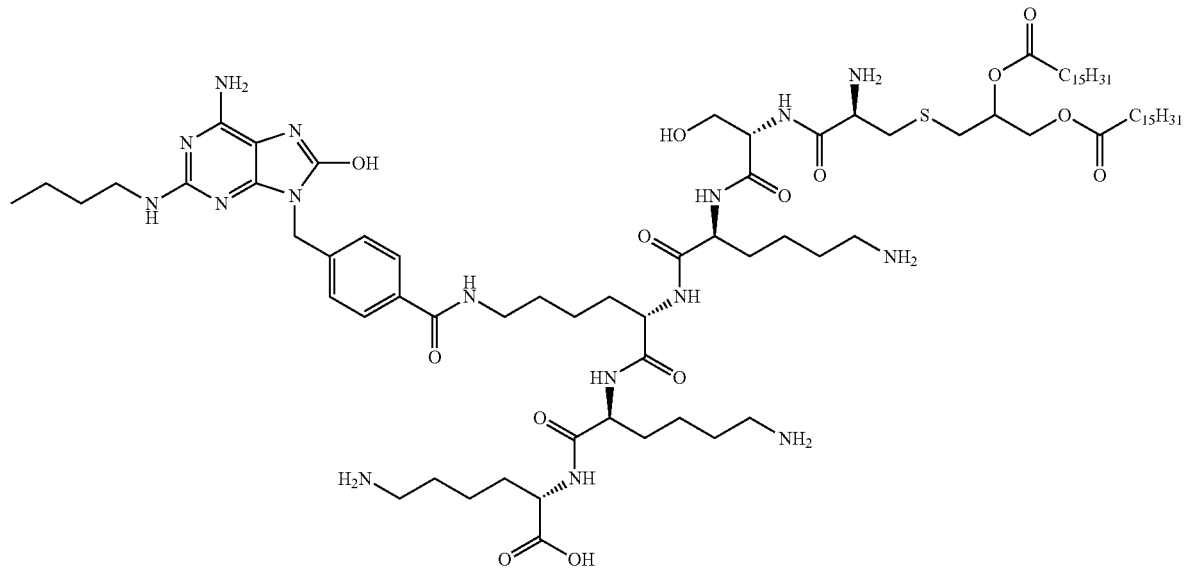
CL531
(2S,5S,8S,11S,14S,17R)-17-amino-5-(4-(4-((6-amino-2-(butylamino)-8-hydroxy-9H-purin-9-yl)methyl)benzamido)butyl)-2,8,11-tris(4-aminobutyl)-14-(hydroxymethyl)-4,7,10,13,16,24-hexaoxo-21-(palmitoyloxy)-23-oxa-19-thia-3,6,9,12,15-pentaazanona triacontan-1-oic acid,
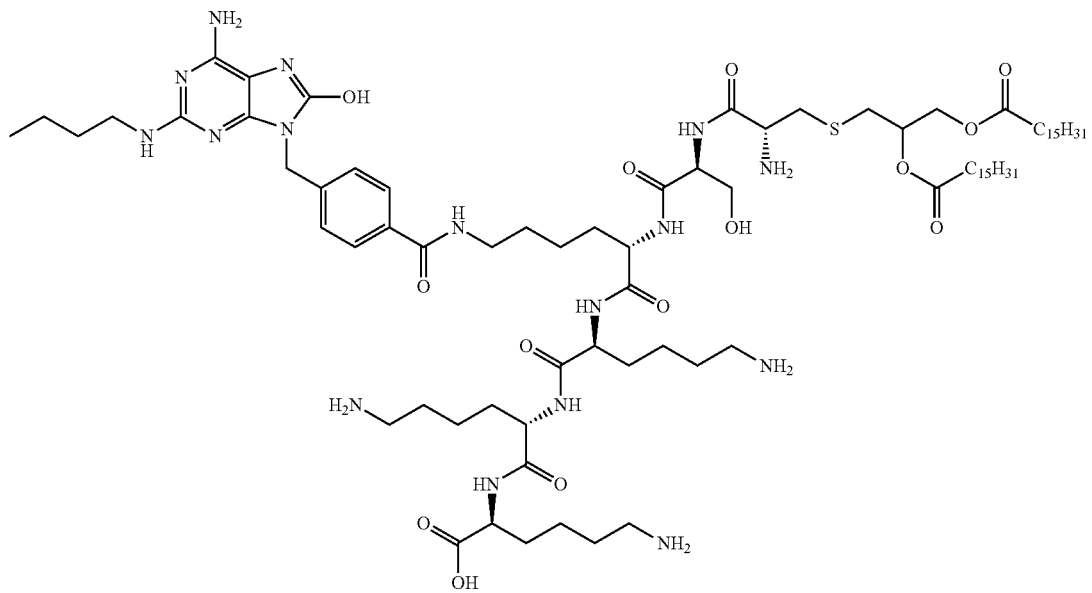
CL533

29
(2S,5S,8S,11S,14S,17R)-17-amino-11-(4-(4-((6-amino-2-(butylamino)-8-hydroxy-9H-purin-9-yl)methyl)benzamido)butyl)-2,5,8-tris(4-aminobutyl)-14-(hydroxym-
30
ethyl)-4,7,10,13,16,24-hexaoxo-21-(palmitoyloxy)-23-oxa-19-thia-3,6,9,12,15-pentaazanona triacontan-1-oic acid,
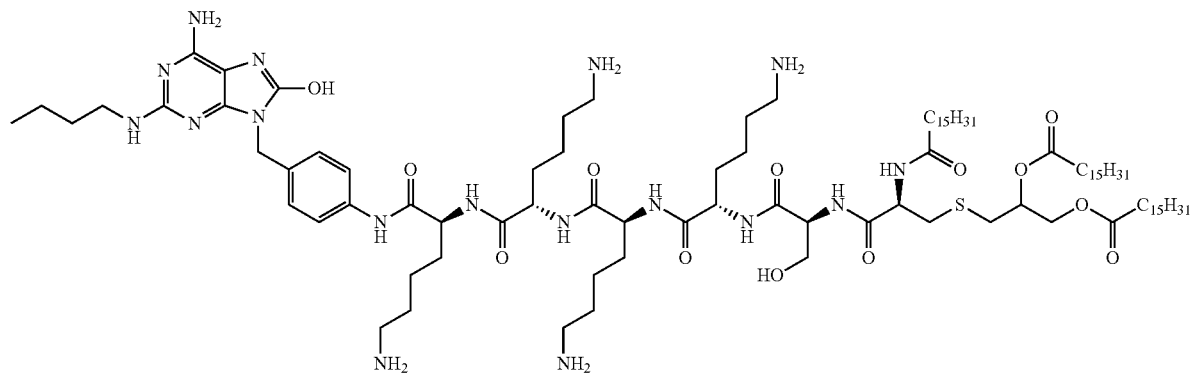
CL534
(((6R,9S,12S,15S,18S,21S)-25-amino-21-(4-((6-amino-2-(butylamino)-8-hydroxy-9H-purin-9-yl)methyl)phenylcarbamoyl)-12,15,18-tris(4-aminobutyl)-9-(hydroxymethyl)-7,10,13,16,19-pentaoxo-6-palmitamido-4-thia-8,11,14,17,20-pentaazapentacosane-1,2-diyldipalmitate,
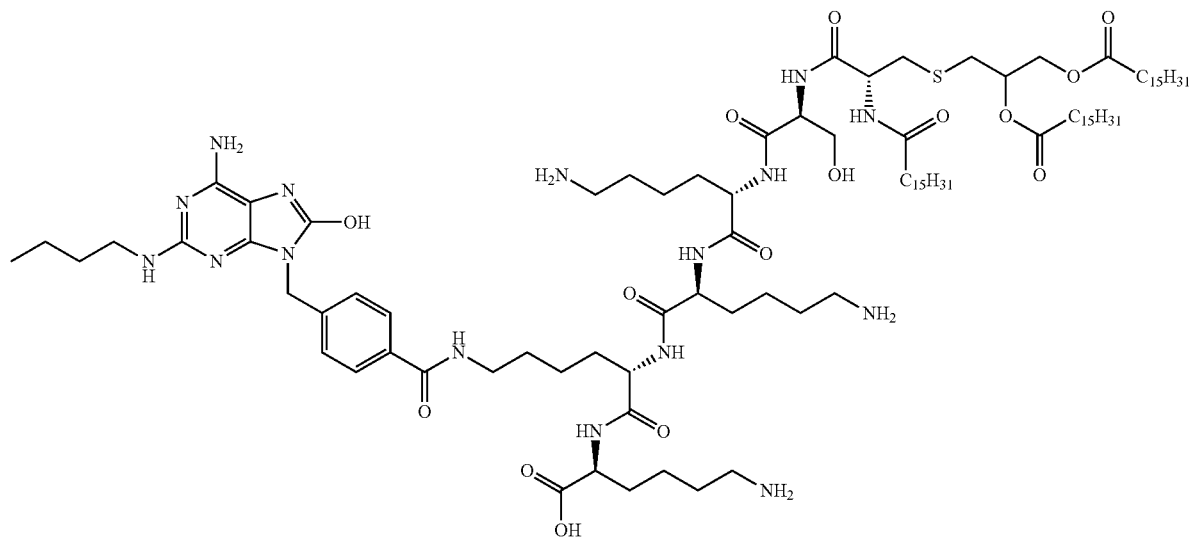
CL535

31

(2S,5S,8S,11S,14S,17R)-5-(4-(4-((6-amino-2-(buty-lamino)-8-hydroxy-9H-purin-9-yl)methyl)benzamido)butyl)-2,8,11-tris(4-aminobutyl)-14-(hydroxymethyl)-4,

32

7,10,13,16,24-hexaoxo-17-palmitamido-21-(palmitoyloxy)-23-oxa-19-thia-3,6,9,12,15-pentaazanonatriacontan-1-oic acid,

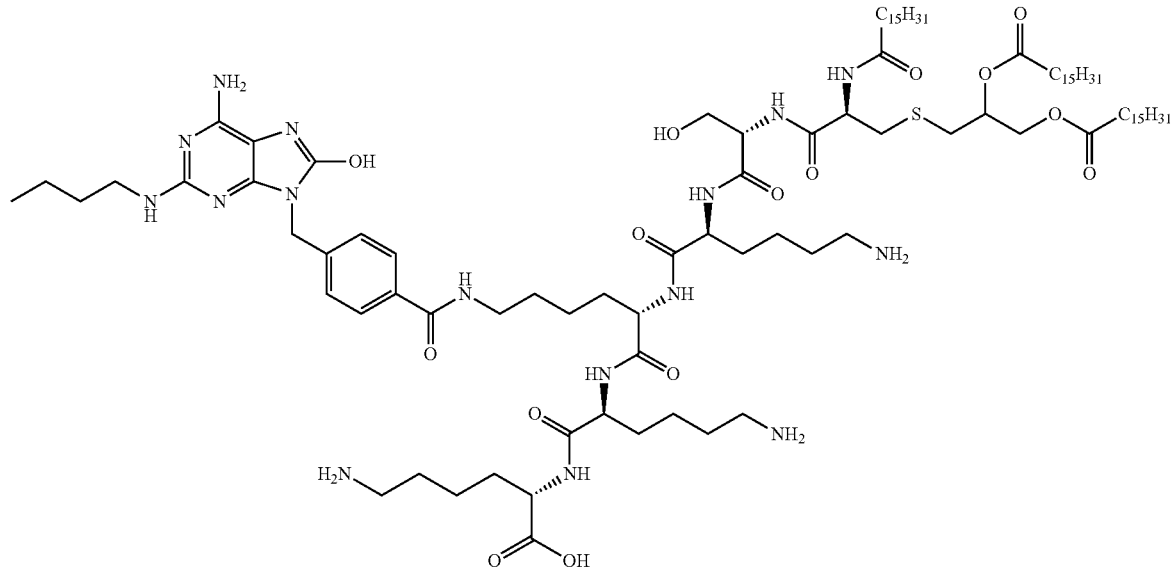

CL536

(2S,5S,8S,11S,14S,17R)-8-(4-(4-((6-amino-2-(buty-lamino)-8-hydroxy-9H-purin-9-yl)methyl)benzamido)butyl)-2,5,11-tris(4-aminobutyl)-14-(hydroxymethyl)-4,7,10,13,16,24-hexaoxo-17-palmitamido-21-(palmitoyloxy)-23-oxa-19-thia-3,6,9,12,15-pentaazanonatriacontan-1-oic acid,

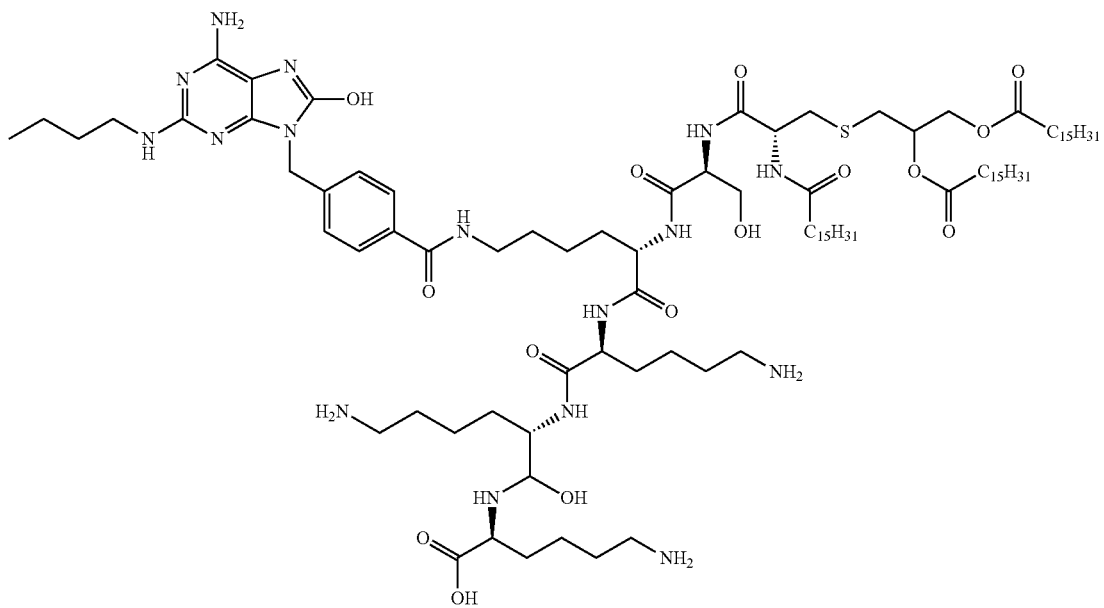

CL537

(2S,5S,8S,11S,14S,17R)-11-(4-(4-((6-amino-2-(butylamino)-8-hydroxy-9H-purin-9-yl)methyl)benzamido)butyl)-2,5,8-tris(4-aminobutyl)-14-(hydroxymethyl)-4,7,10,13,16,24-hexaoxo-17-palmitamido-21-(palmitoyloxy)-23-oxa-19-thia-3,6,9,12,15-pentaazanonatriacontan-1-oic acid,

CL580

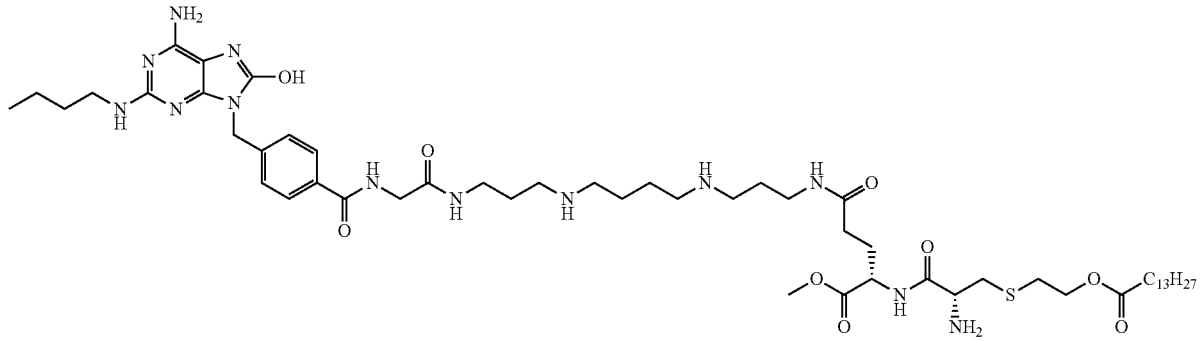

(S)-methyl 1-(4-((6-amino-2-(butylamino)-8-hydroxy-9H-purin-9-yl)methyl)phenyl)-22-((R)-2-amino-3-(2-(tetradecanoyloxy)ethylthio)propanamido)-1,4,19-trioxo-2,5,9,14,18-pentaazatricosan-23-oate.

a tautomer thereof or a pharmaceutically acceptable salt, solvate or polymorph of said compound or tautomer.

A preferred class of compounds of Formula I or II is any combination of the specific classes defined above.

Another object of the invention is a compound of formula XIII:

$$H\text{—}Z\text{—}R^4 \qquad \qquad XIII$$

a tautomer thereof or a pharmaceutically acceptable salt, solvate or polymorph of said compound or tautomer, wherein $Z\text{—}R^4$ is selected from the group consisting of:

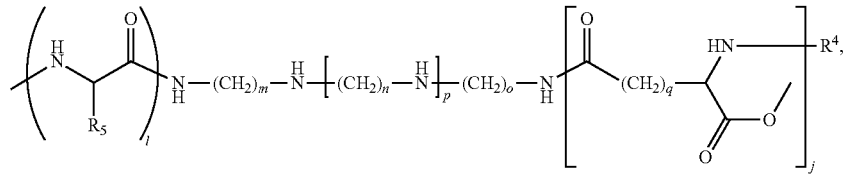

Formula III

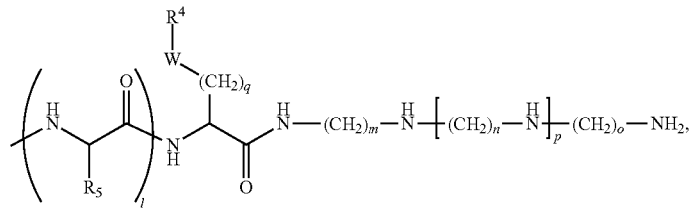

Formula IV

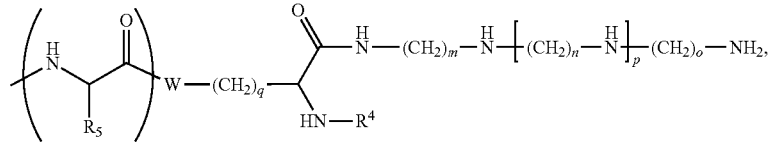

Formula V

Formula VI

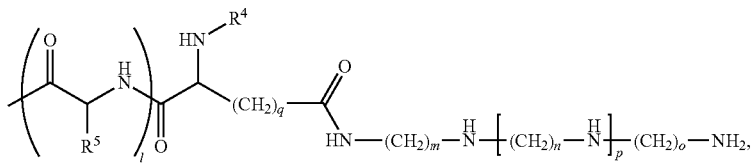

Formula VII

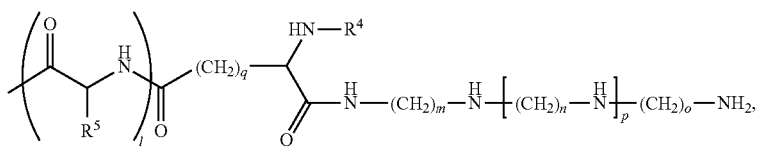

wherein:
R$^5$ and R$^6$, identical or different, are the specific side chain of an amino acid;
W is —O—, —NH—, or —S—;
j and l, identical or different, are 0 or 1;
p is integer from 0 to 6;
f, g, k, m, n, o, and q, identical or different, are integers from 1 to 4;
r and t, identical or different, are integers from 1 to 6; and
R$^4$ is a lipid of Formula XI:

Formula XI

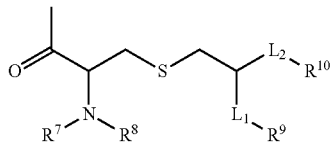

wherein:
R$^7$ and R$^8$ are independently from each other H, C$_1$-C$_{30}$alkyl, C$_2$-C$_{30}$alkylenyl, —C(O)—C$_1$-C$_{30}$alkyl, —C(O)—C$_2$-C$_{30}$alkylenyl, or —C(O)—O—C$_1$-C$_{30}$alkyl;
R$^9$ is H, C$_1$-C$_{30}$alkyl or C$_2$-C$_{30}$alkylenyl;
R$^{10}$ is H, C$_1$-C$_{30}$alkyl or C$_2$-C$_{30}$alkylenyl;
R$^9$ and R$^{10}$ are not both H;
L$_1$ is absent, —OC(O)—, —O—, —NR$^{11}$C(O)—, —OC(O)NR$^{11}$— or —CH2- wherein R$^{11}$ is H, C$_1$-C$_{30}$alkyl or C$_2$-C$_{30}$alkylenyl;
L$_2$ is —CH$_2$OC(O)—, —CH$_2$O—, —CH$_2$NR$^{11}$C(O)— or —CH$_2$—, if L$_1$ is absent L$_2$ is —OC(O)—, —O—, —NR$^{11}$C(O)—, —NR$^{10}$R$^{11}$, —OC(O)NR$^{11}$— or —CH2- wherein R$^{11}$ is as defined above.

The compounds of Formula XIII are TLR2 agonists.
The compounds of Formula XIII are able to form a complex with polyanionic molecules and conserve immunomodulatory activity via TLR2 agonistic properties. Some of these compounds, particularly compounds wherein Z—R$^4$ is of Formula III to VII, have the ability of transfecting cells with nucleic acids of interest.

A specific class of compounds of Formula XIII comprises those where R$^4$ is a lipid of formula XI wherein:
R$^7$ and R$^8$ are independently from each other H or —C(O)—C$_1$-C$_{30}$alkyl such as —COCH$_3$, —COC$_{13}$H$_{27}$, —COC$_{15}$H$_{31}$, or —COC$_{17}$H$_{35}$;
R$^9$ and R$^{10}$ are independently from each other H or C$_1$-C$_{30}$alkyl, such as —C$_{13}$H$_{27}$, —C$_{14}$H$_{29}$, —C$_{15}$H$_{31}$, —C$_{16}$H$_{33}$, or —C$_{17}$H$_{35}$, —C$_{18}$H$_{37}$; and
L$_1$ is absent and L$_2$ is —O— or —OC(O)—; or
L$_1$ and L$_2$ are —O— or —OC(O)—.

A specific class of compounds of Formula XIII comprises those wherein:
Z is of formula III wherein l=1, R$^5$=H, m=3, n=4, p=1, o=3 and j=0 or 1 and q=2;
Z is of formula IV wherein l=0 or 1, R$^5$=H, W=NH, q=4, m=3, n=4 p=1, and o=3;
Z is of formula V wherein l=0 or 1, R$^5$=H, W=NH or O, q=1 or 4, m=3, n=4, p=1, and o=3;
Z is of formula VI wherein l=0, q=2, m=3, n=4, p=1, and o=3;
Z is of formula VII wherein l=0, q=2, m=3, n=4, p=1, and o=3;

The compounds of Formula XIII are preferably selected from the group consisting of:

CL419

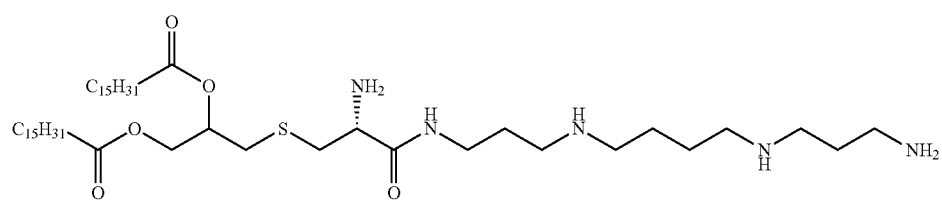

(6R)-6,20-diamino-7-oxo-4-thia-8,12,17-triazaicosane-1,2-diyldipalmitate
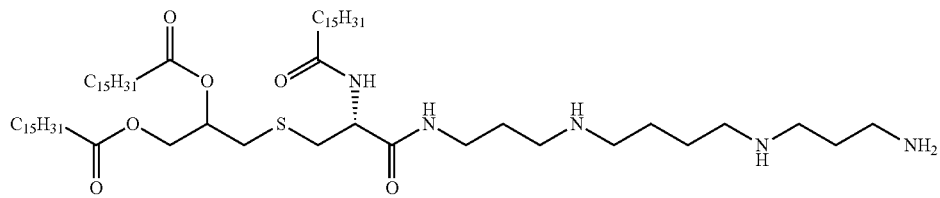
CL438
(6R)-20-amino-7-oxo-6-palmitamido-4-thia-8,12,17-triaza-icosane-1,2-diyldipalmitate
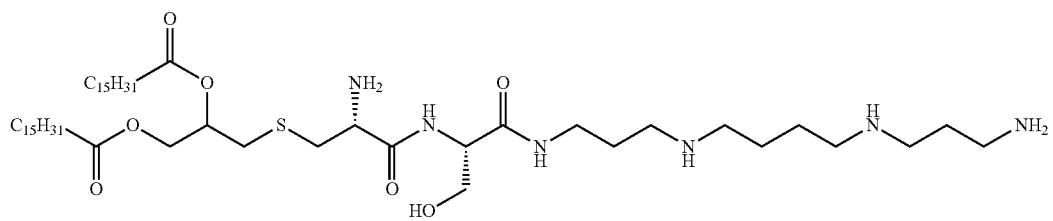
CL462
(6R,9S)-6,23-diamino-9-(hydroxymethyl)-7,10-dioxo-4-thia-8,11,15,20-tetraazatricosane-1,2-diyl dipalmitate
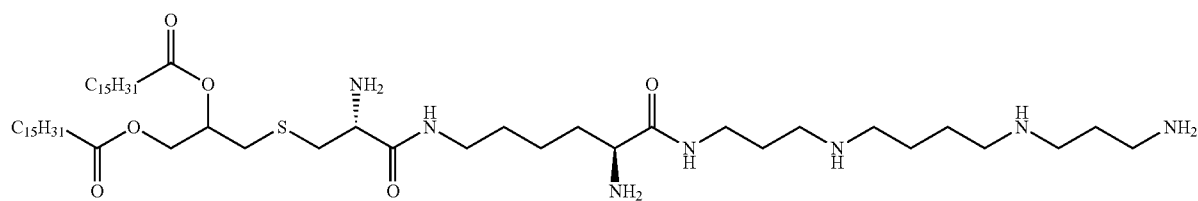
CL576
(6R,13S)-6,13,27-triamino-7,14-dioxo-4-thia-8,15,19,24-tetraazaheptacosane-1,2-diyl dipalmitate
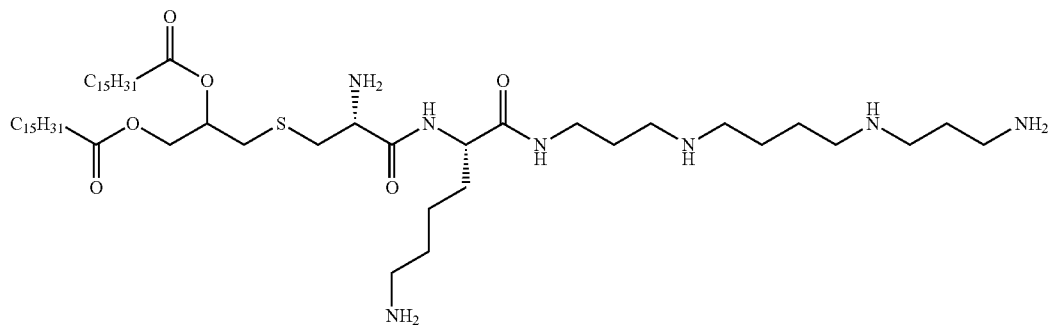
CL577

(6R,9S)-6,23-diamino-9-(4-aminobutyl)-7,10-dioxo-4-thia-8,11,15,20-tetraazatricosane-1,2-diyl dipalmitate

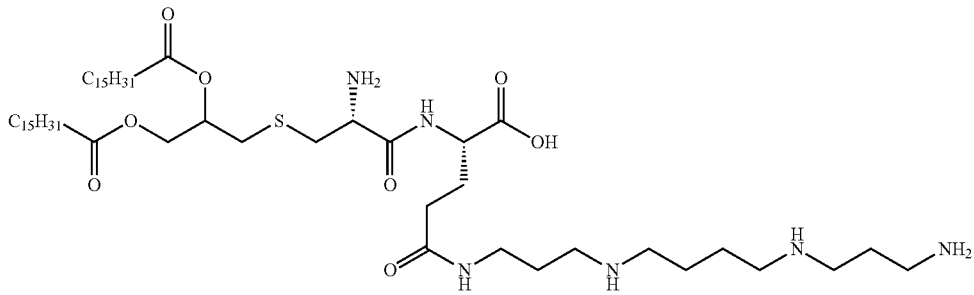

(2S)-2-((2R)-2-amino-3-(2,3-bis(palmitoyloxy)propylthio)propanamido)-5-(3-(4-(3-aminopropylamino)butylamino)propylamino)-5-oxopentanoic acid

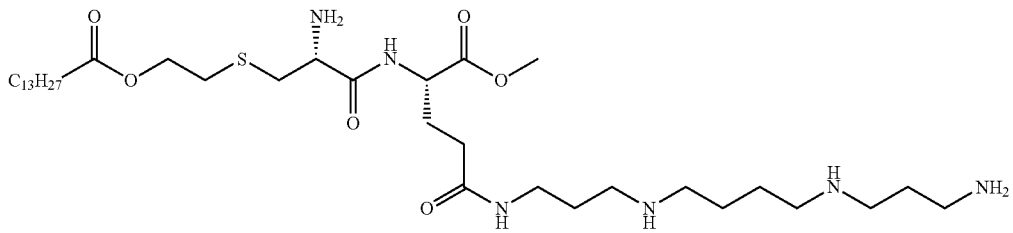

(5R,8S)-5,24-diamino-8-(methoxycarbonyl)-6,11-dioxo-3-thia-7,12,16,21-tetraaza tetracosyl tetradecanoate.

The lipid moiety $R^4$ includes synthetic analogues of a bacterial lipoprotein known as MALP-2, derived from the cytoplasmic membrane of *Mycoplasma fermentans*:

- dipalmitoyl-S-glyceryl cysteine ($Pam_2Cys$). $Pam_2Cys$ is a ligand for both TLR2 and TLR6 (Okusawa et al, 2004);
- tripalmitoyl-S-glyceryl cysteine ($Pam_3Cys$). $Pam_3Cys$ is a ligand for both TLR2 and TLR1;
- or a mono-acylated 2-hydroxythioethyl cysteine, which is a specific ligand for human TLR2 (Agnihotri et al. 2011).

Exemplary fatty acids include, but are not limited to, stearoyl, palmitoyl, myristoyl, lauroyl, and decanoyl groups. More generally, any C2 to C30 saturated, monounsaturated, or polyunsaturated fatty acyl group is thought to be useful, including, but not limited to vinyl, allyl, octenyl, oleyl, or arachidonyl groups.

The lipoamino acid N-palmitoyl-S-[2,3-bis(palmitoyloxy)propyl]cysteine, also known as $Pam_3C$, $Pam_3Cys$ or $Pam_3Cys$-OH (Wiesmuller et al. 1983) is a synthetic version of the N-terminal moiety of Braun's lipoprotein that spans the inner and outer membranes of Gram negative bacteria. $Pam_3Cys$ has the structure of following formula:

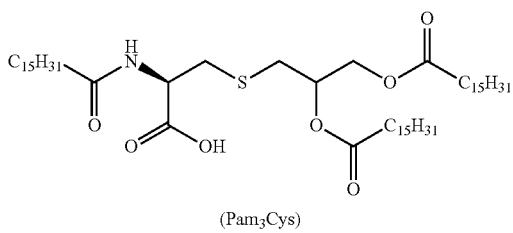

($Pam_3Cys$)

N-acyl-S-(2-hydroxyalkyl) cysteine is an intermediate in the preparation of lipopeptides that are used as synthetic adjuvants, B lymphocyte stimulants, macrophage stimulants, or synthetic vaccines. Metzger et al. (U.S. Pat. No. 5,700,910) teach the use of such compounds as intermediates in the synthesis of $Pam_3Cys$-OH and of lipopeptides that comprise this lipoamino acid or an analog thereof at the N-terminus. The lipopeptides are prepared by coupling a lipoamino acid moiety to the peptide moiety during the synthesis process.

$Pam_2Cys$ (also known as dipalmitoyl-S-glyceryl-cysteine or S-[2,3-bis(palmitoyloxy)propyl]cysteine), an analogue of $Pam_3Cys$, has been synthesized (Metzger et al. 1995) and has been shown to correspond to the lipid moiety of MALP-2, a macrophage-activating lipopeptide isolated from mycoplasma (Muhlradt et al. 1998; Sacht et al. 1998) $Pam_2Cys$ has the structure of following formula:

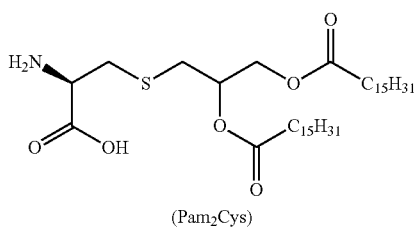

(Pam₂Cys)

Pam₂Cys is reported to be a more potent stimulator of splenocytes and macrophages than Pam₃Cys (Metzger et al. 1995; Muhlradt et al. 1998)

Monoacyl lipopeptides also known as S-(2-acyloxyethyl) cysteinyl]-serine methyl ester is described to have human specific TLR2 agonistic properties (Agnihotri et al. 2011; Salunke et al. 2012)

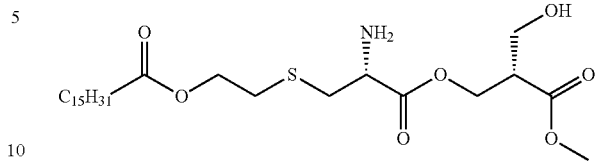

(Pam-Et-S-Cys-SerOMe)

A specific class of compounds of Formula I, II or XIII comprises those wherein Q-Z—R⁴ is selected from the group consisting of:

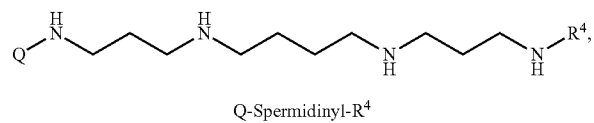

Q-Spermidinyl-R⁴

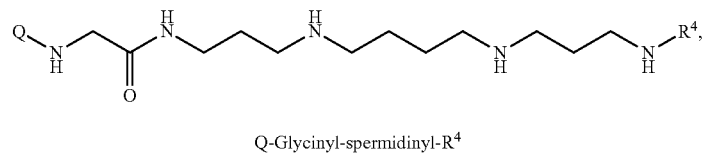

Q-Glycinyl-spermidinyl-R⁴

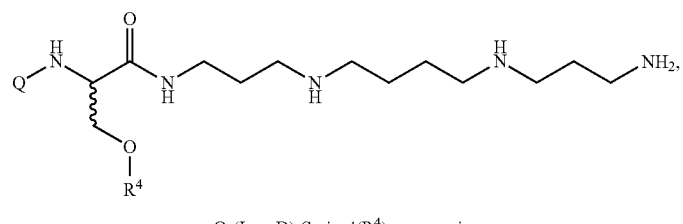

Q-(L or D)-Serinyl(R⁴)-α-spermine

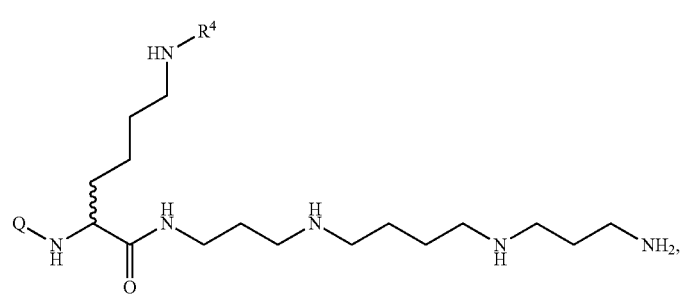

Q-(L or D)-Lysinyl(R⁴)-spermine

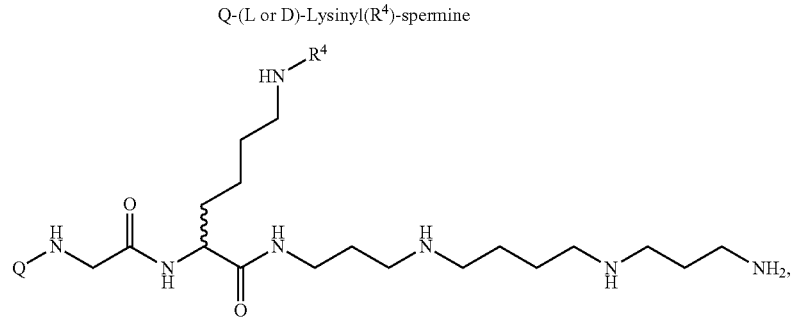

Q-Glycinyl-(L or D)-lysinyl(R⁴)-spermine

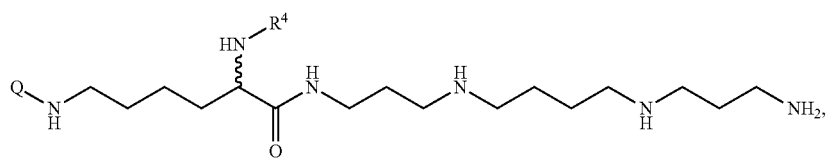
R[4]-(L or D)-Lysinyl(Q)-spermine
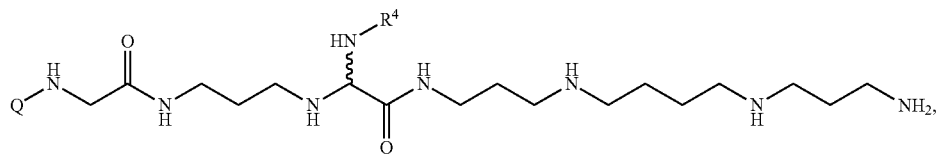
R[4]-(L or D)-Lysinyl(gylcinyl-Q)-spermine
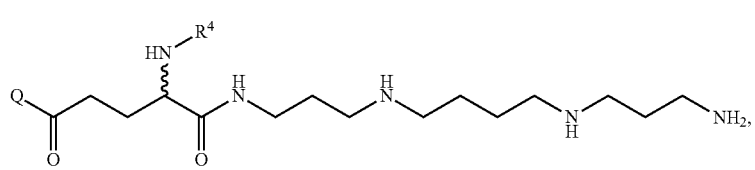
R[4]-(L or D)-Glutamyl(Q)-spermine
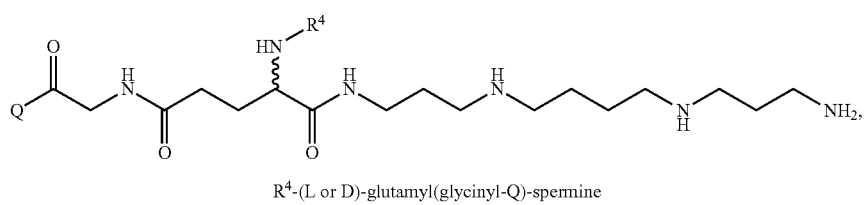
R[4]-(L or D)-glutamyl(glycinyl-Q)-spermine
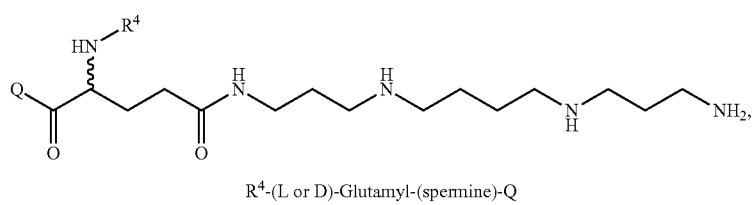
R[4]-(L or D)-Glutamyl-(spermine)-Q
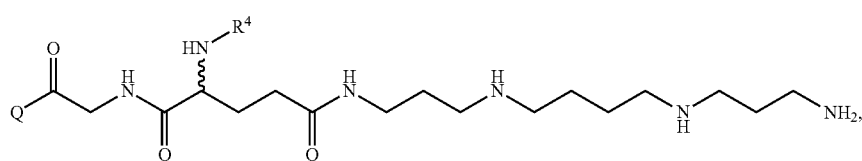
R[4]-(L or D)-glutamyl(sperine)-glycinyl-Q.
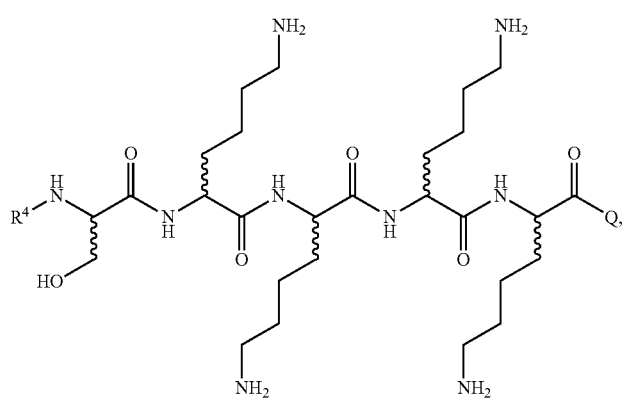
R[4]-(L or D)-Serinyl-[(L or D)-Lysinyl]$_4$-Q

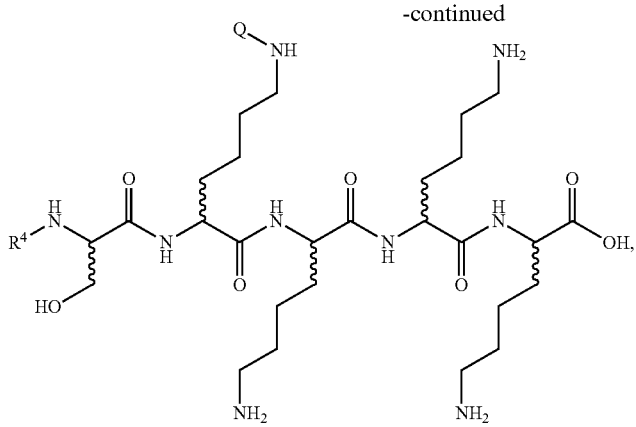

R[4]-(L or D)-Serinyl-(L or D)-Lysinyl(Q)-[(L or D)-lysinyl]₂-(L or D)-Lysine

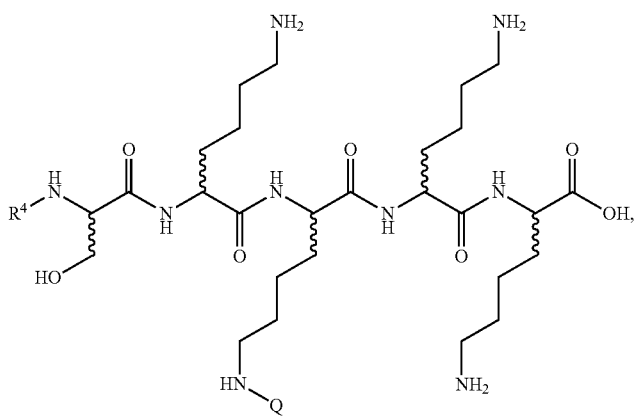

R[4]-(L or D)-Serinyl-(L or D)-Lysinyl-(L or D)-lysinyl(Q)-(L or D)-Lysinyl-(L or D)-Lysine

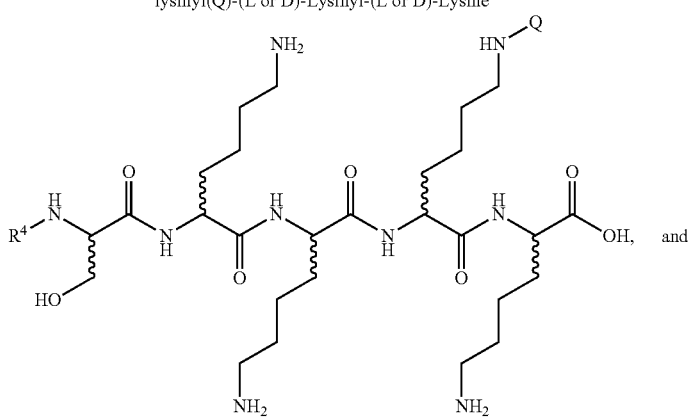 and

R[4]-(L or D)-Serinyl-[(L or D)-Lysinyl]₂-(L or D)-lysinyl(Q)-(L or D)-Lysinyl

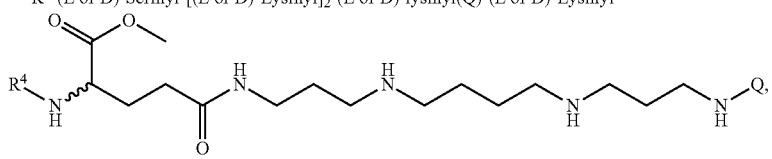

R[4]-(L or D)-Glu(spermidinyl-Q)methyl ester wherein R[4] is as defined previously and Q is H or as defined previously.

The compounds of Formula I, II or XIII containing one or more asymmetric carbon atoms can exist as two or more stereoisomers. Where a compound of Formula I, II or XIII contains an alkenyl or alkenylene group, geometric cis/trans (or Z/E) isomers are possible. Where structural isomers are interconvertible via a low energy barrier, tautomeric isomerism ('tautomerism') can occur. The invention includes the use of conjugated compound of TLR7 and/or TLR8 and TLR2 agonists. The conjugates may include acylated S-glycerylcyteine or acylated S-thioethanol-cysteine linked to a TLR7 or TLR7/8 agonist via a [polyamine or poly(lysine)] spacer which is cationic at physiological pH. The cationic lipid can be used as gene delivery agent.

The molecules of the invention may exist in unsolvated and in solvated forms of pharmaceutically acceptable salts. The compounds of Formula I, II or XIII and their pharmaceutically acceptable salts, solvates and polymorphs are useful because they have pharmacological activity in animals, including humans. More particularly, they are useful in the immune modulation for the treatment of a disease. In one aspect, the compounds of the invention are useful in the treatment of a viral, bacterial, fungal, and protozoal infections, tumors or cancer, or immunological diseases. In yet another aspect, the compounds of the invention are useful as vaccine adjuvants. Accordingly the invention provides a compound of Formula I, II or XIII or a pharmaceutically acceptable salt, solvate or derivative thereof for use as a medicament, in immune modulation for the treatment of a disease.

At physiological pH, the compounds of the invention are positively charged on their Z moiety, thereby being able to form a complex with a polyanionic molecule, such as a nucleic molecule.

The molecules of the invention are typically provided in aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water. The preparation of compound of Formula I, II or XIII under sterile conditions, for example, by lyophilisation, may readily be accomplished using standard pharmaceutical techniques well known to those skilled in the art. Due to the lipid moiety $R^4$ of Formula XI, the compounds of the invention may form liposomes in aqueous solution.

Another object of the present invention is a complex formed between a polyanionic molecule and the compound of Formula I, II or XIII as defined above in a medium having a physiological pH, i.e. a pH comprised between 4 and 8. In this range of pH, the compound of formula I, II or XIII is in cationic form and is capable of forming a complex with a nucleic acid.

Preferably, the polyanionic molecule, e.g., pDNA, mRNA, polynucleotide or nucleic acid oligomer can be solubilized in any of various buffers prior to mixing or complexing with the compound of the invention, e.g., cationic compound of Formula I, II or XIII. Suitable buffers include phosphate buffered saline (PBS), normal saline, carbohydrates buffer such as Glucose 5% or Bionolyte G5, Tri-buffer, and sodium phosphate. Insoluble polynucleotides can be solubilized in a weak acid or weak base, and then diluted to the desired volume with a buffer. The pH of the buffer may be adjusted as appropriate. In addition, a pharmaceutically acceptable additive can be used to provide an appropriate osmolarity. Such additives are within the purview of one skilled in the art.

According to the present disclosure, the polyanionic molecule can be complexed with the compound of the present invention in cationic form by any means known in the art, e.g., by mixing a pDNA solution and a solution of the compound of the present invention in the liposome form.

In one embodiment, the concentration of each of the constituent solutions is adjusted prior to mixing such that the desired final pDNA/cationic lipid ratio and the desired pDNA final concentration will be obtained upon mixing the two solutions. For example, if the desired final solution is Glucose 5% or physiological saline (Bionolyte G5), a nonionic surfactant, such as Pluronic® F-68 (PF-68) can be used to stabilized the complex, both pDNA and cationic lipid liposomes are prepared in Glucose 5% or Bionolyte G5 with PF-68 (2%) and then simply mixed to produce the desired complex. The cationic lipid liposomes of the compounds of the invention can be prepared by any means known in the art.

Preferably, the polyanionic molecule is a nucleic acid, such as a coding or non-coding plasmid DNA, a double-stranded DNA, a single-stranded DNA, a double-stranded RNA, a single-stranded RNA, a oligodeoxynucleotide or a mixture thereof.

Since nucleic acids, due to the phosphate groups within the backbone of nucleic acids, are net negatively charged molecules, they are bound by the positively charged groups of the cationic conjugated molecules of the present invention, via electrostatic interaction, to form a stable complex.

According to the invention, a complex between a cationic molecule and a nucleic acid suggests that the nucleic acid is linked to a cationic molecule by non-covalent bonds, because of the ability of nucleic acids, both RNAs and DNAs, to interact with positively charged substances.

Hence, a cationic molecule according to the invention is a compound comprising
  at least one lipophilic hydrocarbon chain and
  at least one chemical group that is positively charged at physiological pH, said compound being capable of forming a complex with a nucleic acid.

This composition forms a lipophilic complex with nucleic acids of interest, which include non-coding or coding DNA.

According to the present invention, a gene of interest can be complexed with the compounds of the invention by mixing a pDNA (plasmid DNA) solution. The concentration of each of the constituent solutions is adjusted prior to mixing such that the desired final pDNA/cationic lipid ratio and the desired pDNA final concentration will be obtained upon mixing the two solutions. Complexes of the compounds of the invention with pDNA provide further immunogenic compositions of the present disclosure.

Compounds of the invention may be administered alone or in combination with one or more other drugs (complexed with pDNA or as any combination thereof). The compounds of the invention, or the compounds of the invention complexed with a pDNA of interest may be administered directly into the site of disease. In one aspect, immunogenic compositions of the compounds of the invention may be administered intratumorally. Suitable devices for intratumoral administration include needle (including microneedle) injectors, needle-free injectors and infusion techniques. The preparation of intratumoral formulations under sterile conditions may readily be accomplished using standard pharmaceutical techniques well known to those skilled in the art.

Another object of the present invention is a pharmaceutical composition comprising the compounds of the invention as defined previously or the complex as defined above and a pharmaceutically acceptable excipient or carrier.

A pharmaceutically acceptable excipient or carrier means an excipient or carrier that is useful in preparing a pharmaceutical composition that is safe, non-toxic and neither biologically nor otherwise undesirable, and includes and excipient that is acceptable for human use as well as veterinary use.

Treatment

Immune responses stimulated by TLR7 and/or TLR8, TLR2 and cytosolic nucleic acid sensors pathway(s) lead to the production and activation of pro-inflammatory cytokines, TNF-α and type I IFNs and are useful for the treatment of infections, immune-disorders and diseases such as cancer.

Another object the invention is a vaccine comprising the compound of the invention as defined previously or the complex as defined previously.

Another object of the present invention is a compound of Formula I, II or XIII as defined previously or a complex as defined above, for use in a therapeutic treatment in human or animals.

Another object of the present invention is a compound of the invention as defined previously or a complex as defined above, for use in the treatment of a pathology selected from the group consisting of an infection, a cancer and an immune disorder.

Another object of the present invention is a compound of Formula I or II as defined previously or complex as defined above, for use in the treatment of a pathology which may be alleviated by the induction of an immune response via TLR7 and/or TLR8, TLR2 and cytosolic nucleic acid sensors pathway(s).

Another object of the present invention is a compound of Formula XIII as defined previously or complex as defined above, for use in the treatment of a pathology which may be alleviated by the induction of an immune response via TLR2 pathway(s).

The conjugated compounds of Formula I, II or XIII and their pharmaceutically acceptable salts, solvates and polymorphs are useful because they have pharmacological activity in animals, including humans. More particularly, the compounds of the invention are useful in the treatment of a disorder in which the modulation, especially agonism, of TLR7 and/or TLR2 is implicated. In one aspect, the compounds of the invention are useful in the treatment of infections caused by an adenovirus, a herpesvirus (e.g., HSV-I, HSV-II, CMV, or VZV), a poxvirus (e.g., an orthopoxvirus such as variola or vaccinia, or molluscum contagiosum), a picornavirus (e.g., rhinovirus or enterovirus), an orthomyxovirus (e.g., influenzavirus), a paramyxovirus (e.g., parainfluenzavirus, mumps virus, measles virus, or respiratory syncytial virus (RSV)), a coronavirus (e.g., SARS), a papovavirus (e.g., papillomaviruses, such as those that cause genital warts, common warts, or plantar warts), a hepadnavirus (e.g., hepatitis B virus), a flavivirus (e.g., hepatitis C virus or Dengue virus), a retrovirus (e.g., a lentivirus such as HIV) or a filovirus (e.g., Ebola virus or Marburg virus).

In another aspect, the compounds of the invention are useful to treat tumors or cancers including but not limited to carcinomas, sarcomas, and leukemia, e.g. squamous cell carcinoma, pancreatic carcinoma, hepatocarcimona, renal cell carcinoma, Kaposi's sarcoma, skins cancers such as basal cell carcinoma and melanoma, renal cell carcinoma, myelogeous leukemia, chronic lymphocytic leukemia, multiple myeloma, non-Hodgkin's lymphoma.

In yet another aspect, the compounds of the invention are useful to treat bacterial, fungal, and protozoal infections including but not limited to infections caused by bacteria of the genus *Escherichia, Enterobacter, Salmonella, Staphylococcus, Klebsiella, Proteus, Pseudomonas, Streptococcus, Chlamydia*; or fungal infections such as candidiasis, aspergillosis, histoplasmosis, cryptococcal meningitis.

In yet another aspect, the compounds of the invention are useful to treat Th2-mediated diseases (Dabbagh et al. 2003), including but not limited to atopic diseases, such as atopic dermatitis or eczema, eosinophilia, asthma, allergy, allergic rhinitis.

In yet another aspect, the compounds of the invention are useful in the treatment of autoimmune diseases.

Another object of the present invention is a method for treating pathology selected from the group consisting of an infection, a cancer and an immune disorder in a subject in need thereof comprising administering to said subject a therapeutically effective amount of the compound of the invention as defined previously or of the complex as defined previously.

Another object of the present invention is a method for inducing an immune response via TLR7 and/or TLR8, TLR2 and cytosolic nucleic acid sensors pathway(s) in a patient, comprising administering to said patient a therapeutically effective amount of the conjugated compound as defined previously or of the complex as defined previously.

Another object of the present invention is a method for inducing an immune response via TLR2 pathway(s) in a patient, comprising administering to said patient a therapeutically effective amount of the conjugated compound of Formula XIII as defined previously or of the complex as defined previously.

Another object of the present invention is the use of a conjugated compound of Formula I, II or XIII as defined previously or a complex as defined above for the preparation of a medicament for the treatment of an infection, a cancer or an immune disorder.

Methods of Administration

The therapeutically effective amount of the compound of the invention of Formula I, II, or XIII as defined previously or of the complex as defined above may be administered directly into the blood stream, into muscle, into tumor, or into an internal organ. Suitable means for parenteral administration include intravenous, intraarterial, intraperitoneal, intrathecal, intraventricular, intraurethral, intrasternal, intracranial, intramuscular, intrasynovial and subcutaneous. Suitable devices for administration include needle (including microneedle) injectors, needle-free injectors and infusion techniques.

In another embodiment, the therapeutically effective amount of the compound of the present invention of Formula I, II, or XIII or of complex as defined previously may also be administered topically as creams or as other topical forms known to those skilled in the art.

The dosage can vary within wide limits and will, of course, be fitted to the individual requirements in each particular case. In general, in the case of administration to adults a convenient daily dosage of the compound of the invention should be about 1 μg to about 500 mg, preferably about 100 μg to about 1 mg. The daily dosage may be administered as a single dose or in divided doses and, in addition, the upper dosage limit referred to earlier may be exceeded when this is found to be indicated.

Chemistry

The compounds of the present invention can be synthesized by an appropriate combination of generally well known synthetic methods. Techniques employed in synthesizing the compounds of the disclosure are both readily apparent and accessible to those of skill in the relevant art. The discussion below is offered to illustrate a number of the diverse methods available for use in assembling the compounds of the disclosure. However, the discussion is not intended to define the scope of reactions or reaction sequences that are useful in preparing the compounds of the present disclosure. The conjugated compounds of this disclosure may be made by the procedures and techniques disclosed in the Examples section below, as well as by known organic synthesis techniques.

The compounds of the present disclosure may be synthesized using one or more protecting groups generally known in the art of chemical synthesis. The term "protecting group" refers to chemical moieties that block some or all reactive moieties of a compound and prevent such moieties from participating in chemical reactions until the protective group is removed. Examples of the moieties listed are described in 'Protective Groups in Organic Synthesis' by Green and Wuts, third edition, (John Wiley and Sons, 1999). Where different protecting groups were employed, each (different) protective group was removable by a different means. Protective groups that were cleaved under totally disparate reaction conditions allowed for differential removal of such protecting groups. For example, protective groups can be removed by acid, base, and hydrogenolysis.

An object of the present invention is a process for the manufacture of the compounds of Formula I as defined previously, which process comprises reacting a compound of Formula XII:

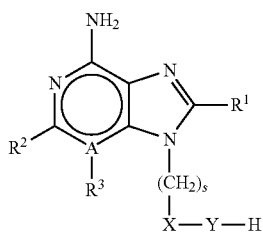

Formula XII wherein $R^1$, $R^2$, $R^3$, A, s, X and Y are as defined previously, with a compound of Formula XIII:

Formula XIII wherein Z and $R^4$ are as defined previously,
or reacting a compound of Formula XIV:

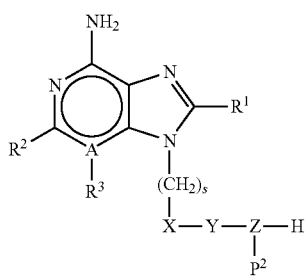

Formula XIV wherein $R^1$, $R^2$, $R^3$, A, s, X, Y and Z are as defined in claim 3, and $P^2$ is a protecting group, with a compound of Formula XV:

Formula XV wherein $R^4$ is as defined above, followed by a deprotection step.

These processes provide:
TLR7/TLR2 purine derivatives of Formula XVI:

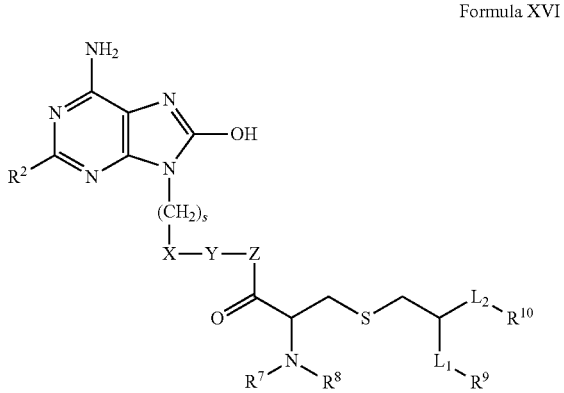

Formula XVI

TLR7 and/or TLR8/TLR2 imidazoquinoline derivatives of Formula XVII:

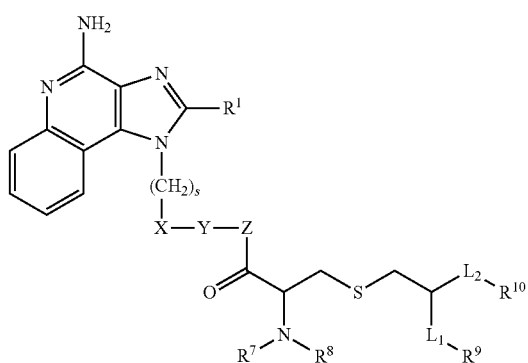

Formula XVII

TLR7 and/or TLR8/TLR2 3-deazapurine derivatives of Formula XVIII:

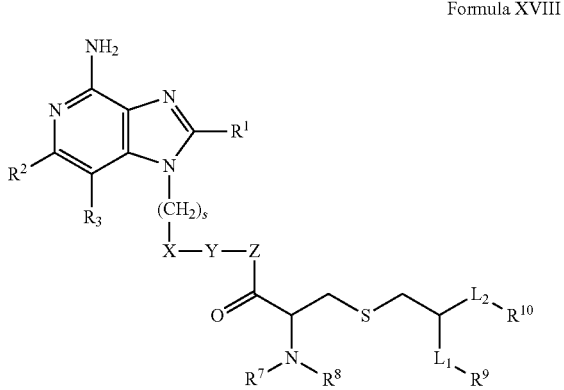

Formula XVIII

The compounds of Formula I or II containing one or more asymmetric carbon atoms can exist as two or more stereoisomers. Where a compound of Formula I or II contains an alkenyl or alkenylene group, geometric cis/trans (or Z/E) isomers are possible. Where structural isomers are interconvertible via a low energy barrier, tautomeric isomerism ('tautomerism') can occur. This can take the form of proton tautomerism in compounds of Formula I containing, for example, an imino, keto, or oxime group, or so-called valence tautomerism in compounds which contain an aromatic moiety. It follows that a single compound may exhibit more than one type of isomerism.

In particular, a compound of Formula $XVI_A$ is the tautomer of the compound of Formula $XVI_B$:

It will be still further appreciated by those skilled in the art that it may be necessary or desirable at any stage in the synthesis of compounds of Formula I to protect one or more sensitive groups in the molecule so as to prevent undesirable side reactions. In particular, it may be necessary or desirable to protect amino groups. The protecting groups used in the preparation of compounds of Formula I may be used in conventional manner. See, for example, those described in 'Pro- Scheme 1

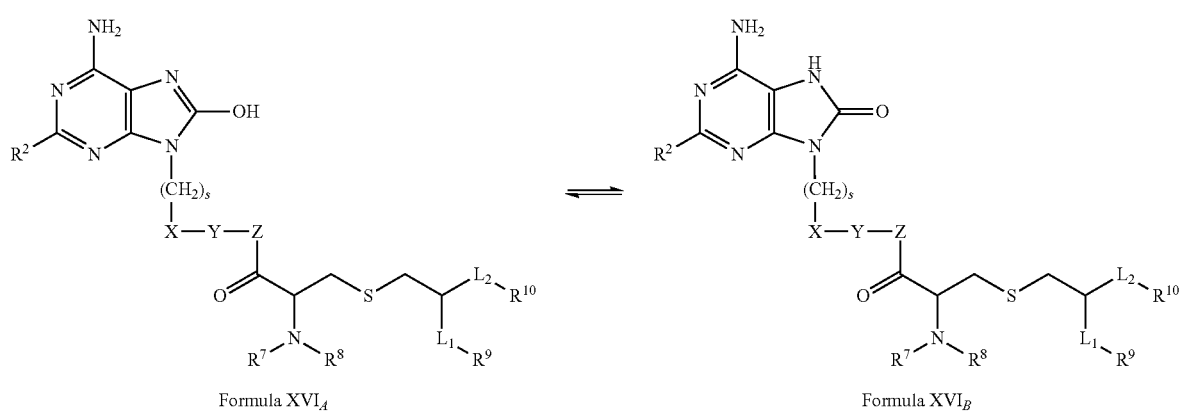

It will be appreciated by those skilled in the art that certain of the procedures described in the schemes for the preparation of compounds of Formula I or intermediates thereof may not be applicable to some of the possible substituents. It will be further appreciated by those skilled in the art that it may be necessary or desirable to carry out the transformations described in the schemes in a different order from that described, or to modify one or more of the transformations, to provide the desired compound of Formula I.

tective Groups in Organic Synthesis' by Green and Wuts, third edition, (John Wiley and Sons, 1999), in particular chapter 7, pages 494-653 ("Protection for the Amino Group"), incorporated herein by reference, which also describes methods for the removal of such groups.

The TLR2 agonist lipid derivatives of Formula XI as described previously can be prepared according to reaction Scheme 2 to provide the compounds HO—$R^4$ of Formula 9 or 12:

Scheme 2

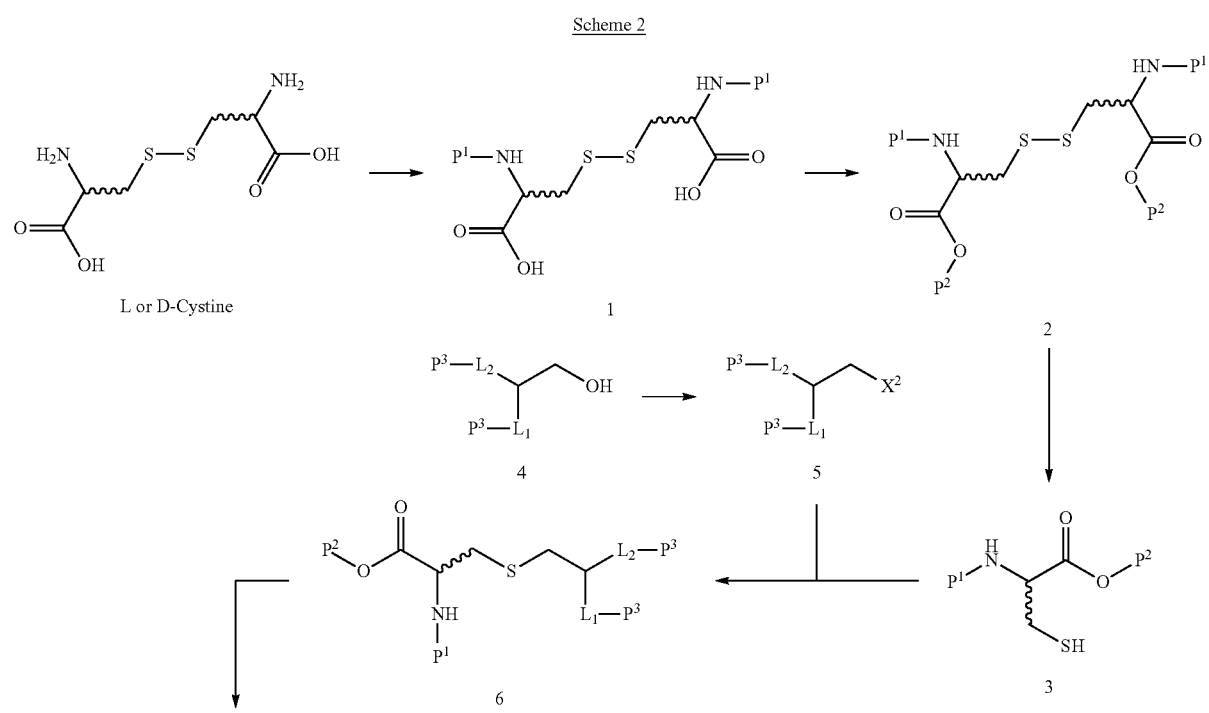

-continued

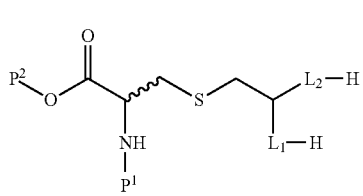
7

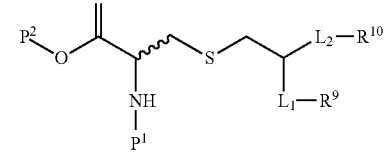
8

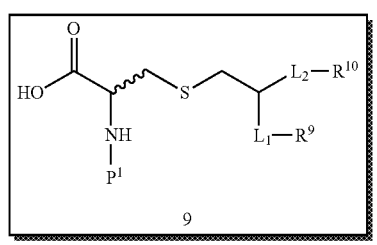
9

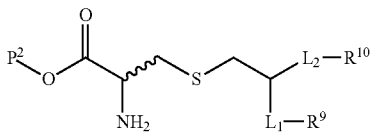
10

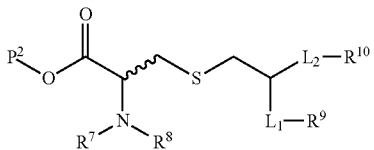
11

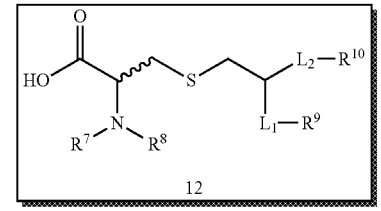
12

In the above formulas, $X^2$ is halogen or leaving group $P^1$, $P^2$, $P^3$ are different protecting groups, $L_1$, $L_2$, $R^7$, $R^8$, $R^9$, and $R^{10}$ are same as defined previously.

The amine function of the commercially available L or D-Cystine can be, suitably, protected as known in the peptide art. For example, the tert-butoxycarbonyl (Boc) group is preferred for protection of the two amino group at the α position of the cystine to provide the compound 1.

The carboxylic acid function of compound 1 can be, then, protected by conventional methods. Typically, the carboxylic acid is treated with an alcohol in the presence of an acid catalyst. Alternatively, the carboxylic acid may be converted to an activated salt, such as a cesium salt, and treated with an alkyl or alkylene halide. In the practice of this invention the acid is protected with the allylic group. Typically, the acid or a salt thereof is reacted with the allyl bromide or iodide in a polar aprotic solvent such as dimethylformamide to provide compound 2.

The disulphide bond of the correctly protected cystine 2 can be reduced with PBu₃, DTT, or other suitable reductant to give the free thiol 3.

The primary hydroxyl group of the correctly protected glycerol 4 (wherein L1 is —CH2-O— and L2-O) can be easily converted into an eliminable group, for example a sulphonyloxy group, by reaction with a methanesulphonyl chloride in the presence of triethylamine in dichloromethane or of p-toluenesulphonyl chloride in pyridine. Preferably, the selective activation of the primary alcohol is carried out to halogenation type reactions which are practically prepared by reaction with iodide, triphenylphosphine, and imidazole (Garegg, P J. et al. 1982). This reaction provides the compound 5 in which $X^2$ is an iodine atom.

The condensation reaction between compound 3 and 5 in presence of base (for example triethylamine in DMF) provides totally protected the thioethanol or thioglycerol motif with the cysteine compound 6.

The protection on glycerol moiety can be, then, selectively removed to provide the compound 7.

The alcohol function of compound 7 can be, preferably, acylated. The reaction is carried out by adding a fatty acid to a solution of the compound 7 dissolved in a suitable organic solvent, such as dichloromethane, in the presence of a suitable catalyst, such as ethyldimethylaminopropylcarbodiimide (EDCl)-DMAP to provide diacylester 8.

The carboxylic protection of compound 8 can be removed by acid, base or hydrogenolysis. In the case of the allylic ester protecting group, the organic soluble palladium complex is used. The complex of choice is tetrakis (triphenylphosphine) palladium-(0). Other utilizable soluble palladium complexes are palladium(II), dichloro-di[benzonitrile]palladium(II) and palladium(II) diacetate in conjunction with several equivalents of triphenylphosphine (see Fieser and Fieser, "Reagents for Organic Synthesis", Vol V, pp. 497, 503, 504). The quantity of catalyst utilized in the process of this invention is typically 0.25-5 mole percent of the allylic ester. This reaction provides the compound 9 which can be used as $R^4$—H derivatives.

Alternately, the protection of the amino group of compound 8 can be removed. Preferably, the Boc group is cleaved with HCl in organic solvents or with TFA in organic solvents. This reaction provides the compound 10.

The free amine function of compound 10 can be, then, acylated. The N-acylated compound can be prepared using acylating reagents such as organic acid halides or organic acid anhydrides or using fatty acid with a coupling reagent such as DCC, CDI, EDC, or optionally with a tertiary amine base and/or catalyst, e.g., DMAP. Preferably, fatty acid is introduced on amine of compound 10 using a coupling agent such as HATU in the presence of an amine such as DIEA in polar solvent such as DMF or dichloromethane to provide compound 11.

The carboxylic protection of compound 11 can be removed to provide compound 12 as described below for compound 9. The compound 12 can be used as $R^4$—H derivatives.

The TLR2 polycationic agonist of Formula XIII as described previously can be prepared according to reaction Scheme 3 to provide the compounds H—Z—$R^4$ of Formula 15 or 16:

esters (OPfp, Odhbt, OSu), phosphonium salts (BOP, PyBOP, AOP, PyAOP) and uronium/guanidinium-mediated salt built around processes using HOBt and HAOt (HBTU, HATU, HBPyU, COMU etc). HATU reacts exclusively with carboxylate salts (R—COO—); mixtures of HATU and a carboxylic acid (R—COOH) remain stable. This procedure eliminates the requirement for a separate neutralization step saving time and minimizing diketopiperazine formation. Three equivalents of base (DIEA or NMM) are necessary to neutralize the carboxylic acid, the amine salt, and the acidic hydroxybenzotriazole. When using HATU, the reaction mixture has to be kept near basic pH in order to ensure a fast coupling. Under such conditions, the coupling rate is so high that racemization is negligible using urethane-protected amino acid couplings and fairly low in segment coupling. The excess of acid and "onium" salt (HATU) is typically 1.1 molar equivalent in solution synthesis. This reaction is preferably carried out in a solvent such as methylene chloride, chloroform, tetrahydrofuran, dioxane, ethyl acetate, or the like under ice-cooling to at ambient temperature and the reaction in the presence of an inert gas is usually carried out in an anhydrous, but not critical, conditions. The reaction temperature is selected from the range between about room temperature and around boiling point of the solvent.

The protection $P^5$ on compound 14 can be removed selectively by acid, base or hydrogenolysis to afford the compound 15. The compound 15 can be used as H—Z—$R^4$ derivatives.

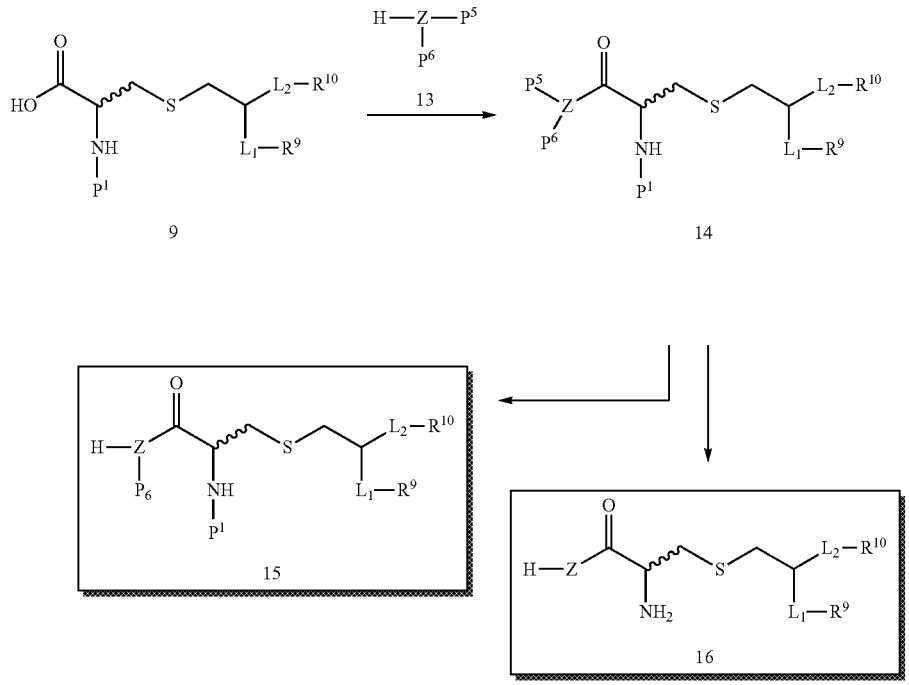

In the above formulas, $P^1$, $P^5$, $P^6$ are different protecting groups, $L_1$, $L_2$, $R^7$, $R^8$, $R^9$, and $R^{10}$ are same as defined previously.

The compound 14 is prepared from respectively compounds 9 and 13 by any well-known peptide synthesis procedure in the art. The most commonly employed methods for peptide bond formation in solution include: the carbodiimide method (DCC, DIC), symmetric or mixed anhydrides, active The total deprotection of compound 14 by acid, base or hydrogenolysis can afford the compound 16. The compound 16 can be used as H—Z—$R^4$ derivatives.

The purine derivatives of Formula XVI can be prepared by the following methods. The starting compounds not disclosed below can be prepared by a similar method to the following method or by a known method and similar methods to that.

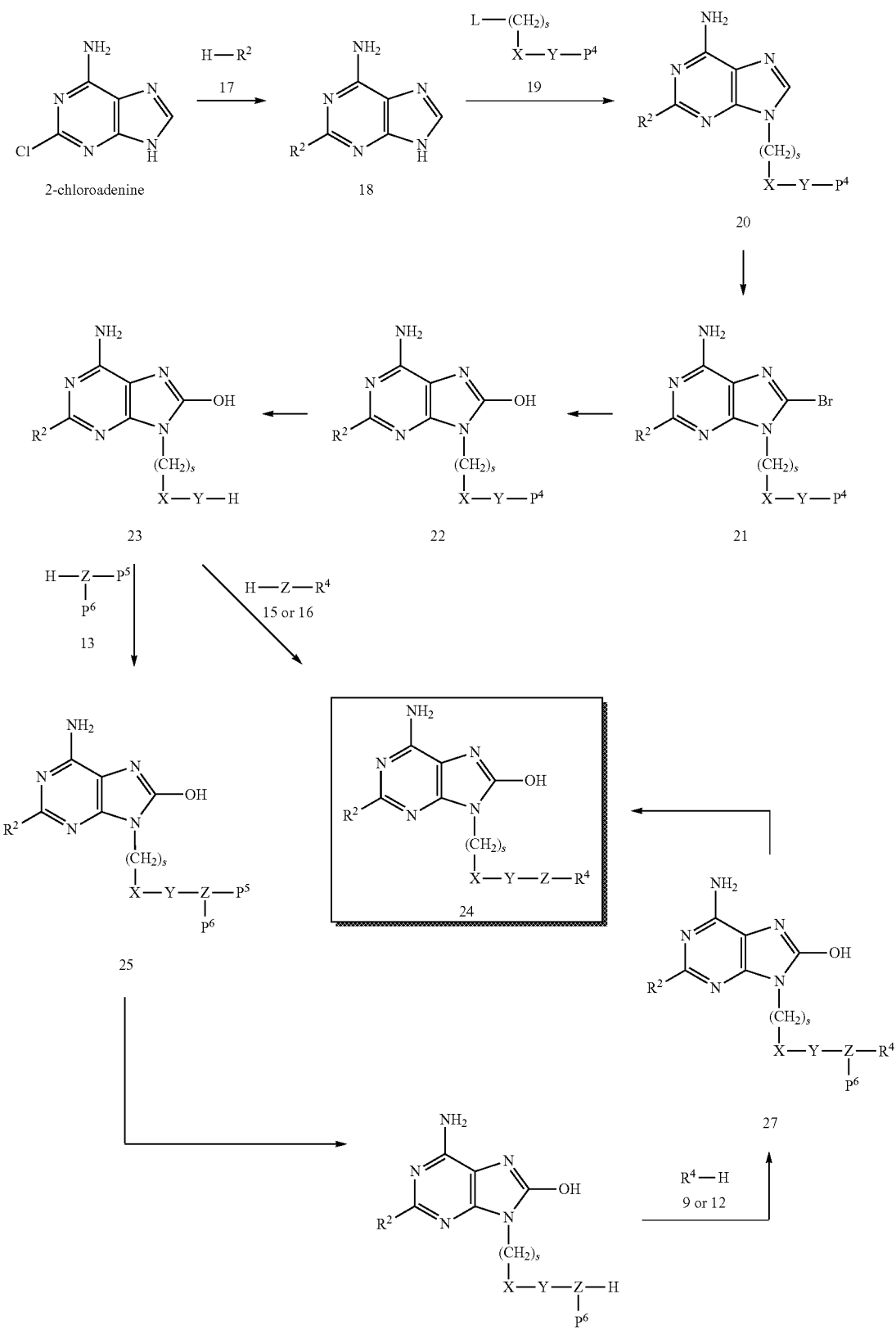

In the above formulas, L is a leaving group, $P^4$, $P^5$ and $P^6$ are different protecting groups $R^2$, s, X, Y, Z and $R^4$ are same as defined previously.

Commercially available 2-Chloroadenine can be reacted with compound 17 in an organic solvent. When compound 17 is an amine, the reaction is preferably carried out in the amine as solvent. Reaction vessels such as an autoclave etc. may be used in the reaction, if necessary. When compound 13 is alcohol or thioalcohol, the reaction is preferably carried out in the presence of a base. The bases are alkali metals, such as sodium or potassium, alkali metal hydrides, such as sodium hydride or potassium hydride, organometalic compounds, such as methyl lithium, butyl lithium or lithium diisopropylamide. The base is preferably used about equimolar to compound 17. The organic solvents are aprotic solvents, such as dimethylformamide, acetonitrile or hexamethylphosphoroustriamide, or ethers such as diethyl ether, tetrahydrofuran or 1,4-dioxane or diglyme. The reaction temperature is selected from the range between about room temperature and around the boiling point of the solvent.

The chlorine atom of 2-chloroadenine can be also coupled under a variety of conditions in which a reactive organometallic reagent can be treated with 2-chloroadenine in the presence of a transition metal catalyst, for example a stannane, zincate or boronic acid in the presence of a palladium catalyst, to give the 2-substituted adenine 18.

Compound 18 and compound 19 can react in the presence of a base in an organic solvent. Compound 19 can be used about equal molar or several molars to compound 18. Bases are inorganic bases such as alkali metal carbonates (e.g. sodium carbonate, potassium carbonate, cesium carbonate), or organic bases, such as tertiary amines (e.g. triethylamine, diisopropylethylamine) or pyridines (e.g. 4-dimethylaminopyridine, pyridine). The base is preferably used about equimolar to compound 19. The organic solvents are halogenated hydrocarbons such as tetrachloromethane, chloroform or methylene chloride, ethers such as diethyl ether, tetrahydrofuran or 1,4-dioxane, or aprotic solvents, such as dimethylformamide, dimethyl sulfoxide, acetonitrile or hexamethylphosphoroustriamide. The reaction temperature is selected from the range between about 0° C. and around the boiling point of the solvent.

Compound 20 can react with a brominating reagent such as bromine, hydrobromic acid perbromide, N-bromo succinimide, etc. in an organic solvent. A reaction promoter such as sodium acetate may be added to the reaction mixture. The brominating reagent is used from equimolar to several moles of compound 20, preferably from equimolar to one and one-half moles. The organic solvents are halogenated hydrocarbons, such as tetrachloromethane, chloroform or methylene chloride, ethers such as diethyl ether, acetic acid, or carbon disulfide. The reaction temperature is selected from the range between about 0° C. and around boiling point of the solvent.

Compound 21 can react with an alcohol such as methanol in the presence of a base in an organic solvent. The bases are alkali metals, such as sodium or potassium, alkali metal hydrides, such as sodium hydride or potassium hydride, organometallic compounds, such as methyl lithium, butyl lithium or lithium diisopropylamide. The base is preferably used from about equal molar to about two times as much to compound 21. The organic solvents are ethers, such as diethyl ether, tetrahydrofuran or 1,4-dioxane, or aprotic solvents, such as dimethylformamide, dimethyl sulfoxide, acetonitrile or hexamethylphosphoroustriamide. The alcohol as the reagent, such as methanol, ethanol, propanol or butanol may serve as a solvent. The reaction temperature is selected from the range between about room temperature and around boiling point of the solvent. This intermediate can be hydrolysed under either acidic or basic conditions, typically with an acid in water or a mixture of water and an organic solvent. The acids are inorganic acids, such as hydrochloric acid or hydrobromic acid, or organic acids such as trifluoroacetic acid. The organic solvents are ethers, such as diethyl ether or tetrahydrofuran, aprotic solvents such as dimethylformamide, alcohols, such as methanol, ethanol or propanol, or acetic acid. The reaction temperature is selected from the range between about room temperature and around boiling point of the solvent.

The protection on compound 22 can be removed by acid, base or hydrogenolysis.

The compounds 24 and 25 are prepared from compound 23 and respectively compounds 15 or 16 and 13 by any well-known peptide synthesis as described previously for compound 14.

The protection $P^5$ on compound 25 can be removed selectively by acid, base or hydrogenolysis to afford the compound 26.

Compound 26 and compounds 9 or 12 can react by any well-known peptide synthesis as described previously for compound 14.

The protection on compound 27 can be removed by acid, base or hydrogenolysis to afford the desired compound 24.

Imidazoquinolines derivatives of Formula XVII of the invention can be prepared according to reaction Scheme 5:

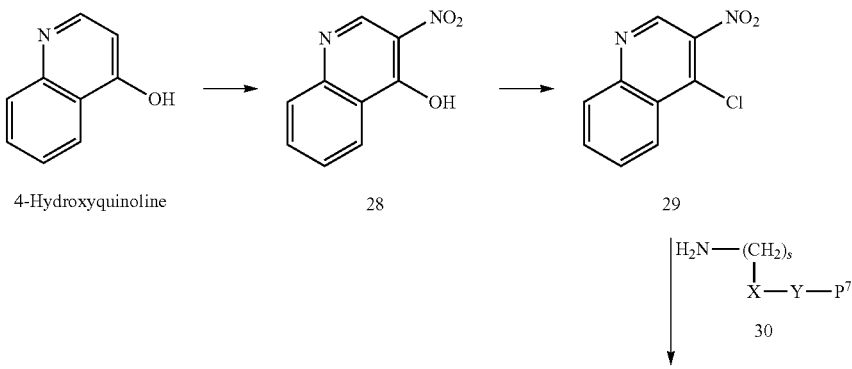

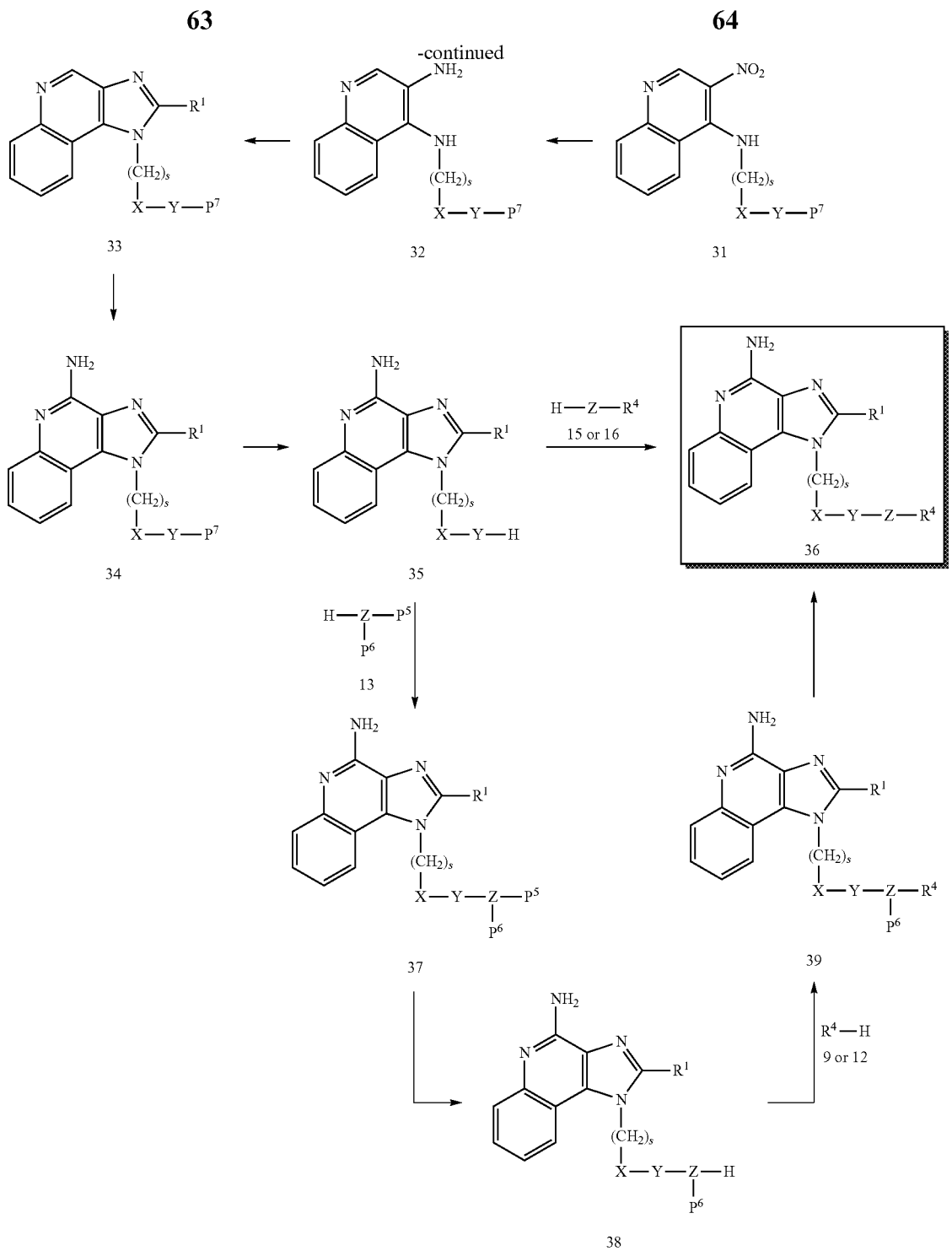

In the above formulas $P^7$ is a protecting group $P^5$, $P^6$, L, $R^1$, $R^4$, s, X, Y, and Z are same as defined previously.

The reaction scheme begins with a commercially available 4-hydroxyquinoline. The nitration of a 4-hydroxyquinoline provide the 3-nitro-4-hydroxyquinoline compound 28. Conventional conditions for such reactions are well known. Preferred conditions in the instance afford a product of Formula 28 in superior yield compared with conditions used in the prior art, involve heating at about 125° C.-130° C. in propionic acid in the presence of nitric acid.

Compound 28 is chlorinated at the 4-position to provide a 3-nitro-4chloroquinoline compound 29. Preferred conditions involve chlorination in methylene chloride with a Vilsmeier reagent prepared from thionyl chloride and N,N-dimethylformamide. In such a reaction, the compound of Formula 28 is suspended in methylene chloride, and a slight molar excess of thionyl chloride and N,N-dimethylformamide is added to the suspension. Heating to reflux facilitates the chlorination.

Compound 29 is reacted with an amine of Formula 30. The reaction can be carried out by adding amine to a solution of compound 29 in a suitable solvent such as chloroform or dichloromethane in presence of base such as triethylamine or diisopropyl-ethylamine and optionally heating.

Compound 31 is reduced to provide a quinoline-3,4-diamine compound 32. Compound 31 may then be reduced under any of the conditions known in the literature to reduce a nitro aromatic compound to an amine using for example iron or tin in HCl, hydrogenation in the presence of a transition metal catalyst such as palladium, platinum or nickel or a chemical reductant such as lithium aluminium hydride to give 32. Preferably, the reduction is carried out using a conventional heterogeneous hydrogenation catalyst such as platinum on carbon or palladium on carbon. The reaction can conveniently be carried out in a suitable solvent such as ethanol, isopropyl alcohol or toluene.

Compound 32 is reacted with a carboxylic acid or an equivalent thereof to provide a 1H-imidazo[4,5-c]quinoline compound 33. Suitable equivalents to carboxylic acid include acid halides, orthoesters, and 1,1-dialkoxyalkyl alkanoates. The carboxylic acid or equivalent is selected such that it will provide the desired $R^1$ substituent in a compound 33. For example, triethyl orthoformate will provide a compound where $R^1$ is hydrogen and triethyl orthoacetate will provide a compound where $R^1$ is methyl. The reaction can be run in the absence of solvent or in an inert solvent such as toluene. The reaction is run with sufficient heating to drive off any alcohol or water formed as a byproduct of the reaction.

Compound 33 is oxidized to provide a 1H-imidazo[4,5-c]quinoline-5N-oxide using a conventional oxidizing agent that is capable of forming N-oxides. Preferred reaction conditions involve by reacting a solution of a compound 33 in chloroform with 3-chloroperoxybenzoic acid at ambient conditions. The intermediate 1H-imidazo[4,5-c]quinoline-5N-oxide is then directly aminated to provide a 1H-imidazo[4,5-c]quinolin-4-amine compound 34. In this step the N-oxide compound is reacted with an acylating agent such as: alkyl- or arylsulfonyl chlorides (e.g., benzenesulfonyl chloride, methanesulfonyl chloride, p-toluenesulfonyl chloride). Arylsulfonyl chlorides are preferred. Para-toluenesulfonyl chloride is most preferred. The product obtained is mixed with an excess of an aminating agent. Suitable aminating agents include ammonia (e.g., in the form of ammonium hydroxide) and ammonium salts (e.g., ammonium carbonate, ammonium bicarbonate, ammonium phosphate). Ammonium hydroxide is preferred. The reaction is preferably carried out by dissolving the N-oxide compound in an inert solvent such as dichloromethane, adding the aminating agent to the solution, and then slowly adding the acylating agent. The product or a pharmaceutically acceptable salt thereof can be isolated using conventional methods.

The protection on compound 34 can be removed by acid, base or hydrogenolysis to provide compound 35.

The compounds 36 and 37 are prepared from compound 35 with respectively compounds 15 or 16 and 13 by any well-known peptide synthesis procedure in the art as described above for compound 14.

The protection $P^5$ on compound 37 can be removed selectively by acid, base or hydrogenolysis to provide the compound 38.

Compound 38 and compounds 9 or 12 can react by any well-known peptide synthesis procedure in the art as described above for compound 14.

The protection on compound 39 can be removed by acid, base or hydrogenolysis to provide compound 36.

3-deazapurine derivatives of Formula XVIII of the invention can be prepared according to reaction Scheme 6:

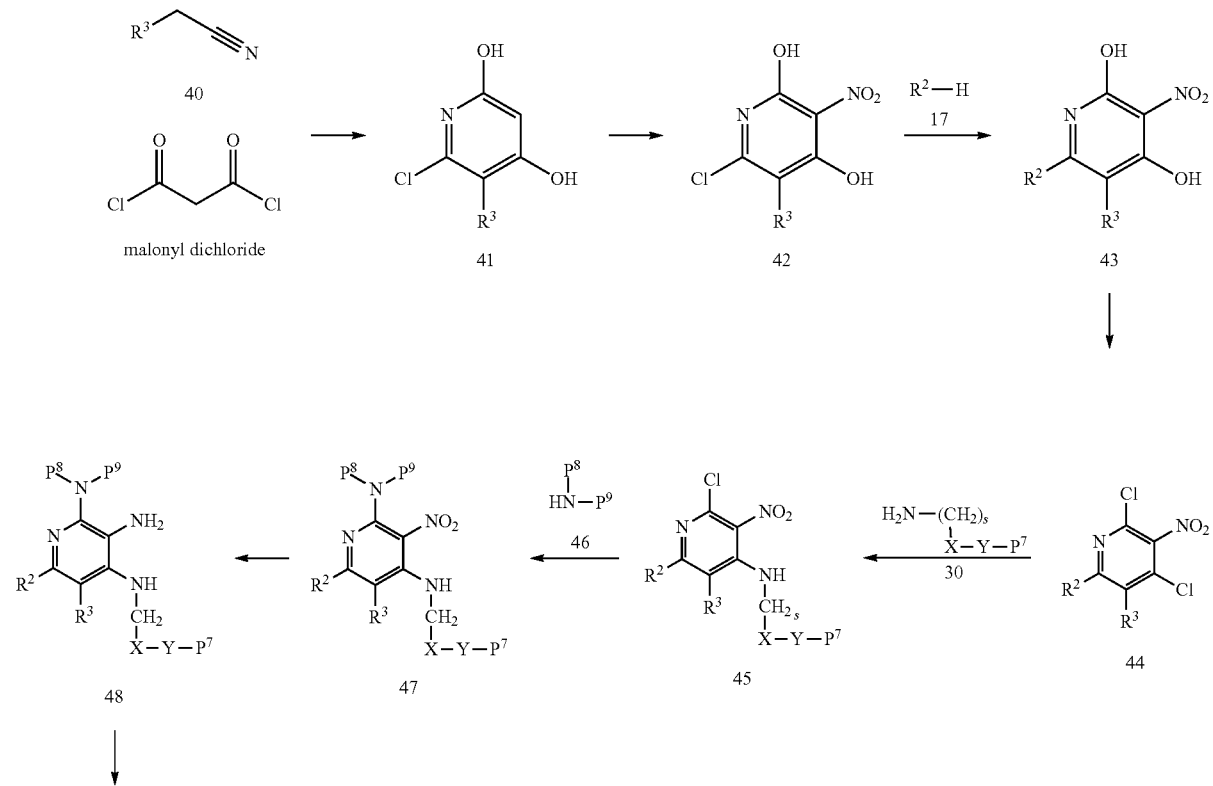

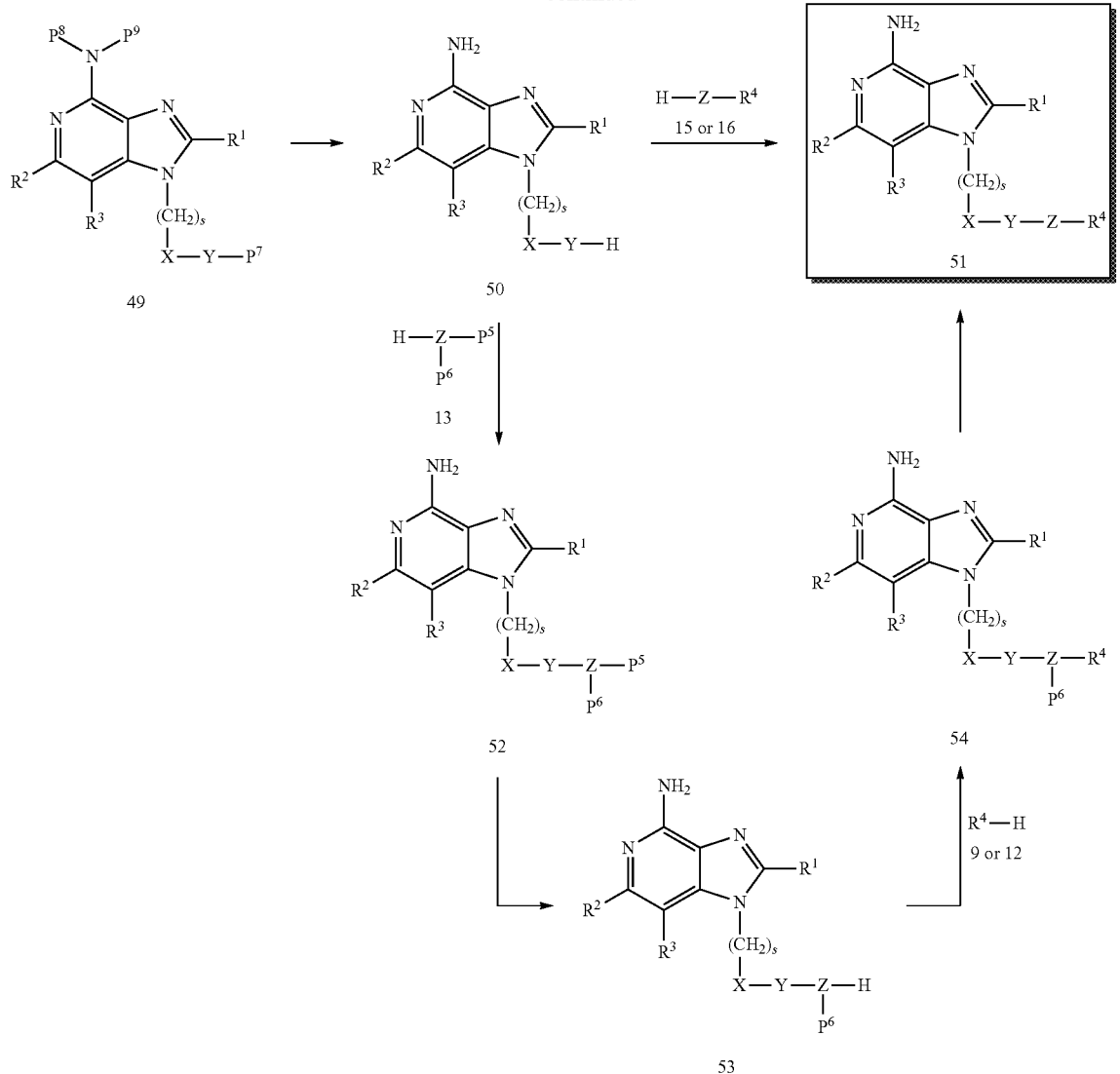

In the above formulas, $P^8$ and $P^9$ are different protecting groups, $P^5$, $P^6$, $P^7$, L, $R^1$, $R^2$, $R^3$, $R^4$, s, X, Y, and Z are same as defined previously.

A commercially available nitrile 40 which possesses a methylene group adjacent to the nitrile function is reacted with malonyl dichloride to provide the pyridines 41. (Nguyen et al. 1984).

The pyridines 41 is then nitrated using method described above for the 4-hydroxyquinoline.

The chlorine atom of compound 42 is then reacted with compound 17 as described above for the preparation of compound 18.

Compound 43 is chlorinated using a variety of conditions which convert hydroxyl groups to chlorines, such as thionyl chloride or phosphorus oxychloride to give 44. Preferred condition is described above for the preparation of compound 29.

Compound 44 is reacted with an amine of general Formula 30, as described above for the preparation of compound 31. This amine preferentially reacts at the 4-chloro group to give 45.

Some displacement of the two chlorine groups or a minor amount of displacement at the 2-chloro group can occur, but does not detract from the ability to secure predominantly compound 45.

Compound 45 is then reacted with ammonia $P^8$=$P^9$=H in methanol at 150° C. under pressure to give compound 47. Alternatively, compound 45 can be reacted with a protected form of ammonia 46, in which $P^5$ and $P^9$ protecting group which can later be removed under mild conditions, such as dibenzylamine or diallylamine.

The compound 47 is then reduced under conditions as described above for compound 31 to give compound 48.

Compound 48 is then reacted with a source of C=O such as 1,1-carbonyldiimidazole or phosgene. Alternatively, compound 48 can be reacted with a carboxylic acid or an equivalent, as described for compound 32, to provide a 1H-imidazo[4,5-c]pyridine compound 49.

The protection on compound 49 can be removed by acid, base or hydrogenolysis to provide compound 50.

The compounds 51 and 52 are prepared from compound 50 with respectively compounds 15 or 16 and 13 by any well-known peptide synthesis procedure in the art as described above for compound 14.

The protection P⁵ on compound 52 can be removed selectively by acid, base or hydrogenolysis to provide compound 53.

Compound 53 and compounds 9 or 12 can react by any well-known peptide synthesis procedure in the art as described above for compound 14.

The protection on compound 54 can be removed by acid, base or hydrogenolysis to provide compound 51.

The invention will be further illustrated by the following figures and examples. However, these examples and figures should not be interpreted in any way as limiting the scope of the present invention.

Peptide Synthesis

The peptide fragments of the invention are preferably made using solid phase synthesis techniques. However, it will be understood that the peptide fragments of the invention may be synthesized or prepared by techniques well known in the art.

Preferably, the peptide fragments of the present invention are synthesized by solid phase peptide synthesis (SPPS) techniques using standard FMOC protocols. (Carpino et al. 1970; Carpino et al. 1972). In a preferred embodiment, the solid phase synthesis of the peptide fragments of the present invention is carried out on super acid sensitive solid supports which include, but are not limited to, 2-chlorotrityl chloride resin (Barlos et al. 1989).

General, non-limiting procedures for production and loading of resins which can be utilized in solid phase peptide synthesis are described herein.

Resin loading can be performed, for example, via the following techniques: The resin, preferably a super acid sensitive resin such as 2-chlorotrityl resin, is charged to the reaction chamber. The resin is washed with a chlorinated solvent such as dichloromethane (DCM). The bed is drained and a solution of 0.5-1.5 equivalents of an amino acid with an 0.2 to 0.5 excess of diisopropylethylamine (DIEA) in about 8-10 volumes of N,N-dimethylformamide (DMF) is added. The N-terminus of the amino acid should be protected, preferably with Fmoc, and the side chain of the amino acid should be protected where necessary or appropriate. The mixture is agitated with nitrogen bubbling for 2-24 hours.

After agitation, the bed is drained and washed with DCM. The active sites on the resin are endcapped with a 9:1 MeOH:DIEA solution for about 20-30 minutes. The bed is drained, washed four times with DCM and dried with a nitrogen purge to give the loaded resin.

Fmoc is the preferred protecting group for the N-terminus of the amino acid. Depending on which amino acid is being loaded, its side chain may or may not be protected. For example, when lysine (Lys) are protected as t-butoxycarbonyl carbamates (Boc) and serine (Ser) are protected as t-butyl ethers or t-butyl esters.

The Fmoc-protected amino acids used in loading the resin and in peptide synthesis are available, with or without side-chain protecting groups as required, from multiple vendors, including Novabiochem or Iris Biotech. As an alternative to the above procedure, the resin may be purchased already loaded with the appropriate amino acid.

Solid phase peptide synthesis techniques can be performed as, for example, according to the following, non-limiting techniques: The loaded resin is added to the reaction chamber and conditioned with a solvent, preferably methylene chloride (DCM; at preferably about 10 vol.) with stirring for about 15 minutes to swell the resin beads. DCM is required for adequate swelling of the 2-chlorotrityl resin. The resin volume will increase 3-6 fold in the reaction chamber as the beads swell and the active sites unfold and become accessible to reaction. After the resin is swelled, the solvent is drained from the reaction chamber.

Removal of the Fmoc (9-fluroenyl-methyloxycarbonyl) protecting group from the terminal amine or the resin can be accomplished by treating the resin with 2 aliquots of a 20% solution of piperidine in DMF for about ten minutes each. The volume of the 20% solution of piperidine in DMF required for each aliquot will depend on the scale of the reaction being run. The resin is then washed 5-7 times with aliquots of DMF (about 10 vol.) to remove the Fmoc by-products (i.e., dibenzofulvene and its piperidine adduct) and residual piperidine.

Meanwhile, the subsequent amino acid in the sequence to be added to the resin is activated for reaction at its carboxy terminus. The amine terminus of each amino acid should be protected with Fmoc. Depending on which amino acid is being added, its side chain may or may not be protected. Preferably, the side-chains of Ser(S), is protected with tBu, and the side-chains of Lys(K) is protected with Boc.

The amino acid can be activated as follows. The Fmoc-protected amino acid (to 1.5-3 eq) and diisopropyl-ethylamine (DIEA) (to 1.5-3 eq) are dissolved in a polar, aprotic solvent such as dimethyl formamide (DMF) or N-methyl pyrrolidinone (NMP), or dimethyl acetamide (DMAC) (about 7.5 vol.) at room temperature. The solution is chilled to 0-10° C., and then 2-(1H-7-Azabenzotriazol-1-yl)-1,1,3,3-tetramethyl uronium hexafluorophosphate Methanaminium (HATU) or O-benzotriazol-1-yl-N,N,N',N'-tetramethyluronium hexafluorophosphate (HBTU) or 0-benzotriazol-1-yl-tetramethyltetrafluoroborate (TBTU) (to 1.5-3 eq) is added followed by stirring for 5-15 minutes to dissolve. It is important that activation is carried out at 1-10° C. to minimize racemization of the amino acid. The HATU is the last reagent added to the cold solution since activation and racemization cannot take place in its absence.

The solution of activated amino acid is charged to the drained resin, washing in with DCM (approximately 2.5 vol). Note that activation of the amino acid is carried out in DMF due to the insolubility of HATU in DCM. However, DCM is added to the reaction at this point to maintain adequate swelling of the resin beads. Coupling completion may be monitored with a qualitative ninhydrin test as described below.

To check for completion of the reaction using the qualitative ninhydrin test, a 2-20 mg sample of the resin can be withdrawn and washed clean with methanol. To the sample is added 3 drops of a 76% solution of phenol in ethanol, 4 or 5 drops of a 0.2 mM KCN solution in pyridine, and 3 drops of a 0.28 M solution of ninhydrin in ethanol. The sample is diluted with ethanol to a volume of about 0.5 mL and placed in a heat block at about 75° C. for 5-10 minutes. A blue or violet color is a positive indication for the presence of free amines, indicating that the reaction is not yet complete. The sample can be diluted further to a volume of about 3 mL to more easily gauge the degree of color change in the concentrated sample.

If a positive ninhydrin test is observed after one hour, the coupling reaction is continued for an additional hour. If the positive ninhydrin test persists after 3 hours, the resin is drained, washed one time in approximately 10 volumes of DMF, and the coupling reaction is repeated using 0.5-1 equivalent of activated amino acid.

If the resin is to be stored overnight between coupling cycles, the resin bed may be drained and covered with DMF under a nitrogen blanket. Alternatively, the bed may be drained, stored under a nitrogen blanket, and then conditioned with a DCM wash prior to proceeding with the next coupling cycle.

After the coupling is judged complete, the resin is drained and washed with 3 aliquots (approximately 10 vol.) of DMF. The cycle is repeated for subsequent mers (i.e., amino acids) of the peptide fragment. Following the final coupling reaction, the resin is washed with 4 aliquots (about 10 vol.) of DMF, then with 2 aliquots (approximately 10 vol.) of DCM. The resin-bound peptide may be dried with a nitrogen purge or in an oven.

Peptides synthesized via solid phase synthesis techniques can be cleaved and isolated according to, for example, the following non-limiting techniques: The peptide may be cleaved from the resin using techniques well known to those skilled in the art. For example, solutions of 1% or 2% trifluoroacetic acid (TFA) in DCM or a combination of a 1% and a 2% solution of TFA in DCM may be used to cleave the peptide. Acetic acid (HOAc), hydrochloric acid (HCl) or formic acid may also be used to cleave the peptide. The specific cleavage reagent, solvents and time required for cleavage will depend on the particular peptide being cleaved. After cleavage the cleavage fractions are subjected to standard work-up procedures to isolate the peptide.

Solution phase peptide synthesis techniques well known to those of skill in the art may be utilized for synthesis of the peptide intermediate fragments of the invention.

FIGURES

Figure 1B:
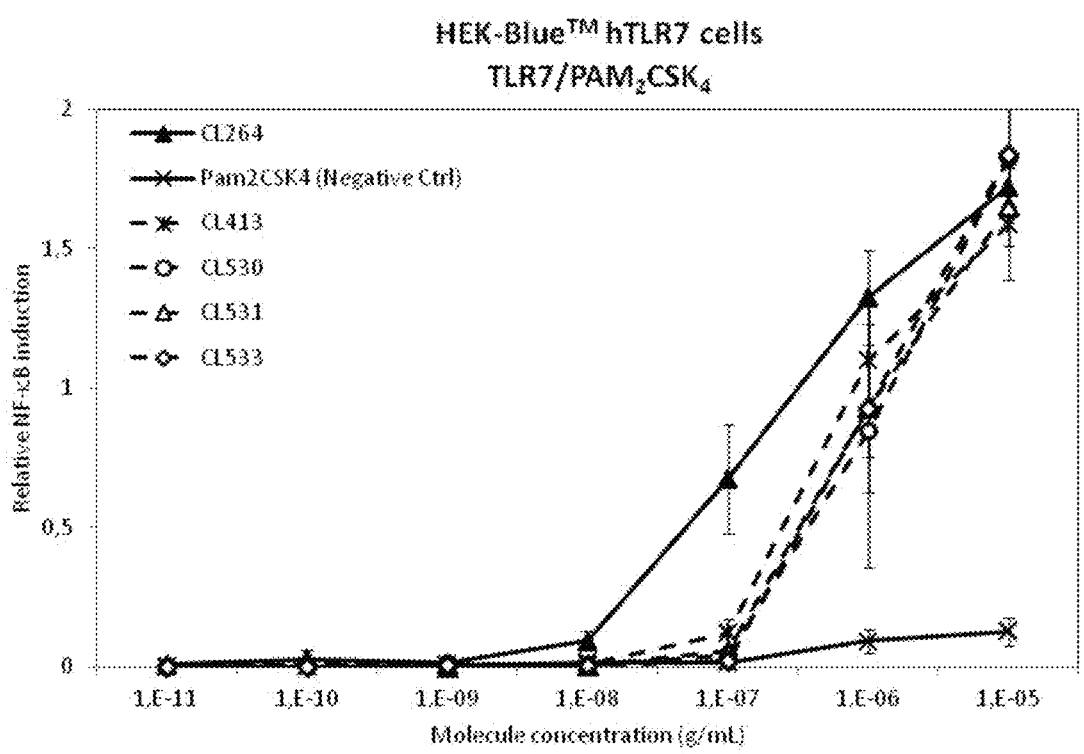
Figure 1C:
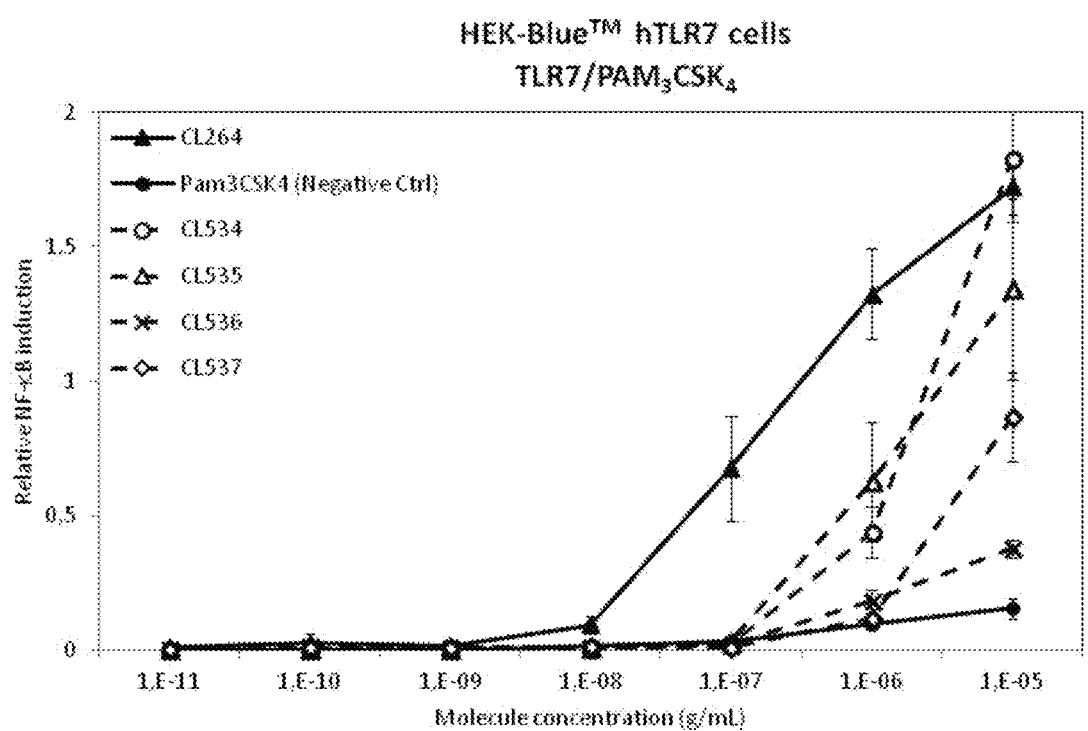

FIG. 1 demonstrates the ability of the molecules of the invention to activate hTLR7. The TLR7 ligand CL264 was employed as a positive control and $Pam_2CSK_4$ and $Pam_3CSK_4$ as negative controls. FIG. 1A illustrates activity induced by TLR7-TLR2 spermine molecules (CL475, CL486, CL487, CL514, CL527, CL553). FIG. 1B illustrates the activity induced by TLR7-TLR2 $Pam_2CSK_4$-based molecules (CL413, CL530, CL531, CL533). FIG. 1C illustrates the activity induced by TLR7-TLR2 $Pam_3CSK_4$-based molecules (CL534, CL535, CL536, CL537).

Figure 2A:
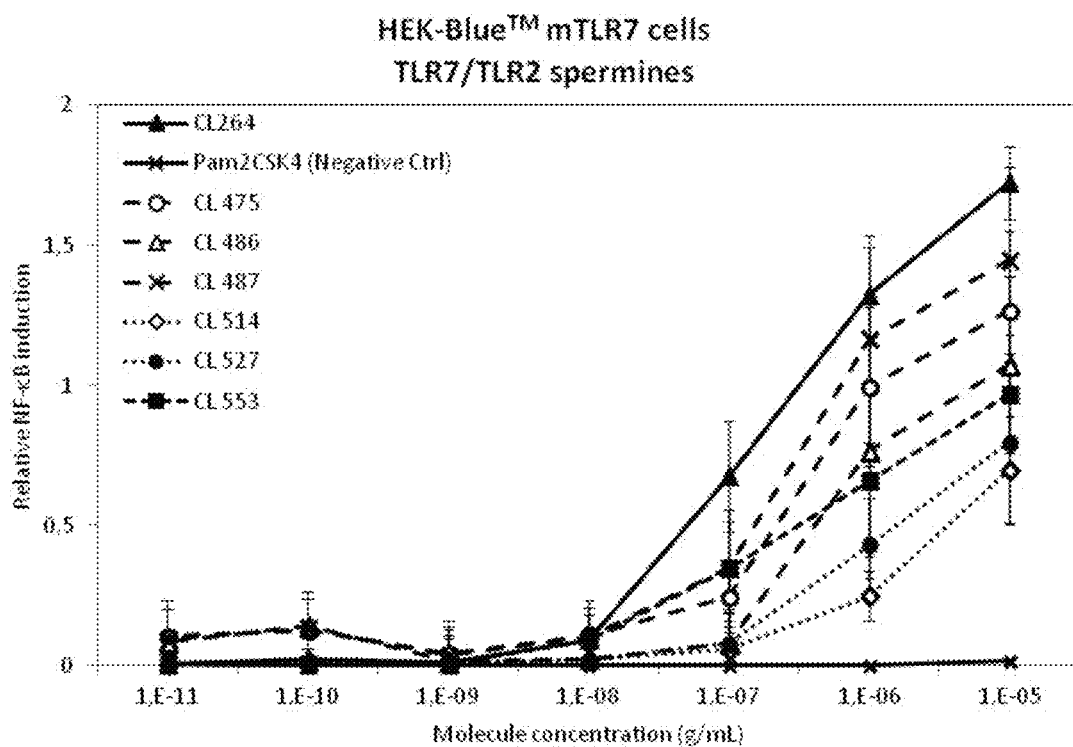
Figure 2B:
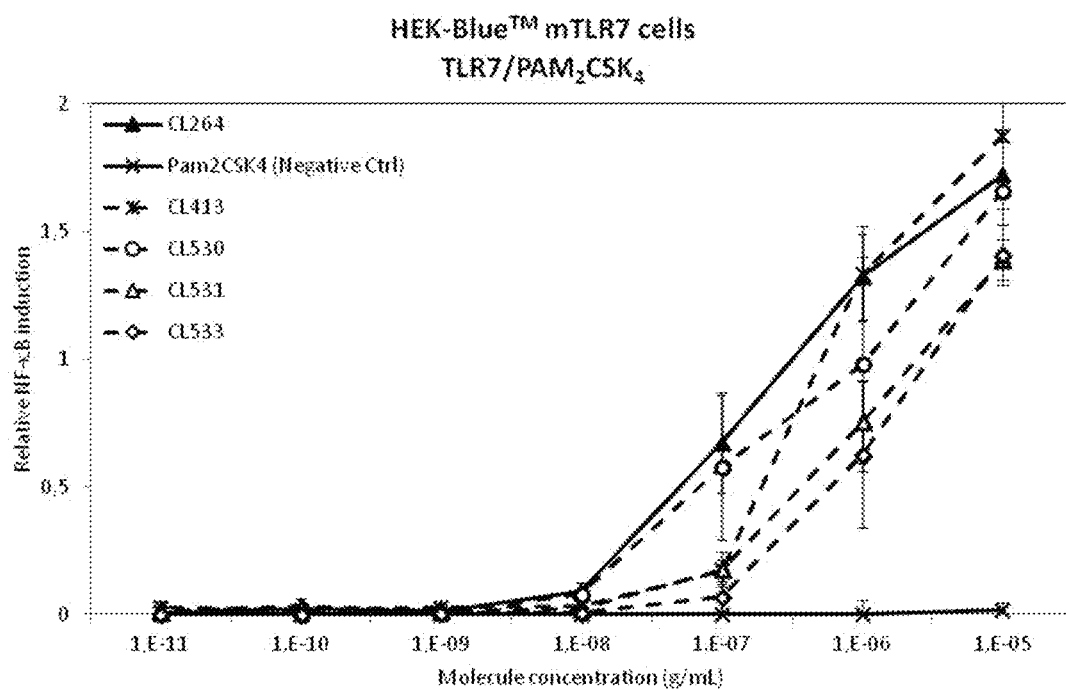
Figure 2C:
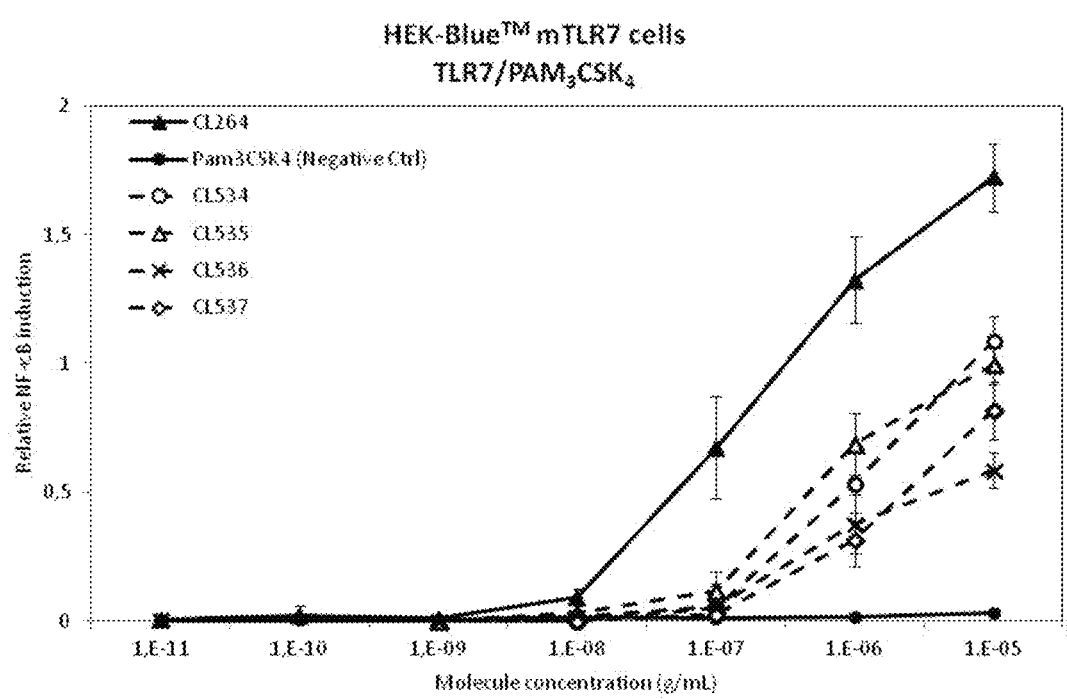

FIG. 2 demonstrates the ability of the molecules of the invention to activate mTLR7 (categorized; FIG. 2A, TLR7-TLR2 spermine molecules (CL475, CL486, CL487, CL514, CL527, CL553); FIG. 2B, TLR7-TLR2 $Pam_2CSK_4$-based molecules (CL413, CL530, CL531, CL533); FIG. 2C, TLR7-TLR2 Pam3CSK4-based molecules (CL534, CL535, CL536, CL537)). The TLR7 ligand CL264 was employed as a positive control and $Pam_2CSK_4$ and $Pam_3CSK_4$ as a negative controls.

Figure 3A:
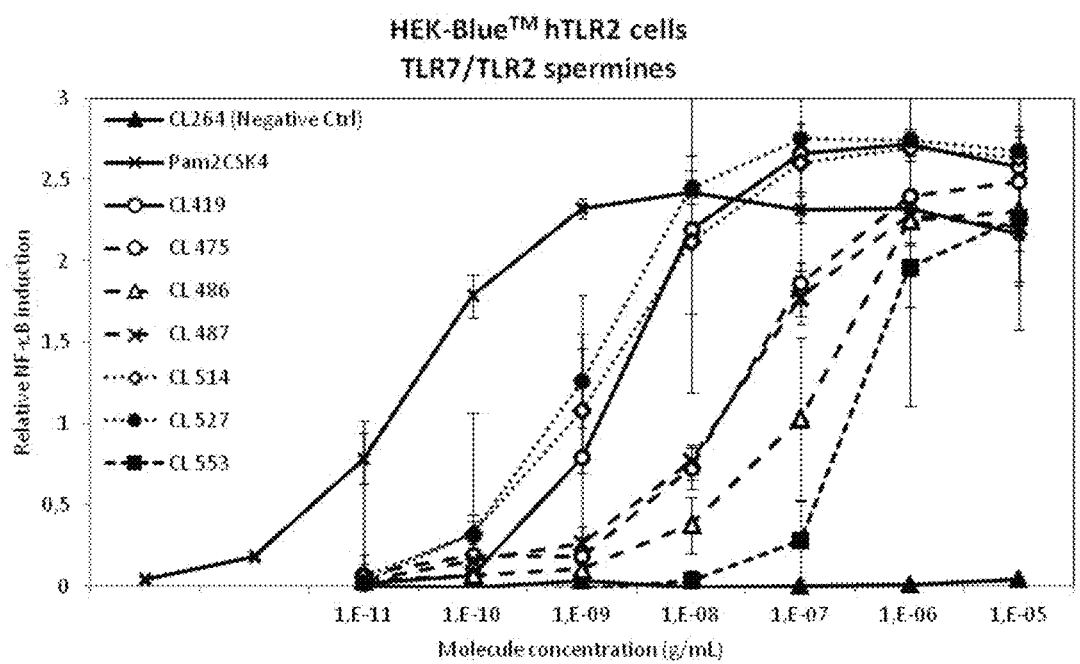
Figure 3B:
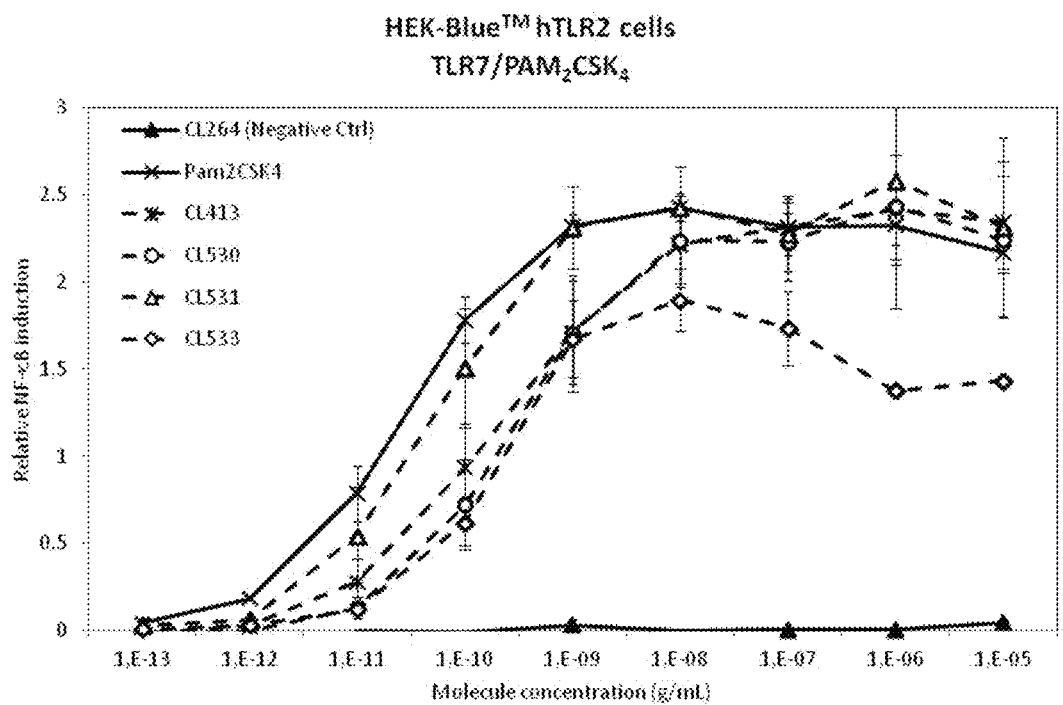
Figure 3C:
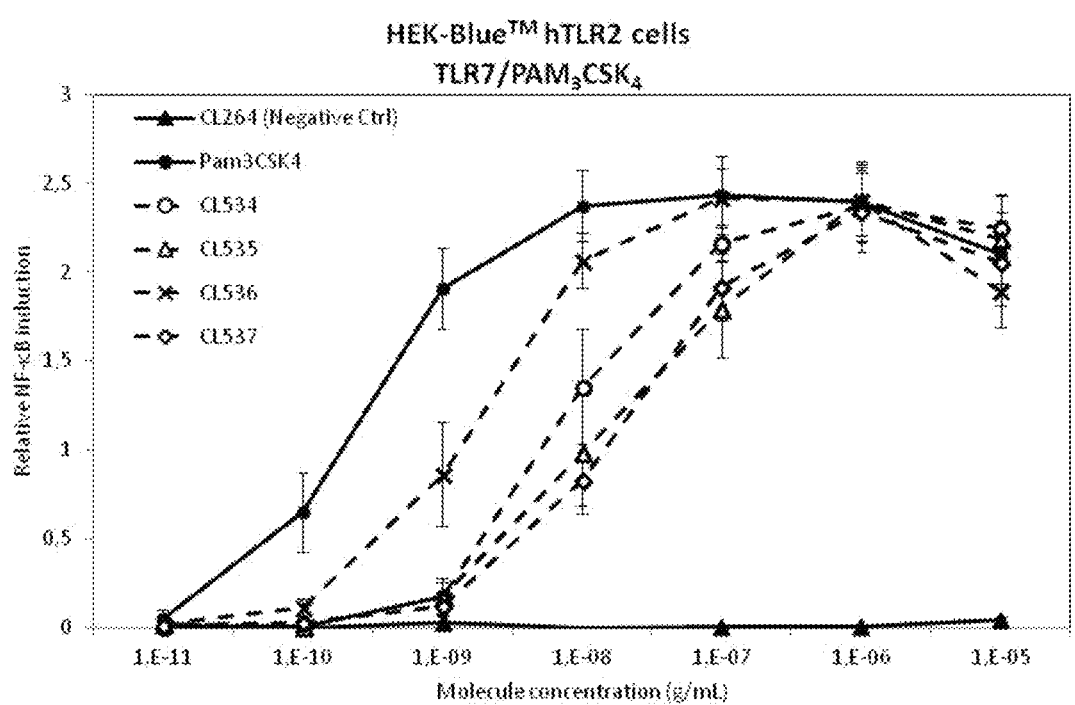

FIG. 3 demonstrates the ability of the molecules of the invention to activate hTLR2 (categorized; FIG. 3A, TLR7-TLR2 spermine molecules (CL475, CL486, CL487, CL514, CL527, CL553) along-side the intermediary compound CL419 employed as an additional positive control; FIG. 3B, TLR7-TLR2 $Pam_2CSK_4$-based molecules (CL413, CL530, CL531, CL533); FIG. 3C, TLR7-TLR2 $Pam_3CSK_4$-based molecules (CL534, CL535, CL536, CL537)). $Pam_2CSK_4$ and $Pam_3CSK_4$ were employed as positive controls and the TLR7 ligand CL264 as a negative control.

Figure 4A:
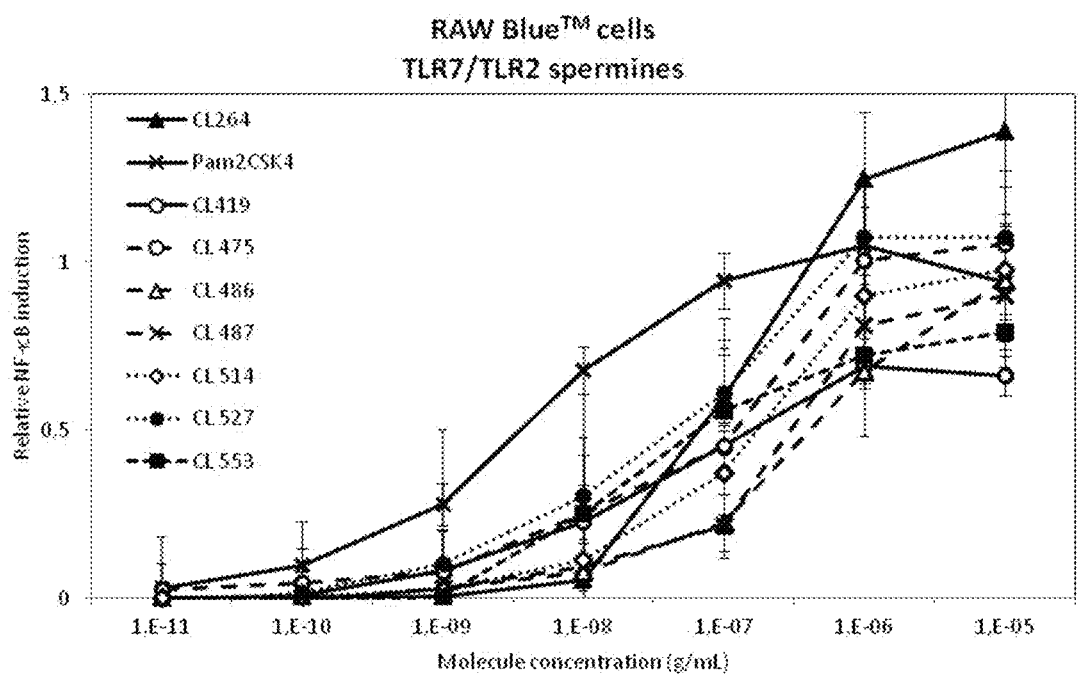
Figure 4B:
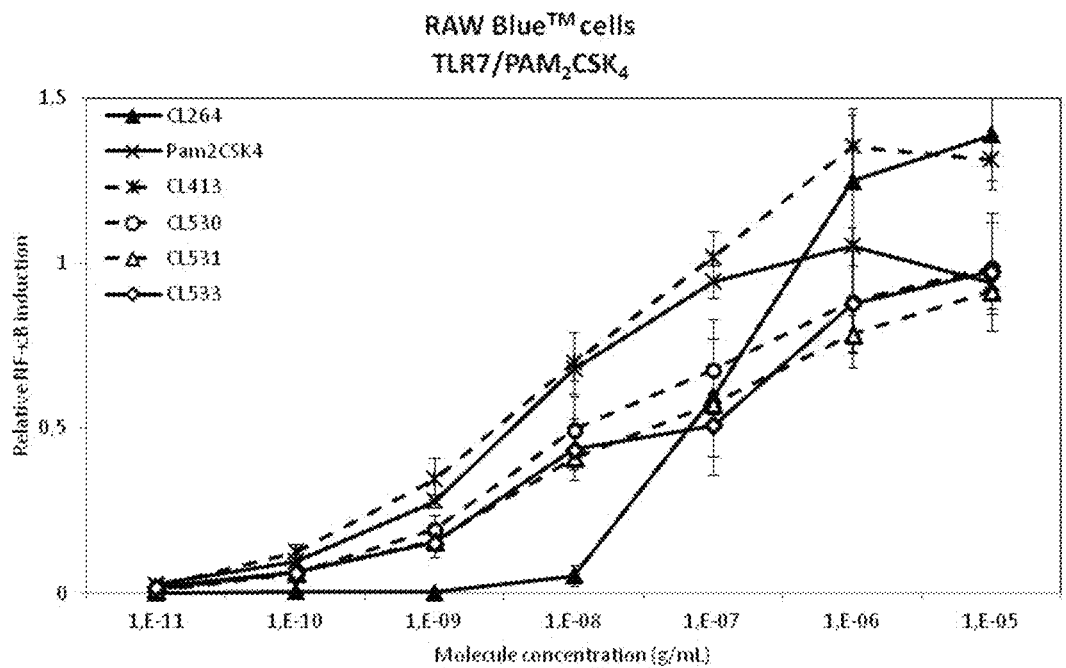
Figure 4C:
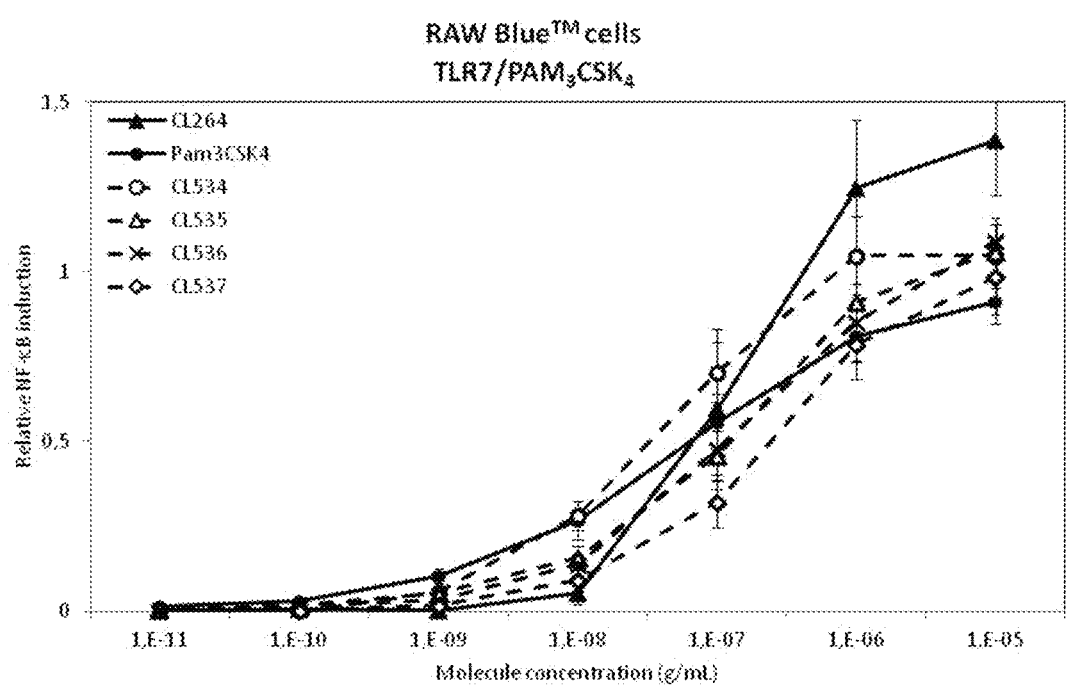

FIG. 4 demonstrates the ability of the molecules of the invention to activate endogenous TLR2 and TLR7 in RAW-Blue™ Cells (categorized; FIG. 4A, TLR7-TLR2 spermine molecules (CL475, CL486, CL487, CL514, CL527, CL553) along-side the intermediary compound CL419 employed as an additional positive control; FIG. 4B, TLR7-TLR2 $Pam_2CSK_4$-based molecules (CL413, CL530, CL531, CL533); FIG. 4C, TLR7-TLR2 $Pam_3CSK_4$-based molecules (CL534, CL535, CL536, CL537)). The TLR7 ligand CL264 and the TLR2 ligands $Pam_2CSK_4$ and $Pam_3CSK_4$ were employed as positive controls.

Figure 5A:
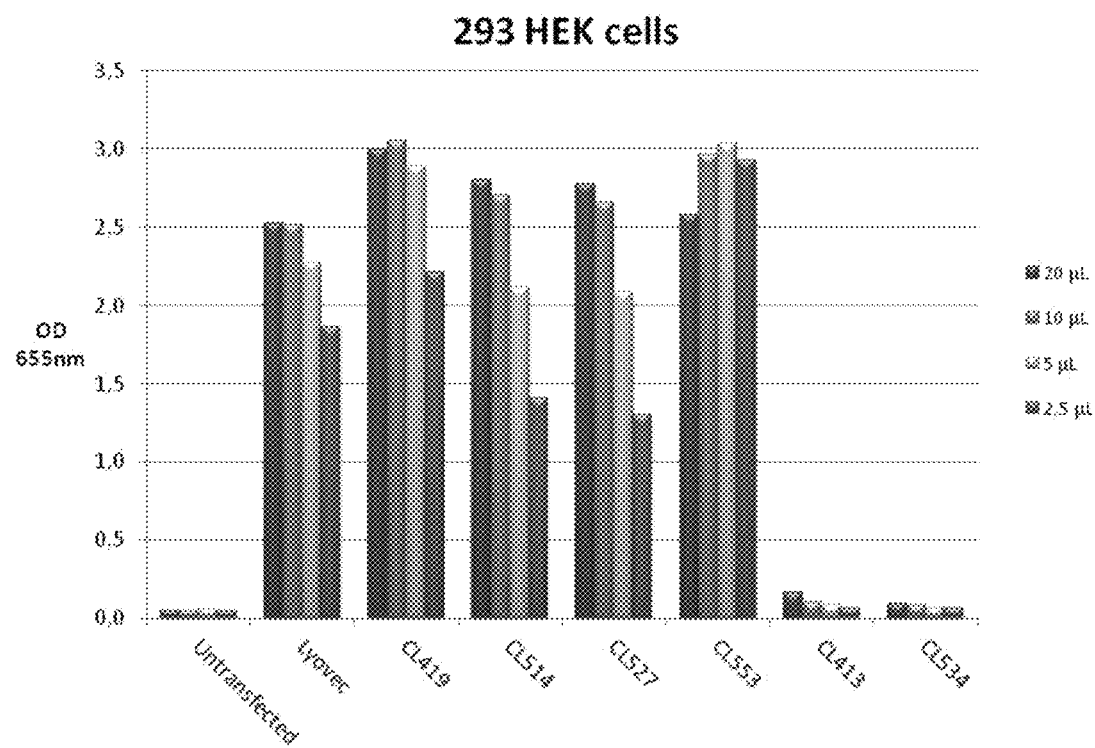
Figure 5B:
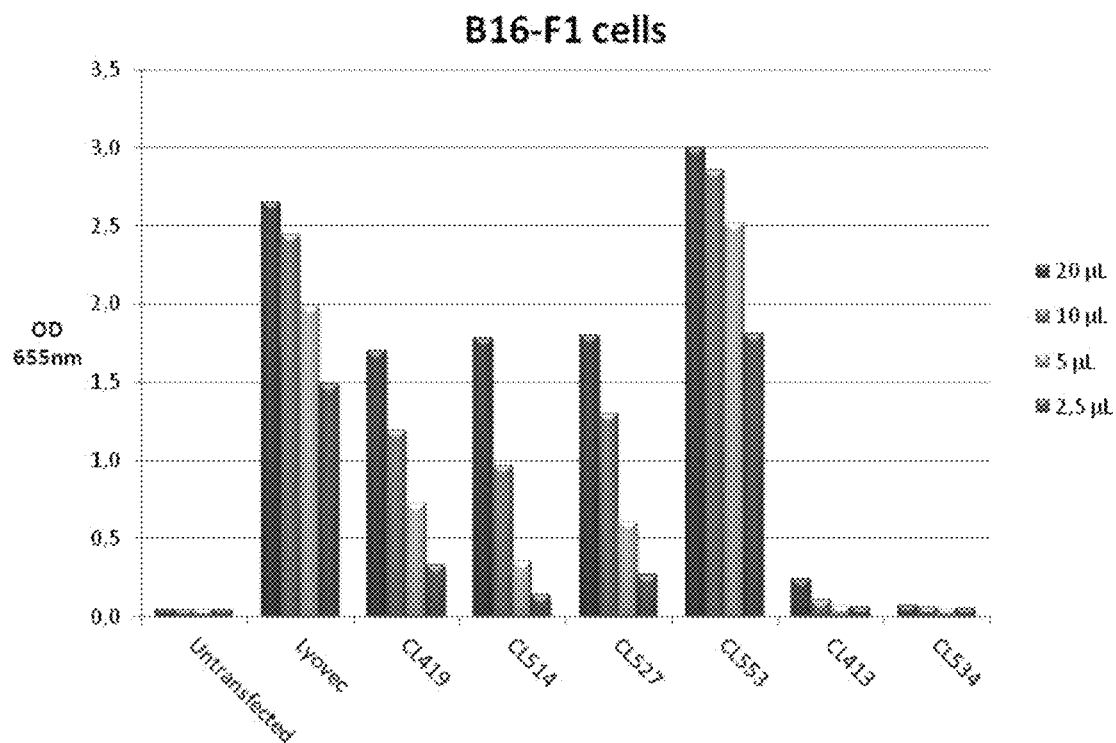

FIG. 5 shows the ability of TLR7-TLR2 polyamine molecules to transfect two different cell lines with pDNA. TLR7-TLR2 molecules that contain spermine and which form uniform nanoparticle complexes with pDNA (see tables above), had the ability to transfect the two cell lines comparable to the control LyoVec™ cationic lipid complex. The intermediary compound CL419 was also employed as an additional positive control. The negative controls used were CL413, a TLR7-TLR2 $Pam_2CSK_4$-based molecule and CL534, a TLR7-TLR2 $Pam_3CSK_4$-based molecule, in complex with pDNA. FIG. 5A demonstrates the ability of TLR7-TLR2 spermine molecules of the invention able to form nanoparticles with pDNA (CL514, CL527, and CL553) to transfect HEK293 cells. FIG. 5B shows the ability of the mentioned spermine molecules of the invention to transfect B16-F1 cells. TLR7-TLR2 poly-lysine molecules CL413 and CL534, although with the ability to form uniform nanoparticle complexes with pDNA, lack the ability to transfect cells due to the absence of the spermine moiety.

Figure 6A:
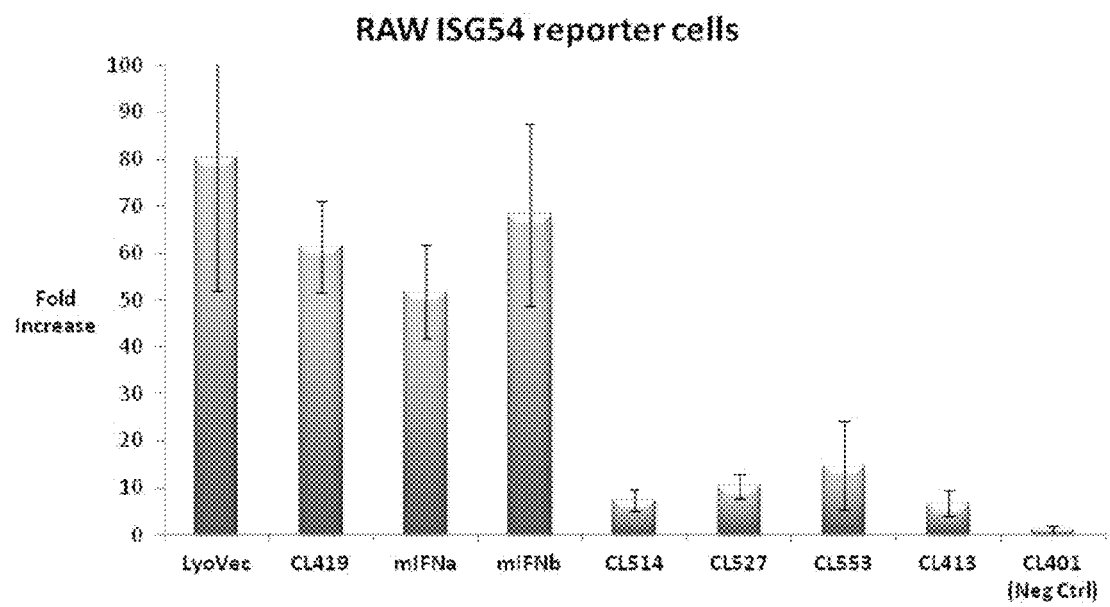
Figure 6B:
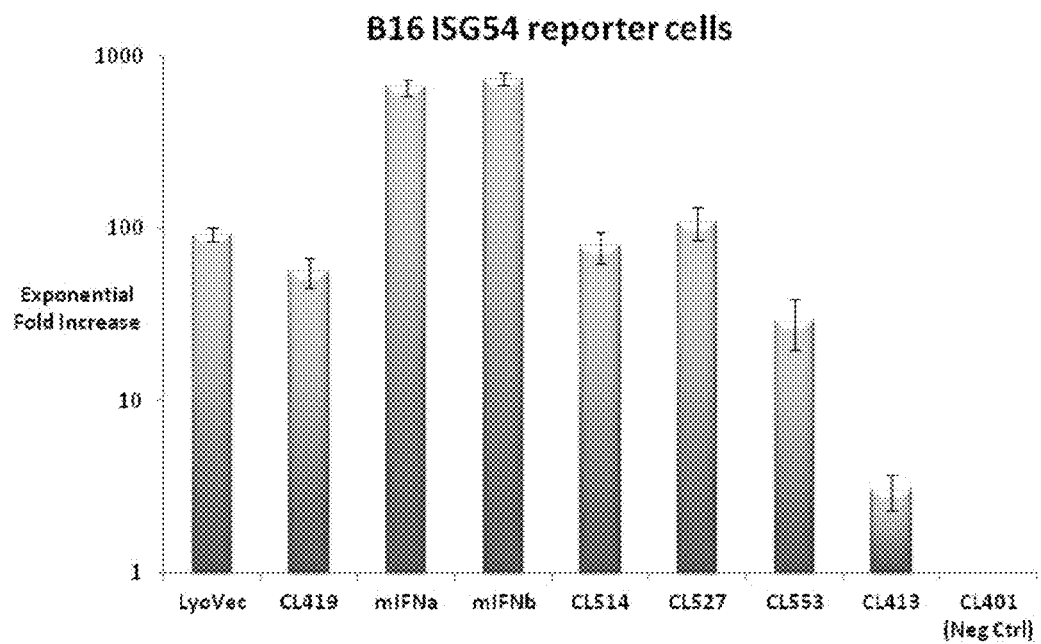

FIG. 6 exemplifies TLR7-TLR2 polyamine molecules with the ability to induce ISG54 promoter activity. FIG. 6A shows the ability of molecules (CL413, CL514, CL527, CL553) in complexes with pDNA to induce an IFN response in RAW-ISG54 reporter cells when contacted with cells. The positive controls included are LyoVec complexed with pDNA and mouse IFNα and mouse IFNβ. The intermediary compound CL419 was employed as an additional positive control. The negative control employed is CL401, a TLR7-TLR2 molecule which lacks the ability to complex pDNA. FIG. 6B shows the ability of molecules (CL413, CL514, CL527, and CL553) in complexes with pDNA to induce an IFN response in B16-ISG54 reporter cells. Differences in the extent of promoter activity induced by the pDNA complexed molecules were observed between the two reporter cell lines. In general, pDNA:TLR7-2 polyamine molecule complexes that conformed as nanoparticles and demonstrated ability to transfect cells, correlated with the induction of ISG54 promoter activity by the production of type 1 interferons, interferons α and β.

Figure 7A:
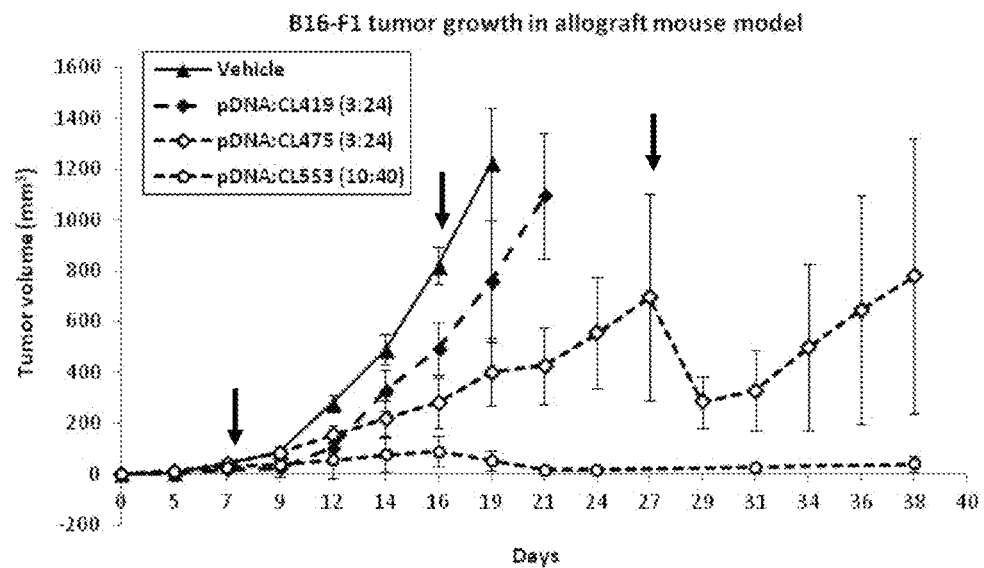
Figure 7B:
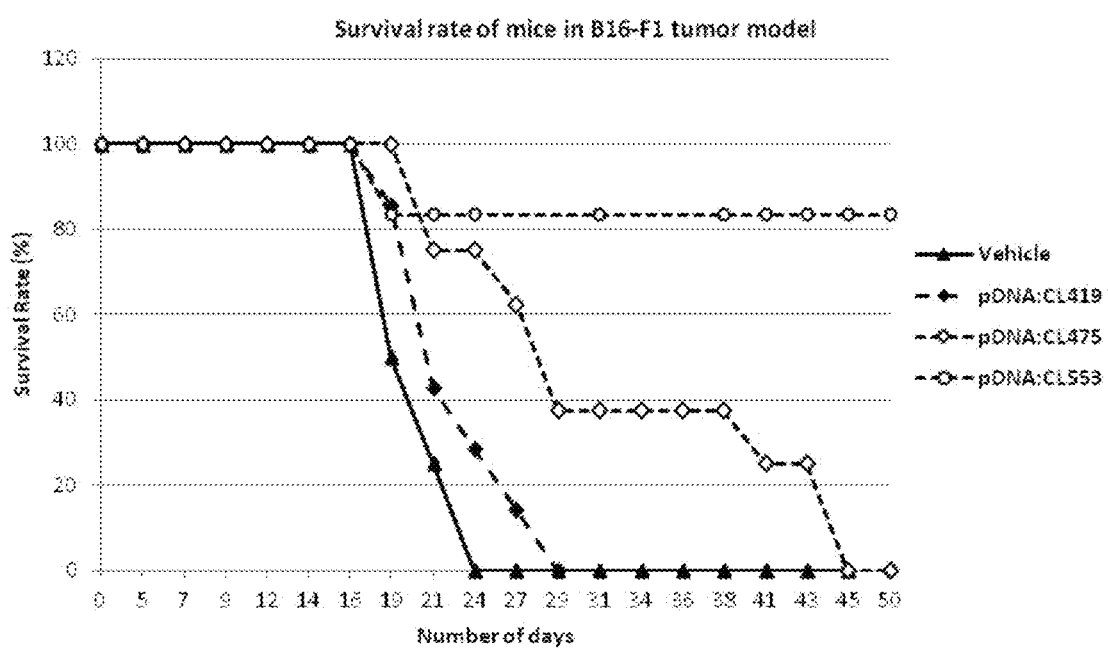

FIG. 7A shows B16-F1 tumor growth curves and FIG. 7B shows the survival rate of mice treated with pDNA:CL475 and pDNA:CL553 TLR7-TLR2 polyamine molecule complexes and pDNA:CL419 the intermediary compound TLR7-TLR2 complexes. Mice treated with pDNA:CL475 TLR7-TLR2 polyamine molecule complexes showed significant reduction in tumor growth compared to pDNA:CL419 complexes and vehicle control. Tumor growth was significantly reduced in pDNA:CL553-treated mice compared to other treated groups. By day 24 following tumor cell graft, over 70% and 80% of mice in the pDNA:CL475 and pDNA:CL553 TLR7-TLR2 polyamine complexes treated group respectively, were still alive. In contrast, by day 24, there was no survival of mice from the control groups of vehicle treated and only less than 30% of mice treated with pDNA:CL419.

Figure 8A:
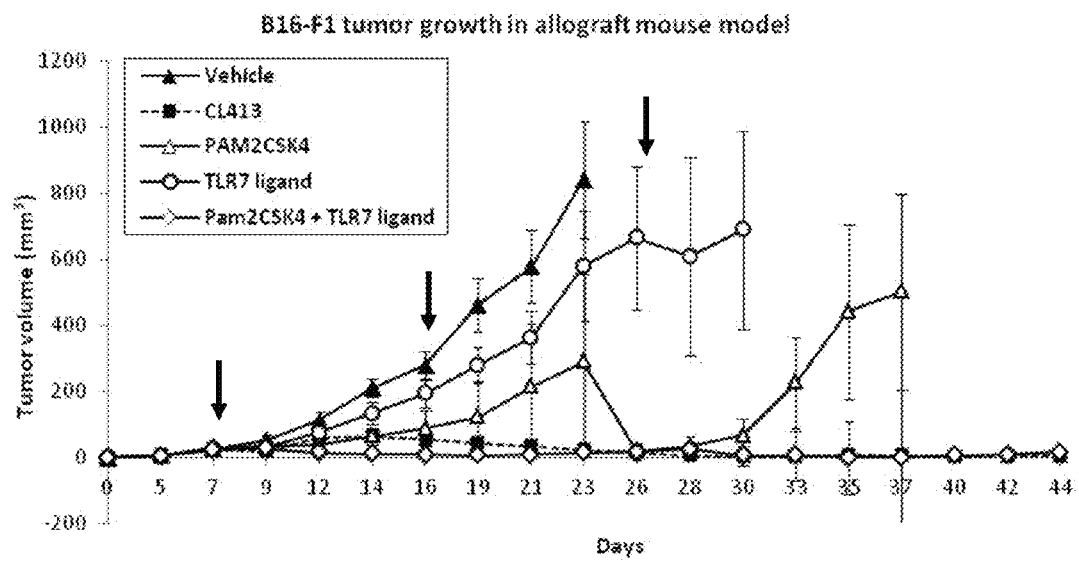
Figure 8B:
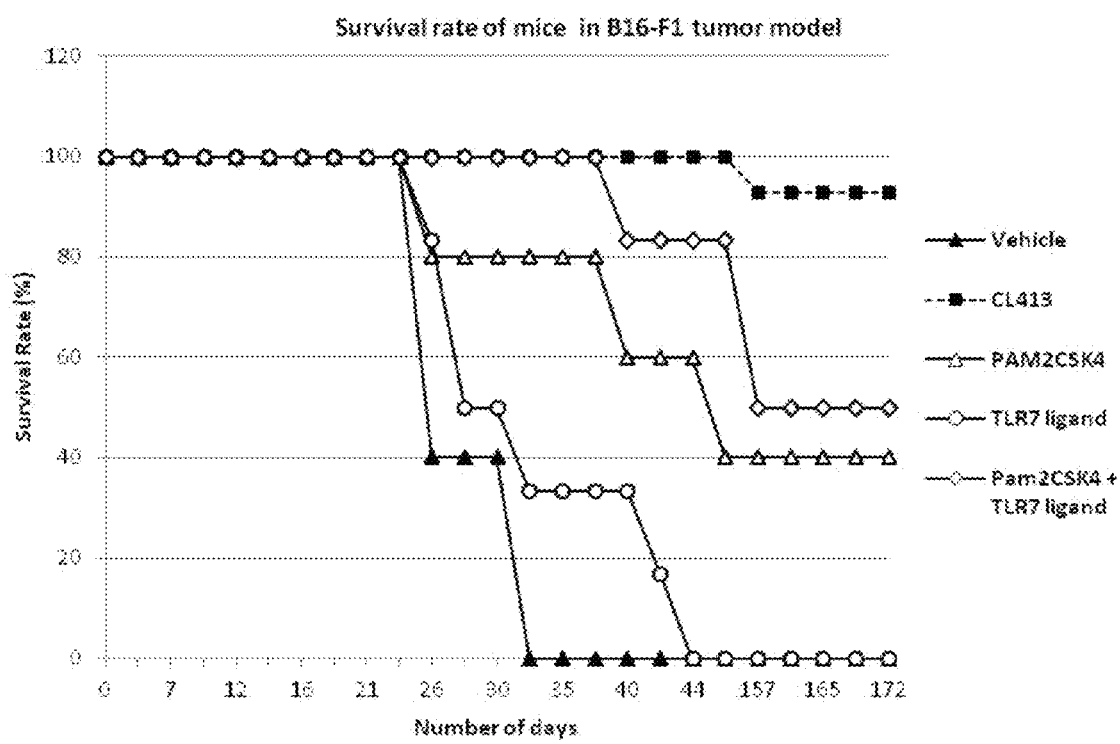

FIG. 8 demonstrates the in vivo data of mice treated with CL413 alone, compared to TLR2 ligand $Pam_2CSK_4$ alone, a TLR7 ligand alone, and the combined treatment of $Pam_2CSK_4$ and TLR7 ligand in the B16-F1 tumor model. FIG. 8A shows the effectiveness of CL413 and the combined treatment of $Pam_2CSK_4$ and TLR7 ligand on reducing tumor volume. By day 23 mice treated with these molecules showed no increase in tumor volume compared to $Pam_2CSK_4$ treatment alone, TLR7 ligand treatment alone and vehicle control. FIG. 8B demonstrates the superior effect of CL413, and therefore the covalent attachment of TLR7 and TLR2 $Pam_2CSK_4$-based agonists, on mice survival compared to the combined treatment of the two separate agonists. By day 42, 100% of mice treated with CL413 were still alive compared to less than 90% of the combined Pam$_2$CSK$_4$ and TLR7 ligand treated group, 60% of mice treated with Pam$_2$CSK$_4$, over 30% of mice treated with TLR7 ligand, and 0% of survival in the vehicle group.

EXAMPLES

Methods of Synthesis

The present invention is next described by means of the following examples. However, the use of these and other examples anywhere in the specification is illustrative only, and in no way limits the scope and meaning of the invention or of any exemplified form. Likewise, the invention is not limited to any particular preferred embodiments described herein. Indeed, many modifications and variations of the invention may be apparent to those skilled in the art upon reading this specification, and can be made without departing from its spirit and scope. The invention is therefore to be limited only by the terms of the appended claims, along with the full scope of equivalents to which the claims are entitled.

ABBREVIATIONS

As used herein, the symbols and conventions used in these processes, schemes and examples, regardless of whether a particular abbreviation is specifically defined, are consistent with those used in the contemporary scientific literature, for example, the Journal of the American Chemical Society or the Journal of Biological Chemistry. Specifically, but without limitation, the following abbreviations may be used in the examples and throughout the specification:

2-CTC for 2-Chlorotritylchloride polymer resin; AcOH for acetic acid; All for allyl; Boc for tert-butyloxy carbonyl; Boc$_2$O for di-tert-butyl dicarbonate; CDCl$_3$-d$_1$ for deuterated chloroform; Cs$_2$CO$_3$ for cesium carbonate; ° C. for degree Celsius; D$_2$O for deuterium oxide; DCM for dichloromethane; δ for Chemical shift; DIEA for N,N-Diisopropylethylamine; DMAP for N,N-dimethylamino pyridine; DMF for N,N-dimethyl formamide; DMSO-d$_6$ for deuterated dimethylsulfoxide; EDCl for 1-(3-diethylaminopropyl)-3-ethylcarbodiimide hydrochloride; EtOH for ethanol; Et$_2$O for diethyl ether; EtOAc for ethyl acetate; ES for electrospray ionization; eq. for equivalent; Fmoc for Fluorenylmethyloxy-carbonyl; Gly for glycine; Glu for glutamic acid; g grams; $^1$H for hydrogen-1; HATU for O-(7-Azabenzotriazol-1-yl)-N,N,N',N'-tetramethyluronium hexafluorophosphate; HCl for hydrochloric acid; HPLC for high performance liquid chromatography; h for hours; LiOH for lithium hydroxide; Lys for lysine; mg for milligrams; MgSO$_4$ for magnesium sulfate; MeOD for deuterated methanol; MeOH for methanol; mL for milliliters; mmol for millimoles; MHz for megahertz; min for minutes; MTBE for methyl-tert-butyl ether; m/z for mass-to-charge ratio; µL for microliters; MS for mass spectrometry; N for normality of a solution; NaOH for sodium hydroxide; Na$_2$S$_2$O$_3$ for sodium thiosulfate; NaHCO$_3$ for sodium hydrogenocarbonate; NH$_4$Cl for ammonium chloride; NMR for nuclear magnetic resonance; OMe for methoxy; OtBu for tert-butoxy; P$_2$O$_5$ for phosphorus pentoxide; Pd/C for Palladium on activated charcoal; ppm for parts per million; Py BOP for benzotriazol-1-yl-oxytripyrrolidinophosphonium hexafluorophosphate; rt for room temperature; Ser for serine; SPPS for Solid-phase peptide synthesis; TES for triethylsilane; TFA for trifluoroacetic acid; THF for tetrahydrofuran; TLC for thin layer chromatography; v/v for and Z for benzyloxy carbonyl.

General Information
Characterization:
1. Preparative HPLC Method: Unless otherwise indicated, the compounds described herein were purified by RP-MPLC ARMEN® Spot Flash Liquid Chromatography (ARMEN Instrument, Saint Ave, France) on a preparative column (SVF D26) packed with 25-40 µm C18 resin (Merck chimie SAS), by applying a linear gradient of 0-10% MeCN in NH$_4$OAc (10 mM) solution (pH=9) over 60 min at a 15 mL/min flow rate. The purification was monitored at 254 nm. Suitable fractions were pooled and lyophilised.
2. Proton NMR Spectra: Unless otherwise indicated, all $^1$H NMR spectra were run on a Bruker series 300 MHz instrument. Where so characterized, all observed protons are reported as parts-per-million (ppm) downfield from tetramethylsilane (TMS) or other internal reference in the appropriate solvent indicated. NMR spectra were recorded on a Brucker 300 spectrometer. For $^1$H (300 MHz) spectra δ values were referenced to CDCl3-d$_1$ (7.26 ppm), DMSO-d$_6$ (2.50 ppm), D$_2$O-d$_2$ (4.79 ppm) or MeOD-d$_4$ (3.31 ppm). The peak patterns are indicated as follows: s: singlet, sl: large singlet, d: doublet, t: triplet, q: quartet, m: multiplet.
3. Mass Spectra (MS): Analyses were run on an Agilent Model 6130 quadrupole MS. Unless otherwise indicated, all mass spectral data for starting materials, intermediates and/or exemplary compounds are reported as mass/charge (m/z), having an (M+H)$^+$ molecular ion. The molecular ion reported was obtained by electrospray detection method (commonly referred to as an ESI MS). Compounds having an isotopic atom, such as bromine and the like, are generally reported according to the detected isotopic pattern, as appreciated by those skilled in the art.
4. Particle size: Particle size was determined using a Malvern Nanosizer (Malvern, Worcestershire, UK) and Malvern ZETASIZER® (Malvern, Worcestershire, UK).
5. Naming Convention The compounds disclosed and described herein have been named using the naming convention provided with Chem-Draw Ultra 11.0 software, available in Chem. Office. In some instances, compounds were named with the term "spermine" inserted where appropriate. For example, where the spermine is substituted with Boc, "N$_1$,N$_5$,N$_{10}$-TriBoc-spermine" is added to the Chem-Draw nomenclature in the appropriate place. Chem-Draw utilizes the ISIS Draw software compound naming convention, as appreciated by those skilled in the art.

Reagents and Solvents:
All commercially available reagents and protected amino acids were purchased and used without further purification. All the solvents used for reactions were distilled over appropriate drying reagents prior to use. Commercially available ACS grade solvents (>99.0% purity) were used for column chromatography without any further purification.

Reactions and Purifications:
For all of the following examples, standard work-up and purification methods known to those skilled in the art can be utilized. Unless otherwise indicated, all temperatures are expressed in ° C. (degrees Centigrade). All reactions conducted at room temperature unless otherwise noted. All reactions and fractions from column chromatography were monitored by thin layer chromatography (TLC) using glass plates with a UV fluorescent indicator (normal SiO$_2$, Merck 60 F254). One or more of the following methods were used for visualization: UV absorption by fluorescence quenching; (Ninhydrin/Ethanol or H₂SO₄/Ethanol) solution. Flash chromatography was performed using Merck type 60, 230-400 mesh silica gel.

Example 1

Molecule CL553

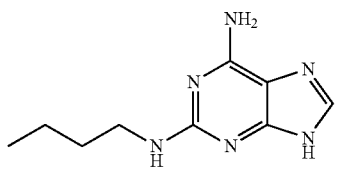

Intermediate 1

6-amino-2-butylamino-9H-purine

2-Chloroadenine (10.0 g, 59 mmol), butylamine (43 mL, 589 mmol) and water (40 mL) were placed in an autoclave (250 mL), and the content of the autoclave was allowed to react at 180° C. for 18 h. The reaction solution was concentrated under reduced pressure, and water was poured into the residue to precipitate a solid. The precipitated solid was sequentially washed with water, EtOH and acetone. Thus, 10.39 g of the title compound was obtained as a yellowish orange powdery solid (yield: 86%). Intermediate 1 was characterized by the following spectroscopic data: $^1$H NMR (DMSO-$d_6$, 300 MHz): 11.92 (br. S, 1H), 7.63 (s, 1H), 6.51 (br. s, 2H), 6.04 (s, 1H), 3.19 (q, 2H), 1.51 (m, 2H), 1.33 (m, 2H), 0.92 (t, 3H).

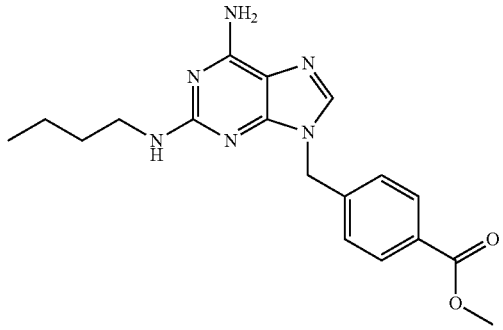

Intermediate 2

Methyl 4-((6-amino-2-(butylamino)-9H-purin-9-yl)methyl)benzoate

The intermediate 1 (10.39 g, 50.4 mmol) and Cs₂CO₃ (16.42 g, 50.4 mmol) were suspended in DMF (200 mL). 4-bromomethyl benzoate (13.85 mg, 60.4 mmol) was added thereto and the mixture was stirred at rt for 18 h. After condensing the suspension in vacuo, to the residue was added brine and the mixture was extracted with EtOAc. The organic layer was washed the mixture was with brine, dried on MgSO₄, filtered and the solvent was evaporated in vacuo. The residue was purified on column of silica gel (5% MeOH/DCM) to give the subject compound (14.67 g, yield 82%).

Intermediate 2 was characterized by the following spectroscopic data: $^1$H NMR (DMSO-$d_6$, 300 MHz) δ (ppm) 7.91 (d, 2H), 7.81 (s, 1H), 7.40 (d, 2H), 6.66 (br. s, 2H), 6.22 (t, 1H), 5.27 (s, 2H), 3.83 (s, 1H), 3.19 (q, 2H), 1.44 (m, 2H), 1.26 (m, 2H), 0.85 (t, 3H).

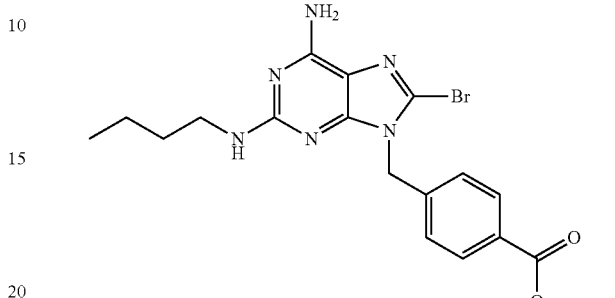

Intermediate 3

Methyl 4-((6-amino-8-bromo-2-(butylamino)-9H-purin-9-yl)methyl)benzoate

The intermediate 2 (14.67 g, 41.9 mmol) and bromine (7.94 mL, 49.7 mmol) were dissolved in 300 mL of CHCl₃ and the solution was stirred at rt for 18 h. Aqueous Na₂S₂O₃ was added to the reaction mixture. The precipitate obtained was filtered off and washed with water and DCM. The solid was purified on column of silica gel (3% MeOH/DCM) to give the subject compound (15.41 g, yield 86%). Intermediate 3 was characterized by the following spectroscopic data: $^1$H NMR (DMSO-$d_6$, 300 MHz) δ (ppm) 7.95 (d, 2H), 7.38 (d, 2H), 6.67 (br. s, 2H), 6.24 (t, 1H), 5.30 (s, 2H), 3.84 (s, 1H), 3.28 (q, 2H), 1.45 (m, 2H), 1.25 (m, 2H), 0.85 (t, 3H).

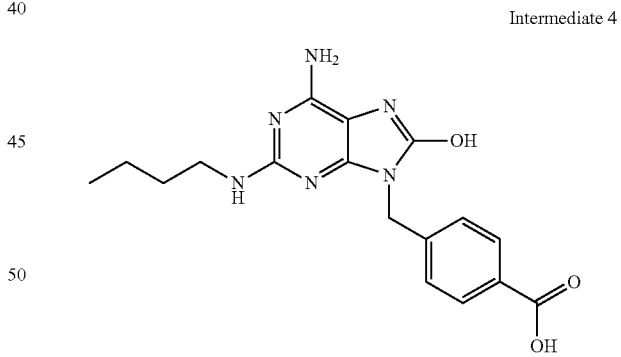

Intermediate 4

4-((6-amino-2-(butylamino)-8-hydroxy-9H-purin-9-yl)methyl)benzoic acid

To the intermediate 3 (15.41 g, 35.6 mmol) in 150 mL of MeOH was added 6 N aqueous NaOH (150 mL). The mixture was refluxed on heating under stirring for 18 h. The residue was dissolved in 12 N HCl solution and stirred at room temperature for 18 h. The mixture was concentrated in vacuo and the pH was adjusted to 5 with 2 N aqueous NaOH to precipitate a solid. The solid was filtered, washed with water and dried in vacuo in presence of P₂O₅ to give the subject compound (12.2 g, yield 97%). Intermediate 4 was characterized by the following spectroscopic data: ¹H NMR (DMSO-d₆, 300 MHz) δ (ppm) 11.10 (s, 1H), 8.18 (br. s, 2H), 7.97 (t, 1H), 7.89 (d, 2H), 7.40 (d, 2H), 4.93 (s, 2H), 3.27 (q, 2H), 1.47 (m, 2H), 1.27 (m, 2H), 0.85 (t, 3H).

Intermediate 5

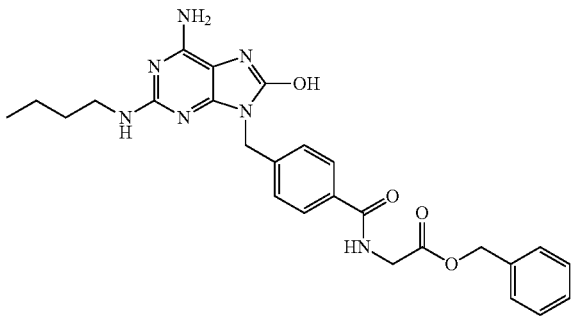

Benzyl 2-(4-((6-amino-2-(butylamino)-8-hydroxy-9H-purin-9-yl)methyl)benzamido)acetate To a suspension of intermediate 4 (4 g, 11 mmol) in dry DMF (20 mL) was added Glycine benzyl ester hydrochloride (2.7 g, 13 mmol), followed by PyBOP (6.4 g, 12 mmol) and N-methylmorpholine (5.68 g, 56.1 mmol). The mixture was stirred at rt for 18 h. The solvent was then removed in vacuo and the residue was dissolved in EtOAc (50 mL) and was washed with water, saturated solution of NH₄Cl and brine. The organic layer was dried over MgSO₄, filtered and concentrated in vacuo. The crude material was purified on column of silica gel (5% MeOH/DCM) to give the subject compound (5.65 g, yield 100%). Intermediate 5 was characterized by the following spectroscopic data: ¹H NMR (DMSO-d₆, 300 MHz) δ (ppm) 9.68 (sl, 1H), 8.89 (m, 1H), 7.81 (d, 2H), 7.37 (m, 7H), 6.25 (t, 1H), 6.04 (sl, 2H), 5.15 (s, 2H), 4.86 (s, 2H), 4.06 (d, 2H), 3.15 (m, 2H), 1.49 (m, 2H), 1.33 (m, 2H), 0.86 (t, 3H).

Intermediate 6

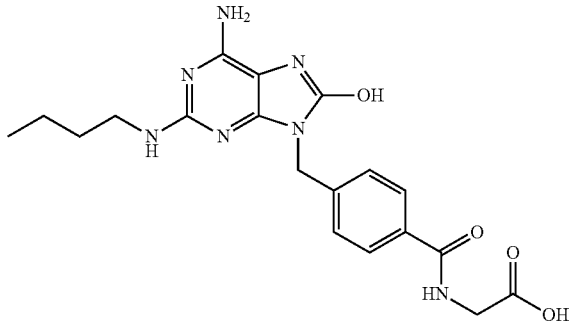

2-(4-((6-amino-2-(butylamino)-8-hydroxy-9H-purin-9-yl)methyl)benzamido)acetic acid To a solution of intermediate 5 (5.65 g, 11 mmol) in a mixture of THF/MeOH (1/1) (20 mL) was added palladium on activated carbon 10% (0.05 eq). The reaction mixture was stirred under hydrogen (1 atm) overnight. The palladium was filtered off the filtrate was concentrated in vacuo. The crude mixture was purified on column of silica gel (12% MeOH/DCM) to give the subject compound (3.58 g, yield 77%). Intermediate 6 was characterized by the following spectroscopic data: ¹H NMR (DMSO-d₆, 300 MHz) δ (ppm) 12.3 (sl, 1H), 10.60 (sl, 1H), 8.83 (m, 1H), 7.82 (d, 2H), 7.38 (m, 2H), 4.89 (s, 2H), 3.91 (d, 2H), 3.24 (m, 2H), 1.46 (m, 2H), 1.31 (m, 2H), 0.85 (t, 3H).

Intermediate 7

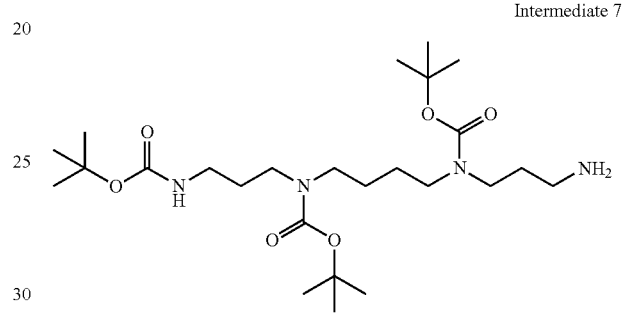

N1,N5,N10-triBoc-spermine

N1,N5,N10-triBoc-spermine was prepared according to the process described in the literature [Blagbrough, I. S.; Geall, A. J. Practical synthesis of unsymmetrical polyamine amides. Tetrahedron Lett. 1998, 39, 439-442. Wellendorph P, Jaroszewski J W, Hansen S H, Franzyk H. A sequential high-yielding large-scale solution-method for synthesis of philanthotoxin analogues. European Journal of Medicinal chemistry 2003, 38, 117-122.]. Intermediate 7 was characterized by the following spectroscopic data: ¹H NMR (CDCl₃-d₁, 300 MHz) δ (ppm) 8.49 (sl, 2H), 3.45 (m, 2H), 3.16 (m, 4H), 3.05 (m, 2H), 2.46 (m, 2H), 1.95 (m, 2H), 1.72 (m, 2H), 1.45 (s, 27H).

Intermediate 8

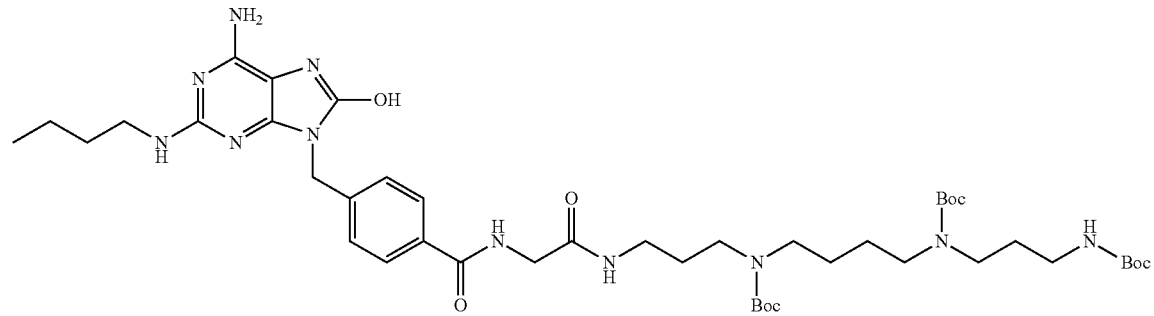

N1-N5-N10-triBoc-N14-[4-((6-amino-2-(butylamino)-8-hydroxy-9H-purin-9-yl)methyl)-N-(2-amino-2-oxoethyl)benzamido]spermine To a solution of intermediate 7 (500 mg, 1.0 mmol) in dry DMF (10 mL) were added intermediate 6 (411 mg, 1.0 mmol), HATU (416 mg, 1.1 mmol), and DIEA (866 μL, 5.0 mmol). The mixture was stirred at rt overnight. The solvent was then removed in vacuo and the residue was dissolved in DCM (50 mL) and washed with saturated NH$_4$Cl solution, water and brine. The organic layer was dried over MgSO$_4$, filtered and concentrated in vacuo. The crude compound was purified on column of silica gel (3% MeOH/DCM) to give the subject compound (777 mg, yield 87%). Intermediate 8 was characterized by the following spectroscopic data: $^1$H NMR (d$_6$-DMSO, 300 MHz) δ (ppm) 9.65 (s, 1H), 8.67 (m, 1H), 7.82 (d, 2H), 7.35 (d, 2H), 6.73 (m, 1H), 6.19 (m, 1H), 6.01 (sl, 2H), 4.85 (s, 2H), 3.80 (d, 2H), 3.15-2.89 (m, 15H), 1.65 (m, 4H), 1.36 (m, 35H), 0.85 (t, 3H).

Intermediate 9

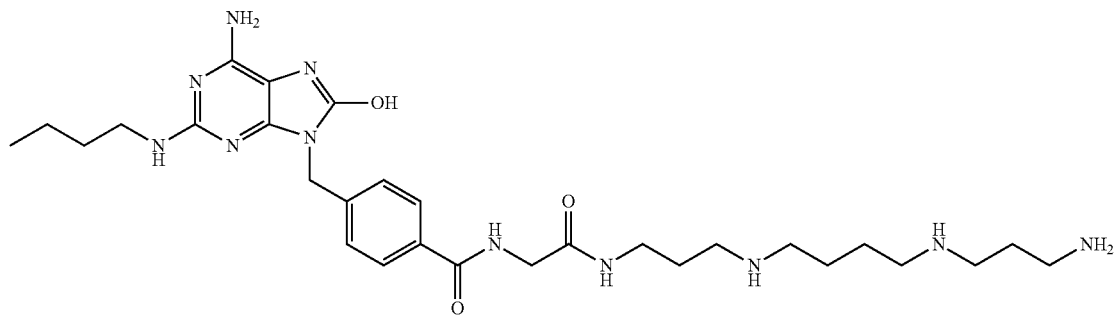

4-((6-amino-2-(butylamino)-8-hydroxy-9H-purin-9-yl)methyl)-N-(2-(3-(4-(3-amino propyl amino)butylamino)propylamino)-2-oxoethyl)benzamide To a solution of intermediate 8 (777 mg, 0.8 mmol) in dioxane (10 mL) was added 4 N HCl solution in dioxane (20 mL). The mixture was stirred at rt overnight. Then the solvent were removed in vacuo, the residue was triturated with Et$_2$O, filtrated, and dried. The crude compound was purified on column of silica gel (6% MeOH/DCM) to give the subject compound (559 mg, yield 99%). Compound 9 was characterized by the following spectroscopic data: $^1$H NMR (DMSO-d$_6$, 300 MHz) δ (ppm) 11.05 (s, 1H), 9.91 (m, 2H), 8.92-8.83 (m, 3H), 8.13 (m, 2H), 7.86 (d, 2H), 7.40 (d, 2H), 4.92 (s, 2H), 3.83 (d, 2H), 3.27 (m, 2H), 3.15 (m, 2H), 2.90 (m, 10H), 1.99 (m, 2H), 1.69 (m, 6H), 1.47 (m, 2H), 1.31 (m, 2H), 0.86 (t, 3H).

N1-benzylcarbamate-N5,N10-diBoc-N14-[4-((6-amino-2-(butylamino)-8-hydroxy-9H-purin-9-yl)methyl)-N-(2-amino-2-oxoethyl)benzamido]spermine To a solution of intermediate 9 (175 mg, 0.3 mmol) in dry DMF (10 mL) were added sodium acetate (240 mg, 0.3 mmol) and benzyl chloroformate (41 μL, 0.3 mmol) at 0° C. The mixture was stirred at this temperature for 2 h. Then Boc$_2$O (192 mg, 0.9 mmol) and Et$_3$N (206 μL, 1.5 mmol) were added to the solution.

The mixture was stirred at rt overnight. The solvent was then removed in vacuo and the residue was dissolved in EtOAc (50 mL) and washed with 0.1 N HCl solution, saturated NaHCO$_3$ solution, water and brine. The organic layer was dried over MgSO$_4$, filtered and concentrated in vacuo. The crude compound was purified on column of silica gel (2%

Intermediate 10

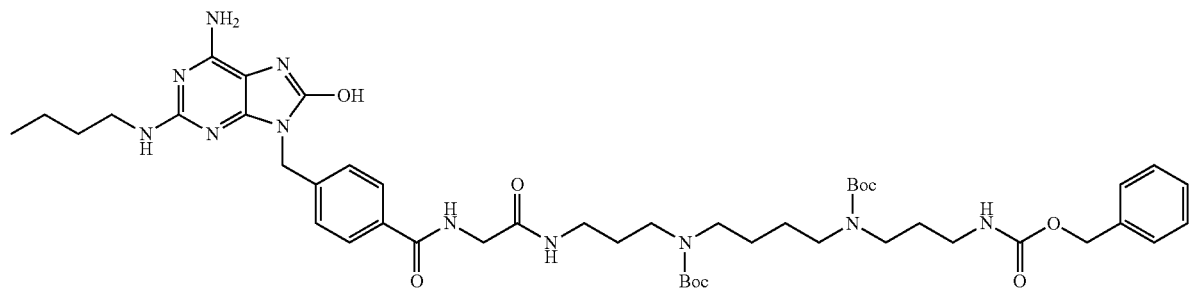

MeOH/DCM) to give the subject compound (108 mg, yield 40%). Intermediate 10 was characterized by the following spectroscopic data: $^1$H NMR (DMSO-$d_6$, 300 MHz) δ (ppm) 9.66 (s, 1H), 8.67 (m, 1H), 7.82 (m, 3H), 7.37-7.33 (m, 7H), 6.76 (m, 1H) 6.21 (m, 1H), 6.03 (sl, 2H), 5.02 (s, 2H), 4.85 (s, 2H), 3.80 (d, 2H), 3.19-3.08 (m, 14H), 1.57 (m, 4H), 1.36 (m, 26H), 0.86 (t, 3H).

organic layer was dried over MgSO$_4$, filtered and concentrated in vacuo. The crude compound was purified on column of silica gel (DCM) to give the subject compound (15.79 g, yield 86%). Intermediate 12 was characterized by the following spectroscopic data: $^1$H NMR (CDCl$_3$-$d_1$, 300 MHz) δ (ppm) 4.33 (m, 1H), 4.19 (m, 1H), 3.82 (m, 1H), 3.32 (m, 1H), 3.27 (m, 1H), 1.49 (s, 3H), 1.38 (s, 3H).

Intermediate 11

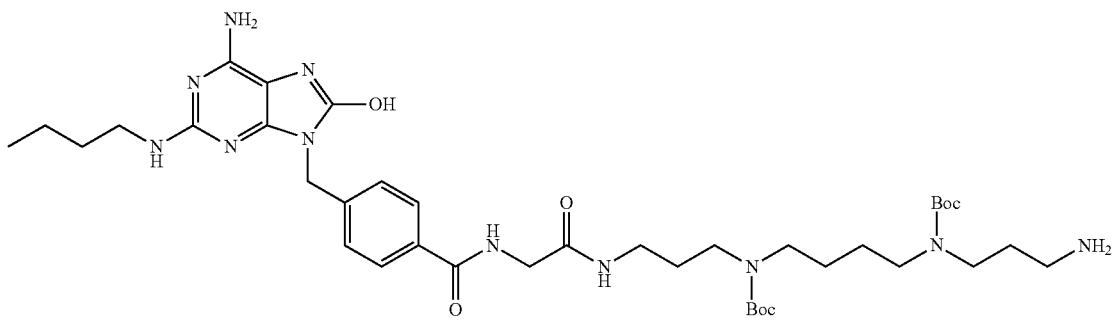

N5,N10-diBoc-N14-[4-((6-amino-2-(butylamino)-8-hydroxy-9H-purin-9-yl)methyl)-N-(2-amino-2-oxo-ethyl)benzamido]spermine To a solution of intermediate 10 (108 mg, 0.11 mmol) in a mixture of THF/MeOH (1/1) (10 mL) was added palladium on activated carbon 10% (0.05 eq). hydrogen gas was introduced via a balloon; the reaction mixture was stirred overnight at RT. The mixture was filtered through Celite and was washed with MeOH, the filtrate was concentrated in vacuo. The resulting solid was used for the next step without any further purification.

Intermediate 12

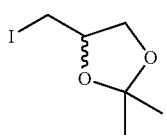

4-(iodomethyl)-2,2-dimethyl-1,3-dioxolane

To a solution of (2,2-dimethyl-1,3-dioxolan-4-yl)methanol (10 g, 75.67 mmol) in dry toluene (200 mL) was added triphenylphospine (23.82 g, 90.81 mmol), imidazole (15.45 g, 227 mmol), and iodine (24.97 g, 98.36 mmol). The mixture was stirred at 90° C. for 3 h. The solvent was then removed in vacuo and the residue was dissolved in DCM (200 mL) and washed with saturated Na$_2$S$_2$O$_3$ solution water and brine. The Intermediate 13

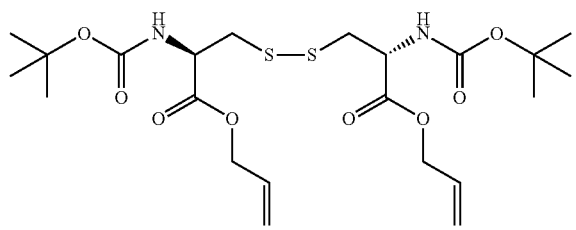

(2R,2'R)-diallyl 3,3'-disulfanediylbis(2-(tert-butoxy-carbonylamino)propanoate)

To a solution of L-cistyne (13 g, 54.1 mmol) in water (200 mL) was added Et$_3$N (22.81 mL, 162.3 mmol). The mixture was stirred at rt for 5 min then was added dropwise a solution of Boc$_2$O (35.42 g, 162.3 mmol) in dioxane. The mixture was stirred at rt overnight. The solvent was then removed in vacuo and the residue was dissolved in EtOAc (200 mL) and washed with 0.1 N HCl solution, water and brine. The organic layer was dried over MgSO$_4$, filtered and concentrated in vacuo. The crude compound was dried and dissolved in dry DMF. To this solution was Cs$_2$CO$_3$ (19.12 g, 58.7 mmol) and allyl bromide (9.92 mL, 117.4). The mixture was stirred at rt overnight. The solvent was removed in vacuo and the residue was dissolved in EtOAc (200 mL), washed with 0.1 N HCl solution, water and brine. The organic layer was dried over MgSO$_4$, filtered and concentrated in vacuo. The crude compound was purified on column of silica gel (2% MeOH/DCM) to give the subject compound (22.53 g, yield 80%). Intermediate 13 was characterized by the following spectroscopic data: $^1$H NMR (DMSO-d6, 300 MHz) δ (ppm) 7.43 (d, 2H), 5.89 (m, 2H), 5.29 (m, 4H), 4.59 (d, 4H), 4.02 (m, 2H), 3.07 (m, 4H), 1.38 (s, 18H).

Intermediate 14

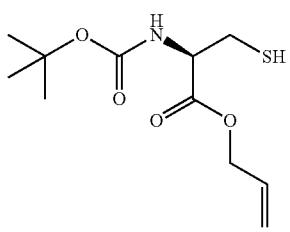

(R)-allyl 2-(tert-butoxycarbonylamino)-3-mercaptopropanoate

The intermediate 13 (20.00 g, 38.4 mmoles) was suspended in a mixture of ethyl acetate/5% w/v aqueous NaHCO$_3$ (1:1, 400 mL) within a suba-sealed 500 mL round bottomed flask. The flask was then purged with nitrogen to displace any air within the vessel. This solution was vigorously stirred and tributylphosphine (20.85 ml, 84.5 mmol) was added by positive displacement. The reaction mixture was then agitated for 2 h. At the end of this time the reaction was quenched by the careful addition of 1 M aqueous KHSO$_4$ (60 mL). The reaction mixture was then transferred to a separating funnel and the crude product was extracted into ethyl acetate (3×200 mL). The organic fractions were then combined and concentrated in vacuo to afford viscous brown oil. The crude oil was purified on column of silica gel (15% EtOAc/Cyclohexane) to give the subject compound (19.00 g, yield 94%). Intermediate 14 was characterized by the following spectroscopic data: $^1$H NMR (CDCl$_3$-d$_1$, 300 MHz) δ (ppm) 5.94 (m, 1H), 5.34 (m, 3H), 4.67 (m, 3H), 4.26 (m, 1H), 3.01 (m, 2H), 1.46 (s, 9H).

Intermediate 15

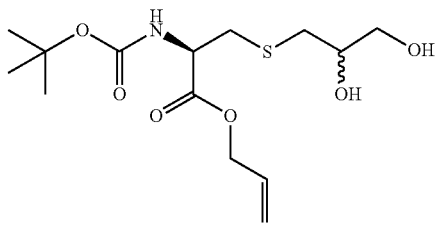

(R)-allyl 2-(tert-butoxycarbonylamino)-3-((2,2-dimethyl-1,3-dioxolan-4-yl)methylthio) propanoate To a solution of intermediate 14 (7.34 g, 28.1 mmol) in dry DMF (100 mL) was added Et$_3$N (15.39 mL, 109.5 mmol) and intermediate 12 (8.83 g, 36.5 mmol). The mixture was stirred at 80° C. overnight. The solvent was then removed in vacuo and the residue was dissolved in DCM (150 mL) and washed with 0.1 N HCl solution water and brine. The organic layer was dried over MgSO$_4$, filtered and concentrated in vacuo. The crude compound was purified on column of silica gel (2% MeOH/DCM) to give the subject compound (7.18 g, yield 68%). Intermediate 15 was characterized by the following spectroscopic data: $^1$H NMR (CDCl$_3$-d$_1$, 300 MHz) δ (ppm) 5.93 (m, 1H), 5.39 (m, 1H), 5.30 (m, 2H), 4.67 (d, 2H), 4.60 (m, 1H), 4.24 (m, 1H), 4.11 (m, 1H), 3.70 (m, 1H), 3.06 (m, 2H), 2.70 (m, 2H), 1.46 (s, 9H), 1.44 (s, 3H), 1.37 (s, 3H).

Intermediate 16

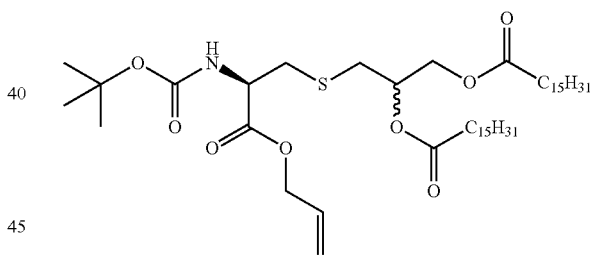

(R)-allyl 2-(tert-butoxycarbonylamino)-3-(2,3-dihydroxypropylthio)propanoate

The intermediate 15 (7.18 g, 19.1 mmol) was dissolved in a solution of AcOH 70% (220 mL). The mixture was stirred at rt overnight. The solvent was then removed in vacuo and the residue was directly applied to a column of silica gel (4% MeOH/DCM) to give the subject compound (5.01 g, yield 78%). Intermediate 16 was characterized by the following spectroscopic data: $^1$H NMR (CDCl$_3$-d$_1$, 300 MHz) δ (ppm) 5.93 (m, 1H), 5.40 (m, 1H), 5.34 (m, 2H), 4.67 (d, 2H), 4.62 (m, 1H), 3.79 (m, 3H), 3.61 (m, 1H), 3.05-2.65 (m, 5H), 1.47 (s, 9H).

Intermediate 17

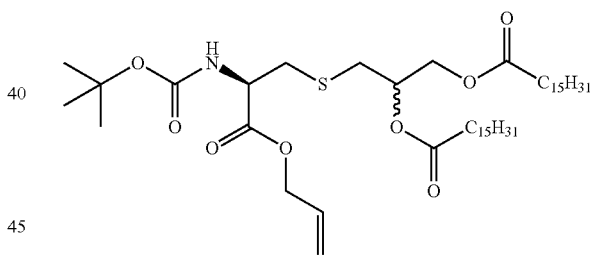

(R)-3-(3-(allyloxy)-2-(tert-butoxycarbonylamino)-3-oxopropylthio)propane-1,2-diyl dipalmitate A solution of intermediate 16 (4.22 g, 12.6 mmol) in dry DCM (150 mL) was cooled in an ice bath. EDCl (6.27 g, 32.7 mmol), DMAP (3.99 g, 32.7 mmol) and palmitic acid (8.38 g, 32.7 mmol) were added to the solution. The mixture was stirred for 10 min then warmed up to rt and stirred overnight. The reaction mixture was diluted with DCM, washed with 0.1 N HCl solution water and brine. The organic layer was dried over MgSO$_4$, filtered and concentrated in vacuo. The crude compound was purified on column of silica gel (DCM) to give the subject compound (9.55 g, yield 93%). Intermediate 17 was characterized by the following spectroscopic data: $^1$H NMR (CDCl$_3$-d$_1$, 300 MHz) δ (ppm) 5.93 (m, 1H), 5.32 (m, 3H), 5.15 (m, 1H), 4.67 (d, 2H), 4.57 (m, 1H), 4.36-4.13 (m, 2H), 3.04 (m, 2H), 2.75 (m, 2H), 2.32 (m, 4H), 1.67 (m, 4H), 1.46 (s, 9H), 1.27 (s, 48H), 0.89 (t, 6H).

Intermediate 18

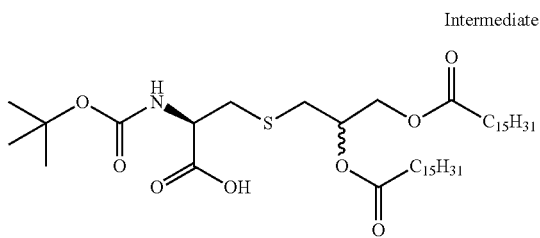

(R)-3-(2,3-bis(palmitoyloxy)propylthio)-2-(tert-butoxycarbonylamino)propanoic acid To a solution of intermediate 17 (7.51 g, 9.2 mmol) in dry THF (120 mL) was added Tetrakis(triphenylphosphine)palladium(0) (2.13 g, 1.8 mmol) and N-methylaniline (2.97 mL, 27.7 mmol). The mixture was stirred at rt for 1 h. The solvent was then removed in vacuo and the residue was dissolved in EtOAc (150 mL) and washed with 0.1 N HCl solution, water and brine. The organic layer was dried over MgSO$_4$, filtered and concentrated in vacuo. The crude compound was purified on column of silica gel (DCM) to give the subject compound (6.94 g, yield 97%). Intermediate 18 was characterized by the following spectroscopic data: $^1$H NMR (CDCl$_3$-d$_1$, 300 MHz) δ (ppm) 5.48 (m, 1H), 5.16 (m, 1H), 4.50 (m, 1H), 4.38-4.13 (m, 2H), 3.04 (m, 2H), 2.77 (m, 2H), 2.33 (m, 4H), 1.61 (m, 4H), 1.46 (s, 9H), 1.27 (s, 48H), 0.89 (t, 6H).

Intermediate 19

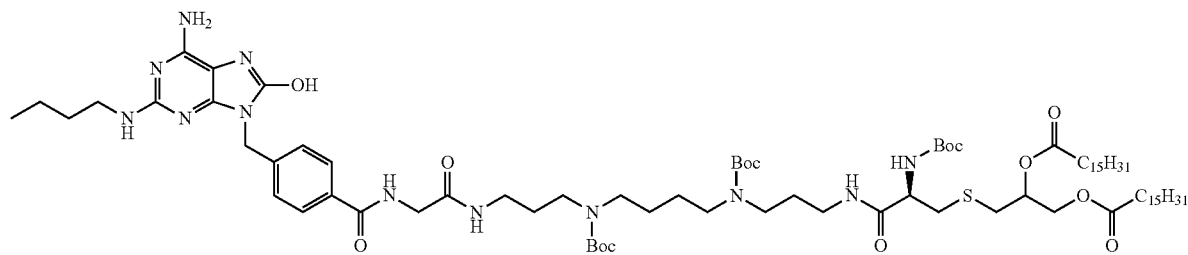

(20R)-1-(4-((6-amino-2-(butylamino)-8-hydroxy-9H-purin-9-yl)methyl)phenyl)-9,14-bis(tert-butoxycarbonyl)-20-(tert-butoxycarbonylamino)-1,4,19-trioxo-22-thia-2,5,9,14,18-pentaazapentacosane-24,25-diyl dipalmitate To a solution of intermediate 11 (69 mg, 0.1 mmol) in dry DMF (5 mL) were added HATU (36 mg, 0.1 mmol), intermediate 18 (67 mg, 0.1 mmol) and DIEA (75 µL, 0.4 mmol). The mixture was stirred at rt overnight. The solvent was removed in vacuo, the residue was dissolved in EtOAc (50 mL) and washed with 0.1 N HCl solution, saturated NaHCO$_3$ solution, water and brine. The organic layer was dried over MgSO$_4$, filtered and concentrated in vacuo. The crude compound was purified on column of silica gel (2% MeOH/DCM) to give the subject compound (49 mg, yield 36%). Intermediate 19 was characterized by the following spectroscopic data: $^1$H NMR (DMSO-d$_6$, 300 MHz) δ (ppm) 9.64 (s, 1H), 8.66 (m, 1H), 7.82 (m, 2H), 7.34 (d, 2H), 6.17 (m, 1H), 5.99 (sl, 2H), 5.07 (m, 1H), 4.85 (s, 2H), 4.26-4.08 (m, 2H), 3.80 (d, 2H), 3.08 (m, 12H), 2.73 (m, 6H), 2.26 (m, 4H), 1.47 (m, 12H), 1.36 (m, 29H), 1.22 (m, 54H), 0.85 (m, 9H).

Compound 20

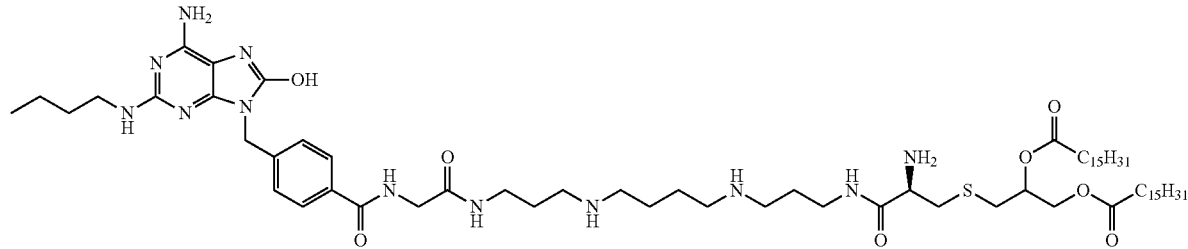

CL553

(20R)-20-amino-1-(4-((6-amino-2-(butylamino)-8-hydroxy-9H-purin-9-yl)methyl)phenyl)-1,4,19-trioxo-22-thia-2,5,9,14,18-pentaazapentacosane-24,25-diyl dipalmitate To a solution of intermediate 19 (49 mg, 0.03 mmol) in dioxane (3 mL) was added 4N HCl solution in dioxane (10 mL). The mixture was stirred at RT overnight. Then the solvent were removed in vacuo, the residue was coevaporated 3 times with toluene. The residue was purified by flash chromatography on an ARMEN® system with C18 column eluting with a gradient of 0-10% MeCN in $NH_4OAc$ (10 mM) solution (pH=9) to give the subject compound (42 mg, yield 97%). $^1$H NMR (DMSO-$d_6$, 300 MHz) δ (ppm) 9.64 (s, 1H), 8.94 (m, 1H), 8.41 (m, 1H), 7.85 (m, 2H), 7.38 (d, 2H), 6.17 (m, 1H), 5.98 (sl, 2H), 5.14 (m, 1H), 4.91 (s, 2H), 4.33-4.12 (m, 4H), 3.81 (d, 2H), 3.27 (m, 6H), 2.88 (m, 10H), 2.26 (m, 6H), 1.78 (m, 4H), 1.48 (m, 12H), 1.26 (m, 52H), 0.85 (m, 9H). MS (+)-ES [M+H]$^+$ 1251.9 m/z.

Example 2

Molecule CL554

Intermediate 21

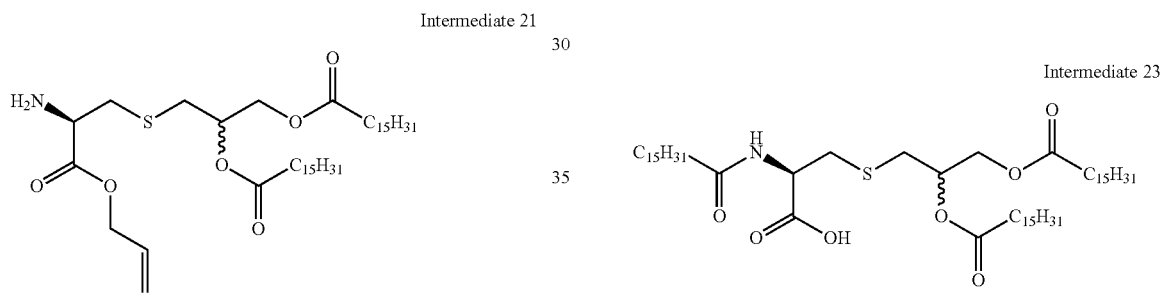

3-((R)-3-(allyloxy)-2-amino-3-oxopropylthio)propane-1,2-diyldipalmitate

To a solution of intermediate 17 (9.55 g, 11.8 mmol) in DCM (100 mL) was added 25 mL of TFA. The mixture was stirred at RT overnight. Then the solvent were removed in vacuo, the residue was coevaporated 3 times with toluene. The residue was precipitated in diethyl ether to give the subject compound (9.71 g, yield 100%). Intermediate 21 was used for the next step without any further purification.

Intermediate 22

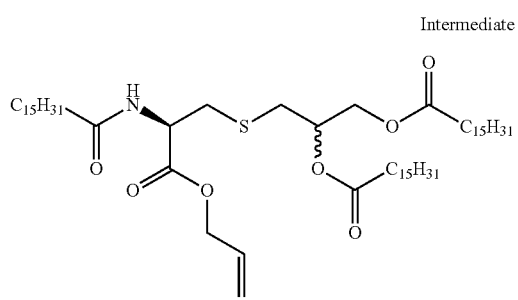

3-((R)-3-(allyloxy)-3-oxo-2-palmitamidopropylthio)propane-1,2-diyl dipalmitate To a solution of intermediate 21 (9.71 g, 11.8 mmol) in dry DMF (120 mL) were added HATU (4.69 g, 12.3 mmol), DIEA (4.07 mL, 23.5 mmol) and palmitic acid (3.16 g, 12.3 mmol). The mixture was stirred at rt overnight. The solvent was removed in vacuo. The residue was dissolved in DCM, washed with 0.1 N HCl solution water and brine. The organic layer was dried over $MgSO_4$, filtered and concentrated in vacuo. The crude compound was purified on column of silica gel (1% MeOH/DCM) to give the subject compound (10.9 g, yield 97%). Intermediate 22 was characterized by the following spectroscopic data: $^1$H NMR (CDCl$_3$-$d_1$, 300 MHz) δ (ppm) 6.35 (t, 1H), 5.92 (m, 1H), 5.34 (m, 2H), 5.14 (m, 1H), 4.87 (m, 1H), 4.67 (d, 2H), 4.33 (m, 1H), 4.16 (m, 1H), 3.09 (m, 2H), 2.73 (d, 2H), 2.33 (m, 6H), 1.61 (m, 6H), 1.28 (m, 72H), 0.89 (t, 9H).

Intermediate 23

(2R)-3-(2,3-bis(palmitoyloxy)propylthio)-2-palmitamidopropanoic acid

To a solution of intermediate 24 (10.9 g, 11.4 mmol) in dry THF (150 mL) was added Tetrakis(triphenylphosphine)palladium(0) (2.72 g, 2.3 mmol) and N-methylaniline (3.83 mL, 35.3 mmol). The mixture was stirred at rt for 1 h. The solvent was then removed in vacuo and the residue was dissolved in EtOAc (150 mL) and washed with 0.1 N HCl solution, water and brine. The organic layer was dried over $MgSO_4$, filtered and concentrated in vacuo. The crude compound was purified on column of silica gel (5% MeOH/DCM) to give the subject compound (10.1 g, yield 97%). Intermediate 23 was characterized by the following spectroscopic data: $^1$H NMR (CDCl$_3$-$d_1$, 300 MHz) δ (ppm) 5.18 (m, 1H), 4.76 (m, 1H), 4.35 (m, 1H), 4.16 (m, 1H), 3.14 (m, 2H), 2.75 (m, 2H), 2.34 (m, 6H), 1.64 (m, 6H), 1.25 (m, 72H), 0.89 (t, 9H).

Intermediate 24

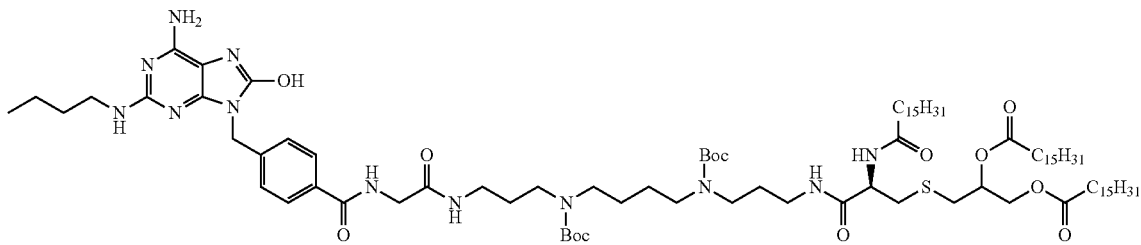

(20R)-1-(4-(((6-amino-2-(butylamino)-8-hydroxy-9H-purin-9-yl)methyl)phenyl)-9,14-bis(tert-butoxycarbonyl)-20-palmitamido-1,4,19-trioxo-22-thia-2,5,9,14,18-pentaazapenta cosane-24,25-diyl dipalmitate The title compound was prepared from intermediate 23 intermediate 11 by following the procedure described for example 1, compound 19. Compound 24 was characterized by the following spectroscopic data: $^1$H NMR (DMSO-d$_6$, 300 MHz) δ (ppm) 9.60 (s, 1H), 8.58 (m, 1H), 7.82 (m, 2H), 7.32 (d, 2H), 6.15 (m, 1H), 5.98 (sl, 2H), 5.06 (m, 1H), 4.83 (s, 2H), 4.27-4.13 (m, 4H), 3.80 (d, 2H), 3.13 (m, 14H), 2.73 (m, 6H), 2.29 (m, 6H), 1.47 (m, 30H), 1.28 (m, 76H), 0.89 (m, 12H). MS (+)-ES [M+H]$^+$ 1290.25.

Compound 25

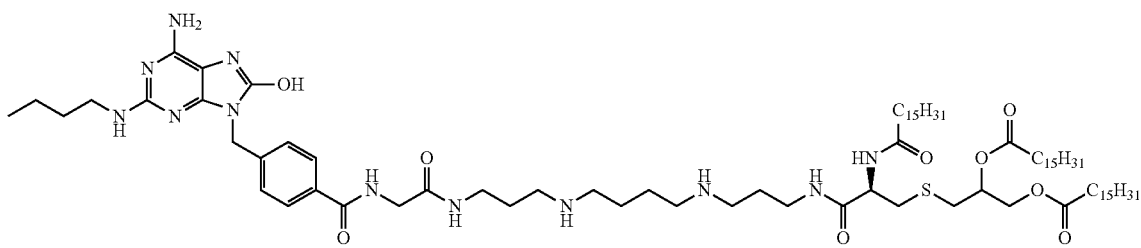

CL554

(20R)-1-(4-(((6-amino-2-(butylamino)-8-hydroxy-9H-purin-9-yl)methyl)phenyl)-1,4,19-trioxo-20-palmitamido-22-thia-2,5,9,14,18-pentaazapentacosane-24,25-diyl dipalmitate The title compound was prepared from intermediate 24 by following the procedure described for example 1, compound 20. Compound 25 was characterized by the following spectroscopic data: $^1$H NMR (DMSO-d$_6$, 300 MHz) δ (ppm) 9.61 (s, 1H), 8.94 (m, 1H), 8.41 (m, 1H), 7.86 (m, 2H), 7.39 (d, 2H), 6.18 (m, 1H), 6.00 (sl, 2H), 5.14 (m, 1H), 4.83 (s, 2H), 4.30-4.13 (m, 4H), 3.82 (d, 2H), 3.27 (m, 6H), 2.88 (m, 12H), 2.29 (m, 6H), 1.78 (m, 4H), 1.48 (m, 12H), 1.26 (m, 76H), 0.86 (m, 12H). MS (+)-ES [M+H]$^+$ 1289.1 m/z.

Example 3

Molecule CL514

Intermediate 26

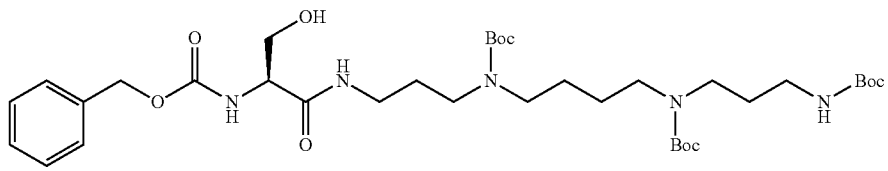

(S)-Benzyl 3-hydroxy-1-oxo-1-(N1,N5,N10-tri Boc-spermine)propan-2-yl carbamate

To a solution of Z-L-SerOH (1.17 mg, 4.9 mmol) in dry DMF (20 mL) was added intermediate 7 (2.47 g, 4.9 mmol), HATU (2.05 g, 5.4 mmol), and DIEA (4.27 mL, 24.6 mmol). The mixture was stirred at rt overnight. The solvent was then removed in vacuo and the residue was dissolved in EtOAc (100 mL) and washed with saturated $NaHCO_3$ solution water and brine. The organic layer was dried over $MgSO_4$, filtered and concentrated in vacuo. The crude compound was purified on column of silica gel (3% MeOH/DCM) to give the subject compound (2.89 g, yield 81%). Intermediate 26 was characterized by the following spectroscopic data: $^1$H NMR (DMSO-$d_6$, 300 MHz) δ (ppm) 7.86 (t, 1H), 7.35 (m, 5H), 7.16 (d, 1H), 6.75 (m, 1H), 5.76 (s, 2H), 5.02 (d, 2H), 4.82 (t, 1H), 3.97 (m, 1H), 3.55 (m, 2H), 3.09 (m, 10H), 2.88 (m, 2H), 1.56 (m, 4H), 1.37 (s, 27H).

Intermediate 27

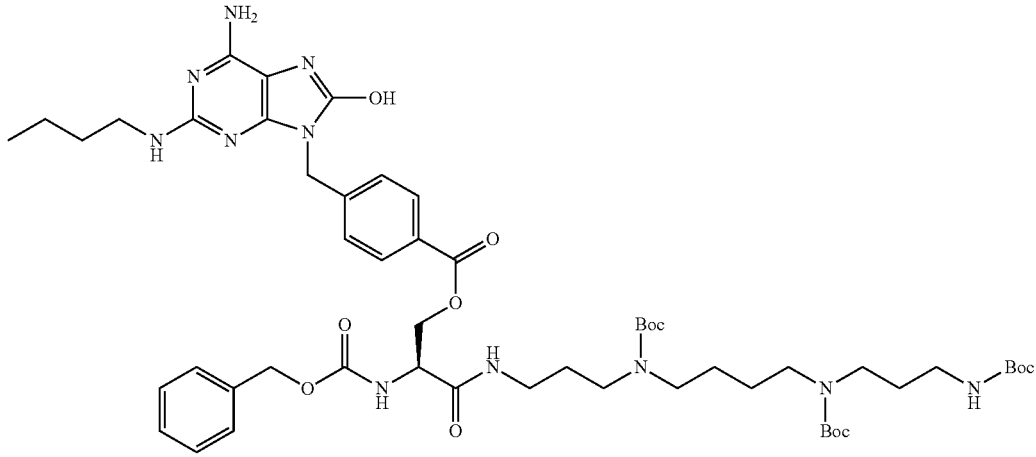

(S)-20-(benzyloxycarbonylamino)-9,14-bis(tert-butoxycarbonyl)-2,2-dimethyl-4,19-dioxo-3-oxa-5,9,14,18-tetraazahenicosan-21-yl-4-((6-amino-2-(butylamino)-8-hydroxy-9H-purin-9-yl)methyl)benzoate To a solution of intermediate 26 (2.14 g, 2.9 mmol) in dry DMF (20 mL) was added intermediate 4 (1.26 g, 3.5 mmol), EDCl (0.680 g, 3.5 mmol), and DMAP (0.433 g, 3.5 mmol). The mixture was stirred at rt overnight. The solvent was then removed in vacuo and the residue was dissolved in EtOAc (50 mL) and washed with 1 M HCl solution water and brine. The organic layer was dried over $MgSO_4$, filtered and concentrated in vacuo. The crude compound was purified on column of silica gel (2% MeOH/DCM) to give the subject compound (590 mg, yield 19%). Intermediate 27 was characterized by the following spectroscopic data: $^1$H NMR (DMSO-$d_6$, 300 MHz) δ (ppm) 9.68 (s, 1H), 8.13 (m, 1H), 7.91 (m, 2H), 7.71 (m, 1H), 7.37 (d, 2H), 7.28 (m, 5H), 6.76 (m, 1H), 6.20 (t, 1H), 6.03 (sl, 2H), 5.06 m, 2H), 4.91 (s, 2H), 4.43 (s, 2H), 4.31 (m, 1H), 4.10 (m, 4), 3.25-2.88 (m, 10H), 2.86 (m, 2H), 1.56 (m, 4H), 1.48-1.20 (m, 33H), 0.83 (t, 3H).

Intermediate 28

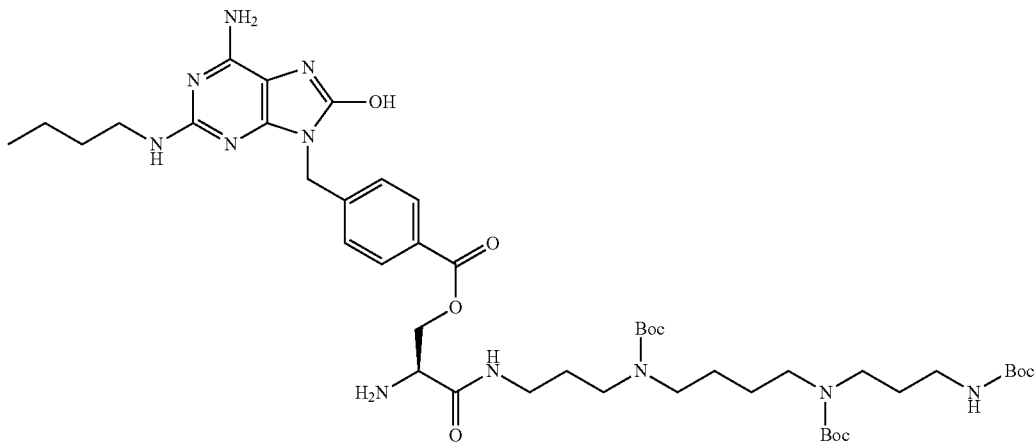

(S)-20-amino-9,14-bis(tert-butoxycarbonyl)-2,2-dimethyl-4,19-dioxo-3-oxa-5,9,14,18-tetraazahenicosan-21-yl-4-((6-amino-2-(butylamino)-8-hydroxy-9H-purin-9-yl)methyl)benzoate To a solution of intermediate 27 (590 mg, 0.5 mmol) in a mixture of THF/MeOH (1/1) (10 mL) was added palladium on activated carbon 10% (0.05 eq). hydrogen gas was introduced via a balloon; the reaction mixture was stirred overnight at rt. The mixture was filtered through Celite and was washed with MeOH, the filtrate was concentrated in vacuo. The resulting solid was used for the next step without any further purification.

Intermediate 29

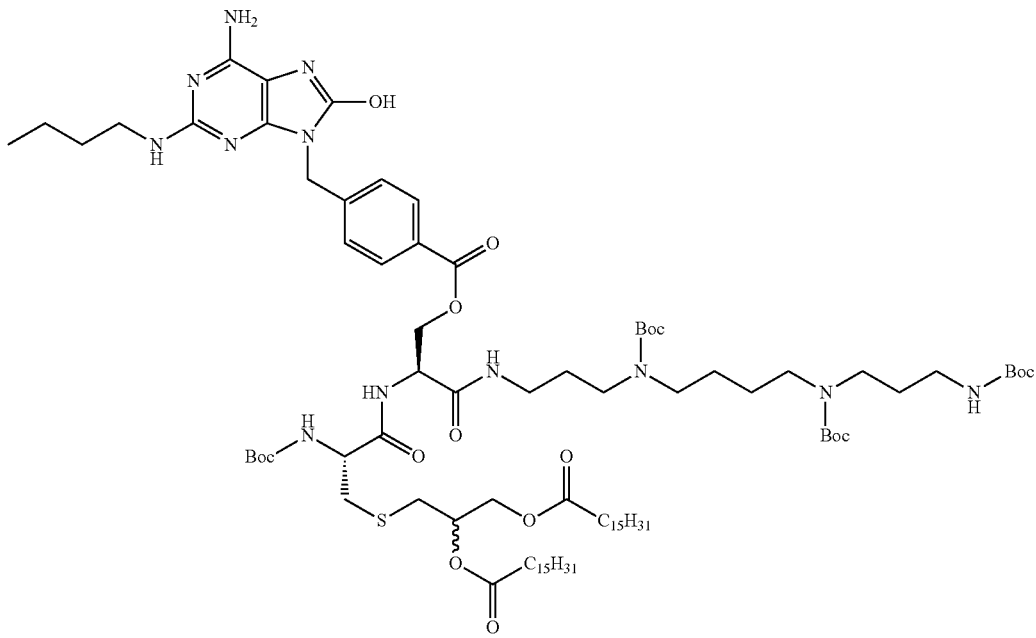

(20S,23R)-20-((4-((6-amino-2-(butylamino)-8-hydroxy-9H-purin-9-yl)methyl)benzoyloxy)methyl)-9,14-bis(tert-butoxycarbonyl)-23-(tert-butoxycarbonylamino)-2,2-dimethyl-4,19,22-trioxo-3-oxa-25-thia-5,9,14,18,21-pentaazaoctacosane-27,28-diyl dipalmitate To a solution of intermediate 28 (114 mg, 0.1 mmol) in dry DMF (10 mL) was added intermediate 18 (95 mg, 0.1 mmol), HATU (51 mg, 0.1 mmol), and DIEA (107 µL, 0.6 mmol). The mixture was stirred at rt overnight. The solvent was then removed in vacuo and the residue was dissolved in EtOAc (50 mL) and washed with saturated NaHCO$_3$ solution water and brine. The organic layer was dried over MgSO$_4$, filtered and concentrated in vacuo. The crude compound was purified on column of silica gel (3% MeOH/DCM) to give the subject compound (95 mg, yield 45%). Intermediate 29 was characterized by the following spectroscopic data: $^1$H NMR (DMSO-d$_6$, 300 MHz) δ (ppm) 9.67 (s, 1H), 8.32 (m, 1H), 8.05 (m, 2H), 7.89 (d, 2H), 7.38 (d, 2H), 7.10 (m, 1H), 6.20 (m, 1H), 6.02 (sl, 2H), 5.06 (m, 1H), 4.87 (s, 2H), 4.63 (m, 1H), 4.38 (m, 2H), 4.13 (m, 1H), 3.25-3.00 (m, 18H), 2.88 (m, 2H), 2.26 (m, 4H), 1.80-1.68 (m, 8H), 1.65-1.35 (m, 40H), 1.34-1.20 (m, 52H), 0.85 (m, 9H).

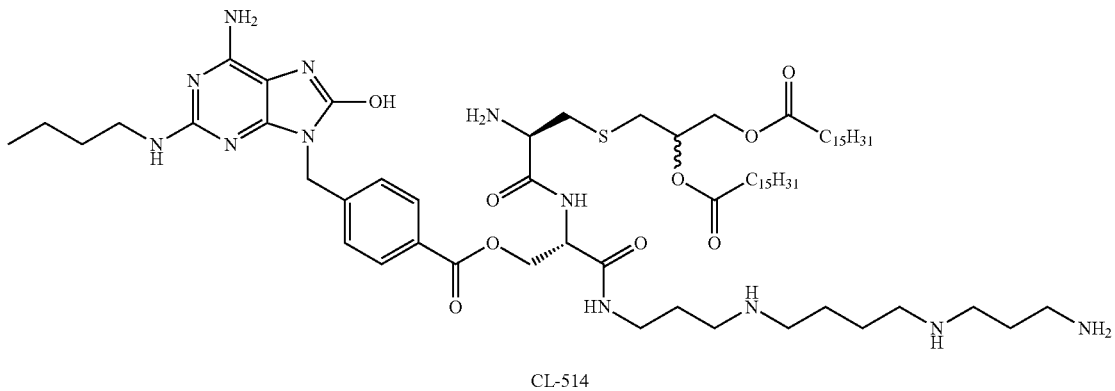

Compound 30

CL-514

(6R,9S)-6,23-diamino-9-((4-((6-amino-2-(butylamino)-8-hydroxy-9H-purin-9-yl)methyl)benzoyloxy)methyl)-7,10-dioxo-4-thia-8,11,15,20-tetraazatricosane-1,2-diyl dipalmitate The title compound was prepared from intermediate 29 by following the procedure described for example 1, compound 20. Compound 30 was characterized by the following spectroscopic data: $^1$H NMR (DMSO-d$_6$, 300 MHz) δ (ppm) 9.19 (m, 2H), 8.94 (m, 2H), 8.56 (m, 1H), 8.44 (m, 1H), 8.10 (m, 2H), 7.95 (d, 2H), 7.44 (d, 2H), 5.14 (m, 1H), 4.94 (s, 2H), 4.67 (m, 1H), 4.49 (m, 2H), 4.10 (m, 2H), 3.76 (m, 2H), 3.25 (m, 4H), 3.07-2.80 (m, 14H), 2.27 (m, 4H), 1.98 (m, 2H), 1.77 (m, 6H), 1.45 (m, 6H), 1.32-1.16 (m, 55H), 0.82 (m, 9H). MS (+)-ES [M+H]$^+$ 1281.9 m/z.

Example 4

Molecule CL486

Intermediate 31

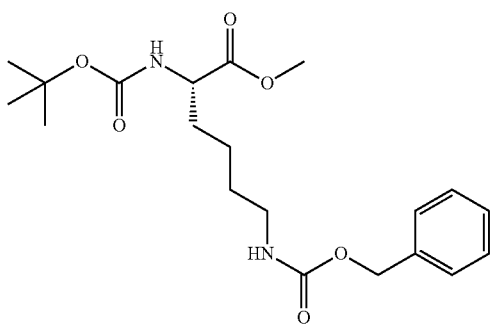

(S)-Methyl 6-(benzyloxycarbonylamino)-2-(tert-butoxycarbonylamino)hexanoate

To a solution of Boc-L-Lys(Z)OH (2.00 g, 5.2 mmol) in dry DMF (50 mL) was added Cs$_2$CO$_3$ (1.71 g, 5.2 mmol). The mixture was stirred at rt for 2 h. To the reaction mixture was then added dropwise methyl iodide (392 μL, 6.3 mmol) and the mixture was stirred at rt overnight. The solvent was removed in vacuo and the residue was dissolved in EtOAc (100 mL) and washed with saturated NaHCO$_3$ solution water and brine. The organic layer was dried over MgSO$_4$, filtered and concentrated in vacuo. The crude compound was purified on column of silica gel (2% MeOH/DCM) to give the subject compound (2.00 g, yield 97%). Intermediate 31 was characterized by the following spectroscopic data: $^1$H NMR (DMSO-d$_6$, 300 MHz) δ (ppm) 7.34 (m, 5H), 7.23 (t, 1H), 4.99 (s, 2H), 3.91 (m, 1H), 3.60 (s, 3H), 3.34 (s, 2H), 2.96 (m, 2H), 1.56 (m, 2H), 1.37 (m, 11H), 1.32 (m, 2H).

Intermediate 32

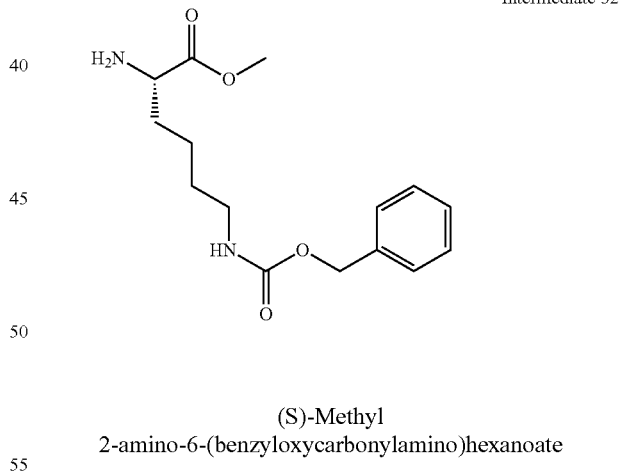

(S)-Methyl 2-amino-6-(benzyloxycarbonylamino)hexanoate

To a solution of Boc-L-Lys(Z)OMe 31 (2.00 g, 12.6 mmol) in DCM (30 mL) was added 30 mL of TFA. The mixture was stirred at rt for 1 h. Then the solvent were removed in vacuo, the residue was coevaporated 3 times with toluene. The residue was precipitated in Et$_2$O to give the subject compound (2.1 g, yield 100%). Intermediate 32 was characterized by the following spectroscopic data: $^1$H NMR (DMSO-d$_6$, 300 MHz) δ (ppm) 8.45 (sl, 2H), 7.33 (m, 5H), 7.31 (t, 1H), 5.00 (s, 2H), 4.03 (m, 1H), 3.74 (s, 3H), 2.97 (m, 2H), 1.75 (m, 2H), 1.39 (m, 4H).

Intermediate 33

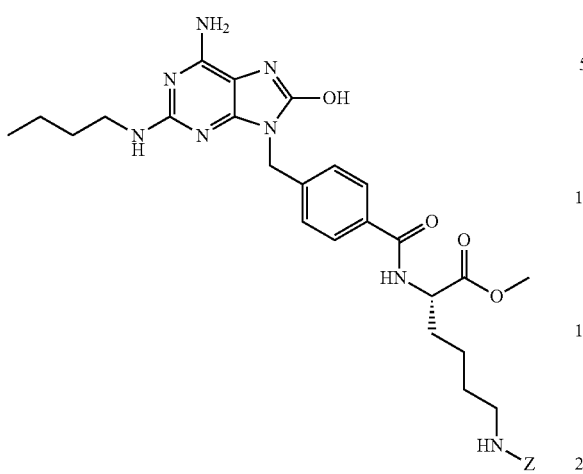

(S)-Methyl 2-(4-((6-amino-2-(butylamino)-8-hydroxy-9H-purin-9-yl)methyl)benzamido)-6-(benzyloxycarbonylamino)hexanoate To a solution of intermediate 4 (1.02 g, 2.9 mmol) in dry DMF (10 mL) was added L-Lys(Z)OMe 32 (1.29 g, 3.2 mmol), HATU (1.20 g, 3.2 mmol), and DIEA (2.50 mL, 14.4 mmol). The mixture was stirred at rt overnight. The solvent was then removed in vacuo and the residue was dissolved in EtOAc (30 mL) and washed with saturated NaHCO$_3$ solution water and brine. The organic layer was dried over MgSO$_4$, filtered and concentrated in vacuo. The crude compound was purified on column of silica gel (4% MeOH/DCM) to give the subject compound (685 mg, yield 38%). Intermediate 33 was characterized by the following spectroscopic data: $^1$H NMR (DMSO-d$_6$, 300 MHz) δ (ppm) 9.67 (s, 1H), 8.65 (d, 1H), 7.81 (d, 2H), 7.32-7.29 (m, 8H), 6.20 (t, 2H), 6.02 (sl, 1H), 4.98 (s, 2H), 4.86 (s, 2H), 4.37 (m, 1H), 3.62 (s, 3H), 3.14 (m, 2H), 2.97 (m, 2H), 1.78 (m, 2H), 1.43-1.26 (m, 8H), 0.88 (t, 3H).

Intermediate 34

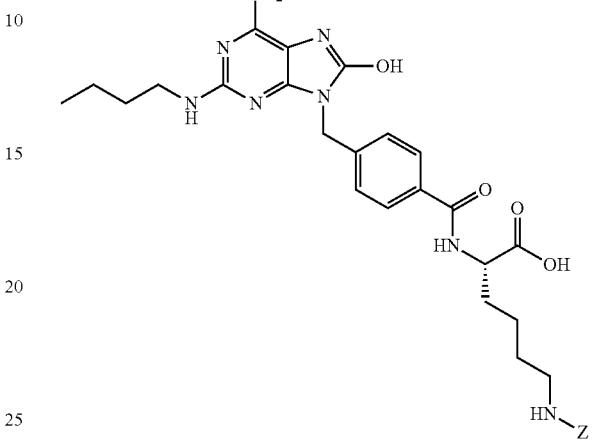

(S)-2-(4-((6-amino-2-(butylamino)-8-hydroxy-9H-purin-9-yl)methyl)benzamido)-6-(benzyl oxycarbonylamino)hexanoic acid To a solution of intermediate 33 (685 mg, 1.08 mmol) in dioxane (10 mL) was added 1 N LiOH solution until pH 10. The mixture was stirred at rt overnight. The mixture was neutralized with 1 M HCl solution (pH 6). The precipitate was filtered off, washed with water, EtOH and Et$_2$O to give the subject compound (668 mg, yield 99%), which was used for the next step without any further purification.

Intermediate 35

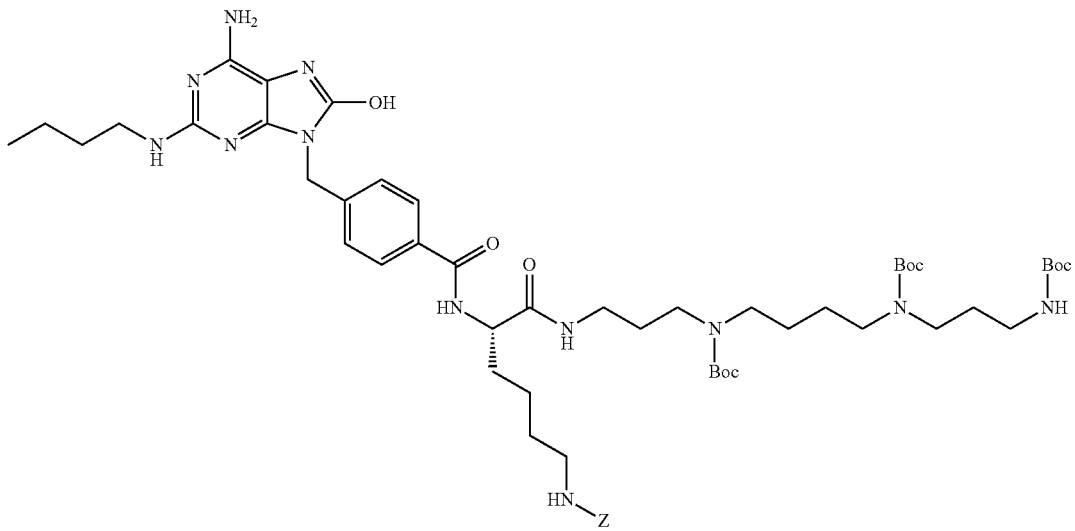

N1,N5,N10-triBoc-spermine (S)-2-(4-(6-amino-2-(butylamino)-8-hydroxy-9H-purin-9-yl)methyl)benzamido)acetamido)-6-(benzyloxycarbonylamino)hexanamide To a solution of intermediate 34 (668 mg, 1.1 mmol) in dry DMF (20 mL) was added intermediate 7 (598 mg, 1.2 mmol), HATU (452 mg, 1.2 mmol), and DIEA (941 μL, 5.4 mmol). The mixture was stirred at rt overnight. The solvent was then removed in vacuo and the residue was dissolved in EtOAc (30 mL) and washed with saturated NaHCO$_3$ solution water and brine. The organic layer was dried over MgSO$_4$, filtered and concentrated in vacuo. The crude compound was purified on column of silica gel (3% MeOH/DCM) to give the subject compound (1.06 g, yield 89%). Intermediate 35 was characterized by the following spectroscopic data: $^1$H NMR (DMSO-d$_6$, 300 MHz) δ (ppm) 9.66 (s, 1H), 8.33 (m, 1H), 7.91 (m, 1H), 7.83 (d, 2H), 7.36-7.32 (m, 7H), 6.76 (t, 1H), 6.19 (t, 1H), 6.01 (sl, 2H), 4.91 (s, 2H), 4.84 (s, 2H), 4.0.4 (m, 1H), 3.25-2.88 (m, 28H), 1.69-1.55 (m, 6H), 1.48-1.20 (m, 37H), 0.87 (t, 3H).

Intermediate 36

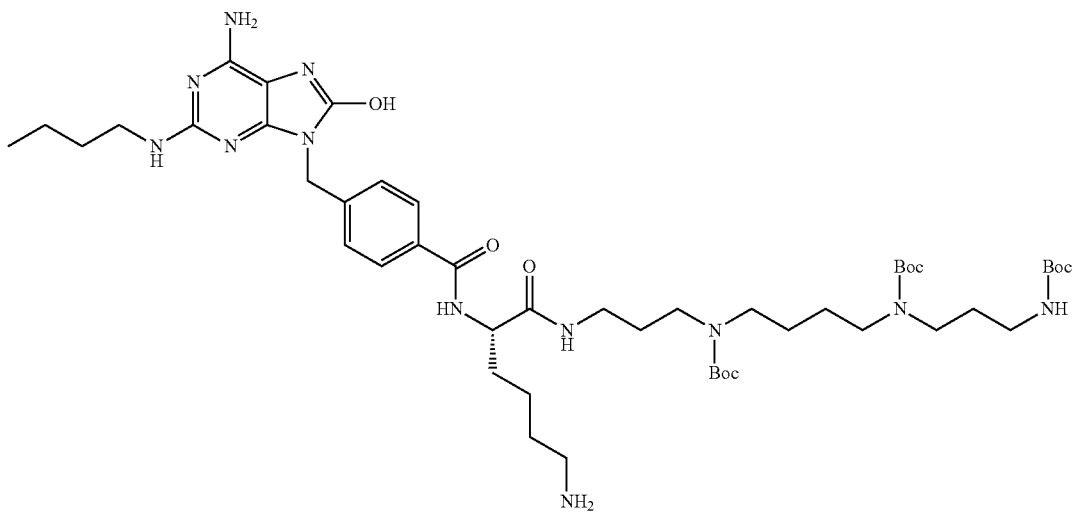

N1,N5,N10-triBoc-spermine (S)-2-(4-(6-amino-2-(butylamino)-8-hydroxy-9H-purin-9-yl)methyl)benzamido)acetamido)-6-amino)hexanamide The title compound was prepared from intermediate 35 by following the procedure described for example 3, intermediate 28.

Intermediate 37

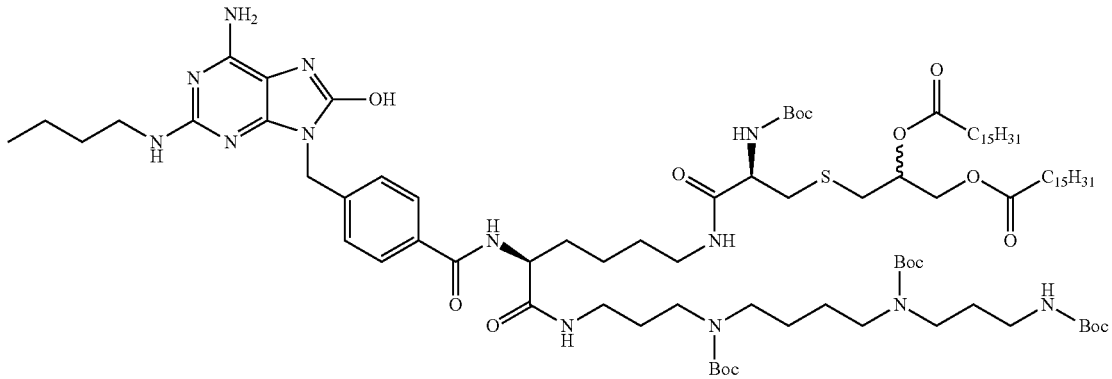

(20S,27R)-20-(4-((6-amino-2-(butylamino)-8-hydroxy-9H-purin-9-yl)methyl)benzamido)-9,14-bis(tert-butoxycarbonyl)-27-(tert-butoxycarbonylamino)-2,2-di methyl-4,19,26-trioxo-3-oxa-29-thia-5,9,14,18,25-pentaazadotriacontane-31,32-diyl dipalmitate To a solution of intermediate 36 (125 mg, 0.1 mmol) in dry DMF (10 mL) was added intermediate 7 (100 mg, 0.1 mmol), HATU (54 mg, 0.1 mmol), and DIEA (112 μL, 0.6 mmol). The mixture was stirred at rt overnight. The solvent was then removed in vacuo and the residue was dissolved in EtOAc (50 mL) and washed with saturated NaHCO₃ solution water and brine. The organic layer was dried over MgSO₄, filtered and concentrated in vacuo. The crude compound was purified on column of silica gel (4% MeOH/DCM) to give the subject compound (45 mg, yield 20%). Intermediate 37 was characterized by the following spectroscopic data: $^1$H NMR (DMSO-d₆, 300 MHz)₆ (ppm) 9.64 (s, 1H), 8.32 (m, 1H), 7.89 (m, 2H), 7.84 (d, 2H), 7.34 (d, 2H), 6.85 (m, 1H), 6.73 (sl, 2H), 5.06 (m, 1H), 4.84 (s, 2H), 4.27 (m, 2H), 4.13 (m, 2H), 3.25-3.00 (m, 18H), 2.88 (m, 6H), 2.25 (m, 4H), 1.80-1.68 (m, 8H), 1.65-1.35 (m, 44H), 1.34-1.20 (m, 52H), 0.85 (m, 9H).

Compound 38

CL-486

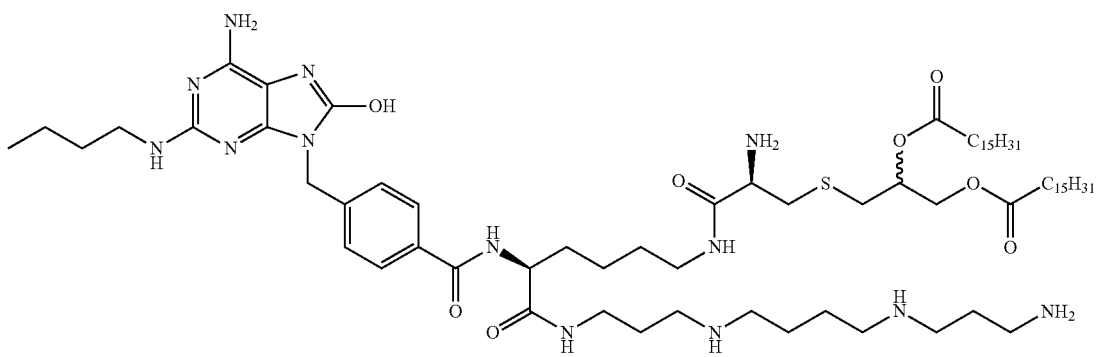

(6R,13S)-6,27-diamino-13-(4-((6-amino-2-(butylamino)-8-hydroxy-9H-purin-9-yl)methyl)benzamido)-7,14-dioxo-4-thia-8,15,19,24-tetraazaheptacosane-1,2-diyl dipalmitate The title compound was prepared from intermediate 37 by following the procedure described for example 1, compound 20. Compound 38 was characterized by the following spectroscopic data: $^1$H NMR (DMSO-d₆, 300 MHz) δ (ppm) 9.10 (m, 2H), 8.83 (m, 2H), 8.46 (m, 1H), 8.50 (m, 1H), 8.32 (m, 2H), 8.04 (m, 4H), 7.91 (d, 2H), 7.37 (d, 2H), 5.11 (m, 1H), 4.91 (s, 2H), 4.28 (m, 2H), 4.12 (m, 2H), 3.28 (m, 2H), 3.16-2.87 (m, 12H), 2.27 (m, 6H), 2.00 (m, 4H), 1.67 (m, 12H), 1.48 (m, 14H), 1.32-1.16 (m, 48H), 0.82 (m, 9H). MS (+)-ES [M+H]⁺ 1322.9 m/z.

Example 5

Molecule CL487

Intermediate 39

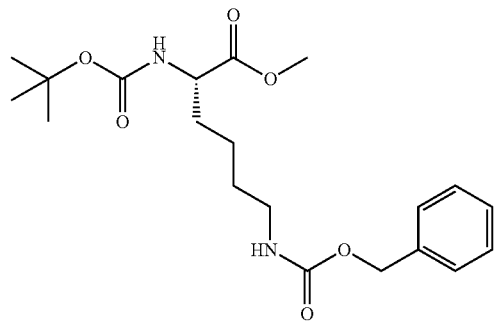

(S)-Methyl 6-(benzyloxycarbonylamino)-2-(tert-butoxycarbonylamino)hexanoate

The title compound was prepared from Boc-L-Lys(Z)OH by following the procedure described for example 4, intermediate 31. Intermediate 39 was characterized by the following spectroscopic data: $^1$H NMR (DMSO-d₆, 300 MHz) δ (ppm) 7.34 (m, 5H), 7.23 (t, 1H), 4.99 (s, 2H), 3.91 (m, 1H), 3.60 (s, 3H), 3.34 (s, 2H), 2.96 (m, 2H), 1.56 (m, 2H), 1.37 (m, 11H), 1.32 (m, 2H).

Intermediate 40

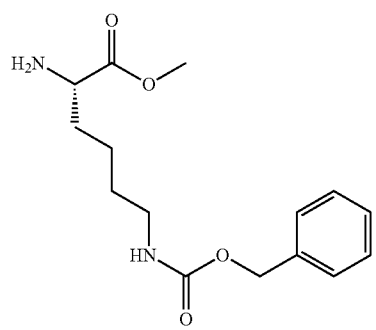

103

(S)-Methyl 2-amino-6-(benzyloxycarbonylamino)hexanoate

The title compound was prepared from intermediate 39 by following the procedure described for example 4, intermediate 32. Intermediate 40 was characterized by the following spectroscopic data: $^1$H NMR (DMSO-$d_6$, 300 MHz) δ (ppm) 8.45 (sl, 2H), 7.33 (m, 5H), 7.31 (t, 1H), 5.00 (s, 2H), 4.03 (m, 1H), 3.74 (s, 3H), 2.97 (m, 2H), 1.75 (m, 2H), 1.39 (m, 4H).

Intermediate 41

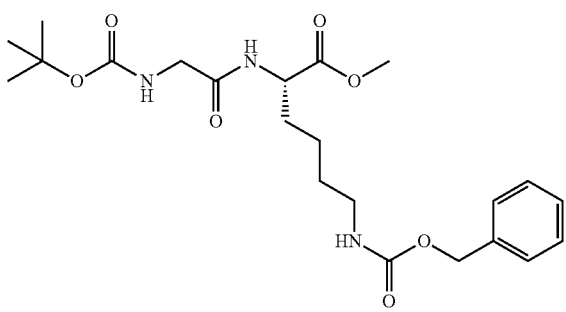

(S)-Methyl 16,16-dimethyl-3,11,14-trioxo-1-phenyl-2,15-dioxa-4,10,13-triazahepta decane-9-carboxylate To a solution of L-Lys(Z)OMe 40 (1.05 g, 2.6 mmol) in dry DMF (40 mL) was added Boc-GlyOH (494 mg, 2.8 mmol), HATU (977 mg, 2.57 mmol), and DIEA (2.03 mL, 11.7 mmol). The mixture was stirred at rt overnight. The solvent was then removed in vacuo and the residue was dissolved in EtOAc (100 mL) and washed with saturated NaHCO$_3$ solution water and brine. The organic layer was dried over MgSO$_4$, filtered and concentrated in vacuo. The crude compound was purified on column of silica gel (2% MeOH/DCM) to give the subject compound (960 mg, yield 90%). Intermediate 41 was characterized by the following spectroscopic data: $^1$H NMR (DMSO-$d_6$, 300 MHz) δ (ppm) 8.12 (t, 1H), 7.98 (t, 1H), 7.47-7.38 (m, 5H), 6.98 (t, 1H), 5.13 (s, 2H), 4.56 (m, 1H), 4.05 (d, 2H), 3.65 (s, 3H), 3.02 (m, 2H), 1.90 (m, 2H), 1.55 (m, 2H), 1.38 (s, 9H), 1.25 (m, 2H).

Intermediate 42

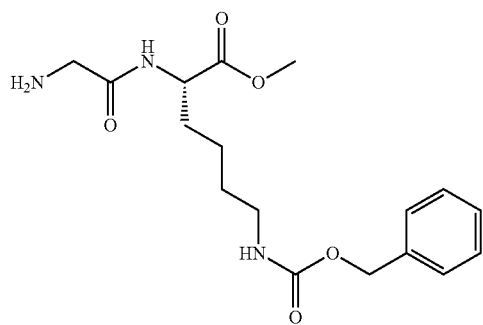

104

(S)-Methyl 2-(2-aminoacetamido)-6-(benzyloxycarbonylamino)hexanoate

The title compound was prepared from intermediate 41 by following the procedure described for example 4, intermediate 32. Intermediate 42 was characterized by the following spectroscopic data: $^1$H NMR (DMSO-$d_6$, 300 MHz) δ (ppm) 8.76 (d, 1H), 8.05 (sl, 2H), 7.34-7.29 (m, 6H), 4.99 (s, 2H), 4.28 (m, 1H), 3.64 (s, 3H), 2.88 (m, 2H), 1.65 (m, 2H), 1.39-1.28 (m, 4H).

Intermediate 43

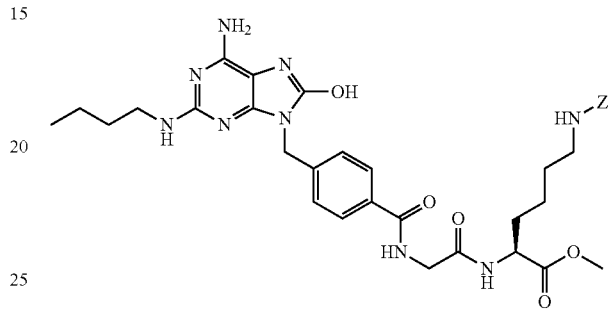

(S)-Methyl 2-(2-(4-((6-amino-2-(butylamino)-8-hydroxy-9H-purin-9-yl)methyl)benzamido) acetamido)-6-(benzyloxycarbonylamino)hexanoate The title compound was prepared from intermediate 42 by following the procedure described for example 4, intermediate 33. Intermediate 43 was characterized by the following spectroscopic data: $^1$H NMR (DMSO-$d_6$, 300 MHz) δ (ppm) 9.88 (s, 1H), 8.68 (t, 1H), 8.31 (d, 1H), 7.82 (d, 2H), 7.34 (m, 9H), 6.19 (t, 1H), 6.13 (sl, 2H), 4.99 (s, 2H), 4.85 (s, 2H), 4.23 (m, 1H), 3.91 (d, 2H), 3.61 (s, 3H), 3.15 (m, 2H), 2.96 (m, 2H), 1.64 (m, 2H), 1.41 (m, 4H), 1.28 (m, 4H), 0.85 (t, 3H).

Intermediate 44

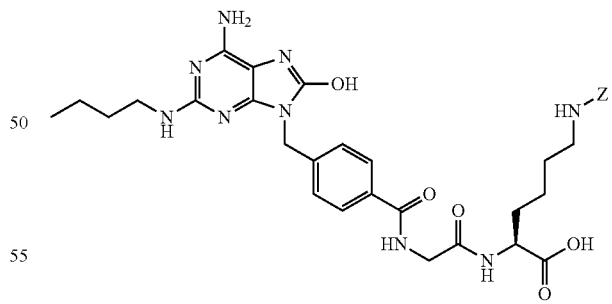

(S)-2-(2-(4-((6-amino-2-(butylamino)-8-hydroxy-9H-purin-9-yl)methyl)benzamido)acetamido)-6-(benzyloxycarbonylamino)hexanoic acid The title compound was prepared from intermediate 44 by following the procedure described for example 4, intermediate 34.

Intermediate 45

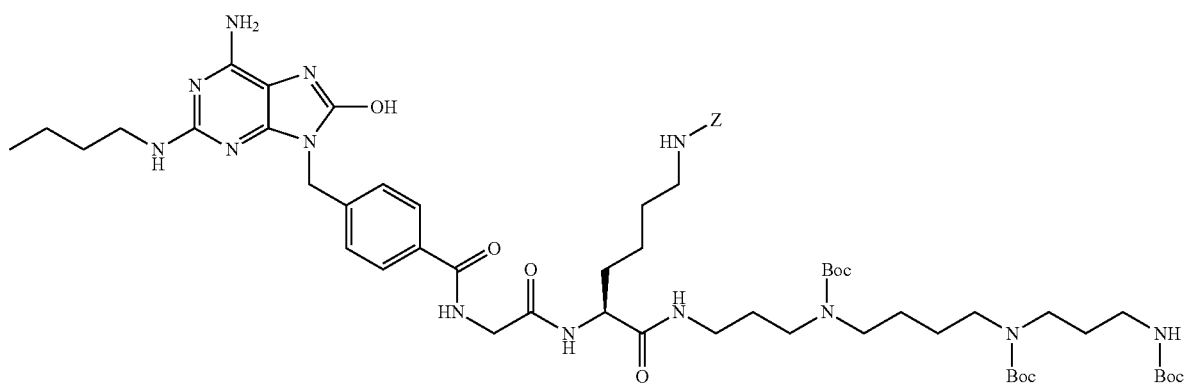

N1,N5,N10-triBoc-spermine (S)-2-(2-(4-((6-amino-2-(butylamino)-8-hydroxy-9H-purin-9-yl)methyl)benzamido)acetamido)-6-(benzyloxycarbonylamino)hexanamide The title compound was prepared from intermediate 44 by following the procedure described for example 4, intermediate 35. Intermediate 45 was characterized by the following spectroscopic data: $^1$H NMR (DMSO-d6, 300 MHz) δ (ppm) 9.70 (s, 1H), 8.73 (t, 1H), 8.04 (d, 1H), 7.87 (m, 1H), 7.80 (d, 2H), 7.32 (m, 7H), 7.22 (t, 1H), 6.76 (t, 1H), 6.20 (t, 1H), 6.04 (sl, 2H), 4.99 (s, 2H), 4.85 (s, 2H), 4.16 (m, 1H), 3.87 (d, 2H), 3.07-2.86 (m, 18H), 1.68-1.52 (m, 6H), 1.48-1.20 (m, 37H), 0.83 (t, 3H).

Intermediate 46

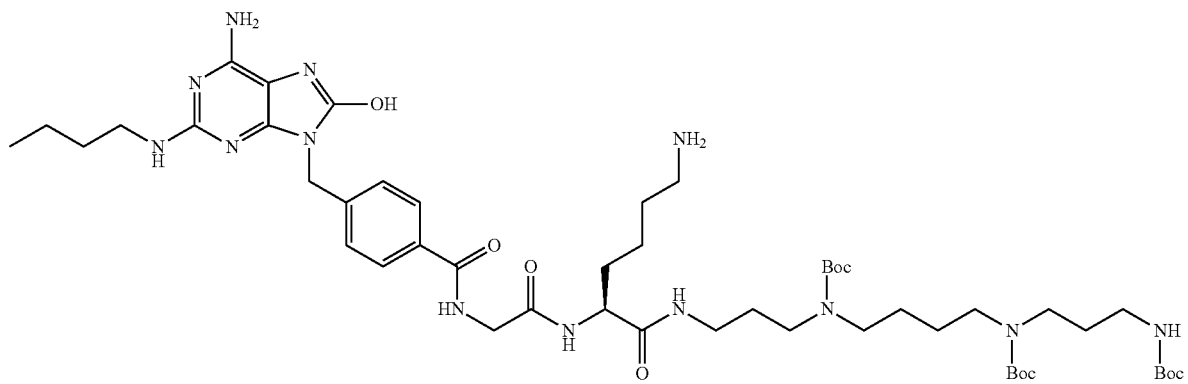

N1,N5,N10-triBoc-spermine (S)-2-(2-(4-((6-amino-2-(butylamino)-8-hydroxy-9H-purin-9-yl)methyl)benzamido)acetamido)-6amino-hexanamide The title compound was prepared from intermediate 45 by following the procedure described for example 4, intermediate 36.

Intermediate 47

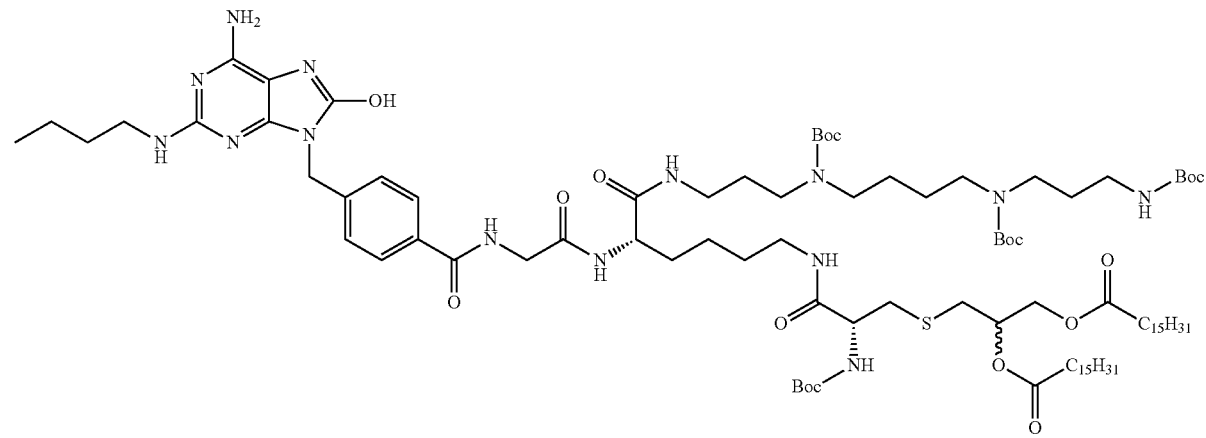

((20S,27R)-20-(2-(4-((6-amino-2-(butylamino)-8-hydroxy-9H-purin-9-yl)methyl)benzamido)acetamido)-9,14-bis(tert-butoxycarbonyl)-27-(tert-butoxycarbonyl amino)-2,2-dimethyl-4,19,26-trioxo-3-oxa-29-thia-5,9,14,18,25-pentaazadotri acontane-31,32-diyl dipalmitate The title compound was prepared from intermediate 46 by following the procedure described for example 4, intermediate 37. Intermediate 47 was characterized by the following spectroscopic data: $^1$H NMR (DMSO-d$_6$, 300 MHz) δ (ppm) 9.65 (s, 1H), 8.72 (m, 1H), 8.03 (m, 2H), 7.80 (d, 2H), 7.34 (d, 2H), 6.85 (m, 1H), 6.74 (sl, 2H), 5.07 (m, 1H), 4.85 (s, 2H), 4.27 (m, 2H), 4.12 (m, 2H), 3.88 (m, 2H), 3.25-3.00 (m, 16H), 2.88 (m, 6H), 2.25 (m, 4H), 1.80-1.70 (m, 8H), 1.65-1.35 (m, 46H), 1.34-1.20 (m, 52H), 0.85 (m, 9H).

Compound 48

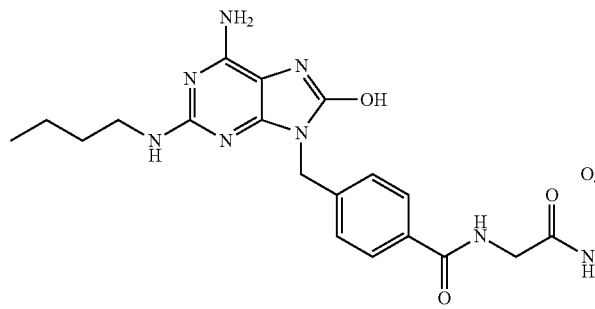

(6R,13S)-6,27-diamino-13-(2-(4-((6-amino-2-(butylamino)-8-hydroxy-9H-purin-9-yl)methyl)benzamido)acetamido)-7,14-dioxo-4-thia-8,15,19,24-tetraazaheptacosane-1,2-diyl dipalmitate The title compound was prepared from intermediate 47 by following the procedure described for example 1, compound 20. Compound 48 was characterized by the following spectroscopic data: $^1$H NMR (DMSO-d$_6$, 300 MHz) δ (ppm) 9.16 (m, 2H), 8.87 (m, 4H), 8.37 (m, 1H), 8.19 (m, 6H), 7.86 (d, 2H), 7.39 (d, 2H), 5.13 (m, 1H), 4.91 (s, 2H), 4.32 (m, 2H), 4.14 (m, 2H), 3.93 (m, 2H), 3.14 (m, 2H), 3.16-2.87 (m, 14H), 2.27 (m, 2H), 1.97 (m, 2H), 1.77 (m, 2H), 1.67 (m, 4H), 1.48 (m, 14H), 1.32-1.16 (m, 54H), 0.82 (m, 9H). MS (+)-ES [M+H]$^+$ 1380.2 m/z.

Example 6

Molecule CL475

Intermediate 49

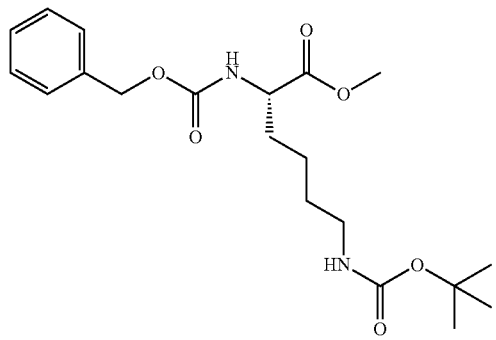

(S)-Methyl 2-(benzyloxycarbonylamino)-6-(tert-butoxycarbonylamino)hexanoate

The title compound was prepared from Z-L-Lys(Boc)OH by following the procedure described for example 4, intermediate 31. Intermediate 49 was characterized by the following spectroscopic data: $^1$H NMR (DMSO-d$_6$, 300 MHz) δ (ppm) 7.47 (m, 5H), 6.76 (t, 1H), 5.09 (s, 2H), 4.51 (m, 1H), 3.68 (s, 3H), 3.18 (m, 2H), 1.90 (m, 2H), 1.55 (m, 2H), 1.38 (s, 9H), 1.25 (m, 2H).

CL-487

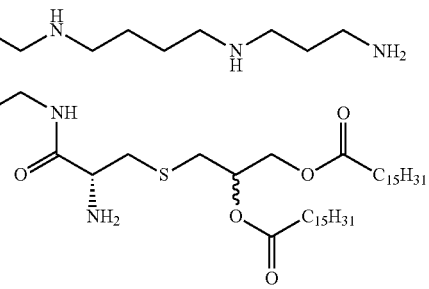

Intermediate 50

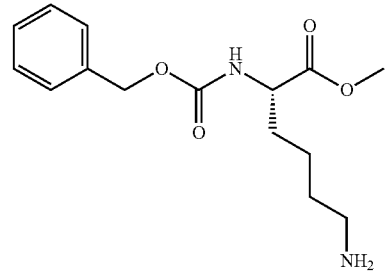

(S)-Methyl-6-amino-2-(benzyloxycarbonylamino)hexanoate

The title compound was prepared from intermediate 49 by following the procedure described for example 4, intermediate 32. Intermediate 50 was characterized by the following spectroscopic data: $^1$H NMR (DMSO-d$_6$, 300 MHz) δ (ppm) 8.45 (sl, 2H), 7.33 (m, 5H), 7.31 (t, 1H), 5.01 (s, 2H), 3.96 (m, 1H), 3.75 (s, 3H), 3.02 (m, 2H), 1.78 (m, 2H), 1.44 (m, 4H).

Intermediate 51

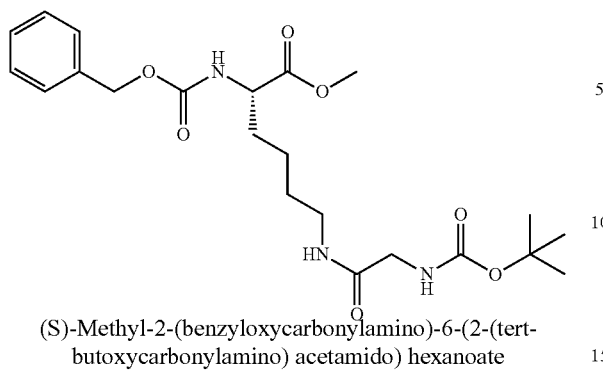

(S)-Methyl-2-(benzyloxycarbonylamino)-6-(2-(tert-butoxycarbonylamino) acetamido) hexanoate The title compound was prepared from intermediate 37 by following the procedure described for example 5, intermediate 41. Intermediate 51 was characterized by the following spectroscopic data: $^1$H NMR (DMSO-$d_6$, 300 MHz) δ (ppm) 8.10 (t, 1H), 7.95 (t, 1H), 7.47-7.38 (m, 5H), 6.95 (t, 1H), 5.11 (s, 2H), 4.55 (m, 1H), 3.95 (d, 2H), 3.70 (s, 3H), 3.02 (m, 2H), 1.90 (m, 2H), 1.55 (m, 2H), 1.38 (s, 9H), 1.25 (m, 2H).

Intermediate 52

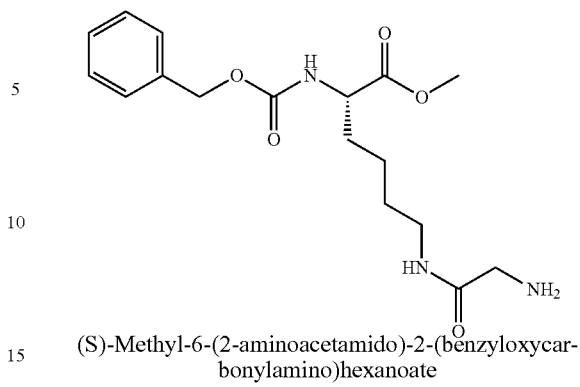

(S)-Methyl-6-(2-aminoacetamido)-2-(benzyloxycarbonylamino)hexanoate

The title compound was prepared from intermediate 51 by following the procedure described for example 4, intermediate 32. Intermediate 52 was characterized by the following spectroscopic data: $^1$H NMR (DMSO-$d_6$, 300 MHz) δ (ppm) 8.35 (sl, 2H), 8.05 (t, 1H), 7.47-7.38 (m, 5H), 7.05 (t, 1H), 5.09 (s, 2H), 4.51 (m, 1H), 3.80 (d, 2H), 3.69 (s, 3H), 3.15 (m, 2H), 1.98 (m, 2H), 1.56-1.44 (m, 4H).

Intermediate 53

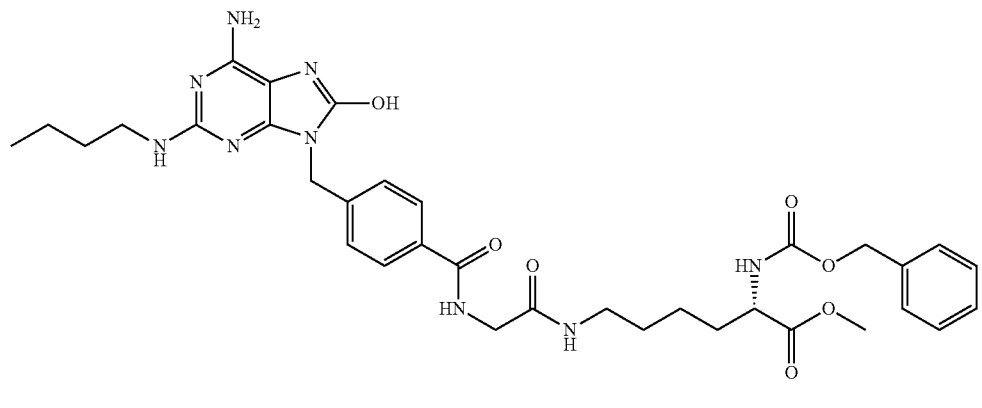

(S)-Methyl-6-(2-(4-((6-amino-2-(butylamino)-8-hydroxy-9H-purin-9-yl)methyl)benzamido) acetamido)-2-(benzyloxycarbonylamino)hexanoate The title compound was prepared from intermediate 52 by following the procedure described for example 4, intermediate 33. Intermediate 53 was characterized by the following spectroscopic data: $^1$H NMR (DMSO-$d_6$, 300 MHz) δ (ppm) 10.20 (s, 1H), 8.68 (t, 1H), 8.33 (d, 1H), 7.36 (d, 2H), 7.32-7.24 (m, 9H), 6.28 (sl, 2H), 6.14 (t, 1H), 4.85 (s, 2H), 4.24 (s, 2H), 4.25 (m, 1H), 3.92 (d, 2H), 3.62 (s, 3H), 3.15 (m, 2H), 2.90 (m, 2H), 1.68-1.61 (m, 2H), 1.46-1.24 (m, 8H), 0.85 (t, 3H).

Intermediate 54

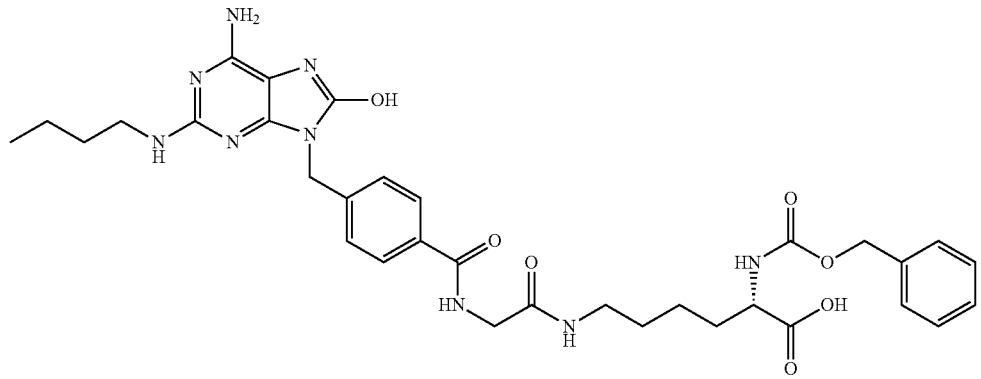

(S)-6-(2-(4-((6-amino-2-(butylamino)-8-hydroxy-9H-purin-9-yl)methyl)benzamido)acetamido)-2-(benzyloxycarbonylamino)hexanoic acid The title compound was prepared from intermediate 53 by following the procedure described for example 4, intermediate 34.

Intermediate 55

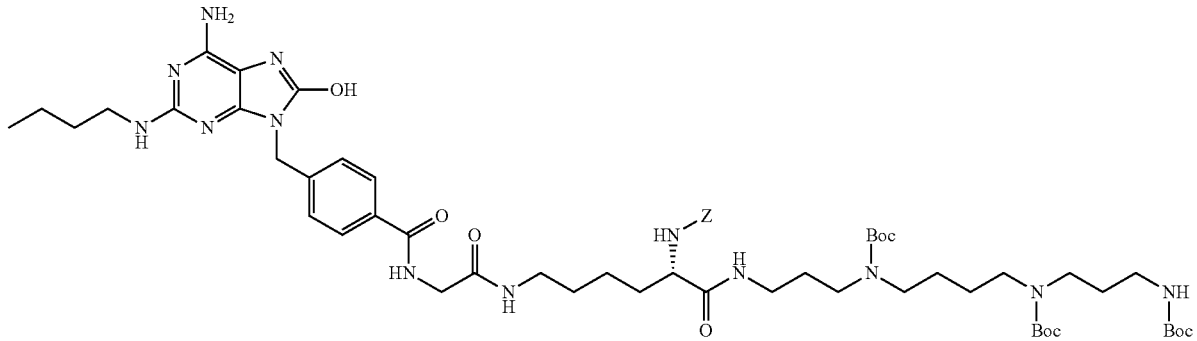

N1,N5,N10-triBoc-spermine (S)-6-(2-(4-((6-amino-2-(butylamino)-8-hydroxy-9H-purin-9-yl)methyl)benzamido)acetamido)-2-(benzyloxycarbonylamino)hexanamide The title compound was prepared from intermediate 54 by following the procedure described for example 4, intermediate 35. Intermediate 55 was characterized by the following spectroscopic data: $^1$H NMR (DMSO-$d_6$, 300 MHz) δ (ppm) 9.69 (s, 1H), 8.71 (t, 1H), 8.03 (d, 1H), 7.86 (d, 2H), 7.36-7.32 (m, 7H), 7.20 (t, 1H), 6.72 (t, 1H), 6.17 (t, 1H), 6.03 (sl, 2H), 4.89 (s, 2H), 4.86 (s, 2H), 4.16 (m, 1H), 3.88 (d, 2H), 3.15 (m, 2H), 3.16-2.85 (m, 16H), 1.68-1.52 (m, 6H), 1.48-1.20 (m, 37H), 0.83 (t, 3H).

Intermediate 56

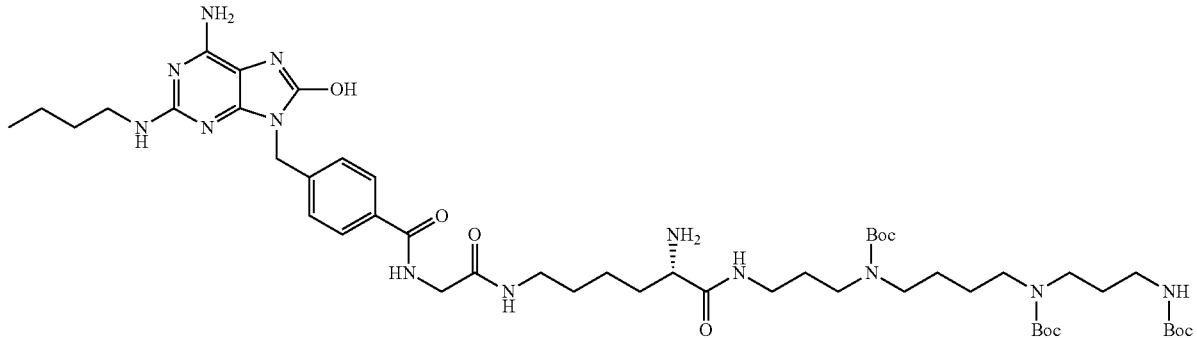

N1,N5,N10-triBoc-spermine (S)-6-(2-(4-((6-amino-2-(butylamino)-8-hydroxy-9H-purin-9-yl)methyl)benzamido)acetamido)hexanamide The title compound was prepared from intermediate 55 by following the procedure described for example 4, intermediate 36.

Intermediate 57

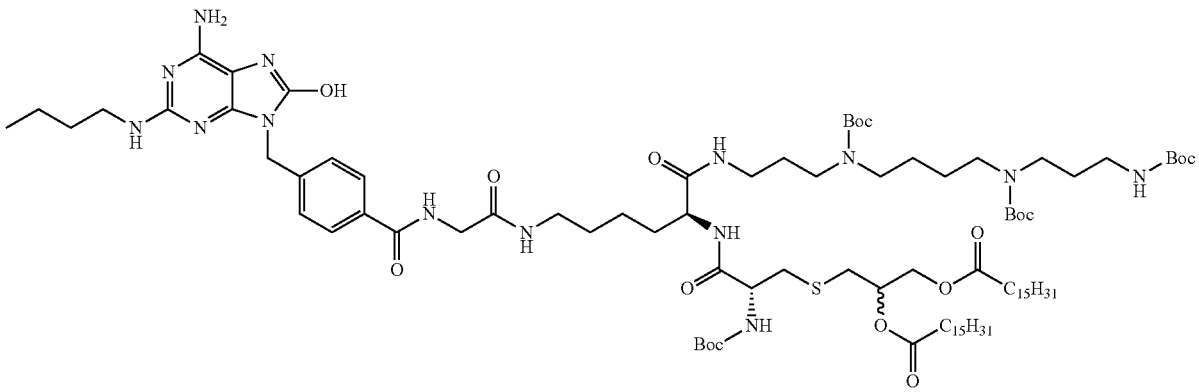

(20S,23R)-20-(4-(2-(4-((6-amino-2-(butylamino)-8-hydroxy-9H-purin-9-yl)methyl)benzamido)acetamido)butyl)-9,14-bis(tert-butoxycarbonyl)-23-(tert-butoxy carbonylamino)-2,2-dimethyl-4,19,22-trioxo-3-oxa-25-thia-5,9,14,18,21-pentaaza octacosane-27,28-diyl dipalmitate The title compound was prepared from intermediate 56 by following the procedure described for example 4, intermediate 37. Intermediate 57 was characterized by the following spectroscopic data: $^1$H NMR (DMSO-d$_6$, 300 MHz) δ (ppm) 9.77 (s, 1H), 8.77 (m, 1H), 8.04 (m, 2H), 7.86 (m, 4H), 7.37 (d, 2H), 6.85 (m, 1H), 6.73 (sl, 2H), 5.10 (m, 1H), 4.87 (s, 2H), 4.33 (m, 1H), 4.18-4.00 (m, 4H), 3.89 (m, 2H), 3.15-3.00 (m, 24H), 2.28 (m, 6H), 1.65-1.05 (m, 100H), 0.85 (m, 9H).

Compound 58

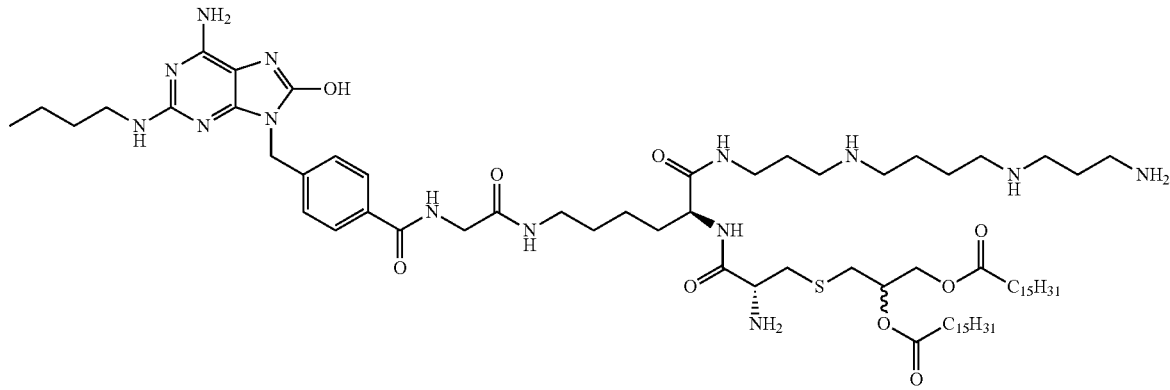

(6R,9S)-6,23-diamino-9-(4-(2-(4-((6-amino-2-(butylamino)-8-hydroxy-9H-purin-9-yl)methyl)benzamido)acetamido)butyl)-7,10-dioxo-4-thia-8,11,15,20-tetraazatrico sane-1,2-diyl dipalmitate The title compound was prepared from intermediate 57 by following the procedure described for example 1, compound 20. Compound 58 was characterized by the following spectroscopic data: $^1$H NMR (DMSO-d$_6$, 300 MHz) δ (ppm) 11.04 (s, 1H), 9.22 (m, 1H), 8.98 (m, 1H), 8.88 (m, 1H), 8.75 (m, 1H), 8.52 (m, 2H), 8.16 (m, 2H), 7.91 (d, 2H), 7.40 (d, 2H), 5.15 (m, 1H), 4.92 (s, 2H), 4.28 (m, 2H), 4.12 (m, 3H), 3.94 (m, 4H), 3.28 (m, 2H), 3.16-2.85 (m, 22H), 2.27 (m, 4H), 2.00 (m, 2H), 1.79-1.69 (m, 6H), 1.53-1.37 (m, 6H), 1.29-1.16 (m, 54H), 0.82 (m, 9H). MS (+)-ES [M+H]$^+$ 1380.0 m/z.

Example 7

Molecule CL527

Intermediate 59

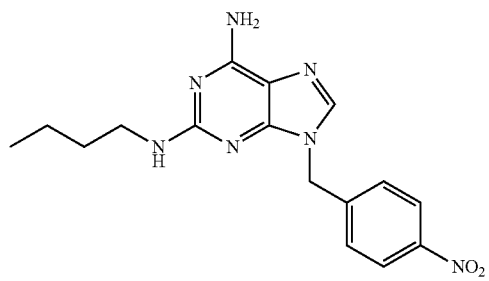

N2-butyl-9-(4-nitrobenzyl)-9H-purine-2,6-diamine

-amino-2-butylamino-9H-purine, intermediate 1 (9.93 g, 48.2 mmol) and Cs$_2$CO$_3$ (15.69 g, 48.2 mmol) were suspended in DMF (200 mL). 4-nitrobenzyl bromide (12.48 mg, 57.8 mmol) was added thereto and the mixture was stirred at rt for 18 h. After condensing the suspension in vacuo, to the residue was added brine and the mixture was extracted with ethyl acetate. The organic layer was washed the mixture was with brine, dried on MgSO$_4$, filtered and the solvent was evaporated in vacuo. The residue was purified on column of silica gel (5% MeOH/DCM) to give the subject compound (11.51 g, yield 70%). Intermediate 59 was characterized by the following spectroscopic data: $^1$H NMR (DMSO-d$_6$, 300 MHz) δ (ppm) 8.19 (d, 2H), 7.83 (s, 1H), 7.49 (d, 2H), 6.69 (sl, 2H), 6.25 (t, 1H), 5.34 (s, 2H), 3.17 (m, 2H), 1.41 (m, 2H), 1.25 (q, 2H), 0.83 (t, 3H).

Intermediate 60

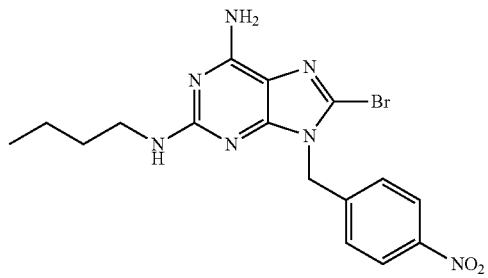

8-bromo-N2-butyl-9-(4-nitrobenzyl)-9H-purine-2,6-diamine

The title compound was prepared from intermediate 59 by following the procedure described for example 1, intermediate 3. Intermediate 60 was characterized by the following spectroscopic data: $^1$H NMR (DMSO-d$_6$, 300 MHz) δ (ppm) 8.21 (d, 2H), 7.51 (d, 2H), 5.39 (s, 2H), 3.15 (m, 2H), 1.44 (m, 2H), 1.27 (q, 2H), 0.82 (t, 3H).

115

Intermediate 61

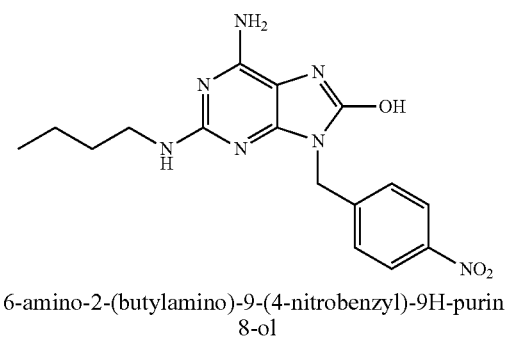

6-amino-2-(butylamino)-9-(4-nitrobenzyl)-9H-purin-8-ol

To a solution of intermediate 60 (14.17 g, 33.72 mmol) in 150 mL of dioxane was added 100 mL of HCl 37% solution. The mixture was refluxed on heating under stirring for 18 h. The mixture was concentrated in vacuo and the pH was adjusted to 5 with 2 N aqueous NaOH to precipitate a solid. The solid was filtered, washed with water and dried in vacuo in presence of $P_2O_5$ to give the subject compound (11.05 g, yield 90%). Intermediate 61 was characterized by the following spectroscopic data: $^1$H NMR (DMSO-$d_6$, 300 MHz) δ (ppm) 10.35 (sl, 1H), 8.19 (d, 2H), 7.53 (d, 2H), 7.23 (sl, 2H), 4.98 (s, 2H), 3.19 (m, 2H), 1.41 (m, 2H), 1.24 (q, 2H), 0.80 (t, 3H).

Intermediate 62

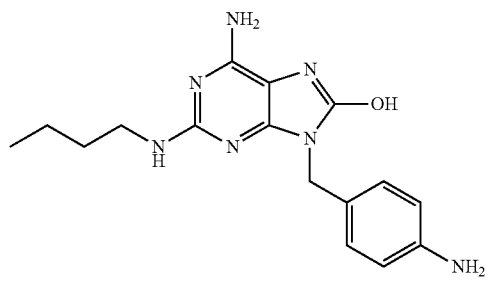

6-amino-9-(4-aminobenzyl)-2-(butylamino)-9H-purin-8-ol

To a solution of intermediate 61 (11.05 g, 30.9 mmol) in a mixture of THF/MeOH (1/1) (200 mL) was added Pd/C (1.79 g, 1.6 mmol), the reaction mixture was stirred at rt under hydrogen atmosphere for 18 h. Then the mixture was filtered off over Celite, washed with MeOH. The filtrate was concentrated in vacuo and the residue was purified on column of silica gel with DCM/MeOH (0-7%) as eluent to give the subject compound (7.52 g, yield 74%). Intermediate 62 was characterized by the following spectroscopic data: $^1$H NMR (DMSO-$d_6$, 300 MHz) δ (ppm) 10.02 (sl, 1H), 7.07 (d, 2H), 6.87 (sl, 2H), 6.77 (sl, 2H), 6.58 (d, 2H), 4.65 (s, 2H), 3.23 (m, 2H), 1.49 (m, 2H), 1.33 (q, 2H), 0.92 (t, 3H).

Intermediate 63

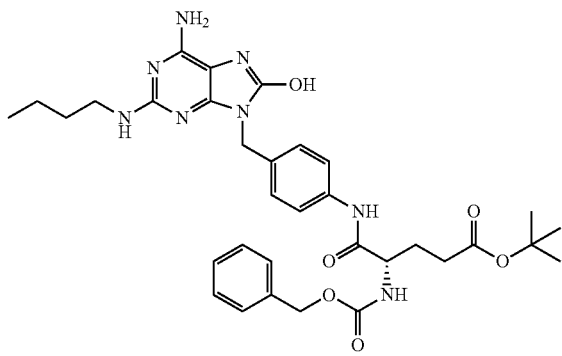

116

(S)-tert-butyl-5-(4-((6-amino-2-(butylamino)-8-hydroxy-9H-purin-9-yl)methyl)phenyl amino)-4-(benzyloxycarbonylamino)-5-oxopentanoate To a solution of Z-L-Glu(OtBu)OH (2.06 g, 6.1 mmol) in dry DMF (50 mL) was added intermediate 62 (2.0 g, 6.1 mmol), HATU (2.55 g, 6.7 mmol), and DIEA (5.23 mL, 30.5 mmol). The mixture was stirred at rt overnight. The solvent was then removed in vacuo and the residue was dissolved in EtOAc (50 mL) and washed with saturated NaHCO$_3$ solution water and brine. The organic layer was dried over MgSO$_4$, filtered and concentrated in vacuo. The crude compound was purified on column of silica gel (3% MeOH/DCM) to give the subject compound (3.12 g, yield 79%). Intermediate 63 was characterized by the following spectroscopic data: $^1$H NMR (DMSO-$d_6$, 300 MHz) δ (ppm) 9.62 (sl, 1H), 8.76 (d, 1H), 8.53 (d, 1H), 7.52 (d, 2H), 7.34 (s, 5H), 7.23 (d, 2H), 6.22 (t, 1H), 6.01 (sl, 2H), 5.02 (s, 2H), 4.74 (s, 2H), 4.12 (m, 1H), 3.15 (m, 2H), 2.26 (m, 2H), 2.08-1.79 (m, 2H), 1.44 (m, 2H), 1.42 (s, 9H), 1.35 (m, 2H), 0.89 (t, 3H).

Intermediate 64

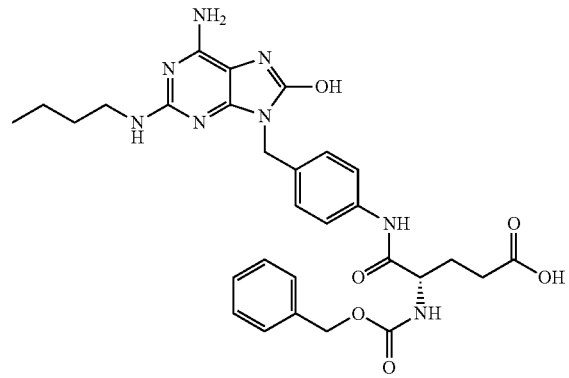

(S)-5-(4-((6-amino-2-(butylamino)-8-hydroxy-9H-purin-9-yl)methyl)phenylamino)-4-(benzyloxycarbonylamino)-5-oxopentanoic acid To a solution of intermediate 63 (3.12 g, 2.13 mmol) in DMF (40 mL) was added 40 mL of TFA. The mixture was stirred at rt overnight. Then the solvent were removed in vacuo, the residue was coevaporated 3 times with toluene. The residue was precipitated in Et$_2$O to give the subject compound (2.33 g, yield 82%). Intermediate 64 was characterized by the following spectroscopic data: $^1$H NMR (DMSO-$d_6$, 300 MHz) δ (ppm) 10.62 (sl, 1H), 10.10 (sl, 1H), 7.82 (sl, 2H), 7.64 (d, 1H), 7.54 (d, 2H), 7.36 (s, 5H), 7.27 (m, 3H), 5.02 (s, 2H), 4.79 (s, 2H), 4.12 (m, 1H), 3.29 (m, 2H), 2.26 (m, 2H), 1.93-1.79 (m, 2H), 1.50 (m, 2H), 1.32 (m, 2H), 0.85 (t, 3H).

Intermediate 65

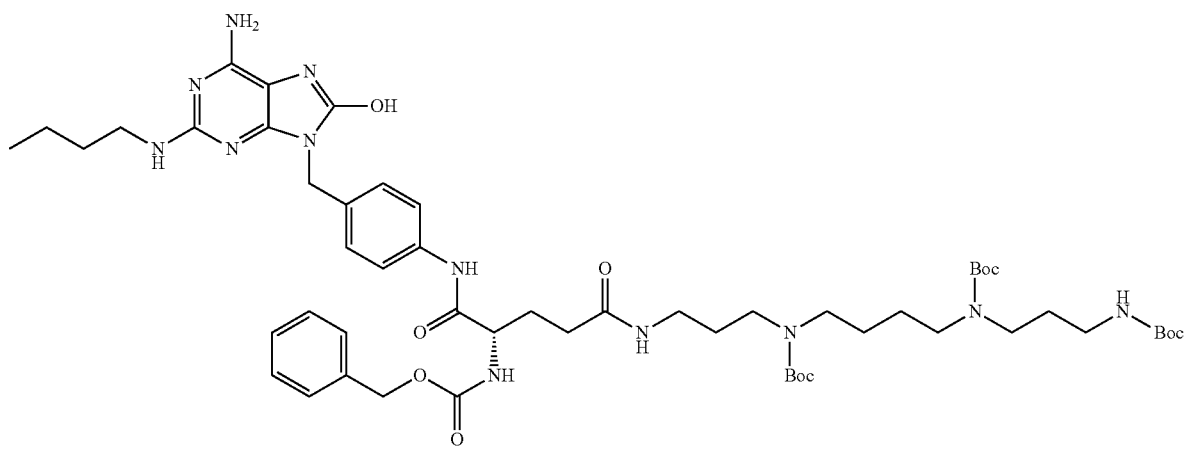

N1,N5,N10-triBoc-spermine (S)-5-(4-((6-amino-2-(butylamino)-8-hydroxy-9H-purin-9-yl)methyl)phenylamino)-4-(benzyloxycarbonylamino)-5-oxopentanamide The title compound was prepared from intermediate 64 by following the procedure described for example 4, intermediate 35. Intermediate 65 was characterized by the following spectroscopic data: $^1$H NMR (DMSO-$d_6$, 300 MHz) δ (ppm) 10.32 (s, 1H), 9.61 (m, 1H), 7.79 (m, 1H), 7.56 (m, 1H), 7.52 (d, 2H), 7.34 (m, 5H), 7.25 (d, 2H), 6.76 (m, 1H), 6.23 (t, 1H), 6.02 (sl, 2H), 5.01 m, 2H), 4.74 (s, 2H), 4.10 (s, 2H), 3.34-3.07 (m, 14H), 2.89 (m, 2H), 1.56 (m, 4H), 1.48-1.20 (m, 33H), 0.83 (t, 3H).

Intermediate 66

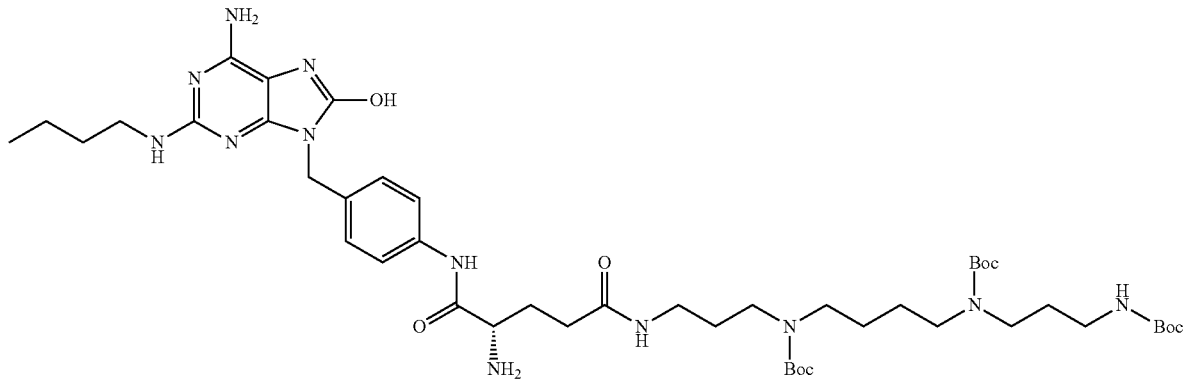

N1,N5,N10-triBoc-spermine (S)-5-(4-((6-amino-2-(butylamino)-8-hydroxy-9H-purin-9-yl)methyl)phenylamino)-4-amino-5-oxopentanamide The title compound was prepared from intermediate 65 by following the procedure described for example 4, intermediate 36.

Intermediate 67

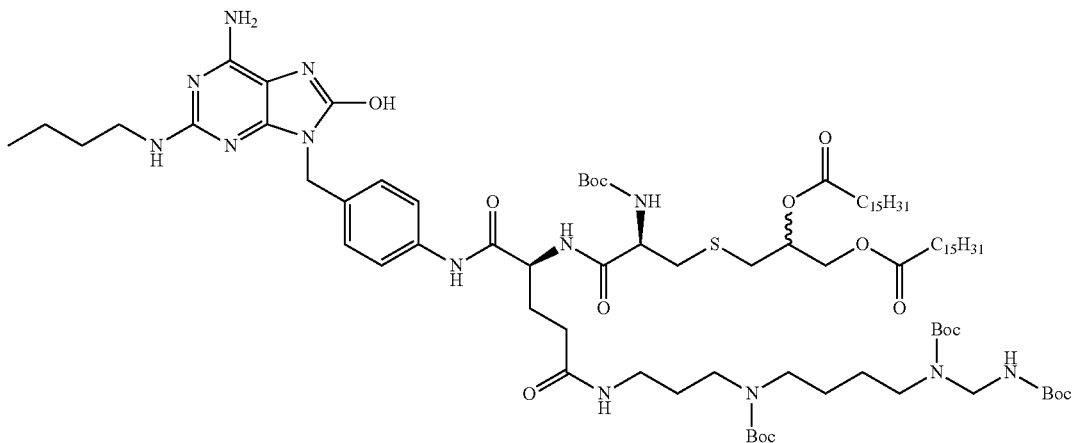

(22S,25R)-22-(4-((6-amino-2-(butylamino)-8-hydroxy-9H-purin-9-yl)methyl)phenyl carbamoyl)-9,14-bis(tert-butoxycarbonyl)-25-(tert-butoxycarbonylamino)-2,2-dimethyl-4,19,24-trioxo-3-oxa-27-thia-5,9,14,18,23-pentaazatriacontane-29,30-diyl dipalmitate The title compound was prepared from intermediate 66 by following the procedure described for example 4, intermediate 37. Intermediate 67 was characterized by the following spectroscopic data: $^1$H NMR (DMSO-$d_6$, 300 MHz) δ (ppm) 10.00 (s, 1H), 9.59 (s, 1H), 8.14 (m, 1H), 7.76 (m, 1H), 7.50 (d, 2H), 7.23 (d, 2H), 7.04 (t, 1H), 6.77 (m, 1H), 6.19 (m, 1H), 5.98 (sl, 2H), 5.07 (m, 1H), 4.73 (s, 2H), 4.36-4.25 (m, 2H), 4.10 (m, 2H), 3.25-3.00 (m, 12H), 2.97-2.72 (m, 6H), 2.24 (m, 4H), 1.47 (m, 7H), 1.36 (m, 46H), 1.22 (m, 50H), 0.86 (m, 9H).

Compound 68

CL-527

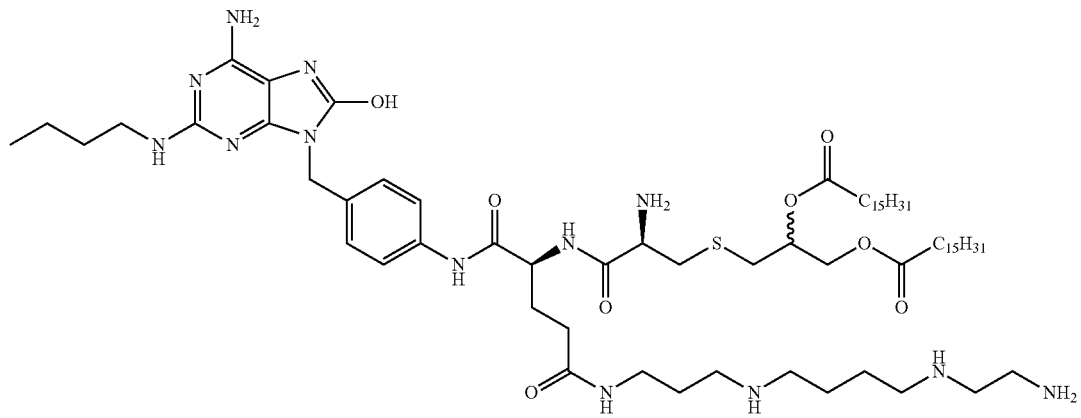

mixture was stirred for 15 min and the solvent was drained this was repeated 2 times, then the resin was suspended in 15 mL of DMF. The resin-DMF mixture was stirred at rt for 30 min. Meanwhile, (2.18 g, 4.6 mmol) Fmoc-Lys(Boc)OH, 10 mL DMF, and (810 μL, 4.6 mmol) of DIEA were charged to a 100 mL flask. The contents of the flask were stirred at rt to dissolve the solid. After the DMF was drained from the reactor, the mixture containing the Fmoc-Lys(Boc)OH was charged to the reactor with the resin and stirred. After 2 h the reactor was drained. Active sites on the resin were end-capped with a mixture of DIEA:MeOH (1:9 mL). This mixture was then stirred at rt for 1 h. The bed was drained, washed with 2 times with 15 mL DMF, 2 times with 15 mL DCM, and one time with 15 mL DMF. The last wash demonstrated a negative UV test.

To the reactor containing Fmoc-Lys(Boc)-O-2-CTC resin was charged 10 mL of 20% piperidine in DMF which was (6R,9S)-6,25-diamino-9-(4-((6-amino-2-(butylamino)-8-hydroxy-9H-purin-9-yl)methyl)phenylcarbamoyl)-7,12-dioxo-4-thia-8,13,17,22-tetraazapentacosane-1,2-diyl dipalmitate The title compound was prepared from intermediate 67 by following the procedure described for example 1, compound 20. Compound 68 was characterized by the following spectroscopic data: $^1$H NMR (DMSO-$d_6$, 300 MHz) δ (ppm) 10.86 (s, 1H), 9.17 (m, 2H), 9.27 (m, 2H), 8.46 (m, 2H), 8.46 (m, 4H), 8.09 (m, 4H), 7.60 (d, 2H), 7.26 (d, 2H), 5.13 (m, 1H), 4.78 (s, 2H), 4.55 (m, 1H), 4.26 (, 1H), 4.08 (m, 2H), 3.08-2.72 (m, 14H), 2.23 (m, 6H), 1.97 (m, 4H), 1.69 (m, 4H), 1.47 (m, 4H), 1.22 (m, 46H), 0.85 (m, 9H). MS (+)-ES [M+H]$^+$ 1294.9 m/z.

Example 8

Molecule CL143

Solid Phase Synthesis of

Intermediate 69

BocCys(Pam$_2$)-Ser(tBu)-Lys(Boc)-Lys(Boc)-Lys(Boc)-Lys(Boc)-2CTC resin

A 20 mL peptide reactor was purged with nitrogen and then charged with 1 g of 2-CTC resin and 15 mL of DCM the then stirred at rt for 30 min. The reactor was drained and then charged with 10 mL of 20% piperidine in DMF. The mixture was stirred for 30 min at rt and the reactor drained. The resin bed was then washed with 3 times with 10 mL DMF, 3 times with 10 mL of DCM, 3 times with 10 mL of MeOH and 3 times with 10 mL of DMF. The last wash was then sampled for piperidine levels by qualitative ninhydrin test.

Then, (2.18 g, 4.6 mmol) of Fmoc-Lys(Boc)OH, (810 μL, 4.6 mmol) of DIEA, and 10 mL DMF were charged to a flask. The contents were stirred at ambient temperature to dissolve the solid which were then cooled to 10° C. Then (1.77 g, 4.6 mmol) of HATU was charged into the flask. The mixture was stirred at 10° C. to dissolve solid. The cooled HATU solution was charged to the solid phase reactor. The flask was then washed with 5 mL of DMF and the wash charged to the SPPS reactor. The mixture was stirred at rt for 3 h. The resin beads were then sampled for the completion of the reaction by a Keiser Test. After the reaction was complete, the reactor was drained and the resin bed washed with 3 times with 10 mL DMF, 3 times with 10 mL of DCM, 3 times with 10 mL of MeOH and 3 times with 10 mL of DMF.

Then, 10 mL 20% piperidine in DMF was charged to the reactor which was then stirred at RT for 30 min. The reactor was drained and 10 mL of 20% piperidine in DMF was added. The mixture was stirred at rt for 30 min and then the reactor was drained. The resin bed was then washed with 3 times with 10 mL DMF, 3 times with 10 mL of DCM, 3 times with 10 mL of MeOH and 3 times with 10 mL of DMF. The last wash was then sampled for piperidine levels by qualitative ninhydrin test.

Then, (2.18 g, 4.6 mmol) of Fmoc-Lys(Boc)OH, (810 μL, 4.6 mmol) of DIEA, and 10 mL DMF were charged to a flask. The contents were stirred at ambient temperature to dissolve the solid which were then cooled to 10° C. Then (1.77 g, 4.6 mmol) of HATU was charged into the flask.

The mixture was stirred at 10° C. to dissolve solid. The cooled HATU solution was charged to the solid phase reactor. The flask was then washed with 5 mL of DMF and the wash charged to the SPPS reactor. The mixture was stirred at rt for 3 h. The resin beads were then sampled for the completion of the reaction by a Keiser Test. After the reaction was complete, the reactor was drained and the resin bed washed with 3 times with 10 mL DMF, 3 times with 10 mL of DCM, 3 times with 10 mL of MeOH and 3 times with 10 mL of DMF.

Then, 10 mL 20% piperidine in DMF was charged to the reactor which was then stirred at rt for 30 min. The reactor was drained and 10 mL of 20% piperidine in DMF was added. The mixture was stirred at rt for 30 min and then the reactor was drained. The resin bed was then washed with 3 times with 10 mL DMF, 3 times with 10 mL of DCM, 3 times with 10 mL of MeOH and 3 times with 10 mL of DMF. The last wash was then sampled for piperidine levels by qualitative ninhydrin test.

Then, (2.18 g, 4.6 mmol) of Fmoc-Lys(Boc)OH, (810 μL, 4.6 mmol) of DIEA, and 10 mL DMF were charged to a flask. The contents were stirred at ambient temperature to dissolve the solid which were then cooled to 10° C. Then (1.77 g, 4.6 mmol) of HATU was charged into the flask. The mixture was stirred at 10° C. to dissolve solid. The cooled HATU solution was charged to the solid phase reactor. The flask was then washed with 5 mL of DMF and the wash charged to the SPPS reactor. The mixture was stirred at rt for 3 h. The resin beads were then sampled for the completion of the reaction by a Keiser Test. After the reaction was complete, the reactor was drained and the resin bed washed with 3 times with 10 mL DMF, 3 times with 10 mL of DCM, 3 times with 10 mL of MeOH and 3 times with 10 mL of DMF.

Then, 10 mL 20% piperidine in DMF was charged to the reactor which was then stirred at rt for 30 min. The reactor was drained and 10 mL of 20% piperidine in DMF was added. The mixture was stirred at rt for 30 min and then the reactor was drained. The resin bed was then washed with 3 times with 10 mL DMF, 3 times with 10 mL of DCM, 3 times with 10 mL of MeOH and 3 times with 10 mL of DMF. The last wash was then sampled for piperidine levels by qualitative Ninhydrin test.

Then, (1.78 g, 4.6 mmol) of Fmoc-Ser(tBu)OH, (810 μL, 4.65 mmol) of DIEA, and 10 mL DMF were charged to a flask. The contents were stirred at ambient temperature to dissolve the solid which were then cooled to 10° C. Then (1.77 g, 4.6 mmol) of HATU was charged into the flask. The mixture was stirred at 10° C. to dissolve solid. The cooled HATU solution was charged to the solid phase reactor. The flask was then washed with 5 mL of DMF and the wash charged to the SPPS reactor. The mixture was stirred at rt for 3 h. The resin beads were then sampled for the completion of the reaction by a Keiser Test. After the reaction was complete, the reactor was drained and the resin bed washed 3 times with 10 mL DMF, 3 times with 10 mL of DCM, 3 times with 10 mL of MeOH and 3 times with 10 mL of DMF.

Then, 10 mL 20% piperidine in DMF was charged to the reactor which was then stirred at rt for 30 min. The reactor was drained and 10 mL of 20% piperidine in DMF was added. The mixture was stirred at rt for 30 min and then the reactor was drained. The resin bed was then washed with 3 times with 10 mL DMF, 3 times with 10 mL of DCM, 3 times with 10 mL of MeOH and 3 times with 10 mL of DMF. The last wash was then sampled for piperidine levels by qualitative Ninhydrin test.

Then, (3.00 g, 4.6 mmol) of intermediate 18, (810 μL, 4.6 mmol) of DIEA, and 10 mL DMF were charged to a flask. The contents were stirred at rt to dissolve the solid which were then cooled to 10° C. Then (1.77 g, 4.6 mmol) of HATU was charged into the flask. The mixture was stirred at 10° C. to dissolve solid. The cooled HATU solution was charged to the solid phase reactor. The flask was then washed with 5 mL of DMF and the wash charged to the SPPS reactor. The mixture was stirred at rt for 3 h. The resin beads were then sampled for the completion of the reaction by a Keiser Test. After the reaction was complete, the reactor was drained and the resin bed washed with 3 times with 10 mL DMF, 3 times with 10 mL of DCM, 3 times with 10 mL of MeOH and 3 times with 10 mL of DMF to give the intermediate 69.

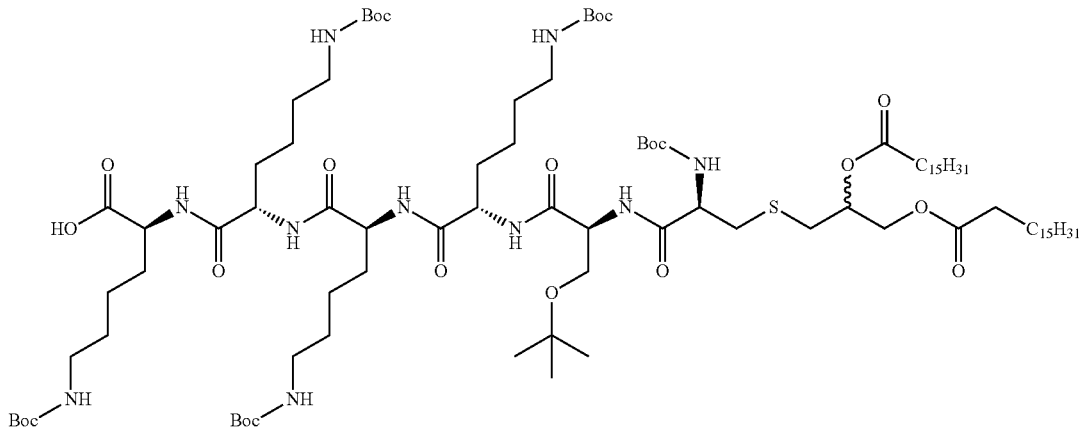

Intermediate 70

123

(2S,5S,8S,11S,14S,17R)-17-(tert-butoxycarbonylamino)-2,5,8,11-tetrakis(4-(tert-butoxy carbonylamino)butyl)-14-(tert-butoxymethyl)-4,7,10,13,16,24-hexaoxo-21-(palmitoyloxy)-23-oxa-19-thia-3,6,9,12,15-pentaazanonatriacontan-1-oic acid Cleavage from resin was achieved with 5 cycles of 15 min each at rt of 15 mL of a solution 2% TFA, 1% TES in dichloromethane. This solution was charged to the solid phase reactor containing the intermediate 69, the reaction was stirred; the colour of the reaction changed from cycle to cycle from yellow/orange to brownish. After each cycle, cleavage reaction was directly quenched by pouring the reaction into dilute pyridine (pyridine/ethanol 1:9 (v/v)). Resin was then removed by filtration with a frit and subjected to the next cycle. All filtrates were pooled, concentrated to an orange semi-liquid under vacuo. The residue was purified on column of silica gel (5% MeOH/DCM) to give the subject compound (1.02 g). Intermediate 70 was characterized by the following spectroscopic data: $^1$H NMR (DMSO-$d_6$, 300 MHz) δ (ppm) 7.94 (m, 4H), 6.73 (m, 4H), 4.31-4.08 (m, 8H), 3.44 (m, 2H), 2.97 (m, 2H), 2.87 (m, 16H), 2.27 (m, 4H), 1.63-1.23 (m, 127H), 0.84 (t, 6H).

Intermediate 71

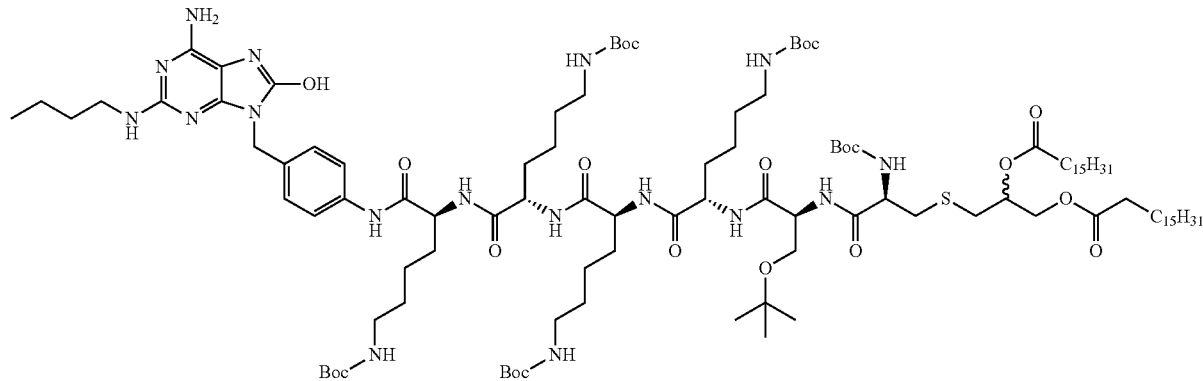

(10S,13S,16S,19S,22S,25R)-10-(4-((6-amino-2-(butylamino)-8-hydroxy-9H-purin-9-yl)methyl)phenylcarbamoyl)-25-(tert-butoxycarbonylamino)-13,16,19-tris(4-(tert-butoxy carbonylamino)butyl)-22-(hydroxymethyl)-2,2-dimethyl-4,12,15,18,21,24-hexaoxo-3-oxa-27-thia-5,11,14,17,20,23-hexaazatriacontane-29,30-diyl dipalmitate To a solution of intermediate 70 (1.00 g, 0.5 mmol) in dry DMF (10 mL) was added intermediate 62 (179 mg, 0.5 mmol), HATU (228 mg, 0.6 mmol), and DIEA (189 µL, 1.1 mmol). The mixture was stirred at rt for 4 h. The solvent was then removed in vacuo and the residue was dissolved in EtOAc (50 mL) and washed with saturated NaHCO$_3$ solution water and brine. The organic layer was dried over MgSO$_4$, filtered and concentrated in vacuo. The crude compound was purified on column of silica gel (2% MeOH/DCM) to give the subject compound (550 mg, yield 47%). Intermediate 71 was characterized by the following spectroscopic data: $^1$H NMR (DMSO-$d_6$, 300 MHz) δ (ppm) 9.59 (s, 1H), 7.91-7.84 (m, 4H), 7.54 (m, 1H), 7.24 (d, 2H), 6.89 (m, 2H), 6.15 (m, 1H), 5.98 (m, 2H), 5.06 (m, 1H), 4.73 (s, 2H), 4.31-4.13 (m, 4H), 3.44 (m, 2H), 3.16 (m, 2H), 2.85 (m, 10H), 2.25 (m, 4H), 1.68-1.42 (m, 12H), 1.36 (m, 56H), 1.08 (m, 56H), 0.88 (m, 12H), 0.84 (t, 9H).

Compound 72

CL413

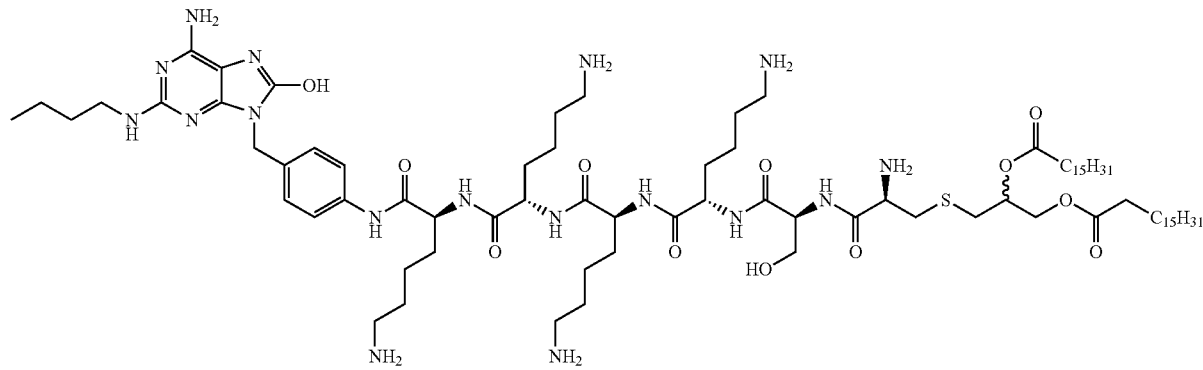

(6S,9S,12S,15S,18S,21R)-6,25-diamino-21-(4-((6-amino-2-(butylamino)-8-hydroxy-9H-purin-9-yl)methyl)phenylcarbamoyl)-12,15,18-tris(4-aminobutyl)-9-(hydroxyl methyl)-7,10,13,16,19-pentaoxo-4-thia-8,11,14,17,20-pentaazapentacosane-1,2-diyl dipalmitate Global deprotection was carried out in DCM diluted with cleavage cocktail: TFA/thioanisole/phenol/water/TES in the mixing ratio (% w/w): 89:2.5:2.5:5:1 in DCM. To a solution of intermediate 71 (527 mg, 0.3 mmol) in 10 ml of DCM was added 5 mL of the cleavage cocktail and the mixture was stirred for 5 hours at room temperature. The product was then recovered by addition of 50 ml MTBE, cooling the reaction down to 0° C. in an ice bath for 30 min under stirring and filtrating off the salt precipitate that has formed in the while time. The filter cake is rinsed with MTBE several times which is then dried at room temperature to give the subject compound (387 mg, yield 98%). Compound 72 was characterized by the following spectroscopic data: $^1$H NMR (MeOD-d$_4$, 300 MHz) δ (ppm) 8.26 (s, 1H), 7.99 (m, 2H), 7.65 (m, 2H), 7.55 (d, 2H), 7.39 (m, 2H), 5.25 (m, 1H), 4.97 (m, 2H), 4.70 (m, 2H), 4.446-4.18 (m, 6H), 3.47 (m, 2H), 2.95 (m, 10H), 2.34 (m, 4H), 1.91-1.41 (m, 30H), 1.00 (m, 50H), 0.93 (m, 9H). MS (+)-ES [M+H]$^+$ 1581.1 m/z.

Example 9

Molecule CL530

Intermediate 73

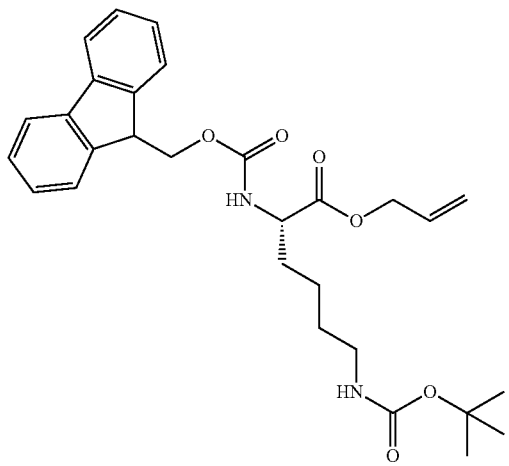

(S)-allyl 2-(((9H-fluoren-9-yl)methoxy)carbonylamino)-6-(tert-butoxycarbonyl amino) hexanoate To a solution of Fmoc-L-Lys(Boc)OH (3.00 g, 6.4 mmol) in dry DMF (40 mL) was added Cs$_2$CO$_3$ (1.15 g, 3.5 mmol). The mixture was stirred at rt for 30 min. To the reaction mixture was then added dropwise allyl bromide (609 μL, 7.1 mmol) and the mixture was stirred at rt for 2 h. The solvent was removed in vacuo and the residue was dissolved in EtOAc (100 mL) and washed with saturated NaHCO$_3$ solution water and brine. The organic layer was dried over MgSO$_4$, filtered and concentrated in vacuo. The crude compound was used for the next step without any further purification. Intermediate 73 was characterized by the following spectroscopic data: $^1$H NMR (DMSO-d$_6$, 300 MHz) δ (ppm) 7.91 (d, 2H), 7.80 (d, 1H), 7.71 (d, 2H), 7.41 (t, 2H), 7.33 (t, 2H), 6.82 (t, 1H), 5.87 (m, 1H), 5.32-5.17 (m, 2H), 4.56 (m, 2H), 4.31-4.20 (m, 3H), 4.01 (m, 1H), 0.2.88 (m, 2H), 1.61 (m, 2H), 1.52 (m, 4H), 1.45 (m, 12H).

Intermediate 74

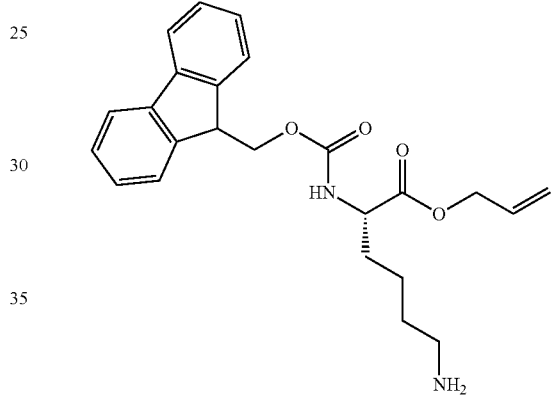

(S)-allyl 2-(((9H-fluoren-9-yl)methoxy)carbonylamino)-6-aminohexanoate

To a solution of Fmoc-L-Lys(Boc)OAll 73 (3.3 g, 6.4 mmol) in DCM (20 mL) was added 10 mL of TFA. The mixture was stirred at rt for 1 h. Then the solvent were removed in vacuo, the residue was coevaporated 3 times with toluene. The residue was precipitated in diethyl ether to give the subject compound (3.3 g, yield 97%). The crude compound was used for the next step without any further purification.

Intermediate 75

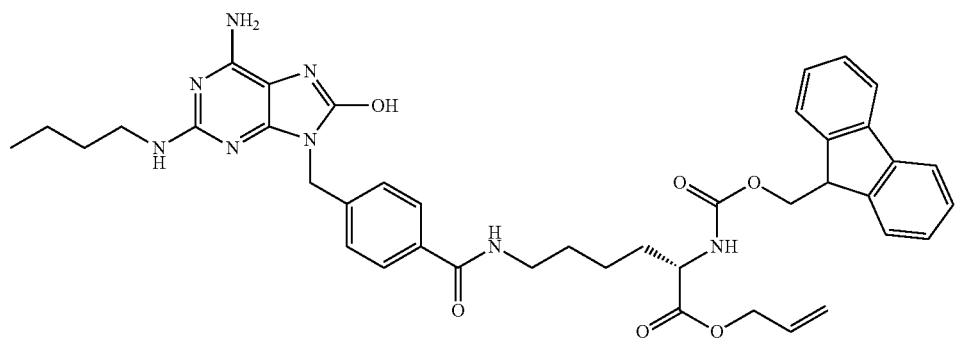

(S)-allyl 2-(((9H-fluoren-9-yl)methoxy)carbonylamino)-6-(4-((4-amino-6-(butyl amino)-2-hydroxy-1H-benzo[d]imidazol-1-yl)methyl)benzamido)hexanoate To a solution of Fmoc-L-LysOAll 74 (3.2 g, 6.1 mmol) in dry DMF (50 mL) was added intermediate 4 (2.31 g, 6.5 mmol), HATU (2.71 g, 7.1 mmol), and DIEA (2.24 mL, 12.9 mmol). The mixture was stirred at rt overnight. The solvent was then removed in vacuo and the residue was dissolved in DCM (150 mL) and washed with saturated NaHCO$_3$ solution water and brine. The organic layer was dried over MgSO$_4$, filtered and concentrated in vacuo. The crude compound was purified on column of silica gel (3% MeOH/DCM) to give the subject compound (2.58 g, yield 53%). Intermediate 75 was characterized by the following spectroscopic data: $^1$H NMR (DMSO-d$_6$, 300 MHz) δ (ppm) 9.66 (s, 1H), 8.39 (t, 1H), 7.88 (d, 2H), 7.80-7.69 (m, 4H), 7.42-7.28 (m, 6H), 6.18 (t, 1H), 6.10 (sl, 2H), 5.30 (m, 1H), 5.15 (m, 2H), 4.84 (s, 2H), 4.55 (d, 2H), 4.27 (m, 3H), 4.01 (m, 1H), 3.32-3.13 (m, 4H), 1.65 (m, 2H), 1.52-1.22 (m, 8H), 0.84 (t, 3H).

ing spectroscopic data: $^1$H NMR (DMSO-d$_6$, 300 MHz) δ (ppm) 9.83 (s, 1H), 8.40 (m, 1H), 7.86-7.23 (m, 15H), 6.39 (m, 3H), 4.85 (s, 2H), 4.25 (s, 2H), 3.91 (m, 1H), 3.42 (m, 1H), 3.32 (m, 4H), 1.68-1.05 (m, 10H), 0.84 (t, 3H).

Solid Phase Synthesis of

Intermediate 77

BocCys(Pam$_2$)-Ser(tBu)-Lys(Boc)-Lys(Boc)-(Intermediate 76)-Lys(Boc)OH

The title peptide was prepared following the procedure described for example 8, intermediate 69 using the intermediate 76 at the 2$^{nd}$ step and the intermediate 18 at last step. Cleavage from resin was achieved with 5 cycles of 15 min each at RT of 15 mL of a solution 2% TFA, 1% TES in dichloromethane. This solution was charged to the solid phase reactor, the reaction was stirred; the colour of the reaction changed from cycle to cycle from yellow/orange to brownish. After each cycle, cleavage reaction was directly

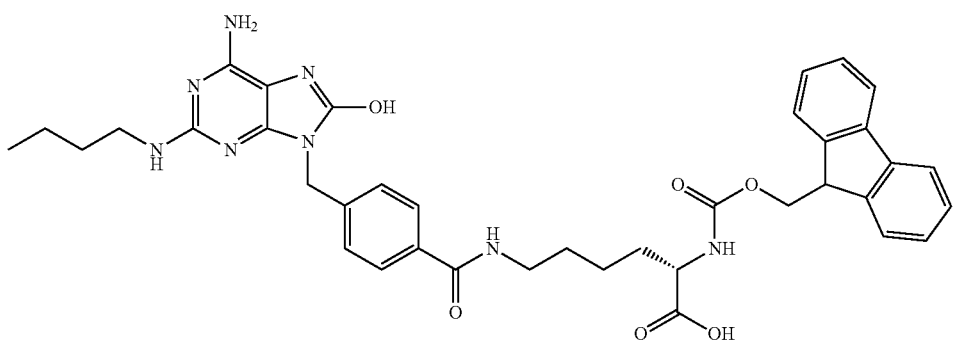

Intermediate 76

(S)-2-(((9H-fluoren-9-yl)methoxy)carbonylamino)-6-(4-((4-amino-6-(butylamino)-2-hydroxy-1H-benzo[d]imidazol-1-yl)methyl)benzamido)hexanoic acid To a solution of intermediate 75 (1.45 g, 1.9 mmol) in a mixture of dry DMF/THF (15/30 mL) was added Tetrakis (triphenylphosphine)palladium(0) (0.67 g, 0.6 mmol), N-methyl aniline (631 μL, 5.8 mmol). The mixture was stirred at rt for 45 min. The solvent was then removed in vacuo and the residue was triturated in a mixture of EtOAc/0.1 N HCl solution (100 mL) the precipitate was filtrated and washed with water EtOH and Et$_2$O to give the subject compound (1.2 g, yield 85%). Intermediate 76was characterized by the followquenched by pouring the reaction into dilute pyridine (pyridine/ethanol 1:9 (v/v)). Resin was then removed by filtration with a frit and subjected to the next cycle. All filtrates were pooled, concentrated to an orange semi-liquid under vacuo. The residue was purified on column of silica gel (8% MeOH/DCM) to give the subject compound (220 mg). Intermediate 77 was characterized by the following spectroscopic data: $^1$H NMR (DMSO-d$_6$, 300 MHz) δ (ppm) 9.75 (s, 1H), 8.39 (s, 1H), 7.83 (m, 2H), 7.73 (d, 2H), 7.27 (d, 2H), 6.69 (m, 2H), 6.13 (t, 1H), 5.95 (sl, 2H), 5.05 (m, 1H), 4.78 (s, 2H), 4.35-4.13 (m, 6H), 3.42 (m, 2H), 2.81 (m, 16H), 2.25 (m, 4H), 1.70 (m, 4H), 1.68-1.42 (m, 12H), 1.36 (m, 48H), 1.12 (m, 56H), 1.03 (s, 9H), 0.85 (t, 9H).

Compound 78

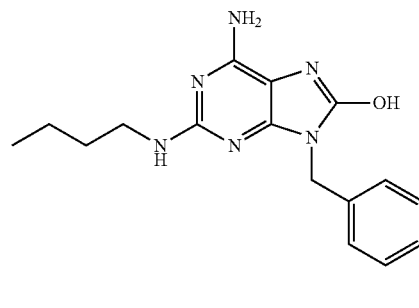
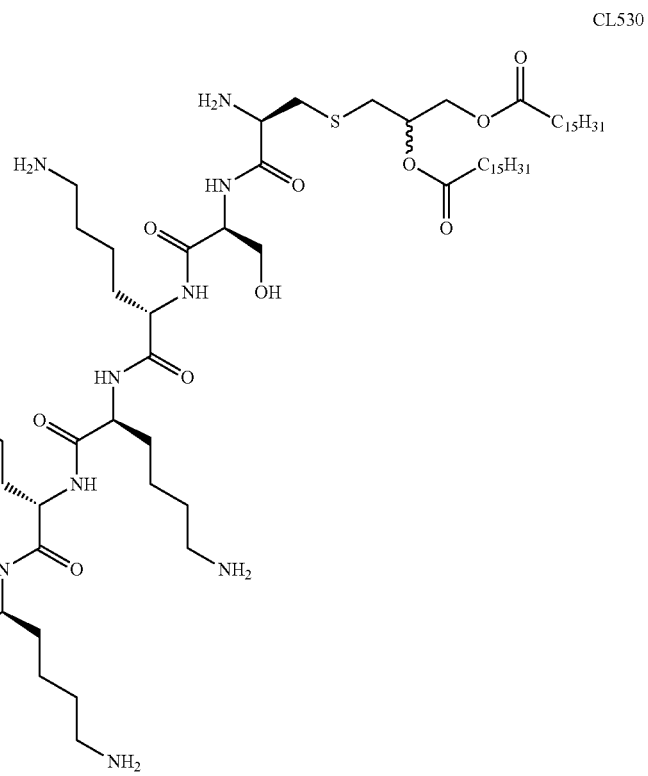

CL530

(2S,5S,8S,11S,14S,17R)-17-amino-5-(4-(4-((6-amino-2-(butylamino)-8-hydroxy-9H-purin-9-yl)methyl)benzamido)butyl)-2,8,11-tris(4-aminobutyl)-14-(hydroxymethyl)-4,7,10,13,16,24-hexaoxo-21-(palmitoyloxy)-23-oxa-19-thia-3,6,9,12,15-pentaaza nonatriacontan-1-oic acid To a solution of intermediate 77 (220 mg, 0.1 mmol) in 5 ml of dioxane was added 10 mL of the 4N HCl dioxane solution. The mixture was stirred at rt overnight. The solvent was removed in vacuo and the residue was then recovered by addition of 50 mL Et$_2$O, cooling the reaction down to 0° C. in an ice bath for 30 min under stirring and filtrating off the salt precipitate that has formed in the while time. The filter cake is rinsed with Et$_2$O several times which is then dried at rt to give the subject compound (169 mg, yield 98%). Compound 78 was characterized by the following spectroscopic data: $^1$H NMR (D$_2$O-d$_2$, 300 MHz) δ (ppm) 7.66 (m, 2H), 7.25 (m, 2H), 4.82 (s, 2H), 4.22-4.13 (m, 6H), 3.57 (m, 2H), 2.88 (m, 16H), 2.28 (m, 4H), 1.73-1.52 (m, 16H), 1.51-1.23 (m, 10H), 1.25 (m, 56H), 0.75 (m, 9H). MS (+)-ES [M+H]$^+$ 1610.1 m/z.

Example 10

Molecule CL531

Solid Phase Synthesis of

Intermediate 79

BocCys(Pam$_2$)-Ser(tBu)-Lys(Boc)-(Intermediate 76)-Lys(Boc)-Lys(Boc)OH

The title peptide was prepared following the procedure described for example 8, intermediate 69 using the intermediate 76 at the 3$^{th}$ step and the intermediate 18 at last step. Cleavage from resin was achieved with 5 cycles of 15 min each at rt of 15 mL of a solution 2% TFA, 1% TES in dichloromethane. This solution was charged to the solid phase reactor, the reaction was stirred; the colour of the reaction changed from cycle to cycle from yellow/orange to brownish. After each cycle, cleavage reaction was directly quenched by pouring the reaction into dilute pyridine (pyridine/ethanol 1:9 (v/v)). Resin was then removed by filtration with a frit and subjected to the next cycle. All filtrates were pooled, concentrated to an orange semi-liquid under vacuo. The residue was purified on column of silica gel (8% MeOH/DCM) to give the subject compound (230 mg). Compound 79 was characterized by the following spectroscopic data: $^1$H NMR (DMSO-d$_6$, 300 MHz) δ (ppm) 9.75 (s, 1H), 8.39 (s, 1H), 7.83 (m, 2H), 7.73 (d, 2H), 7.27 (d, 2H), 6.69 (m, 2H), 6.13 (t, 1H), 5.95 (sl, 2H), 5.05 (m, 1H), 4.78 (m, 6H), 4.35-4.13 (m, 6H), 3.42 (m, 2H), 2.81 (m, 16H), 2.25 (m, 4H), 1.70 (m, 4H), 1.68-1.42 (m, 12H), 1.36 (m, 48H), 1.12 (m, 56H), 1.03 (s, 9H), 0.85 (t, 9H).

Compound 80

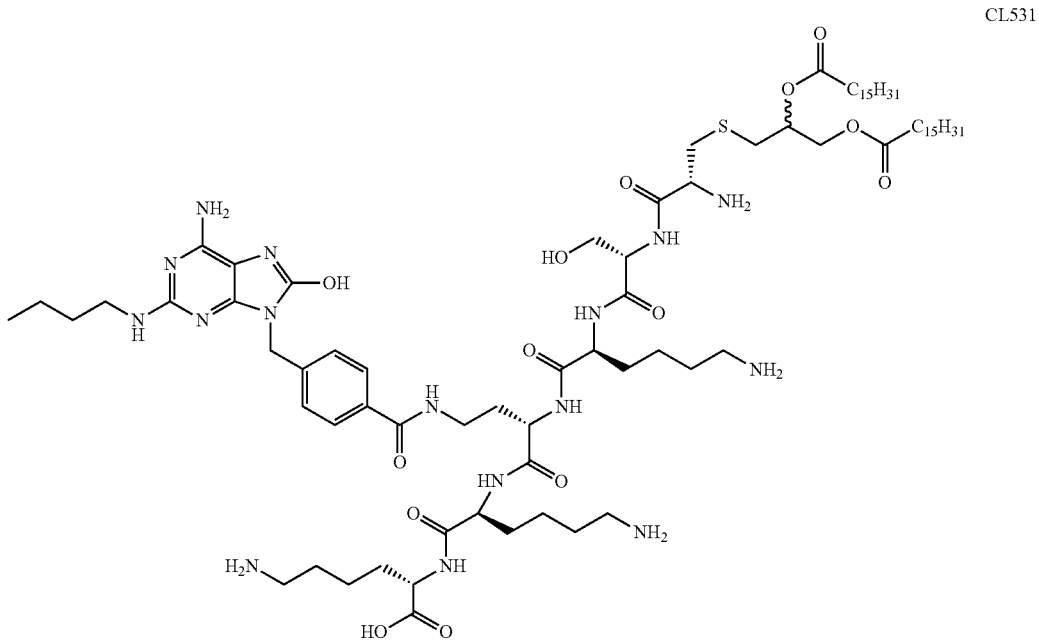

(2S,5S,8S,11S,14S,17R)-17-amino-8-(4-(4-((6-amino-2-(butylamino)-8-hydroxy-9H-purin-9-yl)methyl)benzamido)butyl)-2,5,11-tris(4-aminobutyl)-14-(hydroxymethyl)-4,7,10,13,16,24-hexaoxo-21-(palmitoyloxy)-23-oxa-19-thia-3,6,9,12,15-pentaaza nonatriacontan-1-oic acid The title compound was prepared from intermediate 79 by following the procedure described for example 9, compound 78. Compound 80 was characterized by the following spectroscopic data: $^1$H NMR (D$_2$O-d$_2$, 300 MHz) δ (ppm) 7.65 (d, 2H), 7.25 (d, 2H), 4.84 (s, 2H), 4.23-4.06 (m, 6H), 3.42 (m, 4H), 2.76 (m, 12H), 2.28 (m, 4H), 1.58 (m, 16H), 1.33 (m, 10H), 1.08 (m, 56H), 0.78 (m, 9H). MS (+)-ES [M+H]$^+$ 1610.1 m/z.

Example 11

Molecule CL533

Solid Phase Synthesis of

Intermediate 81

BocCys(Pam$_2$)-Ser(tBu)-(Intermediate 76)-Lys(Boc)-Lys(Boc)-Lys(Boc)OH

The title peptide was prepared following the procedure described for example 8, intermediate 62 using the intermediate 76 at the 4$^{th}$ step and the intermediate 18 at last step. Cleavage from resin was achieved with 5 cycles of 15 min each at rt of 15 mL of a solution 2% TFA, 1% TES in dichloromethane. This solution was charged to the solid phase reactor, the reaction was stirred; the colour of the reaction changed from cycle to cycle from yellow/orange to brownish. After each cycle, cleavage reaction was directly quenched by pouring the reaction into dilute pyridine (pyridine/ethanol 1:9 (v/v)). Resin was then removed by filtration with a frit and subjected to the next cycle. All filtrates were pooled, concentrated to an orange semi-liquid under vacuo. The residue was purified on column of silica gel (8% MeOH/DCM) to give the subject compound (260 mg). Compound 81 was characterized by the following spectroscopic data: $^1$H NMR (DMSO-d$_6$, 300 MHz) δ (ppm) 9.78 (s, 1H), 8.36 (s, 1H), 7.98 (m, 1H), 7.87 (m, 2H), 7.82 (m, 2H), 7.73 (d, 2H), 7.34 (d, 2H), 7.05 (t, 1H), 6.73 (sl, 2H), 5.07 (m, 1H), 4.84 (s, 2H), 4.31-4.22 (m, 7H), 3.45 (m, 10H), 3.16 (m, 4H), 2.86 (m, 6H), 2.28 (m, 4H), 1.78 (m, 4H), 1.68-1.42 (m, 12H), 1.36 (m, 48H), 1.12 (m, 52H), 1.03 (s, 9H), 0.84 (t, 9H).

Compound 82

CL533

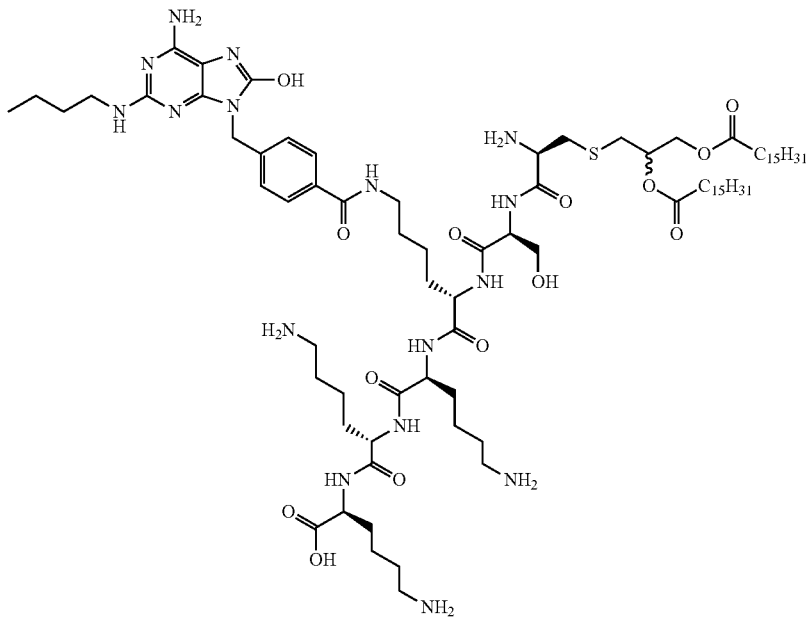

(2S,5S,8S,11S,14S,17R)-17-amino-11-(4-(4-((6-amino-2-(butylamino)-8-hydroxy-9H-purin-9-yl)methyl)benzamido)butyl)-2,5,8-tris(4-aminobutyl)-14-(hydroxyl methyl)-4,7,10,13,16,24-hexaoxo-21-(palmitoyloxy)-23-oxa-19-thia-3,6,9,12,15-pentaazanonatria contan-1-oic acid The title compound was prepared from intermediate 81 by following the procedure described for example 9, compound 78. Compound 82 was characterized by the following spectroscopic data: $^1$H NMR (D$_2$O-d$_2$, 300 MHz) δ (ppm) 7.67 (d, 2H), 7.24 (d, 2H), 4.88 (s, 2H), 4.22-4.02 (m, 6H), 3.42 (m, 4H), 2.86 (m, 12H), 2.28 (m, 4H), 1.58 (m, 16H), 1.27 (m, 10H), 1.06 (m, 56H), 0.73 (m, 9H). MS (+)-ES [M+H]$^+$ 1610.1 m/z.

Example 12

Molecule CL534

Solid Phase Synthesis of

Intermediate 83

PamCys(Pam$_2$)-Ser(tBu)-Lys(Boc)-Lys(Boc)-Lys(Boc)-Lys(Boc)-2CTC resin

The title peptide was prepared following the procedure described for example 8, intermediate 69 using the intermediate 23 at last step.

Intermediate 84

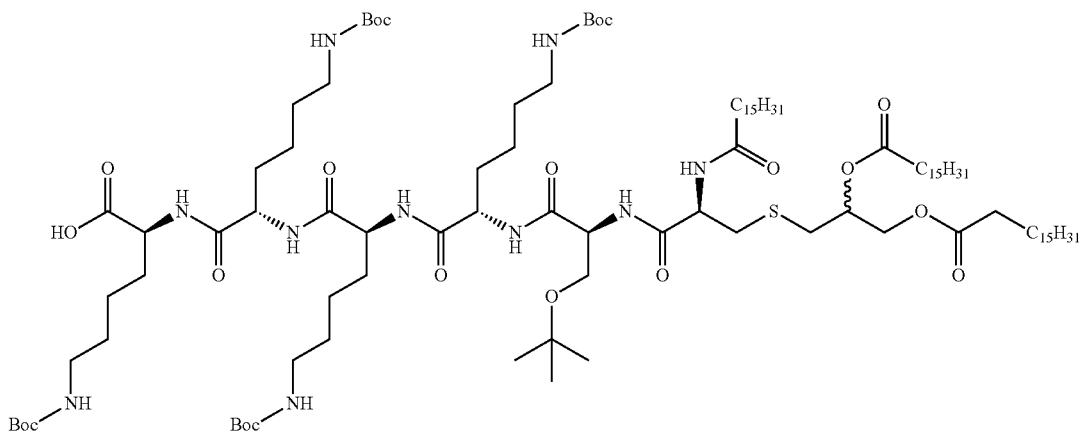

(2S,5S,8S,11S,14S,17R)-2,5,8,11-tetrakis(4-(tert-butoxycarbonylamino)butyl)-14-(tert-butoxymethyl)-4,7,10,13,16,24-hexaoxo-17-palmitamido-21-(palmitoyloxy)-23-oxa-19-thia-3,6,9,12,15-pentaazanonatriacontan-1-oic acid The title compound was prepared from intermediate 83 by following the procedure described for example 8, intermediate 70. Intermediate 84 was characterized by the following spectroscopic data: $^1$H NMR (DMSO-$d_6$, 300 MHz) δ (ppm) 8.04 (m, 5H), 6.83 (m, 5H), 4.31-4.08 (m, 7H), 3.44 (m, 8H), 2.34 (m, 6H), 2.15 (m, 16H), 1.55 (m, 14H), 1.48 (m, 44H), 1.23 (m, 72H), 1.02 (m, 9H), 0.84 (t, 9H).

Intermediate 85

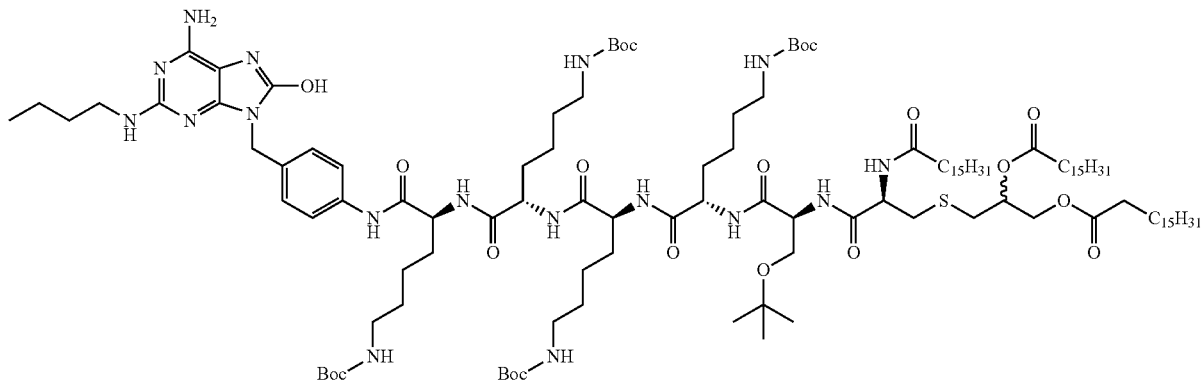

(10S,13S,16S,19S,22S,25R)-10-(4-((6-amino-2-(butylamino)-8-hydroxy-9H-purin-9-yl)methyl)phenylcarbamoyl)-13,16,19-tris(4-(tert-butoxycarbonylamino)butyl)-22-(tert-butoxy methyl)-2,2-dimethyl-4,12,15,18,21,24-hexaoxo-25-palmitamido-3-oxa-27-thia-5,11,14,17,20,23-hexaazatriacontane-29,30-diyl dipalmitate The title compound was prepared from intermediate 84 by following the procedure described for example 8, intermediate 71. Intermediate 85 was characterized by the following spectroscopic data: $^1$H NMR (DMSO-$d_6$, 300 MHz) δ (ppm) 9.66 (s, 1H), 8.30-7.80 (m, 5H), 7.61 (d, 2H), 7.32 (d, 2H), 6.76 (m, 3H), 6.22 (t, 1H), 6.03 (sl, 2H), 5.16 (m, 1H), 4.80 (s, 2H), 4.37-4.07 (m, 6H), 3.54 (m, 2H), 3.26 (m, 2H), 2.95 (m, 8H), 2.35 (m, 8H), 1.68-1.42 (m, 14H), 1.39 (m, 56H), 1.12 (m, 74H), 0.96 (m, 12H), 0.84 (t, 12H).

Compound 86

CL534

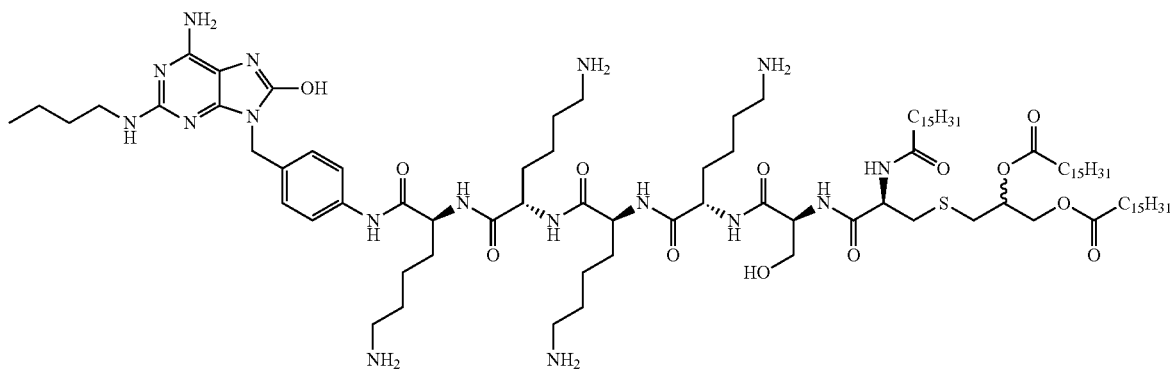

((6R,9S,12S,15S,18S,21S)-25-amino-21-(4-((6-amino-2-(butylamino)-8-hydroxy-9H-purin-9-yl)methyl)phenylcarbamoyl)-12,15,18-tris(4-aminobutyl)-9-(hydroxyl methyl)-7,10,13,16,19-pentaoxo-6-palmitamido-4-thia-8,11,14,17,20-pentaazapentacosane-1,2-diyl dipalmitate The title compound was prepared from intermediate 85 by following the procedure described for example 8, compound 72. Compound 86 was characterized by the following spectroscopic data: $^1$H NMR (DMSO-d$_6$, 300 MHz) δ (ppm) 9.70

Compound 88

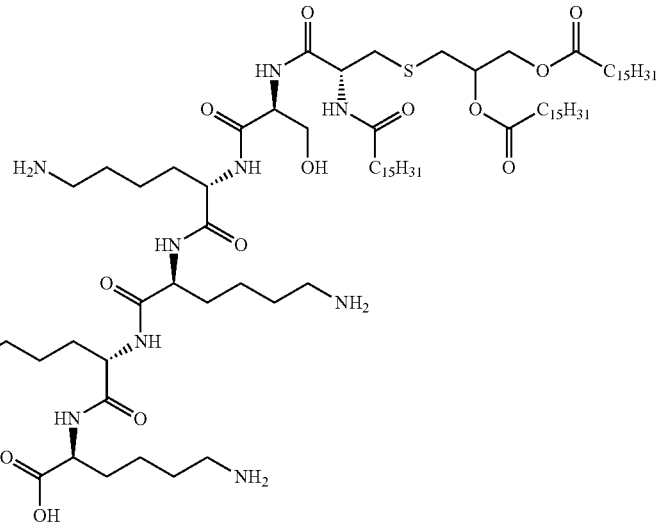

CL535

(s, 1H), 8.06-7.94 (m, 4H), 7.60 (m, 2H), 7.28 (d, 2H), 7.39 (m, 2H), 5.15 (m, 1H), 4.79 (s, 2H), 4.46-4.15 (m, 6H), 3.37 (m, 2H), 2.73 (m, 10H), 2.25 (m, 8H), 1.71-1.39 (m, 30H), 1.25 (m, 68H), 0.83 (m, 12H). MS (+)-ES [M+H]$^+$ 1819.3 m/z.

Example 13

Molecule CL535

Solid Phase Synthesis of

Intermediate 87

PamCys(Pam$_2$)-Ser(tBu)-Lys(Boc)-Lys(Boc)-(Intermediate 76)-Lys(Boc)OH

The title peptide was prepared following the procedure described for example 8, intermediate 69 using the intermediate 76 at the 2$^{nd}$ step and the intermediate 23 at last step. Cleavage from resin was achieved with 5 cycles of 15 min each at rt of 15 mL of a solution 2% TFA, 1% TES in dichloromethane. This solution was charged to the solid phase reactor, the reaction was stirred; the colour of the reaction changed from cycle to cycle from yellow/orange to brownish. After each cycle, cleavage reaction was directly quenched by pouring the reaction into dilute pyridine (pyridine/ethanol 1:9 (v/v)). Resin was then removed by filtration with a frit and subjected to the next cycle. All filtrates were pooled, concentrated to an orange semi-liquid under vacuo. The residue was purified on column of silica gel (8% MeOH/DCM) to give the subject compound (156 mg). Intermediate 87 was characterized by the following spectroscopic data: $^1$H NMR (DMSO-d$_6$, 300 MHz) δ (ppm) 9.75 (s, 1H), 8.39 (s, 1H), 7.83 (m, 2H), 7.83 (d, 2H), 7.42 (d, 2H), 6.75 (m, 2H), 6.23 (t, 1H), 6.05 (sl, 2H), 5.10 (m, 1H), 4.78 (s, 2H), 4.45-4.13 (m, 12H), 3.52 (m, 2H), 3.25 (m, 4H), 2.91 (m, 8H), 2.35 (m, 4H), 1.70 (m, 4H), 1.68-1.42 (m, 14H), 1.35 (m, 35H), 1.12 (m, 79H), 1.09 (s, 9H), 0.90 (t, 12H).

(2S,5S,8S,11S,14S,17R)-5-(4-(4-((6-amino-2-(butylamino)-8-hydroxy-9H-purin-9-yl)methyl)benzamido)butyl)-2,8,11-tris(4-aminobutyl)-14-(hydroxymethyl)-4,7,10,13,16,24-hexaoxo-17-palmitamido-21-(palmitoyloxy)-23-oxa-19-thia-3,6,9,12,15-pentaazanonatriacontan-1-oic acid The title compound was prepared from intermediate 87 by following the procedure described for example 9, compound 78. Compound 88 was characterized by the following spectroscopic data: $^1$H NMR (DMSO-d$_6$, 300 MHz) δ (ppm) 8.52-7.92 (m, 8H), 7.80 (d, 2H), 7.36 (d, 2H), 5.15 (m, 1H), 4.89 (s, 2H), 4.22-4.02 (m, 8H), 3.42 (m, 10H), 2.73 (m, 16H), 2.26 (m, 5H), 1.67-1.58 (m, 20H), 1.34-1.10 (m, 76H), 0.88 (m, 12H). MS (+)-ES [M+H]$^+$ 1848.3 m/z.

Example 14

Molecule CL536

Solid Phase Synthesis of

Intermediate 89

PamCys(Pam$_2$)-Ser(tBu)-Lys(Boc)-(Intermediate 76)-Lys(Boc)-Lys(Boc)OH

The title peptide was prepared following the procedure described for example 8, intermediate 69 using the intermediate 76 at the 3rd step and the intermediate 23 at last step. Cleavage from resin was achieved with 5 cycles of 15 min each at rt of 15 mL of a solution 2% TFA, 1% TES in dichloromethane. This solution was charged to the solid phase reactor, the reaction was stirred; the colour of the reaction changed from cycle to cycle from yellow/orange to brownish. After each cycle, cleavage reaction was directly quenched by pouring the reaction into dilute pyridine (pyridine/ethanol 1:9 (v/v)). Resin was then removed by filtration with a frit and subjected to the next cycle. All filtrates were pooled, concentrated to an orange semi-liquid under vacuo. The residue was purified on column of silica gel (8% MeOH/DCM) to give the subject compound (156 mg). Intermediate 89 was characterized by the following spectroscopic data: $^1$H NMR (DMSO-$d_6$, 300 MHz) δ (ppm) 9.71 (s, 1H), 8.17-7.80 (m, 3H), 7.77 (d, 2H), 7.30 (d, 2H), 6.70 (m, 2H), 6.13 (t, 1H), 6.02 (sl, 2H), 5.11 (m, 1H), 4.82 (s, 2H), 4.50 (m, 1H), 4.45-4.05 (m, 8H), 3.50 (m, 2H), 3.15 (m, 6H), 2.95 (m, 10H), 2.25 (m, 4H), 1.72 (m, 4H), 1.68-1.42 (m, 14H), 1.35 (m, 35H), 1.12 (m, 79H), 1.09 (s, 9H), 0.90 (t, 12H)

Compound 90

Example 15

Molecule CL537

Solid Phase Synthesis of

Intermediate 91

PamCys(Pam$_2$)-Ser(tBu)-(Intermediate 76)-Lys(Boc)-Lys(Boc)-Lys(Boc)OH

The title peptide was prepared following the procedure described for example 8, intermediate 69 using the intermediate 76 at the 4th step and the intermediate 23 at last step. Cleavage from resin was achieved with 5 cycles of 15 min each at rt of 15 mL of a solution 2% TFA, 1% TES in dichloromethane. This solution was charged to the solid phase reac-

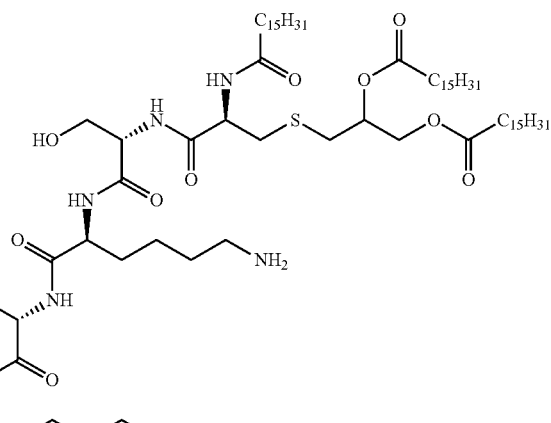

CL536

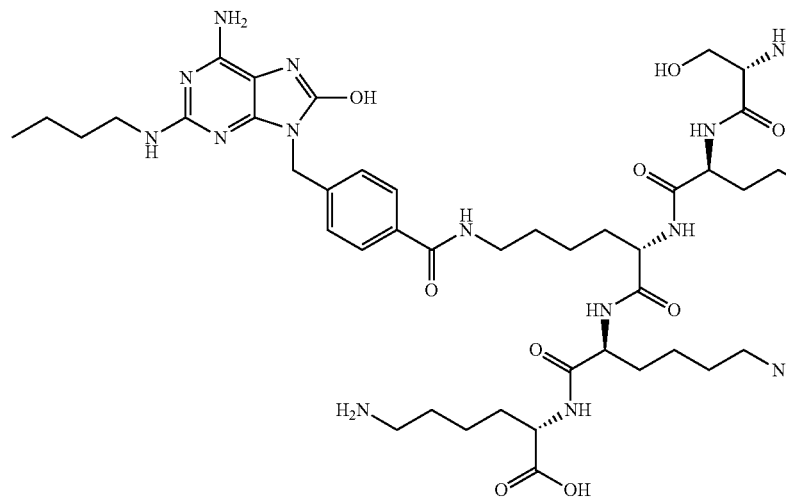

(2S,5S,8S,11S,14S,17R)-8-(4-(4-((6-amino-2-(butylamino)-8-hydroxy-9H-purin-9-yl)methyl)benzamido)butyl)-2,5,11-tris(4-aminobutyl)-14-(hydroxymethyl)-4,7,10,13,16,24-hexaoxo-17-palmitamido-21-(palmitoyloxy)-23-oxa-19-thia-3,6,9,12,15-pentaazanonatriacontan-1-oic acid The title compound was prepared from intermediate 89 by following the procedure described for example 9, compound 78. Compound 90 was characterized by the following spectroscopic data: $^1$H NMR (DMSO-$d_6$, 300 MHz) δ (ppm) 8.50-7.92 (m, 9H), 7.82 (d, 2H), 7.36 (d, 2H), 5.05 (m, 1H), 4.89 (s, 2H), 4.36-4.02 (m, 6H), 3.62 (m, 14H), 3.28 (m, 4H), 2.73 (m, 16H), 2.24 (m, 5H), 1.68 (m, 3H), 1.52 (m, 16H), 1.31 (m, 8H), 1.10 (m, 68H), 0.88 (m, 12H). MS (+)-ES [M+H]$^+$ 1848.3 m/z.

tor, the reaction was stirred; the colour of the reaction changed from cycle to cycle from yellow/orange to brownish. After each cycle, cleavage reaction was directly quenched by pouring the reaction into dilute pyridine (pyridine/ethanol 1:9 (v/v)). Resin was then removed by filtration with a frit and subjected to the next cycle. All filtrates were pooled, concentrated to an orange semi-liquid under vacuo. The residue was purified on column of silica gel (8% MeOH/DCM) to give the subject compound (156 mg). Intermediate 91 was characterized by the following spectroscopic data: $^1$H NMR (DMSO-$d_6$, 300 MHz) δ (ppm) 9.75 (s, 1H), 8.36 (m, 1H), 7.89-7.83 (m, 3H), 7.75 (d, 2H), 7.32 (d, 2H), 6.71 (m, 2H), 6.23 (t, 1H), 6.03 (sl, 2H), 5.07 (m, 1H), 4.83 (s, 2H), 4.30-4.08 (m, 8H), 3.44 (m, 2H), 3.15 (m, 6H), 2.84 (m, 10H), 2.25 (m, 4H), 1.80-1.44 (m, 20H), 1.32 (m, 29H), 1.12 (m, 79H), 1.08 (s, 9H), 0.83 (t, 12H)

Compound 92

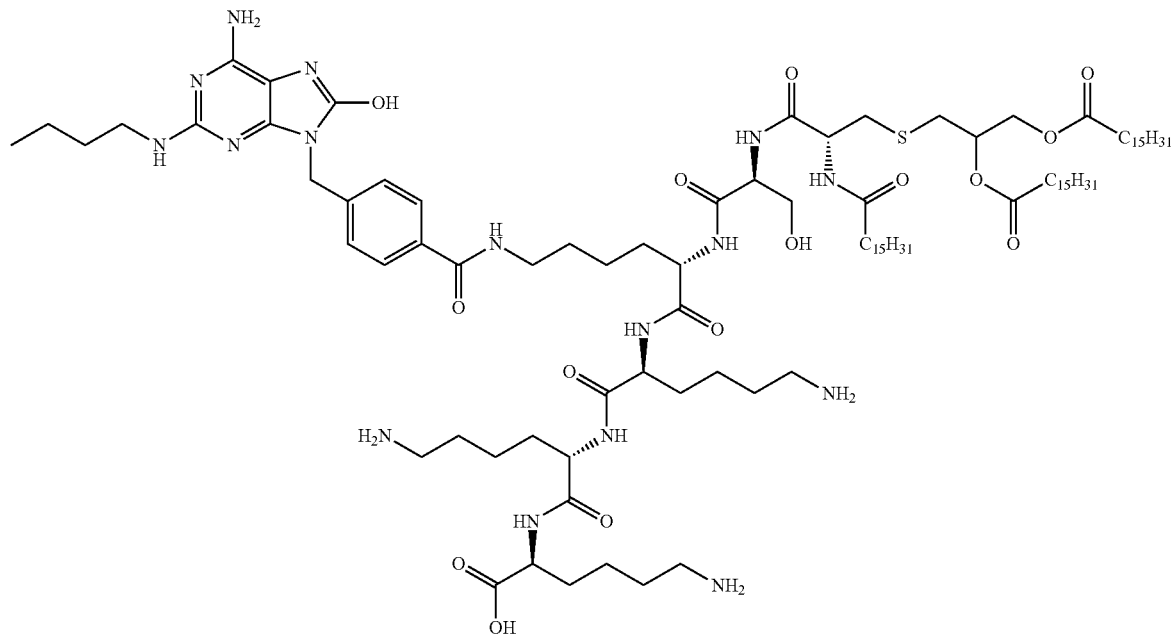

(2S,5S,8S,11S,14S,17R)-11-(4-(4-((6-amino-2-(butylamino)-8-hydroxy-9H-purin-9-yl)methyl)benzamido)butyl)-2,5,8-tris(4-aminobutyl)-14-(hydroxymethyl)-4,7,10,13,16,24-hexaoxo-17-palmitamido-21-(palmitoyloxy)-23-oxa-19-thia-3,6,9,12,15-pentaazanonatria contan-1-oic acid The title compound was prepared from intermediate 91 by following the procedure described for example 9, compound 78. Compound 92 was characterized by the following spectroscopic data: $^1$H NMR (DMSO-d$_6$, 300 MHz) δ (ppm) 8.50-7.94 (m, 10H), 7.81 (d, 2H), 7.35 (d, 2H), 5.06 (m, 1H), 4.89 (s, 2H), 4.36-4.14 (m, 6H), 3.68 (m, 14H), 3.28 (m, 4H), 2.73 (m, 16H), 2.24 (m, 5H), 1.68-1.48 (m, 20H), 1.34 (m, 10H), 1.10 (m, 68H), 0.88 (m, 12H). MS (+)-ES [M+H]$^+$ 1848.3 m/z.

Example 15

Molecule CL580

Intermediate 93

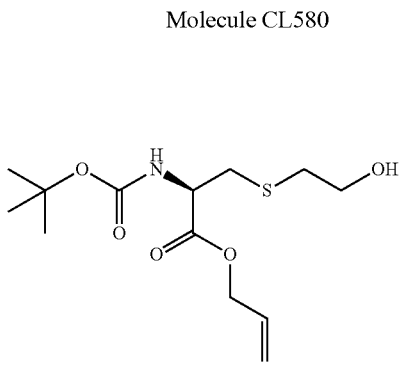

(R)-allyl 2-(tert-butoxycarbonylamino)-3-(2-hydroxyethylthio)propanoate

To a solution of intermediate 14 (10.85 g, 41.5 mmol) in dry DMF (150 mL) was added DIEA (14.37 mL, 83.0 mmol) and 2-bromoethanol (3.53 mL, 49.8 mmol). The mixture was stirred at 90° C. overnight. The solvent was then removed in vacuo and the residue was dissolved in EtOAc (200 mL) and washed with 0.1 N HCl solution water and brine. The organic layer was dried over MgSO$_4$, filtered and concentrated in vacuo. The crude compound was purified on column of silica gel (2% MeOH/DCM) to give the subject compound (10.3 g, yield 81%). Intermediate 93 was characterized by the following spectroscopic data: $^1$H NMR (CDCl$_3$-d$_1$, 300 MHz) δ (ppm) 5.88 (m, 1H), 5.32 (m, 1H), 5.23 (m, 2H), 4.59 (d, 2H), 4.51 (m, 1H), 3.68 (m, 2H), 2.94 (m, 2H), 2.86 (m, 2H), 2.44 (m, 1H), 1.46 (s, 9H).

Intermediate 94

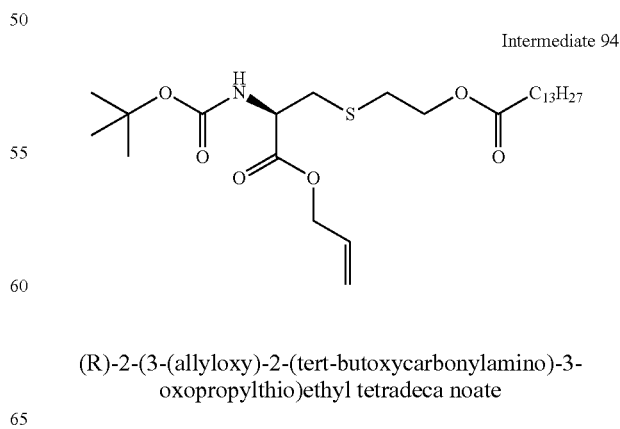

(R)-2-(3-(allyloxy)-2-(tert-butoxycarbonylamino)-3-oxopropylthio)ethyl tetradeca noate A solution of intermediate 93 (1 g, 3.3 mmol) in dry DMF (20 mL) was cooled in an ice bath. EDCl (690 mg, 3.6 mmol), DMAP (440 mg, 3.6 mmol) and myristic acid (822 mg, 3.6 mmol) were added to the solution. The mixture was stirred for 10 min then warmed up to rt and stirred overnight. The reaction mixture was diluted with EtOAc, washed with 0.1 N HCl solution water and brine. The organic layer was dried over MgSO$_4$, filtered and concentrated in vacuo. The crude compound was purified on column of silica gel (1% DCM/MeOH) to give the subject compound (1.49 g, yield 88%). Intermediate 94 was characterized by the following spectroscopic data: $^1$H NMR (CDCl$_3$-d$_1$, 300 MHz) δ (ppm) 5.90 (m, 1H), 5.41-5.30 (m, 3H), 4.68 (d, 2H), 4.59 (m, 1H), 4.21 (t, 2H), 3.04 (m, 2H), 2.77 (m, 2H), 2.32 (m, 2H), 1.63 (m, 2H), 1.47 (s, 9H), 1.29 (s, 20H), 0.89 (t, 3H).

Intermediate 95

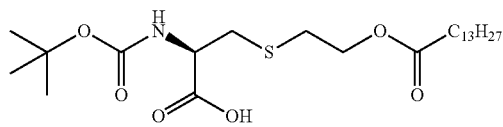

(R)-2-(tert-butoxycarbonylamino)-3-(2-(tetradecanoyloxy)ethylthio)propanoic acid The title compound was prepared from intermediate 94 by following the procedure described for example 1, compound 18. Intermediate 95 was characterized by the following spectroscopic data: $^1$H NMR (CDCl$_3$-d$_1$, 300 MHz) δ (ppm) 5.44 (m, 1H), 4.54 (m, 1H), 4.23 (t, 2H), 3.08 (m, 2H), 2.80 (t, 2H), 2.32 (t, 2H), 1.62 (m, 2H), 1.49 (s, 9H), 1.25 (s, 20H), 0.89 (t, 3H).

Intermediate 96

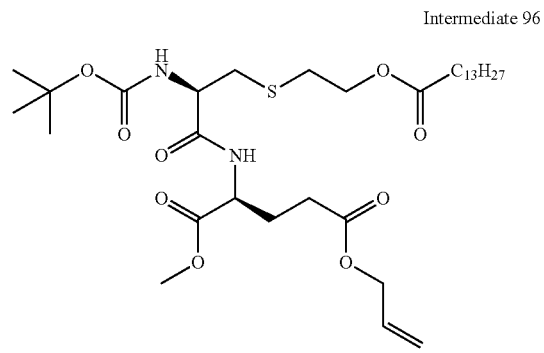

(S)-5-allyl 1-methyl 2-((R)-2-(tert-butoxycarbonylamino)-3-(2-(tetradecanoyloxy)ethylthio)propanamido)pentanedioate The title compound was prepared from intermediate 95 and intermediate H-Glu(OAll)OMe by following the procedure described for example 1, compound 19. Intermediate 96 was characterized by the following spectroscopic data: $^1$H NMR (CDCl$_3$-d$_1$, 300 MHz) δ (ppm) 6.03 (m, 1H), 5.42-5.30 (m, 2H), 4.81 (m, 1H), 4.51 (m, 1H), 4.44 (m, 2H), 4.03 (m, 2H), 3.68 (s, 3H), 3.04 (m, 2H), 2.77 (m, 2H), 2.35 (m, 2H), 2.30 (m, 1H), 2.25 (m, 3H), 1.63 (m, 2H), 1.47 (s, 9H), 1.29 (s, 20H), 0.89 (t, 3H).

Intermediate 97

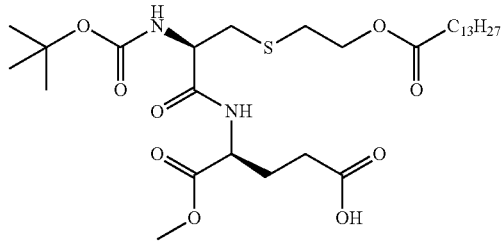

(R)-2-(tert-butoxycarbonylamino)-3-(2-(tetradecanoyloxy)ethylthio)propanoic acid The title compound was prepared from intermediate 96 by following the procedure described for example 1, compound 18. Intermediate 97 was characterized by the following spectroscopic data: $^1$H NMR (DMSO-d$_6$, 300 MHz) δ (ppm) 4.61 (m, 1H), 4.44 (m, 1H), 4.03 (m, 2H), 3.58 (s, 3H), 3.04-2.81 (m, 2H), 2.75 (m, 2H), 2.33 (m, 2H), 2.17 (m, 2H), 2.15 (m, 2H), 1.64 (m, 2H), 1.48 (s, 9H), 1.29 (s, 20H), 0.88 (t, 3H).

Intermediate 98

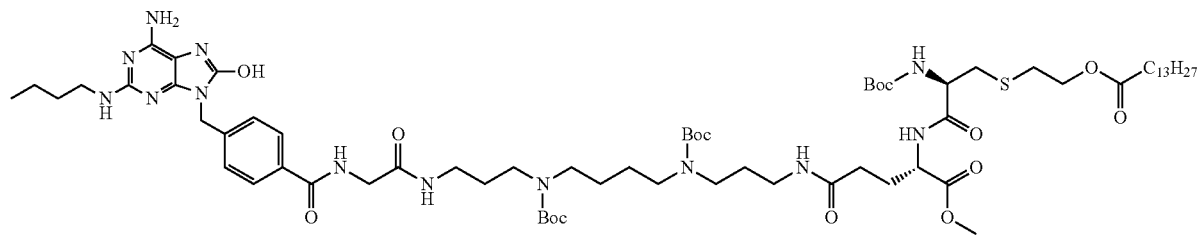

(S)-methyl 1-(4-((6-amino-2-(butylamino)-8-hydroxy-9H-purin-9-yl)methyl)phenyl)-9,14-bis(tert-butoxycarbonyl)-22-((R)-2-(tert-butoxycarbonylamino)-3-(2-(tetradecanoyloxy)ethylthio)propanamido)-1,4,19-trioxo-2,5,9,14,18-pentaaza tricosan-23-oate The title compound was prepared from intermediate 97 and intermediate 11 by following the procedure described for example 1, compound 19. Intermediate 98 was characterized by the following spectroscopic data: $^1$H NMR (DMSO-$d_6$, 300 MHz) δ (ppm) 9.61 (s, 1H), 8.56 (m, 1H), 7.78 (m, 2H), 7.34 (d, 2H), 6.17 (m, 1H), 5.99 (sl, 2H), 5.08 (m, 1H), 4.85 (s, 2H), 4.51 (m, 1H), 4.08 (m, 2H), 3.80 (d, 2H), 3.64 (s, 3H), 3.35 (m, 2H), 3.08 (m, 14H), 2.73 (m, 10H), 2.15 (m, 2H), 2.10 (m, 2H), 1.98 (m, 1H), 1.95 (m, 1H), 1.86 (m, 4H), 1.64 (m, 2H), 1.48 (s, 27H), 1.29 (s, 24H), 0.85 (t, 6H).

Compound 99

CL-580

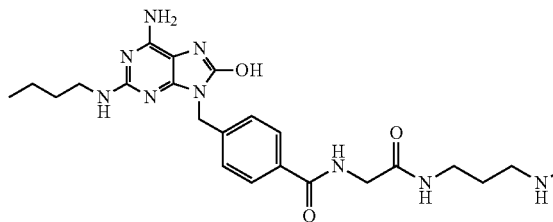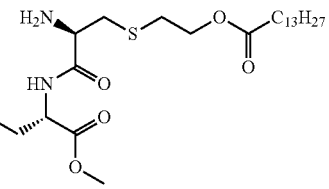

(S)-methyl 1-(4-((6-amino-2-(butylamino)-8-hydroxy-9H-purin-9-yl)methyl)phenyl)-22-((R)-2-amino-3-(2-(tetradecanoyloxy)ethylthio)propanamido)-1,4,19-trioxo-2,5,9,14,18-pentaazatricosan-23-oate The title compound was prepared from intermediate 98 by following the procedure described for example 1, compound 20. Intermediate 99 was characterized by the following spectroscopic data: $^1$H NMR (DMSO-$d_6$, 300 MHz) δ (ppm) 9.63 (s, 1H), 8.95 (m, 1H), 8.46 (m, 1H), 7.85 (m, 2H), 7.35 (d, 2H), 6.17 (m, 1H), 5.98 (sl, 2H), 5.14 (m, 1H), 4.93 (s, 2H), 4.51 (m, 1H), 4.02 (m, 2H), 3.78 (d, 2H), 3.64 (s, 3H), 3.27 (m, 4H), 3.00-2.88 (m, 12H), 2.73 (m, 10H), 2.15 (m, 2H), 2.10 (m, 2H), 1.98 (m, 1H), 1.95 (m, 1H), 1.86 (m, 4H), 1.64 (m, 2H), 1.26 (s, 24H), 0.88 (t, 6H). MS (+)-ES [M+H]$^+$ 1098.7 m/z.

Biological Testing of the Conjugated TLR7 and/or TLR8 and TLR2 Polyamine Molecules of the Invention Example 16

In Vitro Testing of Conjugated Compounds of the Invention

Testing Activation of TLR7 and TLR2 Receptors

The conjugated compounds of the invention were tested for their ability to activate TLR7 and TLR2 receptor signaling, alongside the known TLR7 activator CL264 (InvivoGen) and the TLR2 agonists Pam$_2$CSK$_4$ or Pam$_3$CSK$_4$ (InvivoGen).

Cell-based assays were carried out using TLR7 and TLR2 reporter cell lines (InvivoGen). The reporter cell lines are engineered HEK293 cells, a human embryonic kidney cell line (ATCC, CRL-1573) that stably express either murine TLR7 (HEK-Blue™ mTLR7) or human TLR7 (HEK-Blue™ hTLR7) or human TLR2 (HEK-Blue™ hTLR2) with an NF-κB-inducible secreted embryonic alkaline phosphatase (SEAP) as the reporter gene. The SEAP reporter gene is under the control of the NF-κB and AP-1-inducible promoter, which, upon treatment with a corresponding TLR ligand and activation of NF-κB and AP-1, induces the production of SEAP. Detection of SEAP is measured following culturing cells in HEK-Blue™ Detection media (InvivoGen). HEK-Blue™ Detection contains a SEAP substrate that when hydrolysed by SEAP produces a colorimetric change allowing for detection of SEAP as the protein is secreted. The conjugated compounds were also assayed for their ability to activate both TLR7 and TLR2 in a physiological relevant cell line that naturally expresses these receptors to demonstrate their function as conjugated TLR7-TLR2 polyamine agonists. These assays were carried out using RAW-Blue™ Cells (InvivoGen), derived from RAW 264.7 mouse leukemic monocyte macrophage cell line (ATCC, CRL 2278) stably overexpressing a NF-B/AP-1 inducible SEAP reporter constructs.

To perform the assay, cells were seeded on 96 well microliter plates at 50,000 or 100,000 cells per well for HEK-Blue™ Cells and RAW-Blue™ Cells respectively, and cultured at 37° C. in the presence of the conjugated compounds The TLR7-TLR2 polyamine molecules were prepared as follows: First, stock solutions of the conjugated compounds of the invention were prepared in ethanol or water to a concentration of 10 mg/ml.

The working dilutions of the conjugated TLR7-TLR2 polyamine agonists made up in water or PBS were directly added to the reporter cell lines at a final concentration ranging from 10 µg/mL to 10 pg/ml and incubated at 37° C. for 24 hours. After 24 hours of incubation, the effect on reporter gene activity was determined by reading the OD at 655 nm using iMark™ Microplate Reader (BIO-RAD).

The ability of the molecules of the invention to activate hTLR7 is demonstrated at FIG. 1. The ability of the molecules of the invention to activate mTLR7 is demonstrated in FIG. 2 (categorized; FIG. 2A, TLR7-TLR2 spermine molecules (CL475, CL486, CL487, CL514, CL527, CL553); FIG. 2B, TLR7-TLR2 Pam$_2$CSK$_4$-based molecules (CL413, CL530, CL531, CL533); FIG. 2C, TLR7-TLR2 Pam3CSK4-based molecules (CL534, CL535, CL536, CL537)). The ability of the molecules of the invention to activate hTLR2 is demonstrated at FIG. 3 (categorized; FIG. 3A, TLR7-TLR2 spermine molecules (CL475, CL486, CL487, CL514, CL527, CL553) along-side the intermediary compound CL419 employed as an additional positive control; FIG. 3B, TLR7-TLR2 Pam$_2$CSK$_4$-based molecules (CL413, CL530, CL531, CL533); FIG. 3C, TLR7-TLR2 Pam$_3$CSK$_4$-based molecules (CL534, CL535, CL536, CL537)). Pam$_2$CSK$_4$ and Pam$_3$CSK$_4$ were employed as positive controls and the TLR7 ligand CL264 as a negative control.

The ability of the molecules of the invention to activate endogenous TLR2 and TLR7 in RAW-Blue™ Cells is demonstrated in FIG. 4 (categorized; FIG. 4A, TLR7-TLR2 spermine molecules (CL475, CL486, CL487, CL514, CL527, CL553) along-side the intermediary compound CL419 employed as an additional positive control; FIG. 4B, TLR7-TLR2 Pam$_2$CSK$_4$-based molecules (CL413, CL530, CL531, CL533); FIG. 4C, TLR7-TLR2 Pam$_3$CSK$_4$-based molecules (CL534, CL535, CL536, CL537)). The specificity of the TLR activity was determined by use of a panel of reporter cell lines to the other TLRs (data not shown).

In summary, the results demonstrate that conjugation of TLR7 and/or TLR8 agonist moieties to the TLR2 polyamine agonists generate conjugated compounds that retain TLR7 and TLR2 activity. The molecules show a tendency to activate mouse TLR7 with greater sensitivity than human TLR7. Furthermore, dose-dependent responses of the conjugated compounds indicate significant TLR activities of TLR7 and TLR2 compared to the corresponding controls.

All the variant conjugated compounds exhibit dual activities to TLR7 and TLR2. These results indicate that the conjugation of TLR2 polyamine agonists to a TLR7 agonist moiety does not abrogate TLR7 or TLR2 activity.

Gel Shift Assay and Determination of Nanoparticle Size

To demonstrate that the TLR7-TLR2 polyamine molecules effectively bind to plasmid DNA (pDNA) at a pH comprised between 4 and 8, we performed an in vitro mobility shift assay. To perform this assay, pDNA:TLR7-TLR2 polyamine molecule complexes were prepared as described hereafter.

For pDNA:TLR7-TLR2 polyamine molecules complexes, a ratio pDNA:TLR7-TLR2 polyamine molecules of 3:24 (w:w) was prepared in serum-free culture medium or in 5% glucose. The TLR7-TLR2 conjugated compound of interest was prediluted in serum-free culture medium or in 5% glucose and incubated for 5 minutes at room temperature, prior to the addition of an endotoxin-free, salt-free preparation of pDNA. In these experiments, the pBsr2pCpGLacZh plasmid was used in the pDNA:TLR7-TLR2 polyamine molecule complexes. The pDNA:TLR7-TLR2 polyamine molecule mixtures were incubated at room temperature for 30 minutes to allow the formation of the complex. The control used in these experiments was the cationic lipid transfection agent LyoVec™ (InvivoGen) prepared in a similar manner.

Then, 10 μl of pDNA:TLR7-TLR2 polyamine molecule complexes and 2 μl of charge buffer were mixed and loaded into wells of a 0.8% agarose gel. Samples were migrated through the gel in TAE buffer under 135 voltage for 21 mins and the migration of the pDNA was visualized following ethidium bromide staining under UV light. The ability of TLR7-TLR2 polyamine molecules to complex/associate with the pDNA was identified by partial or complete retardation of the pDNA migration toward the anode in the gel compared to pDNA alone. Gel shift assays demonstrate that pDNA complexes with molecules of the invention that are TLR7-TLR2 spermine molecules (CL475, CL486, CL487, CL514, CL527, CL553), TLR7-TLR2 Pam$_2$CSK$_4$-based molecules (CL413, CL530, CL531, CL533) or TLR7-TLR2 Pam$_3$CSK$_4$-based molecules (CL534, CL535, CL536, CL537) through the inability to migrate through an agarose gel compared to the control of pDNA alone. Ethidium bromide intercalation of pDNA in complex with molecules allowed visualization of complexed pDNA as a smear in the wells of the gel. Some instances pDNA in complexes could not be visualized, despite observing migration of the dye front, likely due to compact complex formation that prevents ethidium bromide intercalation (data not shown).

In order to confirm that TLR7-TLR2 polyamine molecules complex DNA, lipoplex size was determined. The physical characterization of complex was achieved by dynamic light scattering using the analytical equipment for laser diffraction Zetasizer Nano-ZS (Malvern). pDNA:TLR7-TLR2 polyamine molecule complexes were prepared as described above. Subsequently, 50 μl of pDNA: TLR7-TLR2 polyamine molecule complexes were placed into a disposable sizing cuvette and measurements were made under conditions defined according to manufacturer's instructions. The measurements were made at 25° C. in triplicate and a size distribution report was obtained.

A panel of TLR7-TLR2 polyamine molecules and their ability to form complexes with pDNA were tested. The tables hereafter show examples of the sizes of complexes formed of pDNA:TLR7-TLR2 polyamine molecules.

| Complexes | Mean Diameter (nm) | PDI | Conformity (C)/ Non-conformity (NC) |
|---|---|---|---|
| TLR7-TLR2 spermines | | | |
| CL475 | 145.9 | 0.193 | C |
|  | 155.8 | 0.176 | |
|  | 153.5 | 0.158 | |
| CL486 | 209.2 | 0.236 | C |
|  | 179.7 | 0.232 | |
|  | 202.0 | 0.234 | |
| CL487 | 165.6 | 0.255 | C |
|  | 160.0 | 0.241 | |
|  | 148.1 | 0.23 | |
| CL514 | 249.1 | 0.303 | C |
|  | 309.6 | 0.354 | |
|  | 258.3 | 0.372 | |
| CL527 | 175.1 | 0.253 | C |
|  | 156.9 | 0.239 | |
|  | 168.3 | 0.258 | |
| CL553 | 170.0 | 0.226 | C |
|  | 190.0 | 0.230 | |
|  | 180.2 | 0.237 | |
| Positive control molecules | | | |
| CL419 | 147.0 | 0.185 | C |
|  | 148.5 | 0.193 | |
|  | 156.7 | 0.210 | |
| LyoVec ™ | 141.3 | 0.190 | C |
|  | 145.2 | 0.197 | |
|  | 146.6 | 0.203 | |
| TLR7-TLR2 Pam$_2$CSK$_4$-based molecules | | | |
| CL413 | 140.1 | 0.178 | C |
|  | 140.2 | 0.187 | |
|  | 139.1 | 0.229 | |
| CL530 | 188.0 | 0.332 | NC |
|  | 187.6 | 0.351 | |
|  | 213.1 | 0.315 | |
| CL531 | 145.0 | 0.144 | C |
|  | 143.8 | 0.153 | |
|  | 140.1 | 0.138 | |
| CL533 | 140.4 | 0.195 | C |
|  | 149.8 | 0.198 | |
|  | 141.5 | 0.185 | |
| TLR7-TLR2 Pam$_3$CSK$_4$-based molecules | | | |
| CL534 | 165.5 | 0.352 | C |
|  | 187.1 | 0.394 | |
|  | 182.3 | 0.354 | |
| CL535 | 229.5 | 0.351 | NC |
|  | 232.3 | 0.336 | |
|  | 226.8 | 0.396 | |
| CL536 | 231.9 | 0.465 | NC |
|  | 236.1 | 0.583 | |
|  | 225.8 | 0.65 | |

-continued

| Complexes | Mean Diameter (nm) | PDI | Conformity (C)/ Non-conformity (NC) |
|---|---|---|---|
| CL537 | 198.1 | 0.704 | NC |
|  | 203.5 | 0.618 |  |
|  | 219.3 | 0.626 |  |

The tables describe the conformity or non-conformity of the complexes tested related to the polydispersity index (PDI) PDI is a number calculated from a simple two parameter fit to the correlation data called a cumulants analysis. The PDI is dimensionless and scaled such that values smaller than 0.05 are rarely seen other than with latex standards. The maximum value is arbitrarily limited to 1.0. A PDI value of 1 indicates that the sample has a very broad size distribution and may contain large particles or aggregates that could be slowly sedimenting. Generally, the TLR7-TLR2 polyamine molecules forming complexes with pDNA that ranged between 140 and 200 nm in diameter were considered to show conformity, whereas larger sizes were considered to show aggregates or non-conformity. TLR7-TLR2 polyamine molecules in complex with pDNA showing conformity correlated with their ability to transfect cells due to their nanoparticle size.

Cell Transfection

The TLR7-TLR2 molecules were tested for their ability as polyamine molecules to transport plasmid DNA (pDNA) into cells. The pVitro14 LGFP SEAP plasmid (InvivoGen) was complexed to TLR7-TLR2 polyamine molecules and to the control cationic lipid transfection agent, LyoVec™ (InvivoGen). The human HEK293 (ATCC, CRL-1573) and mouse B16-F1 melanoma (ATCC, CRL-6323) cell lines were seeded at a density of 50 000 cells/well and 20 000 cells/well respectively, in the absence or presence of different volumes of the plasmid encoding for the SEAP protein in complex with TLR7-TLR2 polyamine molecules for 48 hours at 37° C. and 10% $CO_2$. Transfection efficiency was assessed by measuring SEAP reporter gene expression: 20 µl of supernatant was sampled and mixed with 180 µl of QUANTI-Blue™ Detection (InvivoGen). In the presence of alkaline phosphatase SEAP, the color of QUANTI-Blue™ changes from pink to purple/blue. The intensity of the blue hue reflects the activity of SEAP. The levels of SEAP secretion were determined quantitatively by reading the OD at 620-655 nm using a spectrophotometer, iMark™ Microplate Reader (BIO-RAD).

The ability of TLR7-TLR2 polyamine molecules to transfect two different cell lines with pDNA is demonstrated in FIG. 5. TLR7-TLR2 molecules that contain spermine and which form uniform nanoparticle complexes with pDNA (see tables above), had the ability to transfect the two cell lines comparable to the control LyoVec™ cationic lipid complex. The intermediary compound CL419 was also employed as an additional positive control. The negative controls used were CL413, a TLR7-TLR2 $Pam_2CSK_4$-based molecule and CL534, a TLR7-TLR2 $Pam_3CSK_4$-based molecule, in complex with pDNA. FIG. 5A demonstrates the ability of TLR7-TLR2 spermine molecules of the invention able to form nanoparticles with pDNA (CL514, CL527, and CL553) to transfect HEK293 cells. FIG. 5B shows the ability of the mentioned spermine molecules of the invention to transfect B16-F1 cells. TLR7-TLR2 poly-lysine molecules CL413 and CL534, although with the ability to form uniform nanoparticle complexes with pDNA, lack the ability to transfect cells due to the absence of the spermine moiety.

IFN Response Assay

The effect of the pDNA:TLR7-TLR2 polyamine molecules complexes on inducing an interferon response was examined. pDNA:TLR7-TLR2 polyamine molecules mixtures (pDNA:TLR7-TLR2 polyamine molecules ratio 3:24, w:w) in serum-free medium or 5% glucose were prepared as described above and added to IFN reporter cells. Luciferase reporter cell lines were used to assay interferon response. A plasmid containing an interferon-inducible luciferase reporter gene was introduced into mouse RAW 264.7 macrophages and mouse B16 melanoma cells, giving rise to the RAW-ISG54 and B16-ISG54 reporter cell lines respectively. Expression of the luciferase reporter gene by the plasmid is under the control of an interferon-inducible promoter (I-ISG54) comprising five interferon-stimulated response elements (ISRE) and the minimal promoter of the human ISG-54K (Interferon Stimulation of a Gene encoding a 54 kDa protein) gene. The ISG-54K gene is induced by interferon regulatory factor 3 (IRF3), which has a key involvement in anti-inflammatory responses (Grandvaux et al. 2002) and the minimal promoter of the human ISG-54K gene contains two ISRE sites and fully inducible by type I interferons (IFN-α and IFN-β) and interferon regulatory factors (IRFs) (Wathelet et al. 1988; Grandvaux et al. 2002).

The RAW-ISG54 and B16-ISG54 reporter cell lines were seeded onto 96 well microtiter plates at 100,000 cells per well and 75,000 cells per well respectively. Cells were cultured in DMEM supplemented with 10% (v/v) heat inactivated fetal bovine serum (30 min at 56° C.), 4.5 g/l glucose, 2 mM L-glutamine, 50 U/ml penicillin, 50 µg/ml streptomycin, 100 µg/ml Normocin™ (InvivoGen) together with pDNA:TLR7-TLR2 polyamine complexes at 37° C. overnight. pDNA:TLR7-TLR2 polyamine molecules complexes were prepared as described above prior to adding to the IFN reporter cells. The induced luciferase expression was assessed in the reporter cell lines using a coelenterazine-base luminescence assay reagent, the Quanti-Luc™ (InvivoGen). Secreted luciferase activity was determined by bioluminescence quantification of the cell culture media using a microplate luminometer (FLUOstar OPTIMA from BMG Labtech).

TLR7-TLR2 polyamine molecules with the ability to induce ISG54 promoter activity is exemplified in FIG. 6. FIG. 6A shows the ability of molecules (CL413, CL514, CL527, CL553) in complexes with pDNA to induce an IFN response in RAW-ISG54 reporter cells when contacted with cells. The positive controls included are LyoVec complexed with pDNA and mouse IFNα and mouse IFNβ. The intermediary compound CL419 was employed as an additional positive control. The negative control employed is CL401, a TLR7-TLR2 molecule which lacks the ability to complex pDNA. FIG. 6B shows the ability of molecules (CL413, CL514, CL527, and CL553) in complexes with pDNA to induce an IFN response in B16-ISG54 reporter cells. Differences in the extent of promoter activity induced by the pDNA complexed molecules were observed between the two reporter cell lines. In general, pDNA:TLR7-2 polyamine molecule complexes that conformed as nanoparticles and demonstrated ability to transfect cells, correlated with the induction of ISG54 promoter activity by the production of type 1 interferons, interferons α and β.

Example 17

In Vivo Testing of the Molecules of the Invention in Complex with pDNA

In Vivo Evaluation of TLR7-TLR2 Spermine Molecules in Complex with pDNA on a Mouse B16-F1 Tumor Model To investigate whether administering in vivo a therapeutically effective amount of a composition concerned by the invention into a tumor environment affects tumor growth, C57BL/6 mice (Janvier S.A.S.) were shaved (on their backs) and were injected subcutaneously with approximately 50 μl ($5\times10^5$) of viable B16-F1 cells (ATCC, CRL-6323) under anesthesia, using 6 to 7 mice per group. Once the tumor volume reached about 5 mm in diameter, around day 7 after tumor cells were grafted, the mice were divided into 4 groups. All animal work was carried out at the animal facility at the Institut de Pharmacologie et de Biologie Structurale (IPBS) in Toulouse, in accordance with institutional guidelines. A first group (control) received intra-tumoral injections of vehicle (Bionolyte G5® with Pluronic® PF68 2% that is often used to facilitate drug solubilization and so enhance delivery), for a total of 3 injections. The second and third groups received intra-tumoral injections of pDNA:CL475 and pDNA:CL419 complexes at ratio pDNA:lipidic polyamines molecules of 3:24 (w:w), for a total of 3 injections. A fourth group received intra-tumoral injections of pDNA:CL553 complexes at ratio pDNA:TLR7-TLR2 polyamine molecule of 10:40 (w:w), for a total of 2 injections. Tumor growth was monitored and measured with calipers after day 5 of grafting tumor cells into mice and then every 2 days after. Measurements were performed under gas anesthesia. Tumor volume in mm$^3$ was determined according to the formula $V=W^2 \times L/2$, where L=length (mm) and W=width (mm).

B16-F1 tumor growth curves are shown in FIG. 7A and the survival rate of mice treated with pDNA:CL475 and pDNA:CL553 TLR7-TLR2 polyamine molecule complexes and pDNA:CL419 the intermediary compound TLR7-TLR2 complexes is shown in FIG. 7B. Mice treated with pDNA:CL475 TLR7-TLR2 polyamine molecule complexes showed significant reduction in tumor growth compared to pDNA:CL419 complexes and vehicle control. Tumor growth was significantly reduced in pDNA:CL553-treated mice compared to other treated groups. By day 24 following tumor cell graft, over 70% and 80% of mice in the pDNA:CL475 and pDNA:CL553 TLR7-TLR2 polyamine complexes treated group respectively, were still alive. In contrast, by day 24, there was no survival of mice from the control groups of vehicle treated and only less than 30% of mice treated with pDNA:CL419.

This example demonstrates that the molecules of the invention that are TLR7 and/or TLR8 agonists covalently conjugated to TLR2 agonists, which have the ability to complex pDNA at pH between 4 and 8, significantly suppress tumor growth in an in vivo mouse model. These molecules of the invention that are polyamine molecules having affinity for DNA, have the ability to trigger a strong interferon response in cells to provide anti-tumor response.

Example 18

In Vivo Testing of the Molecules of the Invention Alone

In Vivo Evaluation of TLR7-TLR2 Pam$_2$CSK$_4$-Based Molecule Alone on a Mouse B16-F1 Tumor Model The investigation of administering in vivo a therapeutically effective amount of a molecule of the invention alone into a tumor environment affects tumor growth, was carried out as described above.

A first group (control) received intra-tumoral injections of vehicle (Bionolyte G5® with Pluronic® PF68 2%), for a total of 3 injections. The second group received intra-tumoral injections of CL413 molecule alone (a TLR7-TLR2 Pam$_2$CSK$_4$-based molecule). Third and forth groups received intra-tumoral injections of the TLR2 ligand, Pam$_2$CSK$_4$ alone, and the TLR7 ligand alone, respectively. A fifth group received a combined treatment of Pam$_2$CSK$_4$ and TLR7 ligand, in solution at the equivalent molecule quantity of the respective TLR2 and TLR7 moieties in CL413 (in 100 μl Bionolyte G5® with Pluronic® F-68 2%) for a total of 3 injections.

The in vivo data of mice treated with CL413 alone, compared to TLR2 ligand Pam$_2$CSK$_4$ alone, a TLR7 ligand alone, and the combined treatment of Pam$_2$CSK$_4$ and TLR7 ligand in the B16-F1 tumor model is demonstrated in FIG. 8. FIG. 8A shows the effectiveness of CL413 and the combined treatment of Pam$_2$CSK$_4$ and TLR7 ligand on reducing tumor volume. By day 23 mice treated with these molecules showed no increase in tumor volume compared to Pam$_2$CSK$_4$ treatment alone, TLR7 ligand treatment alone and vehicle control. FIG. 8B demonstrates the superior effect of CL413, and therefore the covalent attachment of TLR7 and TLR2 Pam$_2$CSK$_4$-based agonists, on mice survival compared to the combined treatment of the two separate agonists. By day 42, 100% of mice treated with CL413 were still alive compared to less than 90% of the combined Pam$_2$CSK$_4$ and TLR7 ligand treated group, 60% of mice treated with Pam$_2$CSK$_4$, over 30% of mice treated with TLR7 ligand, and 0% of survival in the vehicle group.

This example illustrates that the molecules of the invention used, which are TLR7 and/or TLR8 agonists covalently conjugated to TLR2 agonists, when used alone in treatment are more effective than combining the counterpart ligands in the treatment of tumors in an in vivo mouse model.

Included are examples illustrating that the molecules of the invention that are TLR7 and/or TLR8 agonists covalently conjugated to TLR2 agonists, either used alone or in complex with pDNA, significantly suppress tumor growth in an in vivo mouse model.

Among the molecules of the invention that are TLR7 and/or TLR8 agonists covalently conjugated to TLR2 agonists, are polyamine molecules that have affinity for DNA, which when introduced into cells, trigger a strong interferon response known to suppresses tumor growth.

Altogether the examples illustrate that covalently conjugating TLR7 and/or TLR8 agonists to TLR2 agonists are useful in vivo demonstrated by theft anti-tumor ability using a syngenic mouse tumor model. In addition, some of the novel TLR7-TLR2 polyamine molecules of the invention can be used as transfection agents to deliver polyanionic molecules such as nucleic acids including coding or non-coding DNA into cells while concomitantly activating multiple sensors of the innate immune system, namely TLR7, TLR8, TLR2 and cytosolic nucleic acid sensors. As indicated by the results of the in vivo mouse tumor model, one application of the molecules can be useful in the treatment of cancer. Other applications include the use of the molecules and compositions of for the treatment of immune disorders and for use as vaccine adjuvants.

REFERENCES

Throughout this application, various references describe the state of the art to which this invention pertains. The disclosures of these references are hereby incorporated by reference into the present disclosure.

Biggadike et al., US 2011/0229500 A1 (Glaxo). Sep. 22, 2011. Purine derivatives for use in the treatment of allergic, inflammatory and infectious diseases.

Carson et al., US 2010/0210598 A1. Aug. 19, 2010. Toll-like modulators and treatment of diseases.

Cook et al., US 2010/0240623 (AstraZeneca). Sep. 23, 2010. 8-oxoadenine derivatives acting as modulator of TLR7.

Finberg et al., US 2011/0152251. Jun. 23, 2011. Compounds for modulating TLR2.

Fink et al., U.S. Pat. No. 7,485,432 B2 (3M). Feb. 3, 2009. Selective Modulation of TLR-mediated biological Activity.

Gerster et al. U.S. Pat. No. 4,689,338. (Riker) Aug. 25, 1987. 1H-Imidazo[4,5-c]quinolin-4-amines and antiviral use.

Gorden et al., US 2011/0070575 A1 (Coley). Mar. 24, 2011. Immunomodulatory compositions, combinations and Methods (TLR7).

Isobe et al., US 2011/8044056 B2 (Sumitomo). Oct. 25, 2011. Adenine Compound.

Jackson et al., US 2010/0310595 A1. Dec. 9, 2010. Methods of Transfection and compositions therefor.

Johnson et al., US 2011/0282061 A1.(Glaxo). Nov. 17, 2011. Lipidated imidazoquinoline derivatives.

Jones et al., WO/2007/093901. Aug. 28, 2007. 3-Dezazapurine derivatives as TLR7 modulators.

Nakaar et al., US 2009/0028889 (Vaxinnate). Novel polypeptide ligands for Toll-like receptor 2.

Wu et al., US 2011/0053893 A1 (Novartis). Mar. 3, 2011. Compounds and compositions as TLR activity modulators.

Adams S. 2009. Toll-like receptor agonists in cancer therapy. Immunotherapy 1: 949-964.

Aliprantis A O, Yang R B, Mark M R, Suggett S, Devaux B, Radolf J D, Klimpel G R, Godowski P, Zychlinsky A. 1999. Cell activation and apoptosis by bacterial lipoproteins through toll-like receptor-2. *Science.* 285(5428):736-9.

Agnihotri G, Crall B M, Lewis T C, Day T P, Balakrishna R, Warshakoon H J, Malladi S S, David S A. 2011. Structure-activity relationships in toll-like receptor 2-agonists leading to simplified monoacyl lipopeptides. *Journal of medicinal chemistry* 54: 8148-8160.

Ambach A, Bonnekoh B, Nguyen M, Schon M P, Gollnick H. 2004. Imiquimod, a Toll-like receptor-7 agonist, induces perforin in cytotoxic T lymphocytes in vitro. Molecular immunology 40: 1307-1314.

Barber G N. 2011a. Innate immune DNA sensing pathways: STING, AIMII and the regulation of interferon production and inflammatory responses. Current opinion in immunology 23: 10-20.

Barber G N. 2011 b. STING-dependent signaling. Nature immunology 12: 929-930.

Barlos, K., Gatos, D., Kallitsis, J., Papaphotiu, G., Sotiriu, P., Wengqing, Y., and Schafer, W 1989. *Tetrahedron Letters,* 30, 3943-3946.

Bennaceur K, Chapman J A, Touraine J L, Portoukalian J. 2009. Immunosuppressive networks in the tumour environment and their effect in dendritic cells. *Biochimica et biophysica acta* 1795: 16-24.

Beutler B A. 2009. TLRs and innate immunity. Blood 113: 1399-1407.

Bourquin C, Hotz C, Noerenberg D, Voelkl A, Heidegger S, Roetzer L C, Storch B, Sandholzer N, Wurzenberger C, Anz D et al. 2011. Systemic cancer therapy with a small molecule agonist of toll-like receptor 7 can be improved by circumventing TLR tolerance. *Cancer research* 71: 5123-5133.

Burdette D L, Monroe K M, Sotelo-Troha K, Iwig J S, Eckert B, Hyodo M, Hayakawa Y, Vance R E. 2011. STING is a direct innate immune sensor of cyclic di-GMP. Nature 478: 515-518.

Caproni E, Tritto E, Cortese M, Muzzi A, Mosca F, Monaci E, Baudner B, Seubert A, De Gregorio E. 2012. MF59 and Pam3CSK4 boost adaptive responses to influenza subunit vaccine through an IFN type I-independent mechanism of action. *J Immunol* 188: 3088-3098.

Carpino L A, Han G Y. 1970. The 9-fluorenylmethoxycarbonyl function, a new base-sensitive amino-protecting group. *J. Am. Chem. Soc.* 92(19):5748-5749.

Carpino L A, Han G Y. 1972, The 9-Fluorenylmethoxycarbonyl Amino-Protecting Group. *J. Org. Chem.* 37(22):3404-3409.

Caviar T, Ablasser A, Hornung V. 2012. Induction of type I IFNs by intracellular DNA-sensing pathways. Immunology and cell biology.

Chiu Y H, Macmillan J B, Chen Z J. 2009. RNA polymerase III detects cytosolic DNA and induces type I interferons through the RIG-I pathway. Cell 138: 576-591.

Curtin J F, Liu N, Candolfi M, Xiong W, Assi H, Yagiz K, Edwards M R, Michelsen K S, Kroeger K M, Liu C et al. 2009. HMGB1 mediates endogenous TLR2 activation and brain tumor regression. *PLoS medicine* 6: e10.

Dabbagh K, Lewis D B. 2003. Toll-like receptors and T-helper-1/T-helper-2 response. *Curr Opin Infect Dis.* 16(3):199-204.

Duggan J M, You D, Cleaver J O, Larson D T, Garza R J, Guzman Pruneda F A, Tuvim M J, Zhang J, Dickey B F, Evans S E. 2011. Synergistic interactions of TLR2/6 and TLR9 induce a high level of resistance to lung infection in mice. *J Immunol* 186: 5916-5926.

El-Omar E M, Ng M T, Hold G L. 2008. Polymorphisms in Toll-like receptor genes and risk of cancer. *Oncogene* 27: 244-252.

Garaude J, Kent A, van Rooijen N, Blander J M. 2012. Simultaneous targeting of toll- and nod-like receptors induces effective tumor-specific immune responses. *Science translational medicine* 4: 120ra116.

Garay R P, Viens P, Bauer J, Normier G, Bardou M, Jeannin J F, Chiavaroli C. 2007. Cancer relapse under chemotherapy: why TLR2/4 receptor agonists can help. *European journal of pharmacology* 563: 1-17.

Garegg, P. J.; Johansson, R.; Ortega, C.; Samuelsson, B. 1982. *J. Chem. Soc., Perkin Trans* 1, 681-683.

Garland S M. 2003. Imiquimod. Current opinion in infectious diseases 16: 85-89.

Grandvaux N, Servant M J, tenOever B, Sen G C, Balachandran S, Barber G N, Lin R, Hiscott J. 2002. Transcriptional profiling of interferon regulatory factor 3 target genes: direct involvement in the regulation of interferon-stimulated genes. Journal of virology 76: 5532-5539.

Hemmi H, Kaisho T, Takeuchi O, Sato S, Sanjo H, Hoshino K, Horiuchi T, Tomizawa H, Takeda K, Akira S. 2002. Small anti-viral compounds activate immune cells via the TLR7 MyD88-dependent signaling pathway. *Nature immunology* 3: 196-200.

Hoebe K, Janssen E, Beutler B. 2004. The interface between innate and adaptive immunity. *Nature immunology* 5: 971-974.

Hotz C, Bourquin C. 2012. Systemic cancer immunotherapy with Toll-like receptor 7 agonists: Timing is everything. *Oncoimmunology* 1: 227-228.

Huang B, Zhao J, Unkeless J C, Feng Z H, Xiong H. 2008. TLR signaling by tumor and immune cells: a double-edged sword. *Oncogene* 27: 218-224.

Janeway C A, Jr., Medzhitov R. 2002. Innate immune recognition. Annual review of immunology 20: 197-216.

Jayakumar A, Castilho T M, Park E, Goldsmith-Pestana K, Blackwell J M, McMahon-Pratt D. 2011. TLR1/2 activation during heterologous prime-boost vaccination (DNA- MVA) enhances CD8+ T Cell responses providing protection against *Leishmania* (Viannia). *PLoS neglected tropical diseases* 5: e1204.

Jin M S, Kim S E, Heo J Y, Lee M E, Kim H M, Paik S G, Lee H, Lee J O. 2007. Crystal structure of the TLR1-TLR2 heterodimer induced by binding of a tri-acylated lipopeptide. *Cell.* 130(6):1071-82.

Jones P, Pryde D C, Tran T D, Adam F M, Bish G, Calo F, Ciaramella G, Dixon R, Duckworth J, Fox D N et al. 2011. Discovery of a highly potent series of TLR7 agonists. *Bioorganic & medicinal chemistry letters* 21: 5939-5943.

Kanzler H, Barrat F J, Hessel E M, Coffman R L. 2007. Therapeutic targeting of innate immunity with Toll-like receptor agonists and antagonists. Nature medicine 13: 552-559.

Kauffman E C, Liu H, Schwartz M J, Scherr D S. 2012. Toll-like receptor 7 agonist therapy with imidazoquinoline enhances cancer cell death and increases lymphocytic infiltration and proinflammatory cytokine production in established tumors of a renal cell carcinoma mouse model. *Journal of oncology* 2012: 103298.

Kawai T, Akira S. 2011. Toll-like receptors and their crosstalk with other innate receptors in infection and immunity. *Immunity* 34: 637-650.

Keating S E, Baran M, Bowie A G. 2011. Cytosolic DNA sensors regulating type I interferon induction. Trends in immunology 32: 574-581.

Kellner J, Erhard M, Schranner I, Losch U. 1992. The influence of various adjuvants on antibody synthesis following immunization with an hapten. *Biol Chem Hoppe Seyler.* 373(1):51-5.

Krieg A M. 2008. Toll-like receptor 9 (TLR9) agonists in the treatment of cancer. *Oncogene* 27: 161-167.

Kurimoto A, Ogino T, Ichii S, Isobe Y, Tobe M, Ogita H, Takaku H, Sajiki H, Hirota K, Kawakami H. 2004. Synthesis and evaluation of 2-substituted 8-hydroxyadenines as potent interferon inducers with improved oral bioavailabilities. *Bioorganic & medicinal chemistry* 12: 1091-1099.

Kutikhin A G. 2011. Association of polymorphisms in TLR genes and in genes of the Toll-like receptor signaling pathway with cancer risk. *Human immunology* 72: 1095-1116.

Leah E. 2011. Rheumatoid arthritis: spontaneous release of cytokines from synovial tissue is blocked by anti-TLR2. *Nature Reviews Rheumatology* 7: 254.

Lee J, Chuang T H, Redecke V, She L, Pitha P M, Carson D A, Raz E, Cottam H B. 2003. Molecular basis for the immunostimulatory activity of guanine nucleoside analogs: activation of Toll-like receptor 7. *Proceedings of the National Academy of Sciences of the United States of America* 100: 6646-6651.

Lee J Y, Plakidas A, Lee W H, Heikkinen A, Chanmugam P, Bray G, Hwang D H. 2003. Differential modulation of Toll-like receptors by fatty acids: preferential inhibition by n-3 polyunsaturated fatty acids. *J Lipid Res.* 4-((3):479-486.

Lombardi V, Van Overtvelt L, Horiot S, Moussu H, Chabre H, Louise A, Balazuc A M, Mascarell L, Moingeon P. 2008. Toll-like receptor 2 agonist Pam3CSK4 enhances the induction of antigen-specific tolerance via the sublingual route. *Clinical and experimental allergy journal of the British Society for Allergy and Clinical Immunology* 38: 1819-1829.

MacLeod H, Wetzler L M. 2007. T cell activation by TLRs: a role for TLRs in the adaptive immune response. *Science's STKE: signal transduction knowledge environment* 2007: pe48.

Mandal R K, George G P, Mittal R D. 2012. Association of Toll-like receptor (TLR) 2, 3 and 9 genes polymorphism with prostate cancer risk in North Indian population. *Molecular biology reports* 39: 7263-7269.

Metzger J W, Beck-Sickinger A G, Loleit M, Eckert M, Bessler W G, Jung G. 1995. Synthetic 5-(2,3-dihydroxypropyl)-cysteinyl peptides derived from the N-terminus of the cytochrome subunit of the photoreaction centre of *Rhodopseudomonas viridis* enhance murine splenocyte proliferation. *Journal of peptide science: an official publication of the European Peptide Society* 1: 184-190.

Meyer T, Stockfleth E. 2008. Clinical investigations of Toll-like receptor agonists. *Expert opinion on investigational drugs* 17: 1051-1065.

Muhlradt P F, Kiess M, Meyer H, Sussmuth R, Jung G. 1998. Structure and specific activity of macrophage-stimulating lipopeptides from *Mycoplasma hyorhinis*. *Infection and immunity* 66: 4804-4810.

Muruve D A, Petrilli V, Zaiss A K, White L R, Clark S A, Ross P J, Parks R J, Tschopp J. 2008. The inflammasome recognizes cytosolic microbial and host DNA and triggers an innate immune response. Nature 452: 103-107

Newton K, Dixit V M. 2012. Signaling in innate immunity and inflammation. *Cold Spring Harbor perspectives in biology* 4.

Nguyen C H, Bisagni E. 1984. A general route to 5- and 6-substituted 4-amino-2-oxo-1,2-dihydropyridines. Synthesis. 9:765-766.

Okusawa T, Fujita M, Nakamura J, Into T, Yasuda M, Yoshimura A, Hara Y, Hasebe A, Golenbock D T, Morita M, Kuroki Y, Ogawa T, Shibata K. 2004. Relationship between structures and biological activities of mycoplasmal diacylated lipopeptides and their recognition by toll-like receptors 2 and 6. *Infect Immun.* 72: 1657-1665.

Ozinsky A, Underhill D M, Fontenot J D, Hajjar A M, Smith K D, Wilson C B, Schroeder L, Aderem A. 2000. The repertoire for pattern recognition of pathogens by the innate immune system is defined by cooperation between toll-like receptors. *Proc Natl Acad Sci USA.* 97(25):13766-13771.

Palsson-McDermott E M, O'Neill L A. 2007. The potential of targeting Toll-like receptor 2 in autoimmune and inflammatory diseases. *Ir J Med Sci.* 176; 253-260.

Pasare C, Medzhitov R. 2005. Toll-like receptors: linking innate and adaptive immunity. *Advances in experimental medicine and biology* 560: 11-18.

Rakoff-Nahoum S, Medzhitov R. 2009. Toll-like receptors and cancer. *Nature reviews Cancer* 9: 57-63.

Sacht G, Marten A, Deiters U, Sussmuth R, Jung G, Wingender E, Muhlradt P F. 1998. Activation of nuclear factor-kappaB in macrophages by mycoplasmal lipopeptides. *European journal of immunology* 28: 4207-4212.

Salaun B, Zitvogel L, Asselin-Paturel C, Morel Y, Chemin K, Dubois C, Massacrier C, Conforti R, Chenard M P, Sabourin J C et al. 2011. TLR3 as a biomarker for the therapeutic efficacy of double-stranded RNA in breast cancer. *Cancer research* 71: 1607-1614.

Salunke D B, Shukla N M, Yoo E, Crall B M, Balakrishna R, Malladi S S, David S A. 2012. Structure-activity relationships in human Toll-like receptor 2-specific monoacyl lipopeptides. *Journal of medicinal chemistry* 55: 3353-3363.

Sato Y, Goto Y, Narita N, Hoon D S. 2009. Cancer Cells Expressing Toll-like Receptors and the Tumor Microenvironment. *Cancer microenvironment: official journal of the International Cancer Microenvironment Society* 2 Suppl 1: 205-214.

Satoh T, Kato H, Kumagai Y, Yoneyama M, Sato S, Matsushita K, Tsujimura T, Fujita T, Akira S, Takeuchi O. 2010. LGP2 is a positive regulator of RIG-I- and MDA5-mediated antiviral responses. Proceedings of the National Academy of Sciences of the United States of America 107: 1512-1517.

Schmidt J, Welsch T, Jager D, Muhlradt P F, Buchler M W, Marten A. 2007. Intratumoural injection of the toll-like receptor-2/6 agonist 'macrophage-activating lipopeptide-2' in patients with pancreatic carcinoma: a phase I/II trial. *British journal of cancer* 97: 598-604.

Seifert R, Schultz G, Richter-Freund M, Metzger J, Wiesmüller K H, Jung G, Bessler W G, Hauschildt S. 1990. Activation of superoxide formation and lysozyme release in human neutrophils by the synthetic lipopeptide Pam3Cys-Ser-(Lys)4. Involvement of guanine-nucleotide-binding proteins and synergism with chemotactic peptides. *Biochem J.* 267(3):795-802.

Schon M P, Schon M. 2004. Immune modulation and apoptosis induction: two sides of the antitumoral activity of imiquimod. *Apoptosis: an international journal on programmed cell death* 9: 291-298.

Smits E L, Ponsaerts P, Berneman Z N, Van Tendeloo V F. 2008. The use of TLR7 and TLR8 ligands for the enhancement of cancer immunotherapy. *The oncologist* 13: 859-875.

So E Y, Ouchi T. 2010. The application of Toll like receptors for cancer therapy. *International journal of biological sciences* 6: 675-681.

Sun L, Wu J, Du F, Chen X, Chen Z J. 2012. Cyclic GMP-AMP Synthase is a cytosolic DNA sensor that activates the type I interferon pathway. *Science* (ahead of print) DOI: 10.1126/science.1232458.

Takaoka A, Wang Z, Choi M K, Yanai H, Negishi H, Ban T, Lu Y, Miyagishi M, Kodama T, Honda K et al. 2007. DAI (DLM-1/ZBP1) is a cytosolic DNA sensor and an activator of innate immune response. Nature 448: 501-505.

Takeshita F, Ishii K J. 2008. Intracellular DNA sensors in immunity. Current opinion in immunology 20: 383-388.

Takeuchi O, Akira S. 2009. Innate immunity to virus infection. Immunological reviews 227: 75-86.

Tuvim M J, Gilbert B E, Dickey B F, Evans S E. 2012. Synergistic TLR2/6 and TLR9 activation protects mice against lethal influenza pneumonia. *PloS one* 7: e30596.

Tye H, Kennedy C L, Najdovska M, McLeod L, McCormack W, Hughes N, Dev A, Sievert W, Ooi C H, Ishikawa T O, Oshima H, Bhathal P S, Parker A E, Oshima M, Tan P, Jenkins B J. 2012. STAT3-driven upregulation of TLR2 promotes gastric tumorigenesis independent of tumor inflammation. *Cancer Cell.* 22(4):466-78

Underhill D M, Ozinsky A, Smith K D, Aderem A. 1999. Toll-like receptor-2 mediates mycobacteria-induced proinflammatory signaling in macrophages. *Proc Natl Acad Sci USA.* 96(25):14459-63.

Wang R F, Miyahara Y, Wang H Y. 2008. Toll-like receptors and immune regulation: implications for cancer therapy. *Oncogene* 27: 181-189.

Wathelet M G, Clauss I M, Content J, Huez G A. 1988. Regulation of two interferon-inducible human genes by interferon, poly(rI).poly(rC) and viruses. European journal of biochemistry/FEBS 174: 323-329.

Whitmore M M, DeVeer M J, Edling A, Oates R K, Simons B, Lindner D, Williams B R. 2004. Synergistic activation of innate immunity by double-stranded RNA and CpG DNA promotes enhanced antitumor activity. *Cancer research* 64: 5850-5860.

Wiesmuller K H, Bessler W, Jung G. 1983. Synthesis of the mitogenic S-[2,3-bis(palmitoyloxy)propyl]-N-palmitoyl-pentapeptide from *Escherichia coli* lipoprotein. *Hoppe-Seyler's Zeitschrift fur physiologische Chemie* 364: 593-606.

Wu J, Sun L, Chen X, Du F, Shi H, Chen C, Chen Z J. 2012. Cyclic GMP-AMP is an endogenous second messenger in innate immune signaling by cytosolic DNA. *Science* (ahead of print) DOI:10.1126/science.1229963.

Yang P, An H, Liu X, Wen M, Zheng Y, Rui Y, Cao X. 2010. The cytosolic nucleic acid sensor LRRFIP1 mediates the production of type I interferon via a beta-catenin-dependent pathway. Nature immunology 11: 487-494.

Zahringer U, Lindner B, Inamura S, Heine H, Alexander C. 2008. TLR2—promiscuous or specific? A critical re-evaluation of a receptor expressing apparent broad specificity. *Immunobiology* 213: 205-224.

Zhang Y, Luo F, Cai Y, Liu N, Wang L, Xu D, Chu Y. 2011. TLR1/TLR2 agonist induces tumor regression by reciprocal modulation of effector and regulatory T cells. *J Immunol* 186: 1963-1969.

The invention claimed is:
1. A conjugated compound of Formula I:

Q-Z—$R^4$    Formula I wherein Q is

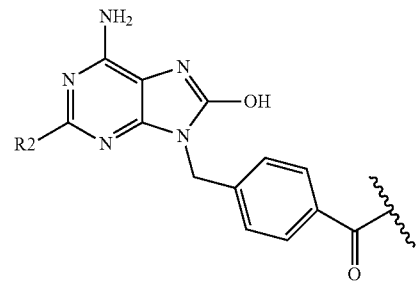

a tautomer thereof or a pharmaceutically acceptable salt, of said compound or tautomer, wherein:
$R_2$ is a $C_1$-$C_{10}$ alkylamino;
Z—$R^4$ is a TLR2 agonist of formula III:

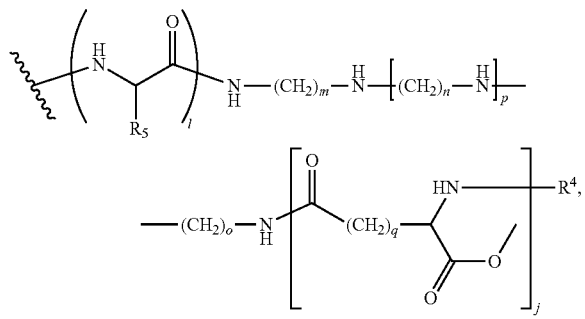

wherein:
$R^5$ is the specific side chain of L or D isomers of an amino acid selected from the group consisting of alanine, valine, leucine, isoleucine, phenylalanine, tryptophan, methionine, glycine, serine, threonine, cysteine, tyrosine, asparagine, glutamine, aspartic acid, glutamic acid, lysine, arginine, proline and histidine;

j and l, identical or different, are 0 or 1;

p is integer from 0 to 6;

m, n, o, and q, identical or different, are integers from 1 to 4;

and $R^4$ is a lipid of Formula XI:

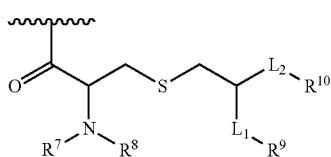

Formula XI wherein:

$R^7$ and $R^8$ are independently from each other H, $C_1$-$C_{30}$alkyl, $C_2$-$C_{30}$lkylenyl, —C(O)—$C_1$-$C_{30}$alkyl, —C(O)—$C_2$-$C_{30}$alkylenyl, or —C(O)—O—$C_1$-$C_{30}$alkyl;

$R^9$ is H, $C_1$-$C_{30}$alkyl or $C_2$-$C_{30}$alkylenyl;

$R^{10}$ is H, $C_1$-$C_{30}$alkyl or $C_2$-$C_{30}$alkylenyl;

$R^9$ and $R^{10}$ are not both H;

$L_1$ is absent, —OC(O)—, —O—, —$NR^{11}$C(O)—, —OC(O)$NR^{11}$— or —CH2- wherein $R^{11}$ is H, $C_1$-$C_{30}$alkyl or $C_2$-$C_{30}$alkylenyl;

If $L_1$ is present, $L_2$ is —$CH_2$OC(O)—, —$CH_2$O—, —$CH_2NR^{11}$C(O)— or —$CH_2$—, and if $L_1$ is absent, $L_2$ is —OC(O)—, —O—, —$NR^{11}$C(O)—, —$NR^{10}R^{11}$, —OC(O)$NR^{11}$— or —CH2- wherein $R^{11}$ is as defined above.

2. The conjugated compound according to claim 1, wherein:

Z is of formula III wherein l=1, $R^5$=H, m=3, n=4, p=1, o=3 and j=0 or 1 and q=2.

3. The conjugated compound according to claim 1, wherein $R^4$ is a lipid of formula XI wherein:

$R^7$ and $R^8$ are independently from each other H or —C(O)—$C_1$-$C_{30}$alkyl;

$R^9$ and $R^{10}$ are independently from each other H or $C_1$-$C_{30}$alkyl;

$R^9$ and $R^{10}$ are not both H and $L_1$ is absent and $L_2$ is —OC(O)—.

4. The conjugated compound according to claim 1, wherein said conjugated compound is selected from the group consisting of:

(20R)-20-amino-1-(4-((6-amino-2-(butylamino)-8-hydroxy-9H-purin-9-yl)methyl)phenyl)-1,4,19-trioxo-22-thia-2,5,9,14,18-pentaazapentacosane-24,25-diyl dipalmitate, (20R)-1-(4-((6-amino-2-(butylamino)-8-hydroxy-9H-purin-9-yl)methyl)phenyl)-1,4,19-trioxo-20-palmitamido-22-thia-2,5,9,14,18-pentaazapentacosane-24,25-diyl dipalmitate, and (S)-methyl 1-(4-((6-amino-2-(butylamino)-8-hydroxy-9H-purin-9-yl)methyl)phenyl)-22-((R)-2-amino-3-(2-(tetradecanoyloxy)ethylthio)propanamido)-1,4,19-trioxo-2,5,9,14,18-pentaazatricosan-23-oate, a tautomer thereof or a pharmaceutically acceptable salt of said compound or tautomer.

* * * * *